US012668813B2

(12) United States Patent
Xu

(10) Patent No.: US 12,668,813 B2
(45) Date of Patent: Jun. 30, 2026

(54) NEUROD1 VECTOR

(71) Applicant: NeuExcell Therapeutics Inc., State College, PA (US)

(72) Inventor: Jie Xu, State College, PA (US)

(73) Assignee: NeuExcell Therapeutics Inc., State College, PA (US)

( * ) Notice: Subject to any disclaimer, the term of this patent is extended or adjusted under 35 U.S.C. 154(b) by 74 days.

(21) Appl. No.: 17/487,699

(22) Filed: Sep. 28, 2021

(65) Prior Publication Data

US 2022/0106613 A1 Apr. 7, 2022

Related U.S. Application Data

(60) Provisional application No. 63/246,545, filed on Sep. 21, 2021, provisional application No. 63/084,908, filed on Sep. 29, 2020.

(51) Int. Cl.
*C12N 15/86* (2006.01)
*A61K 35/761* (2015.01)

(52) U.S. Cl.
CPC ............ *C12N 15/86* (2013.01); *A61K 35/761* (2013.01)

(58) Field of Classification Search
None
See application file for complete search history.

(56) References Cited

U.S. PATENT DOCUMENTS

| | | | |
|---|---|---|---|
| 5,648,097 A | 7/1997 | Nuwayser | |
| 5,695,995 A | 12/1997 | Weintraub et al. | |
| 6,444,463 B1 | 9/2002 | Tapscott | |
| 6,602,680 B2 | 8/2003 | Rubenstein et al. | |
| 6,630,486 B1 | 10/2003 | Royer | |
| 7,041,507 B1 | 5/2006 | Levesque et al. | |
| 8,257,969 B2 * | 9/2012 | Farrar ................ | A61K 48/0066 |
| | | | 435/325 |
| 8,440,431 B2 | 5/2013 | Voytas et al. | |
| 8,440,432 B2 | 5/2013 | Voytas et al. | |
| 8,450,471 B2 | 5/2013 | Voytas et al. | |
| 8,586,363 B2 | 11/2013 | Voytas et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 9,260,752 B1 | 2/2016 | May et al. | |
| 9,410,198 B2 | 8/2016 | May et al. | |
| 9,717,804 B2 | 8/2017 | Chen et al. | |
| 9,725,714 B2 | 8/2017 | May et al. | |
| 9,738,908 B2 | 8/2017 | Wu | |
| 9,803,194 B2 | 10/2017 | May et al. | |
| 9,809,814 B1 | 11/2017 | May et al. | |

| | | | |
|---|---|---|---|
| 10,076,574 B2 | 9/2018 | Wang et al. | |
| 10,201,619 B2 | 2/2019 | Chen et al. | |
| 10,561,742 B2 | 2/2020 | Chen et al. | |
| 10,973,930 B2 | 4/2021 | Chen et al. | |
| 11,014,976 B2 | 5/2021 | Esteves et al. | |
| 11,104,881 B2 | 8/2021 | Ying et al. | |
| 11,167,044 B2 | 11/2021 | Chen et al. | |
| 11,851,491 B2 | 12/2023 | Baeuerle et al. | |
| 2002/0151066 A1 | 10/2002 | Rubenstein et al. | |
| 2002/0172952 A1 | 11/2002 | Henderson et al. | |
| 2002/0187951 A1 | 12/2002 | Aebischer et al. | |
| 2004/0141946 A1 | 7/2004 | Schaebitz et al. | |
| 2004/0192630 A1 | 9/2004 | Kyrkanides | |
| 2005/0265981 A1 | 12/2005 | Salim-Nordstrom | |
| 2006/0127358 A1 | 6/2006 | Muzyczka et al. | |
| 2008/0050393 A1 | 2/2008 | Tang et al. | |
| 2009/0055941 A1 | 2/2009 | Wang et al. | |
| 2009/0238795 A1 | 9/2009 | Sehgal et al. | |
| 2010/0226912 A1 | 9/2010 | Mehtali | |
| 2010/0247487 A1 | 9/2010 | Sehgal et al. | |
| 2011/0003327 A1 | 1/2011 | Chien et al. | |
| 2011/0207828 A1 | 8/2011 | Miller et al. | |
| 2011/0217274 A1 | 9/2011 | Reld | |
| 2011/0223635 A1 | 9/2011 | Deisseroth et al. | |
| 2012/0040393 A1 | 2/2012 | Zhang et al. | |
| 2012/0278912 A1 | 11/2012 | Farrar et al. | |
| 2012/0301446 A1 | 11/2012 | Zhu et al. | |
| 2013/0022583 A1 | 1/2013 | Wernig et al. | |
| 2013/0095118 A1 | 4/2013 | Smith et al. | |
| 2014/0010861 A1 | 1/2014 | Bancel et al. | |

(Continued)

FOREIGN PATENT DOCUMENTS

| | | |
|---|---|---|
| CA | 2903933 A1 | 3/2017 |
| CN | 1756556 A | 4/2006 |

(Continued)

OTHER PUBLICATIONS

Addgene plasmid # 41583, pCAGGS-mCherry (http://n2t.net/addgene:41583 ; RRID:Addgene_41583, accessed on Jul. 2024 (Year: 2024).*

Choi et al. Optimization of AAV expression cassettes to improve packaging capacity and transgene expression in neurons (2014), Molecular Brain, 7, pp. 1-10. (Year: 2014).*

Chen et al., "A NeuroD1 AAV-Based Gene Therapy for Functional Brain Repair after Ischemic Injury through In Vivo Astrocyte-to Neuron Conversion" *Molecular Therapy*, 28(1):217-234, Jan. 2020.

International Search Report and Written Opinion dated Mar. 9, 2022, PCT/US2021/052299.

Abernathy et al., "MicroRNAs Induce a Permissive Chromatin Environment that Enables Neuronal Subtype-Specific Reprogramming of Adult Human Fibroblasts," *Cell Stem Cell*, 21(3), pp. 332-348 (Sep. 2017) (electronic publication).

(Continued)

*Primary Examiner* — Tracy Vivlemore
(74) *Attorney, Agent, or Firm* — Jones Day

(57) ABSTRACT

The present disclosure relates to AAV vectors, compositions, and methods related to converting glial cells to neurons by the use of a NeuroD1 coding sequence in an AAV vector.

19 Claims, 36 Drawing Sheets
(27 of 36 Drawing Sheet(s) Filed in Color)

Specification includes a Sequence Listing.

(56) References Cited

U.S. PATENT DOCUMENTS

| | | | |
|---|---|---|---|
| 2014/0024599 A1 | 1/2014 | Chen et al. | |
| 2014/0051171 A1 | 2/2014 | Christensen et al. | |
| 2014/0068797 A1 | 3/2014 | Doudna et al. | |
| 2014/0273235 A1 | 9/2014 | Voytas et al. | |
| 2014/0315782 A1 | 10/2014 | Tremblay et al. | |
| 2015/0023927 A1 | 1/2015 | Eggan et al. | |
| 2015/0065376 A1* | 3/2015 | Knaut | G01N 33/5041 |
| | | | 435/320.1 |
| 2015/0067922 A1 | 3/2015 | Yang et al. | |
| 2015/0132821 A1 | 5/2015 | Fine et al. | |
| 2015/0190481 A1 | 7/2015 | Finn | |
| 2015/0250900 A1 | 9/2015 | Chen et al. | |
| 2015/0283065 A1 | 10/2015 | Frey, II et al. | |
| 2015/0335708 A1 | 11/2015 | Froelich et al. | |
| 2016/0024600 A1 | 1/2016 | Inglese et al. | |
| 2016/0046700 A1 | 2/2016 | Foster et al. | |
| 2016/0115447 A1 | 4/2016 | Blumenstein et al. | |
| 2016/0175462 A1 | 6/2016 | Zhang et al. | |
| 2016/0194625 A1 | 7/2016 | Hoge et al. | |
| 2016/0199412 A1 | 7/2016 | Tareen | |
| 2016/0234600 A1 | 8/2016 | Kajihara et al. | |
| 2016/0263233 A1 | 9/2016 | Wang et al. | |
| 2016/0296605 A1 | 10/2016 | Zhang | |
| 2016/0355797 A1 | 12/2016 | Konermann et al. | |
| 2017/0035839 A1 | 2/2017 | Miller et al. | |
| 2017/0073382 A1 | 3/2017 | Wong et al. | |
| 2017/0096683 A1 | 4/2017 | Scaria et al. | |
| 2017/0101622 A1 | 4/2017 | Ahlfors et al. | |
| 2017/0152528 A1 | 6/2017 | Zhang | |
| 2017/0216456 A1 | 8/2017 | Alexander et al. | |
| 2017/0224843 A1 | 8/2017 | Deglon et al. | |
| 2017/0239373 A1 | 8/2017 | Chen et al. | |
| 2017/0304463 A1 | 10/2017 | Chen et al. | |
| 2017/0320968 A1 | 11/2017 | Tremblay et al. | |
| 2018/0087052 A1 | 3/2018 | Hung et al. | |
| 2018/0187188 A1 | 7/2018 | Lee et al. | |
| 2018/0282759 A1 | 10/2018 | Hu et al. | |
| 2018/0311290 A1* | 11/2018 | Sena-Esteves | C12N 9/2402 |
| 2018/0320200 A1 | 11/2018 | Hajitou et al. | |
| 2019/0000982 A1 | 1/2019 | Wang et al. | |
| 2019/0024056 A1 | 1/2019 | Ahlfors et al. | |
| 2019/0032078 A1 | 1/2019 | Kielian et al. | |
| 2019/0046664 A1 | 2/2019 | Schnieders et al. | |
| 2019/0055552 A1 | 2/2019 | Davidson et al. | |
| 2019/0111157 A1 | 4/2019 | Stanek et al. | |
| 2019/0117797 A1* | 4/2019 | Chen | A61K 38/1709 |
| 2019/0153412 A1 | 5/2019 | Zhang et al. | |
| 2019/0276540 A1 | 9/2019 | Baeuerle et al. | |
| 2020/0054711 A1 | 2/2020 | Chen et al. | |
| 2020/0056159 A1 | 2/2020 | Wilson et al. | |
| 2020/0080107 A1 | 3/2020 | Rezania | |
| 2020/0106958 A1 | 4/2020 | Yang et al. | |
| 2020/0108193 A1 | 4/2020 | Glaser | |
| 2020/0123517 A1 | 4/2020 | Mijts et al. | |
| 2020/0181592 A1 | 6/2020 | Mijts et al. | |
| 2020/0190494 A1 | 6/2020 | Hou et al. | |
| 2020/0190504 A1 | 6/2020 | Baltes | |
| 2020/0255859 A1 | 8/2020 | Yang et al. | |
| 2020/0270635 A1 | 8/2020 | Hou et al. | |
| 2020/0384076 A1 | 12/2020 | Passini et al. | |
| 2020/0405801 A1 | 12/2020 | Chen et al. | |
| 2021/0032300 A1 | 2/2021 | Chen et al. | |
| 2021/0155664 A1 | 5/2021 | Chen et al. | |
| 2021/0162002 A1 | 6/2021 | Chen et al. | |
| 2021/0162003 A1 | 6/2021 | Chen et al. | |
| 2021/0162072 A1 | 6/2021 | Moullier et al. | |
| 2021/0163985 A1 | 6/2021 | Sah et al. | |
| 2021/0260217 A1 | 8/2021 | Chen et al. | |
| 2021/0324044 A1 | 10/2021 | Esteves et al. | |
| 2021/0346473 A1 | 11/2021 | McIvor et al. | |
| 2021/0395692 A1 | 12/2021 | Ko et al. | |
| 2021/0395777 A1 | 12/2021 | Slack et al. | |
| 2022/0040236 A1 | 2/2022 | Chen | |
| 2022/0064671 A1 | 3/2022 | Maranga et al. | |
| 2022/0072153 A1 | 3/2022 | Chen et al. | |
| 2022/0098254 A1 | 3/2022 | Xu | |
| 2022/0098255 A1 | 3/2022 | Xu | |
| 2022/0098616 A1 | 3/2022 | Xu | |
| 2022/0098617 A1 | 3/2022 | Xu | |
| 2022/0106613 A1 | 4/2022 | Xu | |
| 2022/0106614 A1 | 4/2022 | Xu | |
| 2022/0152224 A1 | 5/2022 | Chen et al. | |
| 2022/0160825 A1 | 5/2022 | Chen et al. | |
| 2022/0175970 A1 | 6/2022 | Kerr et al. | |
| 2022/0186256 A1 | 6/2022 | Danos et al. | |
| 2022/0211871 A1 | 7/2022 | Abeliovich et al. | |
| 2022/0339270 A1 | 10/2022 | Liu et al. | |
| 2022/0395586 A1 | 12/2022 | Stanek et al. | |
| 2023/0021959 A1 | 1/2023 | Small et al. | |
| 2023/0075314 A1 | 3/2023 | Hou et al. | |
| 2023/0084580 A1 | 3/2023 | Passini et al. | |
| 2023/0135379 A1 | 5/2023 | Passini et al. | |
| 2023/0142867 A1 | 5/2023 | Ramu | |
| 2023/0220014 A1 | 7/2023 | Cheng et al. | |
| 2023/0242937 A1* | 8/2023 | Pulé | C12N 15/86 |
| | | | 435/320.1 |
| 2023/0242939 A1 | 8/2023 | Mathur et al. | |
| 2023/0302158 A1 | 9/2023 | Daigle et al. | |
| 2023/0304032 A1 | 9/2023 | Sah et al. | |
| 2023/0330267 A1 | 10/2023 | Cao et al. | |
| 2024/0082352 A1 | 3/2024 | Chen et al. | |
| 2024/0117322 A1 | 4/2024 | Wilson et al. | |

FOREIGN PATENT DOCUMENTS

| | | | |
|---|---|---|---|
| CN | 101553245 A | 10/2007 | |
| CN | 101693107 A | 4/2010 | |
| CN | 102083964 A | 6/2011 | |
| CN | 102858985 A | 1/2013 | |
| CN | 103667190 A | 3/2014 | |
| CN | 104870634 A | 8/2015 | |
| CN | 105377039 A | 3/2016 | |
| CN | 105745326 A | 7/2016 | |
| CN | 102459611 B | 11/2016 | |
| CN | 106170295 A | 11/2016 | |
| CN | 106460054 A | 2/2017 | |
| CN | 107530447 A | 1/2018 | |
| CN | 107683289 A | 2/2018 | |
| CN | 109069544 A | 12/2018 | |
| CN | 110741082 A | 1/2020 | |
| CN | 111630170 A | 9/2020 | |
| CN | 111886343 A | 11/2020 | |
| CN | 112245592 A | 1/2021 | |
| CN | 113966400 A | 1/2022 | |
| CN | 114026242 A | 2/2022 | |
| CN | 114127089 A | 3/2022 | |
| CN | 115997011 A | 4/2023 | |
| CN | 116209768 A | 6/2023 | |
| KR | 10-2016-0143651 A | 12/2016 | |
| WO | WO 2005/021704 A2 | 3/2005 | |
| WO | WO 2005/037226 A2 | 4/2005 | |
| WO | WO 2005/056807 A2 | 6/2005 | |
| WO | WO 2005/113812 A2 | 12/2005 | |
| WO | WO 2008/013737 A2 | 1/2008 | |
| WO | WO 2008/083931 A1 | 7/2008 | |
| WO | WO 2009/100131 A2 | 8/2009 | |
| WO | WO 2009/136168 A1 | 11/2009 | |
| WO | WO 2009/142602 A1 | 11/2009 | |
| WO | WO 2009/143578 A1 | 12/2009 | |
| WO | WO 2010/053522 A2 | 5/2010 | |
| WO | WO 2010/129021 A1 | 11/2010 | |
| WO | WO 2011/011767 A1 | 1/2011 | |
| WO | WO 2011/050476 A1 | 5/2011 | |
| WO | WO 2011/072246 A2 | 6/2011 | |
| WO | WO 2011/097181 A2 | 8/2011 | |
| WO | WO 2012/010675 A2 | 1/2012 | |
| WO | WO 2013/025963 A1 | 2/2013 | |
| WO | WO 2013/071440 A1 | 5/2013 | |
| WO | WO 2014/003553 | 1/2014 | |
| WO | WO 2014/015261 A1 | 1/2014 | |
| WO | WO 2014/153230 A1 | 9/2014 | |
| WO | WO 2014/186579 A1 | 11/2014 | |
| WO | WO 2014/204729 A1 | 12/2014 | |
| WO | WO 2015/060722 A1 | 4/2015 | |

(56)                    References Cited

FOREIGN PATENT DOCUMENTS

| WO | WO 2015/061779 A1 | 4/2015 | | |
|----|-------------------|--------|---|---|
| WO | WO 2015/069736 A1 | 5/2015 | | |
| WO | WO 2015/120776 A1 | 8/2015 | | |
| WO | WO 2015/131788 A1 | 9/2015 | | |
| WO | WO 2015/142293 A1 | 9/2015 | | |
| WO | WO 2016/123142 A1 | 8/2016 | | |
| WO | WO 2016/125148 A1 | 8/2016 | | |
| WO | WO 2016/130591 A2 | 8/2016 | | |
| WO | WO 2016/161124 A1 | 10/2016 | | |
| WO | WO 2017/100671 A1 | 6/2017 | | |
| WO | WO 2017/143207 A1 | 8/2017 | | |
| WO | WO 2018/160582 A1 | 9/2018 | | |
| WO | WO 2018/160712 A1 | 9/2018 | | |
| WO | WO 2019/025984 A1 | 2/2019 | | |
| WO | WO 2019/028306 A2 | 2/2019 | | |
| WO | WO 2019/032320 A1 | 2/2019 | | |
| WO | WO 2019/094694 A1 | 5/2019 | | |
| WO | WO 2019/152857 A1 | 8/2019 | | |
| WO | WO 2019/165050 A1 | 8/2019 | | |
| WO | WO 2019/204503 A1 | 10/2019 | | |
| WO | WO 2020/033601 A1 | 2/2020 | | |
| WO | WO 2020/072873 A1 | 4/2020 | | |
| WO | WO 2020/097155 A1 | 5/2020 | | |
| WO | WO-2020106916 A1 * | 5/2020 | ............ | A61K 48/00 |
| WO | 111448308 A | 7/2020 | | |
| WO | WO 2020/163102 A1 | 8/2020 | | |
| WO | WO 2020/198485 A1 | 10/2020 | | |
| WO | WO 2020/206189 A1 | 10/2020 | | |
| WO | WO 2020/210615 A1 | 10/2020 | | |
| WO | WO 2020/219563 A1 | 10/2020 | | |
| WO | WO 2020/223276 A1 | 11/2020 | | |
| WO | WO 2020/223279 A1 | 11/2020 | | |
| WO | WO 2020/245169 A1 | 12/2020 | | |
| WO | WO 2020/263639 A1 | 12/2020 | | |
| WO | WO 2021/076947 A1 | 4/2021 | | |
| WO | WO 2021/076951 A1 | 4/2021 | | |
| WO | WO 2021/076983 A1 | 4/2021 | | |
| WO | WO2021/108609 A1 | 6/2021 | | |
| WO | WO 2021/154923 A2 | 8/2021 | | |
| WO | WO 2021/216456 A2 | 10/2021 | | |
| WO | WO 2021/216975 A1 | 10/2021 | | |
| WO | WO 2022/003211 A1 | 1/2022 | | |
| WO | WO 2022/036255 A1 | 2/2022 | | |
| WO | WO 2022/051633 A2 | 3/2022 | | |
| WO | WO 2022/072308 | 4/2022 | | |
| WO | WO 2022/072308 A1 | 4/2022 | | |
| WO | WO 2022/072309 A1 | 4/2022 | | |
| WO | WO 2022/072310 A1 | 4/2022 | | |
| WO | WO 2022/072322 A1 | 4/2022 | | |
| WO | WO 2022/072324 A1 | 4/2022 | | |
| WO | WO 2022/072325 | 4/2022 | | |

OTHER PUBLICATIONS

Abraira et al., "The sensory neurons of touch," *Neuron*, 79(4), pp. 618-639 (Aug. 2013) (electronic publication).

Adams et al., "Spasticity after spinal cord injury," *Spinal Cord*, 43(10), pp. 577-586 (Apr. 2005) (electronic publication).

Addis et al., "Efficient conversion of astrocytes to functional midbrain dopaminergic neurons using a single polycistronic vector," *PLoS One*, 6(12): e28719, pp. 1-8 (Dec. 2011) (electronic publication).

Adil et al., "hPSC-derived striatal cells generated using a sealable 3D hydrogel promote recovery in a Huntington disease mouse model," *Stem Cell Reports*, 10(5), pp. 1481-1491 (May 2018) (electronic publication).

Aguirre et al., "NG2-expressing cells in the subventricular zone are type C-likes cells and contribute to interneuron generation in the postnatal hippocampus," *The Journal of Cell Biology*, 165(4), pp. 575-589 (May 2004) (electronic publication).

Aguirre et al., "Postnatal neurogenesis and gliogenesis in the olfactory bulb from NG2-expressing progenitors of the subventricular zone," *The Journal of Neuroscine*, 24(46), pp. 10530-10541 (Nov. 2004) (electronic publication).

Alaoui-Ismaili, et al. "Design of second generation therapeutic recombinant bone morphogenetic proteins," Cytokine & Growth Factor Reviews, vol. 20, pp. 501-507 (2009) (Amsterdam, Netherlands).

Altschul et al., "Gapped BLAST and PSI-BLAST: a new generation of protein database search programs," *Nucleic Acids Research*, 25(17), pp. 3389-3402 (1997) (electronic publication).

Amador-Arjona et al., "SOX2 primes the epigenetic landscape in neural precursors enabling proper gene activation during hippocampal neurogenesis," *PNAS*, 112(15), pp. E1936-E1945 (Mar. 2015) (electronic publication).

AmCyan-P2A-mCherry vector sequence (P2A sequence) (Year: 2023).

Anderson et al., "Astrocyte scar formation aids central nervous system axon regeneration," *Nature*, 532(7598), pp. 195-200 (Mar. 2016) (electronic publication).

Anderson et al., "Differential origins of neocortical projection and local circuit neurons: role of Dlx genes in neocortical interneuronogenesis," *Cerebral Cortex*, 9(6), pp. 646-654 (Sep. 1999) (electronic publication).

Anderson et al., "Interneuron migration from basal forebrain to neocortex: dependence on Dlx genes," *Science*, 278(5337), pp. 474-476 (Oct. 1997) (electronic publication).

Animal Research Info, "Huntington's disease," published Nov. 5, 2014 [retrieved on Oct. 21, 2020], Retrieved from: URL<http://www.animalresearch.info/en/medical-advances/diseases-research/huntingtons-disease/> 5 pages.

Araújo et al., "Direct Reprogramming of Adult Human Somatic Stem Cells Into Functional Neurons Using Sox2, Ascll, and Neurog2," *Frontiers in Cellular Neuroscience*, 12(155), pp. 1-15 (Jun. 2018) (electronic publication).

Ascoli et al., "Petilla terminology: nomenclature of features of GABAergic interneurons of the cerebral cortex," *Nature Review Neuroscience*, 9(7), pp. 557-568 (Jul. 2008) (electronic publication).

Atasoy et al., "A FLEX switch targets Channelrhodopsin-2 to multiple cell types for imaging and long-range circuit mapping," *Journal of Neuroscience*, 28(28), pp. 7025-7030 (Jul. 2008) (electronic publication).

Baird et al., "The staircase test of skilled reaching in mice," *Brain Research Bulletin*, 54(2), pp. 243-250 (Jan. 2001) (electronic publication).

Bani-Yaghoub et al., "Role of Sox2 in the development of the mouse neocortex," *Developmental Biology*, 295(1), pp. 52-66 (Jul. 2006) (electronic publication).

Bardehle et al., "Live imaging of astrocyte responses to acute injury reveals selective juxtavascular proliferation," *Nature Neuroscience*, vol. 16, pp. 580-586 (Mar. 2013) (electronic publication).

Barker et al., "New approaches for brain repair—from rescue to reprogramming," *Nature*, 557(7705), pp. 329-334 (May 2018) (electronic publication).

Barry et al., "Striatal direct and indirect pathway output structures are differentially altered in mouse models of Huntington's disease," *Journal of Neuroscience*, 38(20), pp. 4678-4694 (May 2018) (electronic publication).

Baskin et al., "Two effective behavioral tasks for evaluating sensorimotor dysfunction following traumatic brain injury in mice," *Journal of Neuroscience Methods*, 129(1): 87-93 (Oct. 2003) (electronic publication).

Bates et al., "Huntington disease," *Nature Reviews Disease Primers*, vol. 1, article 15005, pp. 1-21 (Apr. 2015) (electronic publication).

Bayer et al., "Intracellular accumulation of amyloid-Beta-a predictor for synaptic dysfunction and neuron loss in Alzheimer's disease," *Frontiers in Aging Neuroscience*, vol. 2, article 8, pp. 1-10 (Mar. 2010) (electronic publication).

Bermingham et al., "Proprioceptor pathway development is dependent on Isdathi," *Neuron*, 30(2), pp. 411-422 (May 2001) (electronic publication).

Berninger et al., "Functional properties of neurons derived from in vitro reprogrammed postnatal astroglia," *The Journal of Neuroscience*, 27(32), pp. 8654-8664 (Aug. 2007) (electronic publication).

Bertrand et al., "Proneural genes and the specification of neural cell types," *Nature Reviews Neuroscience*, vol. 3, pp. 517-530 (Jul. 2002) (electronic publication).

(56) References Cited

OTHER PUBLICATIONS

Bonnard et al., "Recent advances in Nanomedicine for ischemic and hemorrhagic stroke," Stroke, 50(5), pp. 1318-1324 (Apr. 2019) (electronic publication).

Boulaire et al., "Transcriptional targeting to brain cells: Engineering cell type-specific promoter containing cassettes for enhanced transgene expression." Advanced Drug Delivery Reviews, vol. 61, Apr. 2009, pp. 589-602.

Boutin et al., "NeuroD1 induces terminal neuronal differentiation in olfactory neurogenesis," PNAS, vol. 107, pp. 1201-1206 (Dec. 2010) (electronic publication).

Bowie, et al. "Deciphering the Message in Protein Sequences: Tolerance to Amino Acid Substitutions," Science, New Series, vol. 247, No. 4948. pp. 1306-1313 ((Mar. 1990) (London, UK).

Brandao et al., "Interplay of environmental signals and progenitor diversity on fate specification of cortical GABAergic neurons," Frontiers in Cellular Neuroscience, vol. 9, article 149, pp. 1-11 (Apr. 2015) (electronic publication).

Brennan et al., "The Somatic Genomic Landscape of Glioblastoma," Cell, 155(2), pp. 462-477 (Oct. 2013) (electronic publication).

Brill et al., "A D1x2- and Pax6-Dependent Transcriptional Code for Periglomerular Neuron Specification in the Adult Olfactory Bulb," The Journal of Neuroscience, 28(25), pp. 6439-6452 (Jun. 2008) (electronic publication).

Brulet et al., "NEUROD1 instructs neuronal conversion in non-reactive astrocytes," Stem Cell Reports, 8(6), pp. 1506-1515 (Jun. 2017) (electronic publication).

Buffo et al., "Origin and progeny of reactive gliosis: A source of multipotent cells in the injured brain," PNAS, 105(9), pp. 3581-3586 (Mar. 2008) (electronic publication).

Burda et al., "Reactive gliosis and the multicellular response to CNS damage and disease," Neuron, 81(2):229-248 (Jan. 2014) (electronic publication).

Burgess, et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111, pp. 2129-2138 (Nov. 1990) (New York, NY).

Busch et al., "Alzheimer's disease and retinal neurodegeneration share a consistent stress response of the neurovascular unit," Cellular Physiology and Biochemistry, 30(6), pp. 1436-1443 (Nov. 2012) (electronic publication).

Bush et al., "Leukocyte Infiltration, Neuronal Degeneration, and Neurite Outgrowth after Ablation of Scar-Forming, Reactive Astrocytes in Adult Transgenic Mice," Neuron 23(2), pp. 297-308 (Jun. 1999) (electronic publication).

Bylund et al., "Vertebrate neurogenesis is counteracted by Soxl-3 activity," Nature Neuroscience, 6(11), pp. 1162-1168 (Sep. 2003) (electronic publication).

Cai et al., "Misexpression of basic helix-loop-helix genes in the murine cerebral cortex affects cell fate choices and neuronal survival," Development, 127(14), pp. 3021-3030 (Jul. 2000) (electronic publication).

Caiazzo et al., "Direct generation of functional dopaminergic neurons from mouse and human fibroblasts," Nature, vol. 476, pp. 224-227 (Jul. 2011) (electronic publication).

Cancer Genome Atlas Research Network, "Comprehensive genomic characterization defines human glioblastoma genes and core pathways," Nature, 455(7216), pp. 1061-1068 (Sep. 2008) (electronic publication).

Castillo et al., "Comparative profiling of cortical gene expression in Alzheimer's disease patients and mouse models demonstrates. a link between amyloidosis and neuroinflammation," Scientific Reports, 7(1), pp. 1-6 (Dec. 2017) (electronic publication).

Celis et al., "High-resolution two-dimensional gel electrophoresis of proteins: isoelectric focusing and nonequilibrium pH gradient electrophoresis (NEPHGE)," Cell Biology, A Laboratory Handbook(3): 222-230 (1994) (electronic publication).

Cell biolab pAAV-MCS Expression vector sequence (pAAV-MCS) (Year: 2023).

Chan et al., "Engineered AAVs for efficient noninvasive gene delivery to the central and peripheral nervous systems," Nature Neuroscience, 20(8), pp. 1172-1179 (Jun. 2017) (electronic publication).

Chanda et al., "Generation of Induced Neuronal Cells by the Single Reprogramming Factor ASCL1," Stem Cell Reports, 3(2), pp. 282-296 (Aug. 2014) (electronic publication).

Chen et al., "GAD67-GFP knock-in mice have normal sleep-wake patterns and sleep homeostasis," Neuroreport, 21(3), pp. 216-220 (Feb. 2010) (electronic publication).

Chen, "Functional Brain Repair Through In Vivo Cell Conversion," International Society for Stem Cell Research (ISSCR) 2017 Annual Meeting—Poster Abstract Book, Abstract F-1155 p. 401 (2017) (electronic publication).

Chen et al., "The basic helix-loop-helix transcription factor olig2 is critical for reactive astrocyte proliferation after cortical injury," Journal of Neuroscience, 28(43), pp. 10983-10989 (Oct. 2008) (electronic publication).

Cheng et al., "Lbx1 and Tlx3 are opposing switches in determining GABAergic versus glutamatergic transmitter phenotypes," Nature Neuroscience, 8(11), pp. 1510-1515 (Oct. 2005) (electronic publication).

Cheng et al., "Neurogenin 2 converts mesenchymal stem cells into a neural precursor fate and improves functional recovery after experimental stroke," Cellular Physiology and Biochemistry, 33(3), pp. 847-858 (Apr. 2014) (electronic publication).

Chittajallu et al., "NG2-positive cells in the mouse white and grey matter display distinct physiological properties," The Journal Physiology, 561(1), pp. 109-122 (Nov. 2004) (electronic publication).

Cho et al., "Targeted genome engineering in human cells with the Cas9 RNA-guided endonuclease," Nature Biotechnology, vol. 31, pp. 230-232 (Jan. 2013) (electronic publication).

Cho et al., "The role of BETA2/NeuroD1 in the development of the nervous system," Molecular Neurobiology, 30(1), pp. 35-47 (Aug. 2004) (electronic publication).

Choi et al., "Hippocampus-based contextual memory alters the morphological characteristics of astrocytes in the dentate gyrus," Molecular Brain, 9(1):72 (Jul. 2016) (electronic publication).

Chouchane et al., "Lineage Reprogramming of Astroglial Cells from Different Origins into Distinct Neuronal Subtypes," Stem Cell Reports, 9(1), pp. 162-176 (Jul. 2017) (electronic publication).

Chuang et al., "Partial Reprogramming of Pluripotent Stem Cell-Derived Cardiomyocytes into Neurons," Scientific Reports, 7(44840), pp. 1-10 (Mar. 2017) (electronic publication).

Claassen et al., "Tetrabenazine Treatment Patterns and Outcomes for Chorea Associated with Huntington Disease: A Retrospective Chart Review," Journal of Huntington's Disease, 7(4), pp. 345-353 (Nov. 2018) (electronic publication).

Clarkson et al., "Reducing excessive GABA-mediated tonic inhibition promotes functional recovery after stroke," Nature, 468(7321), pp. 305-309 (Nov. 2010) (electronic publication).

Cobos et al., "Mice lacking Dlx1 show subtype-specific loss of interneurons, reduced inhibition and epilepsy," Nature Neuroscience, vol. 8, pp. 1059-1068 (Jul. 2005) (electronic publication).

Colasante et al., "Rapid Conversion of Fibroblasts into Functional Forebrain GABAergic Interneurons by Direct Genetic Reprogramming," Cell Stem Cell, 17(6), pp. 719-734, (Dec. 2015) (electronic publication).

Cong et al., "Multiplex genome engineering using CRISPR/Cas systems," Science, 339(6121), pp. 819-823 (Jan. 2013) (electronic publication).

Corti et al., "Direct reprogramming of human astrocytes into neural stem cells and neurons," Experimental Cell Research, 318(13), pp. 1528-1541 (Aug. 2012) (electronic publication).

Cregg et al., "Functional regeneration beyond the glial scar," Experimental Neurology, vol. 253, pp. 197-207 (Mar. 2014) (electronic publication).

Crooke, "Zonis: The Leader in RNA-Targeted," [retrieved on Oct. 21, 2020], Retrieved from: Therapeuticshttps://ir.ionispharma. comistatic-files/e034473b-e000-084-88a6-0dfOc5b6a79e>, 94 pages.

Dayton, et al., "More expansive gene transfer to the rat CNS: AAV PHP.EB vector dose-response and comparison to AAV PHP.B," Gene Therapy, vol. 25, pp. 392-400 (Jul. 2018), (Berlin, Germany).

(56) References Cited

OTHER PUBLICATIONS

Deng et al., "Sequential Postsynaptic Maturation Governs the Temporal Order of GABAergic and Glutamatergic Synaptogenesis in Rat Embryonic Cultures," *The Journal of Neuroscience*, 27(40), pp. 1086010869 (Oct. 2007) (electronic publication).

Di Val Cervo et al., "Induction of functional dopamine neurons from human astrocytes in vitro and mouse astrocytes in a Parkinson's disease model," *Nature Biotechnology*, vol. 35, pp. 444-452 (Apr. 2017) (electronic publication).

Di-Carlo et al., "Genome engineering in Saccharomyces cerevisiae using CRISPR-Cas systems," *Nucleic Acids Research*, 41(7), pp. 4336-4343 (Mar. 2013) (electronic publication).

Dittgen et al., "Lentivirus-based genetic manipulations of cortical neurons and their optical and electrophysiological monitoring in vivo," *Proceedings of the National Academy of Sciences*, 101(52), pp. 18206-18211 (Dec. 2004) (electronic publication).

Duff et al., "Transgenic mouse models of Alzheimer's disease: How useful have they been for therapeutic development?," *Briefing in Functional Genomics and Proteomics*, 3(1), pp. 47-59, (Apr. 2004) (electronic publication).

El-Serag, "Epidemiology of viral hepatitis and hepatocellular carcinoma," *Gastroenterology*, 142(6), pp. 1264-1273 (May 2012) (electronic publication).

Escartin et al., "Targeted Activation of Astrocytes: A Potential Neuroprotective Strategy," *Molecular Neurobiology*, vol. 33, pp. 231-241 (Oct. 2008) (electronic publication).

Extended European Search Report in European Patent Application No. 17753935.0, dated Jan. 18, 2019, 277 pages.

Extended European Search Report in European Patent Application No. 19747921.5, dated Oct. 1, 2021, 136 pages.

Extended European Search Report in European Patent Application No. 21156322.4, dated Jun. 23, 2022, 9 pages.

Extended European Search Report in European Patent Application No. 21167319.9, dated Jul. 28, 2021, 8 pages.

Extended European Search Report issued in European Patent Application No. 20777797.0, dated Nov. 25, 2022.

Extended European Search Report issued in European Patent Application No. 20833514.1, dated Mar. 14, 2023.

Fan, Plasmids 101: Multicistronic Vectors, Addgene Blog, Published Sep. 9, 2014, 2 pages.

Fang, "The Molecular Mechanism of the NeuroD1 Gene Regulation Induced by Alt-trans Retinoic Acid in Neural Cells Differential," Dissertation Full-text Database (Electronic Journal) Basic Science, 11: A006-4 (Oct. 2010) (electronic publication).

Ferreira et al., "From the periphery to the brain: Lipocalin-2, a friend or foe?" *Progress in Neurobiology*, vol. 131, pp. 120-136 (Aug. 2015) (electronic publication).

Filous et al., "Determinants of Axon Growth, Plasticity, and Regeneration in the Context of Spinal Cord Injury," *The American Journal of Pathology*, vol. 188, pp. 53-62 (Jan. 2018) (electronic publication).

Foust et al., "Intravascular AAV9 preferentially targets neonatal neurons and adult astrocytes," *Nature Biotechnology*, 27(1), pp. 59-65 (Dec. 2009) (electronic publication).

Freeman, "Specification and morphogenesis of astrocytes," *Science*, 330(6005), pp. 774-778 (Nov. 2010) (electronic publication).

Frost et al., "The role of astrocytes in amyloid production and Alzheimer's disease," *Open Biology*, 7(12), pp. 1-14 (Dec. 2017) (electronic publication).

Fu et al., "MiR-30a-5p ameliorates spinal cord injury-induced inflammatory responses and oxidative stress by targeting Neurod 1 through MAPK/ERK signalling," *Clinical and Experimental Pharmacology and Physiology*, 45(1), pp. 68-74 (Jan. 2018) (electronic publication).

Fuxe et al., "Endothelin-1 induced lesions of the frontoparietal cortex of the rat. A possible model of focal cortical ischemia," *NeuroReport*, 8(11), pp. 2623-2629 (Jul. 1997) (electronic publication).

Gallo et al., "Glial Development: The Crossroads of Regeneration and Repair in the CNS," *Neuron*, 83(2), pp. 283-308 (Jul. 2014) (electronic publication).

Games et al., "Alzheimer-type neuropathology in transgenic mice overexpressing V717F β-amyloid precursor protein," *Nature*, vol. 373, pp. 523-527 (Feb. 1995) (electronic publication).

Gangarossa et al., "Distribution and compartmental organization of GABAergic medium-sized spiny neurons in the mouse nucleus accumbens," *Frontiers in Neural Circuits*, vol. 7, article 22, pp. 1-20 (Feb. 2013) (electronic publication).

Gao et al., "Neurodl is essential for the survival and maturation of adult-born neurons," *Nature Neuroscience*, 12(9), pp. 1090-1092 (Sep. 2009) (electronic publication).

Gascón et al., "Identification and successful negotiation of a metabolic checkpoint in direct neuronal reprogramming," *Cell Stem Cell*, 18(3), pp. 396-409 (Mar. 2016) (electronic publication).

GenBank Accession No. AAB32188.1, "Nrf2 [*Homo sapiens*]," dated Mar. 3, 1995, 2 pages.

GenBank Accession No. AAH06221.2, "NK2 homeobox 1 [*Homo sapiens*]," dated Jan. 30, 2008, 2 pages.

GenBank Accession No. AAH06545.2, "FOXA2 protein, partial [*Homo sapiens*]," dated Oct. 8, 2003, 2 pages.

GenBank Accession No. AAH11780.1, "Forkhead box A2 [*Homo sapiens*]," dated Jul. 15, 2006, 2 pages.

GenBank Accession No. AAH33890.1, "Forkhead box A1 [*Homo sapiens*]," dated Jul. 17, 2006, 2 pages.

GenBank Accession No. AAH36847.1, "Neurogenin 2 [*Homo sapiens*]," dated Jul. 15, 2006, 2 pages.

GenBank Accession No. AAH46460.1, "Forkhead box J1 [*Homo sapiens*]," dated Jul. 15, 2006, 2 pages.

GenBank Accession No. AAH53850.1, "Forkhead box Q1 [*Homo sapiens*]," dated Jul. 15, 2006, 2 pages.

GenBank Accession No. AAH64698.1, "Transcription factor CP2-like 1 [*Homo sapiens*]," dated Jul. 17, 2006, 2 pages.

GenBank Accession No. AAH80524.1, "E4F transcription factor 1 [*Homo sapiens*]," dated Jul. 15, 2006, 3 pages.

GenBank Accession No. AAH80868.1, "Nkx2-1 protein [synthetic construct]," dated Sep. 2, 2016, 2 pages.

GenBank Accession No. AAH89442.1, "Forkhead box F1 [*Homo sapiens*], " dated Jan. 30, 2008, 2 pages.

GenBank Accession No. AAI43480.1, "GATA4 protein [*Homo sapiens*], GATA4 protein [*Homo sapiens*], " dated Jan. 8, 2009, 2 pages.

GenBank Accession No. ACA06111.1, "forkhead box A2 [*Homo sapiens*]" dated Feb. 20, 2008, 1 page.

GenBank Accession No. EAW51092.1, "forkhead box N1 [*Homo sapiens*]," dated Mar. 23, 2015, 2 pages.

GenBank Accession No. EAW55070.1, "forkhead box Q1 [*Homo sapiens*]," dated Mar. 23, 2015, 2 pages.

GenBank Accession No. EAW65844.1, "forkhead box A1 [*Homo sapiens*]," dated Mar. 23, 2015, 2 pages.

GenBank Accession No. EAW95250.1, "transcription factor CP2-like 1, isoform CRA_a [*Homo sapiens*]," dated Mar. 23, 2015, 2 pages.

GenBank Accession No. EAW95251.1, "transcription factor CP2-like 1, isoform CRA_b [*Homo sapiens*], " dated Mar. 23, 2015, 2 pages.

GenBank Accession No. EAW95424.1, "forkhead box F1 [*Homo sapiens*]," dated Mar. 23, 2015, 2 pages.

GenBank Accession No. EAX06278.1, "neurogenin 2 [*Homo sapiens*]," dated Mar. 23, 2015, 2 pages.

GenBank Accession No. NM 001308093.1, "*Homo sapiens* GATA binding protein 4 (GATA4), transcript variant 1, mRNA," dated Apr. 28, 2015, 4 pages.

Gen Bank Accession No. NM 001308093.3, "*Homo sapiens* GATA binding protein 4 (GATA4), transcript variant 1 mRNA," Sep. 16, 2022, 5 pages.

GenBank Accession No. NM 002500.4 "*Homo sapiens* neuronal differentiation 1 (NEUROD1), mRNA," dated May 10, 2014, 4 pages.

GenBank Accession No. NM 004316.3, "*Homo sapiens* achaete-scute family bHLH transcription factor 1 (ASCL1), mRNA," dated May 3, 2014, 4 pages.

(56) References Cited

OTHER PUBLICATIONS

Gen Bank Accession No. NM 004316.4, "*Homo sapiens* achaete-scute family bHLH transcription factor 1 (ASCL1), mRNA," Jun. 26, 2022, 4 pages.

GenBank Accession No. NM 004405, "*Homo sapiens* distal-less homeobox 2 (DLX2), mRNA," May 10, 2014, 5 pages.

GenBank Accession No. NM 021784.4, "*Homo sapiens* forldtead box A2 (FOXA2), transcript variant 1, mRNA," dated Feb. 2, 2014, 4 pages.

Gen Bank Accession No. NM 021784.5, "*Homo sapiens* forkhead box A2 (FOXA2), transcript variant 1, mRNA," Sep. 18, 2022, 4 pages.

GenBank Accession No. NM 024019.3,"*Homo sapiens* neurogenin 2 (NEUROG2), mRNA," dated Mar. 16, 2014, 3 pages.

Gen Bank Accession No. NM 024019.4, "*Homo sapiens* neurogenin 2 (NEUROG2), mRNA," Jun. 1, 2022, 4 pages.

GenBank Accession No. NM 178849.2, "*Homo sapiens* hepatocyte nuclear factor 4, alpha (HNF4A), transcript variant 1, mRNA," Oct. 15, 2014, 4 pages.

Gen Bank Accession No. NM 178849.3, "*Homo sapiens* hepatocyte nuclear factor 4 alpha (HNF4A), transcript variant 1 mRNA," Aug. 16, 2022, 6 pages.

GenBank Accession No. NP 000448.3, "hepatocyte nuclear factor 4-alpha isoform HNF4alpha2 [*Homo sapiens*]," dated Oct. 15, 2014, 3 pages.

GenBank Accession No. NP 000449.1, "hepatocyte nuclear factor 1-beta isoform 1 [*Homo sapiens*]," dated Jan. 16, 2015, 3 pages.

GenBank Accession No. NP 001025174.1, "hepatocyte nuclear factor 4-alpha isoform HNElalpha7 [Fiorito sapiens]" dated Oct. 15, 2014, 3 pages.

GenBank Accession No. NP 001025175.1, "hepatocyte nuclear factor 4-alpha isoform HNF4alpha9 [*Homo sapiens*]," dated Oct. 15, 2014, 3 pages.

GenBank Accession No. NP 001073136.1, "homeobox protein Nkx-2.1 isofisoform1 [*Homo sapiens*]," dated May 10, 2014, 3 pages.

GenBank Accession No. NP001108450.1, "tumor protein 63 isoform 2 [*Homo sapiens*]," dated May 4, 2014, 3 pages.

GenBank Accession No. NP001108451.1, "tumor protein 63 isoform 3 [*Homo sapiens*]," dated May 4, 2014, 3 pages.

GenBank Accession No. NP 001159395.1 "hepatocyte nuclear factor 1-beta isoform 2 [*Homo sapiens*]," dated May 11, 2014, 3 pages.

GenBank Accession No. NP 001230009.1, "ETS-related transcription factor Elf-5 isoform 3 [*Homo sapiens*]," dated Feb. 26, 2014, 3 pages.

GenBank Accession No. NP 001230010.1, "ETS-related transcription factor Elf-5 isoform 4 [*Homo sapiens*]," dated Aug. 9, 2014, 3 pages.

GenBank Accession No. NP 001245284.1, "hepatocyte nuclear factor 4-alpha isoform HNF4alpha4 [*Homo sapiens*], " dated Oct. 15, 2014, 3 pages.

GenBank Accession No. NP 001274111.1, "hepatocyte nuclear factor 4-alpha isoform HNE4alpha10 [*Homo sapiens*], " dated Oct. 15, 2014, 3 pages.

GenBank Accession No. NP 001274112.1, "hepatocyte nuclear factor 4-alpha isoform HNF4alpha11 [*Homo sapiens*]," dated Oct. 15, 2014, 3 pages.

GenBank Accession No. NP 001274113.1, "hepatocyte nuclear factor 4-alpha isoform 1INF4alpha12 [*Homo sapiens*]," dated Jan. 18, 2014, 3 pages.

GenBank Accession No. NP 001291215.1, "hepatocyte nuclear factor 1-beta isoform 3 [*Homo sapiens*]," dated Jan. 15, 2015, 3 pages.

GenBank Accession No. NP 001295022.1, "transcription factor GATA-4 isoform 1 [*Homo sapiens*]," dated Apr. 28, 2015, 3 pages.

GenBank Accession No. NP 001295023.1, "transcription factor GATA-4 isoform 3 [*Homo sapiens*]," dated Apr. 28, 2015, 3 pages.

GenBank Accession No. NP001316073.1, "tumor protein 63 isoform 7 [*Homo sapiens*]," dated Jul. 2, 2016, 3 pages.

GenBank Accession No. NP 001316893.1, "tumor protein 63 isoform 13 [*Homo sapiens*]," dated Aug. 13, 2016, 3 pages.

GenBank Accession No. NP 001350675.1, "LIM/homeobox protein Lhx3 isoform c [*Homo sapiens*]," dated May 30, 2018, 3 pages.

GenBank Accession No. NP 001350793.1, "B-cell lymphoma/leukemia 11A isoform 4 [*Homo sapiens*]," dated Jun. 3, 2018, 3 pages.

GenBank Accession No. NP 001352538.1, "B-cell lymphoma/leukemia 11A isoform 5 [*Homo sapiens*]," dated Sep. 12, 2018, 3 pages.

GenBank Accession No. NP001356298.1, forkhead box protein N1 [*Homo sapiens*], dated Apr. 8, 2019, 3 pages.

GenBank Accession No. NP 001361203.1, "transcription factor GATA-4 isoform 4 [*Homo sapiens*]," dated Sep. 18, 2019, 3 pages.

GenBank Accession No. NP 001413.1, "ETS-related transcription factor Elf-5 isoform 2 [*Homo sapiens*]," dated May 3, 2014, 3 pages.

GenBank Accession No. NP 001442.2, "forkhead box protein F1 [*Homo sapiens*]," dated May 11, 2014, 3 pages.

GenBank Accession No. NP 001445.2, "forkhead box protein J1 [*Homo sapiens*]," dated May 3, 2014, 3 pages.

GenBank Accession No. NP 002043.2, "transcription factor GATA-4 [*Homo sapiens*]," dated Sep. 23, 2014, 3 pages.

GenBank Accession No. NP 002193.2, "insulin gene enhancer protein ISL-1 [*Homo sapiens*], " dated Aug. 26, 2018, 3 pages.

GenBank Accession No. NP 002491.2, "neurogenic differentiation factor 1 [*Homo sapiens*]," dated May 10, 2014, 3 pages.

GenBank Accession No. NP 003308.1, "homeobox protein Nkx-2.1 isoisoform2 [*Homo sapiens*]" dated Apr. 19, 2014, 3 pages.

GenBank Accession No. NP 003584.2, "forkhead box protein N1 [*Homo sapiens*]," dated May 3, 2014, 3 pages.

GenBank Accession No. NP 003713.3, tumor protein 63 isoform 1[*Homo sapiens*], May 4, 2014, 2 pages.

GenBank Accession No. NP 004307.2, "achaete-scute homolog 1 [*Homo sapiens*]," dated May 3, 2014,, 2 pages.

GenBank Accession No. NP 004396.1, "homeobox protein DIA-2 [*Homo sapiens*]," May 10, 2014, 3 pages.

GenBank Accession No. NP 004487.2, "hepatocyte nuclear factor 3-alpha [*Homo sapiens*]," dated May 11, 2014, 3 pages.

GenBank Accession No. NP 055368.1, "transcription factor CP2-like protein 1 [*Homo sapiens*]," dated May 14, 2014, 3 pages.

GenBank Accession No. NP 068556.2, "hepatocyte nuclear factor 3-beta isoform 1 [*Homo sapiens*]," dated Feb. 2, 2014, 3 pages.

GenBank Accession No. NP 075044.2, "B-cell lymphoma/leukemia 11A isoform 1 [*Homo sapiens*]," dated May 24, 2014, 4 pages.

GenBank Accession No. NP 076924.1, "neurogenin-2 [*Homo sapiens*], " dated Mar. 16, 2014, 3 pages.

GenBank Accession No. NP 150285.3, "forkhead box protein Q1 [*Homo sapiens*]," dated May 10, 2014,3 pages.

GenBank Accession No. NP 710141.1, "hepatocyte nuclear factor 3-beta isoform 2 [*Homo sapiens*]" dated Feb. 2, 2014, 3 pages.

GenBank Accession No. NP 787110.2, "hepatocyte nuclear factor 4-alpha isoform [*Homo sapiens*]," dated Oct. 15, 2014, 3 pages.

GenBank Accession No. NP 849180.1, "hepatocyte nuclear factor 4-alpha isoform HNF4alphal [*Homo sapiens*]," Oct. 15, 2014, 3 pages.

GenBank Accession No. NP 849181.1, "hepatocyte nuclear factor 4-alpha isoform IINF4alpha3 [Fiorito sapiens]," dated Oct. 15, 2014, 3 pages.

GenBank Accession No. NP 938195.1, "ETS-related transcription factor Elf-5 isoform 1 [*Homo sapiens*]," dated Jan. 26, 2014, 3 pages.

GenBank Accession No. P27889.2, "RecName: Full=Hepatocyte nuclear factor 1-beta; Short=1INF-1-beta; Short-FINF-1B; AltName: Full=Homeoprotein LFB3; AltName: Full=Transcription factor 2; Short=TCF-2," dated Feb. 4, 2015, 4 pages.

GenBank Accession No. P35680.1, "RecName: Full=Hepatocyte nuclear factor 1-beta; Short=IINF-1-beta; Short=HNF-1.B; AltName: Full=Homeoprotein LFB3; . AltName: Full=Transcription factor 2; Short=TCF-2; AltName: Full=Variant hepatic nuclear factor 1; Short-vHNF1," dated Jan. 7, 2015, 9 pages.

GenBank Accession No. Q12946.2, "RecName: Full=Forkhead box protein F1; AltName: Full=Forkhead-related activator 1; Short-

(56)          References Cited

OTHER PUBLICATIONS

FREAC-1; AltName: Full=Forkhead-related protein FKFIL5: AltName: Full=Forkhead-related transcription factor I," dated Feb. 4, 2015, 6 pages.

GenBank Accession No. Q13562.3, "RecName: Full=Neurogenic differentiation factor 1; Short-NeuroD; Short-NeuroD1; AltName: Full=Class A basic helix-loop-helix protein 3; Short=bHLHa3," dated Feb. 4, 2015, 6 pages.

GenBank Accession No. Q66K89.2, RecName: Full=Transcription factor E4F1; AltName: Full=E4F transcription factor 1; AltName: Full=Putative E3 ubiquitin-protein ligase E4F1; AltName: Full= Transcription factor E4F; AltName: Full=p120E4F; AltName: Full= p50E4F, dated Feb. 4, 2015, 9 pages.

GenBank Accession No. Q9H165.2, "RecName: Full=B-cell lymphoma/ leukemia 11A; Short=BCL-1 IA; AltName: Full=B-cell CEEl-lymphoma 11A: AltName: Full=COUP-TF-interacting protein 1; AltName: Full=Ecotropic viral integration site 9 protein homolog; Short=EVI-9; AltName: Full=Zinc finger protein 856," dated Feb. 4, 2015, 7 pages.

GenBank Accession No. Q9Y261.1, "RecName: Full=Hepatocyte nuclear factor 3-beta; Short=IINF-3-beta: Short=IINF-3B; AltName: Full= Forldiead box protein A2; AltName: Full=Transcription factor 3B: Short=TCF-3B," dated Feb. 4, 2015, 5 pages.

GenBank Accession No. XP 005260464.1, "Predicted: hepatocyte nuclear factor 4-alpha isoform X1 [*Homo sapiens*]," Feb. 3, 2014, 2 pages.

Gentet, "Functional diversity of supragranular GABAergic neurons in the barrel cortex," *Frontiers in Neural Circuits*, vol. 6, article 52, pp. 1-13 (Aug. 2012) (electronic publication).

Ginhoux et al., " Fate mapping analysis reveals that adult microglia derive from primitive macrophages," *Science*, 330(6005), pp. 841-845 (Oct. 2010) (electronic publication).

Goldman, "Stem and Progenitor Cell-Based Therapy of the Central Nervous System: Hopes, Hype, and Wishful Thinking," *Cell Stem Cell*, 18(2), pp. 174-188 (Feb. 2016) (electronic publication).

Gómez-Isla et al., "Profound loss of layer II entorhinal cortex neurons occurs in very mild Alzheimer's disease," *Journal of Neuroscience*, 16(14), pp. 4491-4500 (Jul. 1996) (electronic publication).

Gonzalez-Reyes et al., "Involvement of astrocytes in Alzheimer's disease from a neuroinflammatory and oxidative stress perspective," *Frontiers in Molecular Neuroscience*, vol. 10, article 427, pp. 1-20 (Dec. 2017) (electronic publication).

Graham et al., "SOX2 Functions to Maintain Neural Progenitor Identity," *Neuron*, 39(5), pp. 749-765 (Aug. 2003) (electronic publication).

Grande et al., "Environmental impact on direct neuronal reprogramming in vivo in the adult brain," *Nature Communications*, vol. 4, article 2373, pp. 1-12 (Aug. 2013) (electronic publication).

Gresita et al., "Very Low Efficiency of Direct Reprogramming of Astrocytes Into Neurons in the Brains of Young and Aged Mice After Cerebral Ischemia," *Frontiers in Aging Neuroscience*, 11(334), pp. 1-7 (Dec. 2019) (electronic publication).

Gross et al., "Lbx1 specifies somatosensory association interneurons in the dorsal spinal cord," *Neuron*, 34(4), pp. 535-549 (May 2002) (electronic publication).

Gu et al., "R gene expression induced by a type-III effector triggers disease resistance in ice," *Nature*, 435(7045), pp. 1122-1125 (Jul. 2005) (electronic publication).

Guichet et al., "Cell death and neuronal differentiation of glioblastoma stem-like cells induced by neurogenic transcription factors," *Glia*, 61(2), pp. 225-239 (Feb. 2013) (electronic publication).

Guncova et al., "The neurodegenerative process in a neurotoxic rat model and in patients with Huntington's disease: Histopathological parallels and differences," *Acta Histochemica*, 113(8), pp. 783-792 (Dec. 2011) (electronic publication).

Guo et al., "Protein tolerance to random amino acid change," PNAS, vol. 101, No. 25, pp. 9205-9210 (Jun. 2004) (Washington, DC).

Guo et al., "In vivo direct reprogramming of reactive glial cells into functional neurons after brain injury and in an Alzheimer's disease model," *Cell Stem Cell*, 14(2), pp. 188-202 (Feb. 2014) (electronic publication).

Habekost et al., "MicroRNAs and Ascll facilitate direct conversion of porcine fibroblasts into induced neurons," *Stem Cell Research*, vol. 48, article: 101984, pp. 1-9 (Oct. 2020) (electronic publication).

Halees et al., "PromoSer: a large-scale mammalian promoter and transcription start site identification service," *Nucleic Acids Research*, 31(13), pp. 3554-3559 (Jul. 2003) (electronic publication).

Hays et al., "The Utility of Cerebral Blood Flow as a Biomarker of Preclinical Alzheimer's Disease," *Cellular and Molecular Neurobiology*, 36(2): 167-179 (Feb. 2016) (electronic publication).

He et al., "Intrinsic control of axon regeneration, " *Neuron*, 90(3), pp. 437-451 (May 2016) (electronic publication).

He et al., "Multipotent stem cells from the mouse basal forebrain contribute GABAergic neurons and oligodendrocytes to the cerebral cortex during embryogenesis," *The Journal of Neuroscience*, 21(22), pp. 8854-8862 (Nov. 2001) (electronic publication).

He et al., "The regulation of microRNA expression by DNA methylation in hepatocellular carcinoma," *Molecular BioSystems*, 11(2), pp. 532-539 (Nov. 2014) (electronic publication).

Heinrich et al., "Directing astroglia from the cerebral cortex into subtype specific functional neurons," *PLoS Biology*, 8(5): e1000373, pp. 1-29 (May 2010) (electronic publication).

Heinrich et al., "Generation of subtype-specific neurons from post-natal astroglia of the mouse cerebral cortex," *Nature Protocols*, 6(2), pp. 214-228 (Feb. 2011) (electronic publication).

Heinrich et al. "Reprogramming of postnatal astroglia of the mouse neocortex into functional, synapse-forming neurons," *Methods in Molecular Biology*, vol. 814, pp. 485-498, 2012 (available online Nov. 2011) (electronic publication).

Heinrich et al., "Sox2-mediated conversion of NG2 glia into induced neurons m the injured adult cerebral cortex," *Stem Cell Reports*, 3(6), pp. 1000-1014 (Dec. 2014) (electronic publication).

Heppner et al., "Immune attack: the role of inflammation in Alzheimer disease," *Nature Reviews Neuroscience*, 16(6), pp. 358-372 (May 2015) (electronic publication).

Herrmann et al., "STAT3 is a critical regulator of astrogliosis and scar formation after spinal cord injury," *Journal of Neuroscience*, 28(28), pp. 7231-7243 (Jul. 2008) (electronic publication).

High et al., "Gene Therapy," *The New England. Journal of Medicine*, 381(5), pp. 455-464 (Aug. 2019) (electronic publication).

Hill et al., "Modulation of oligodendrocyte generation during a critical temporal window after NG2 cell division," *Nature Neuroscience*, vol. 17, pp. 1518-1527 (Nov. 2014) (electronic publication).

Holley et al., "Therapeutic effects of stem cells in rodent models of Huntington's disease: Review and electrophysiological findings," *CNS Neuroscience & Therapeutics*, 24(4), pp. 329-342 (Apr. 2018) (electronic publication).

Hong et al., "Complement and microglia mediate early synapse loss in Alzheimer mouse models," *Science*, 352(6286), pp. 712-716 (Mar. 2016) (electronic publication).

Hong et al., "Functional requirement of dicer1 and miR-17-5p in reactive astrocyte proliferation after spinal cord injury in the mouse," *Glia*, 62(12), pp. 2044-2060 (Dec. 2014) (electronic publication).

Horie et al., "Mouse model of focal cerebral ischemia using endothelia-1," *Journal of Neuroscience Methods*, 173(2), pp. 286-290 (Aug. 2008) (electronic publication).

Howard et al., "Tropism and toxicity of adeno-associated viral vector serotypes 1, 2, 5, 6, 7, 8, and 9 in rat neurons and glia in vitro," *Virology*, 372(1), pp. 24-34 (Mar. 2008) (electronic publication).

Hu et al., "Region-Restrict Astrocytes Exhibit Heterogeneous Susceptibility to Neuronal Reprogramming," *Stem Cell Reports*, 12(2), pp. 290-304 (Feb. 2019) (electronic publication).

Huang et al., "Alzheimer mechanisms and therapeutic strategies," *Cell*, 148(6), pp. 1204-1222 (Mar. 2012) (electronic publication).

Huang et al., "Ptf1a, Lbx1 and Pax2 coordinate glycinergic and peptidergic transmitter phenotypes in dorsal spinal inhibitory neurons," *Developmental Biology*, 322(2), pp. 394-405 (Oct. 2008) (electronic publication).

(56) References Cited

OTHER PUBLICATIONS

Hughes et al., "Focal lesions in the rat central nervous system induced by endothelin-1," *Journal of Neuropathology & Experimental Neurology*, 62(12), pp. 1276-1286 (Dec. 2003) (electronic publication).

Hussain et al., "Blood-Brain Barrier Breakdown: An Emerging Biomarker of Cognitive Impairment in Normal Aging and Dementia," *Frontiers in Neuroscience* vol. 15, Article 688090, pp. 1-22; (Aug. 2021) (Lausanne, Switzerland).

Hwang et al., "Efficient genome editing in zebrafish using a CRISPR-Cas system," *Nature Biotechnology*, 31(3), pp. 227-229 (Jan. 2013) (electronic publication).

International Preliminary Report on Patentability in International Application No. PCT/US2018/020251 dated Sep. 3, 2019, 7 pages.

International Preliminary Report on Patentability in International Application No. PCT/US2019/016378 dated Feb. 2, 2018, 10 pages.

International Search Report and Written Opinion in International Application No. PCT/US2017/018398, dated May 8, 2017, 10 pages.

International Search Report and Written Opinion in International Application No. PCT/US2018/020251 dated Jun. 14, 2018, 9 pages.

International Search Report and Written Opinion in International Application No. PCT/US2019/016378 dated Apr. 26, 2019, 14 pages.

International Search Report and Written Opinion in International Application No. PCT/US2020/038050, dated Sep. 17, 2020, 18 pages.

International Search Report and Written Opinion, in International Application No. PCT/US/2020/056059, dated Feb. 25, 2021, 10 pages.

International Search Report and Written Opinion, in International Application No. PCT/US/2020/056064, dated Feb. 25, 2021, 10 pages.

International Search Report and Written Opinion in International Application No. PCT/US2021/052299, dated Mar. 9, 2022, 47 pages.

International Search Report and Written Opinion in International Application No. PCT/US2021/052300, dated Feb. 28, 2022, 7 pages.

International Search Report and Written Opinion in International Application No. PCT/US2021/052302, dated Feb. 18, 2022, 29 pages.

International Search Report and Written Opinion in International Application No. PCT/US2021/052354, dated Mar. 1, 2022, 208 pages.

International Search Report and Written Opinion in International Application No. PCT/US2021/052358, dated Feb. 15, 2022, 31 pages.

International Search Report in International Application No. PCT/US2020/024976, dated Jun. 12, 2020, 5 pages.

International Search Report in International Application No. PCT/US2020/062299, dated Mar. 3, 2021, 4 pages.

International Search Report in International Application No. PCT/US2021/052348, dated Feb. 17, 2022, 7 pages.

International Search Report and Written Opinion issued in International Application No. PCT/US2013/051277, dated Oct. 16, 2013, 12 pages.

Iqbal et al., "Mechanisms of neurofibrillary degeneration and the formation of neurofibrillary tangles," *Journal of Neural Transmission. Supplement*, vol. 53, pp. 169-180 (1998) (electronic publication).

Ivkovic et al. "Expression of the striatal DARPP-32/ARPP-21 phenotype in GABAergic neurons requires neurotrophins in vivo and in vitro. 1," *Neuroscience*, 19(13), pp. 5409-5419 (Jul. 1999) (electronic publication).

Jaunmuktane et al., "Evidence for human transmission of amyloid-(3 pathology and cerebral amyloid angiopathy," *Nature*, 525(7568), pp. 247-250 (Sep. 2015) (electronic publication).

Jessberger et al., "Directed differentiation of hippocampal stem/progenitor cells in the adult brain," *Nature Neuroscience*, 11(8), pp. 888-893 (Aug. 2008) (electronic publication).

Ji et al. "Cell Fate Conversion: Direct Induction of Hepatocyte-Like Cells From Fibroblasts," *Journal of Cellular Biochemistry*, vol. 114, pp. 256-265 (Feb. 2013) (Hoboken, NJ).

Jiang et al., "Motor and behavioral phenotype in conditional mutants with targeted ablation of cortical D1 dopamine receptor-expressing cells," *Neurobiology of Disease*, vol. 76, pp. 137-158 (Apr. 2015) (electronic publication).

Jiang et al., "RNA-guided editing of bacterial genomes using CRISPR-Cas systems," *Nature Biotechnology*, 31(3), pp. 233-239 (Jan. 2013) (electronic publication).

Jinek et al., "A programmable dual-RNA—guided DNA endonuclease in adaptive bacterial immunity," *Science*, 337(6096), pp. 816-821 (Jun. 2012) (electronic publication).

Kang et al., "NO2+ CNS Glial Progenitors Remain Committed to the Oligodendrocyte Lineage in Postnatal Life and following Neurodegeneration," *Neuron*, 68(4), pp. 668-681 (Nov. 2010) (electronic publication).

Karlin et al., "Applications and statistics for multiple high-scoring segments in molecular sequences," *Proceedings of the National Academy of Sciences*, 90(12), pp. 5873-5877 (Jun. 1993) (electronic publication).

Karlin et al., "Methods for assessing the statistical significance of molecular sequence features by using general scoring schemes," *Proc. Natl. Acad. Sci. U.S.A.*, 87(6), pp. 2264-2268 (Mar. 1990) (electronic publication).

Karow et al., "Reprogramming of pericyte-derived cells of the adult human brain into induced neuronal cells," *Cell Stem Cell*, 11(4), pp. 471-476 (Oct. 2012) (electronic publication).

Kawaguchi et al., "Parvalbumin, somatostatin and cholecystokinin as chemical markers for specific GABAergic interneuron types in the rat frontal cortex," *Journal of Neurocytology*, vol. 31, pp. 277-287 (Mar. 2002) (electronic publication).

Kay et al., "A bacterial effector acts as a plant transcription factor and induces a cell size regulator," Science, 318(5850), pp. 648-651, (Oct. 2007) (electronic publication).

Kepecs et al., "Interneuron Cell Types: Fit to form and formed to fit," *Nature*, vol. 505, pp. 318-326 (Jan. 2014) (electronic publication).

Kim et al., "Functional integration of dopaminergic neurons directly converted from mouse fibroblasts," *Cell Stem Cell*, 9(5), pp. 413-419 (Nov. 2011) (electronic publication).

Kim et al., "Hybrid restriction enzymes: zinc finger fusions to Fok I cleavage domain," *Proc. Natl. Acad. Sci. U.S.A.*, 93(3), pp. 1156-1160 (Feb. 1996) (electronic publication).

Kim et al., "Mitochondrial Aging Defects Emerge in Directly Reprogrammed Human Neurons due to Their Metabolic Profile," *Cell Reports*, 23(9), pp. 2550-2558 (May 2018) (electronic publication).

Kim et al., "Modelling APOE ε3/4 allele-associated sporadic Alzheimer's disease in an induced neuron," *Brain*, 140(8), pp. 2193-2209 (Aug. 2017) (electronic publication).

Kimbrough et al., "Vascular amyloidosis impairs the gliovascular unit in a mouse model of Alzheimer's disease," *Brain*, 138(12), pp. 3716-3373 (Nov. 2015) (electronic publication).

Kitagawa, "Therapeutic application of cell transplantation and increased neurogenesis in cerebral infarction," *Rinsho Shinkeigaku Clinical Neurology*, 44(11), pp. 756-759 (Nov. 2004) (electronic publication).

Kogiso et al. "Transdifferentiation of human fibroblasts into hepatocyte-like cells by defined transcriptional factors," *Hepatology International*, vol. 7, No. 3, pp. 937-944 (Mar. 2013) (New Delhi, India).

Kojima et al., "NeuroD-betacellulin gene therapy induces islet neogenesis in the liver and reverses diabetes in mice," *Nature Medicine*, vol. 9, pp. 596-603 (Apr. 2003) (electronic publication).

Koprivica et al., "EGFR activation mediates inhibition of axon regeneration by myelin and chondroitin sulfate proteoglycans," *Science*, 310(5745), pp. 106-110 (Oct. 2005) (electronic publication).

(56)　　　　　References Cited

OTHER PUBLICATIONS

Kordasiewicz et al., "Sustained therapeutic reversal of Huntington's disease by transient repression of huntingtin synthesis," *Neuron*, 74(6), pp. 1031-1044 (Jun. 2012) (electronic publication).

Kreitzer, "Physiology and pharmacology of striatal neurons," *Annual Review of Neuroscience*, vol. 32, pp. 127-147 (Jul. 2009) (electronic publication).

Kunz et al., "Reduced grid-cell-like representations in adults at genetic risk for Alzheimer's disease," *Science*, 350(6259), pp. 430-433 (Oct. 2015) (electronic publication).

Kuwabara et al., "Win-mediated activation of NeuroD1 and retro-elements during adult neurogenesis," *Nature Neuroscience*, 12(9), pp. 1097-1105 (Aug. 2009) (electronic publication).

LaFerla et al., "Intracellular amyloid-13 in Alzheimer's disease," *Nature Reviews Neuroscience*, 8(7), pp. 499-509 (Jul. 2007) (electronic publication).

Lambert et al., "Targeting transcription factors for cancer treatment," *Molecules*, 23(6), article 1479, pp. 1-51 (Jun. 2018) (electronic publication).

Lau et al., "Direct neural conversion from human fibroblasts using self- regulating and nonintegrating viral vectors," *Cell Reports*, 9(5), pp. 1673-1680 (Dec. 2014) (electronic publication).

Le Cong et al., "Multiplex genome engineering using CRISPR/Cas systems," *Science*, 339(6121), pp. 819-823 (Jan. 2013) (electronic publication).

Lee et al., "Conversion of Xenopus Ectoderm into Neurons by NeuroD, a Basic Helix-Loop-Helix Protein," *Science*, 268(5212), pp. 836-844 (May 1995) (electronic publication).

Lei et al., "Non-engineered and engineered adult neurogenesis in mammalian brains," *Frontiers in Neuroscience*, vol. 13, article 131, pp. 1-13 (Feb. 2019) (electronic publication).

Leib et al., "Limited astrocyte-to-neuron conversion in the mouse brain using NeuroD1 overexpression," *Molecular Therapy*, vol. 30, No. 3, pp. 982-986, (Mar. 2022), (Cambridge, MA).

Lennihan et al., "Effect of Hypervolemic Therapy on Cerebral Blood Flow After Subarachnoid Hemorrhage," *Stroke*, 31(2), pp. 383-391 (Feb. 2000) (electronic publication).

Lethbridge Brainiacs, "Team: Lethbridge/project" (online publication) (screenshot from Wayback Machine dated Jul. 2, 2015), 7 pages, retrieved from the internet: Jul. 13, 2022, <https://web.archive.org/web/20150702194117/http://2014.igem.org/Team:Lethbridge/project>.

Li et al., "Conversion of Astrocytes and Fibroblasts into Functional Noradrenergic Neuron," *Cell Reports*, 28(3), pp. 682-697 (Jul. 2019) (electronic publication).

Li et al., "In vivo reprogramming for CNS repair: regenerating neurons from endogenous glial cells," *Neuron*, 91(4), pp. 728-738 (Aug. 2016) (electronic publication).

Liang et al., "Myt11 induced direct reprogramming of pericytes into cholinergic neurons," *CNS Neuroscience & Therapeutics*, 24(9):801-809 (Sep. 2018) (electronic publication).

Liddelow et al., "Neurotoxic reactive astrocytes are induced by activated microglia," *Nature*, 541(7638), pp. 481-487 (Jan. 2017) (electronic publication).

Liddelow et al., "Reactive astrocytes: production, function, and therapeutic potential," *Immunity*, 46(6), pp. 957-967 (Jun. 2017) (electronic publication).

Limon et al., "Loss of functional GABAA receptors in the Alzheimer diseased brain," *Proceedings of the National Academy of Sciences*, 109(25), pp. 10071-10076 (Jun. 2012) (electronic publication).

Liu et al., "Ascl 1 converts dorsal midbrain astrocytes into functional neurons in vivo," *Journal of Neuroscience*, 35(25), pp. 9336-9355 (Jun. 2015) (electronic publication).

Liu et al., "Differential neuronal reprogramming induced by NeuroD1 from astrocytes in grey matter versus white matter," *Neural Regeneration Research*, 15(2), pp. 342-351 (Sep. 2020) (electronic publication).

Liu et al., "Direct Lineage Reprogramming Reveals Disease-Specific Phenotypes of Motor Neurons from Human ALS Patients," *Cell Reports*, 14(1), pp. 115-128 (Jan. 2016) (electronic publication).

Liu et al., "Direct reprogramming of human fibroblasts into dopaminergic neuron-like cells," *Cell Research*, 22(2), pp. 321-332 (Feb. 2012) (electronic publication).

Liu et al., "Small molecules enable neurogenin 2 to efficiently convert human fibroblasts into cholinergic neurons," *Nature Communications*, vol. 4, Article: 2183, pp. 1-10 (Jul. 2013) (electronic publication).

Livingston et al., "Direct reprogramming of astrocytes to neurons leads to functional recovery after stroke," *bioRxiv*, doi: https://doi.org/10.1101/2020.02.02.92909, pp. 1-15 (Feb. 2020) (electronic publication).

Lollo et al., "Poly-L-Lysine Based Gene Delivery Systems: Synthesis, Purification, and Application," in Gene Therapy Protocols, 2nd Edition, Morgan (ed.), Humana Press, Totowa, NJ, pp. 1-30 (Oct. 2001).

Lu et al., "Molecular and cellular development of spinal cord locomotor circuitry," *Frontiers in Molecular Neuroscience*, vol. 8, article 25, pp. 1-18 (Jun. 2015) (electronic publication).

Lu et al., "Prolonged human neural stem cell maturation supports recovery in injured rodent CNS," *The Journal of Clinical Investigation*, 127(9), pp. 3287-3299 (Aug. 2017) (electronic publication).

Lu et al., "Turning reactive glia into functional neurons in the brain," *Cell Stem Cell*, 14(2), pp. 133-134 (Feb. 2014) (electronic publication).

Luo et al., "Global DNA methylation remodeling during direct reprogramming of fibroblasts to neurons," *eLife*, vol. 8, article: e40197, pp. 1-19 (Jan. 2019) (electronic publication).

Ma et al., "Distinct Subtypes of Somatostatin-Containing Neocortical Interneurons Revealed in Transgenic Mice," *Journal of Neuroscience*, 26(19), pp. 5069-5082 (May 2006) (electronic publication).

Ma et al., "Human embryonic stem cell-derived GABA neurons correct locomotion deficits in quinolinic acid-lesioned mice," *Cell Stem Cell*, 10(4), pp. 455-464 (Apr. 2012) (electronic publication).

Maas et al., "Traumatic brain injury: integrated approaches to improve prevention, clinical care, and research," *Lancet Neurol.*, 16(12):987-1048 (2017) (electronic publication).

MacDonald et al., "A novel gene containing a trinucleotide repeat that is expanded and unstable on Huntington's disease chromosomes," *Cell*, 72(6), pp. 971-983 (Mar. 1993) (electronic publication).

Makarova et al., "An updated evolutionary classification of CRISPR-Cas systems," *Nature Reviews Microbiology*, 13(11), pp. 722-736, (Sep. 2015) (electronic publication) (electronic publication).

Makarova et al., "Evolution and classification of the CRISPR-Cas systems," *Nature Reviews Microbiology*, 9(6), pp. 467-477 (May 2011) (electronic publication).

Malankhanova et al., "Modern Genome Editing Technologies in Huntington's Disease Research," *Journal of Huntington's Disease*, vol. 6, pp. 19-31, (Mar. 2017) (Amsterdam, Netherlands).

Mali et al., "RNA-Guided Human Genome Engineering via Cas9," *Science*, 339(6121), pp. 823-826 (Jan. 2013) (electronic publication).

Mangiarini et al., "Exon 1 of the HD Gene with an Expanded CAG Repeat Is Sufficient to Cause a Progressive Neurological Phenotype in Transgenic Mice," *Cell*, 87(3), pp. 493-506 (Nov. 1996) (electronic publication).

Marchesi, "Alzheimer's dementia begins as a disease of small blood vessels, damaged by oxidative-induced inflammation and dysregulated amyloid metabolism: implications for early detection and therapy," *The FASEB Journal*, 25(1), pp. 5-13 (Jan. 2011) (electronic publication).

Margaritsescu et al., "Original Paper: Histopathological changes in acute ischemic stroke," *Romanian Journal of Morphology and Embryology*, vol. 50, No. 3, pp. 327-339 (2009) (online publication).

Marin et al., "Origin and Molecular Specification of Striatal Interneurons," *Journal of Neuroscience*, 20(16), pp. 6063-6076 (Aug. 2000) (electronic publication).

(56) References Cited

OTHER PUBLICATIONS

Markakis et al., "Comparative Transduction Efficiency of AAV Vector Serotypes 1-6 in the Substantia Nigra and Striatum of the Primate Brain," *Molecular Therapy*, 18(3), pp. 588-593 (Mar. 2010) (electronic publication).
Markram et al., "Interneurons of the neocortical inhibitory system," *Nature Reviews Neuroscience*, vol. 5, pp. 793-807 (Oct. 2004) (electronic publication).
Marro et al., "Direct lineage conversion of terminally differentiated hepatocytes to functional neurons," *Cell Stem Cell*, 9(4), pp. 374-382 (Oct. 2011) (electronic publication).
Masserdotti et al., "Transcriptional Mechanisms of Proneural Factors and REST in Regulating Neuronal Reprogramming of Astrocytes," *Cell Stem Cell*, 17(1), pp. 74-88 (Jul. 2015) (electronic publication).
Matsuda et al., "Cerebral blood flow and metabolic abnormalities in Alzheimer's disease," *Annals Nuclear Medicine*, 15(2), pp. 85-92 (Apr. 2001) (electronic publication).
Matsuda et al., "Pioneer Factor NeuroD1 Rearranges Transcriptional and Epigenetic Profiles to Execute Microglia-Neuron Conversion," *Neuron*, vol. 101, pp. 472-485 (Feb. 2019) (electronic publication).
Mazzoni et al., "Synergistic binding of transcription factors to cell-specific enhancers programs motor neuron identity," *Nature Neuroscience*, 16(9):1219-27 (Sep. 2013) (electronic publication).
McKinsey et al., "Dlx1&2-Dependent Expression of Zfhx1b (Sip1, Zeb2) Regulates the Fate Switch between Cortical and Striatal Interneurons," *Neuron*, 77(1), pp. 83-98 (Jan. 2013) (electronic publication).
McLendon et al., Comprehensive genomic characterization defines human glioblastoma genes and core pathways, *Nature*, 455(7216), pp. 1061-1068, (Oct. 2008) (electronic publication).
McPhee, et al. "Immune responses to AAV in a phase I study for Canavan disease," *The Journal of Gene Medicine*, vol. 8, pp. 577-588 (Mar. 2006) (Hoboken, NJ).
McPhee et al., "Effects of AAV-2-mediated aspartoacylase gene transfer in the tremor rat model of Canavan disease," *Molecular Brain Research*, 135(1-2), pp. 112-121 (Apr. 2005) (electronic publication).
Medeiros et al., "Astrocytes: Conductors of the Alzheimer disease neuroinflammatory symphony," *Experimental Neurology*, vol. 239, pp. 133-138 (Jan. 2013) (electronic publication).
Menalled et al., "Systematic behavioral evaluation of Huntington's disease transgenic and knock-in mouse models," *Neurobiology of Disease*, 35(3), pp. 319-336 (Sep. 2009) (electronic publication).
Mertens et al., "Directly Reprogrammed Human Neurons Retain Aging-Associated Transcriptomic Signatures and Reveal Age-Related Nucleocytoplasmic Defects," *Cell Stem Cell*, 17(6), pp. 705-718 (Dec. 2015) (electronic publication).
Miao et al., "Up-regulation of GBP2 is Associated with Neuronal Apoptosis in Rat Brain Cortex Following Traumatic Brain Injury," *Neurochemical Research*, vol. 42, pp. 1515-1523 (May 2017) (electronic publication).
Miniarikova et al., "AAV5-miHTT gene therapy demonstrates suppression of mutant huntingtin aggregation and neuronal dysfunction in a rat model of Huntington's disease," *Gene Therapy*, vol. 24, pp. 630-639 (Aug. 2017) (electronic publication).
Mitew et al., "Altered synapses and gliotransmission in Alzheimer's disease and AD model mice," *Neurobiology of Aging*, 34(10), pp. 2341-2351 (Oct. 2013) (electronic publication).
Miyata et al., "NeuroD is required for differentiation of the granule cells in the cerebellum and hippocampus," *Genes & Development*, vol. 13, pp. 1647-1652 (May 1999) (electronic publication).
Moghimi et al., "Nanomedicine: current status and future prospects," *The FASEB Journal*, 19(3), pp. 311-330 (Mar. 2005) (electronic publication).
Morrow et al., "NeuroD regulates multiple functions in the developing neural retina in rodent," *Development*, 126(1), pp. 23-36 (Jan. 1999) (electronic publication).
Myers et al., "Optimal alignments in linear space," *Bioinformatics*, 4(1), pp. 11-17 (Mar. 1988) (electronic publication).

Nemoto et al., "Direct Neuronal Reprogramming of Common Marmoset Fibroblasts by ASCL1, microRNA-9/9*, and microRNA-124 Overexpression," *Cells*, 10(6), pp. 1-14 (Dec. 2021) (electronic publication).
Ngo et al., "Computational Complexity, Protein Structure Prediction, and the Levinthal Paradox," *The Protein Folding Problem and Tertiary Structure Prediction*, pp. 433-495 (1994) (electronic publication).
Nicoleau et al., "Human Pluripotent Stem Cell Therapy for Huntington's Disease: Technical, Immunological, and Safety Challenges," *Neurotherapeutics*, vol. 8, pp. 562-576 (Oct. 2011) (electronic publication).
Nishimura et al., "Generation of induced neurons by direct reprogramming in the mammalian cochlea," *Neuroscience*, vol. 275, pp. 125-135 (Sep. 2014) (electronic publication).
Nishiyama et al., "Polydendrocytes (NG2 cells): multifunctional cells with lineage plasticity," *Nature Reviews Neuroscience*, vol. 10, pp. 9-22 (Jan. 2009) (electronic publication).
Niu et al., "In vivo reprogramming of astrocytes to neuroblasts in the adult brain," *Nature Cell Biology*, vol. 15, pp. 1164-1175 (Sep. 2013) (electronic publication).
Niu et al., "SOX2 Reprograms Resident Astrocytes into Neural Progenitors in the Adult Brain," *Stem Cell Reports*, 4(5), pp. 780-794 (May 2015) (electronic publication).
Noda et al., "Direct Reprogramming of Spiral Ganglion Non-neuronal Cells into Neurons: Toward Ameliorating Sensorineural Hearing Loss by Gene Therapy," *Frontiers in Cell and Developmental Biology*, 6(16), pp. 1-14 (Feb. 2018) (electronic publication).
Norenberg, et al., "The Pathology of Human Spinal Cord Injury: Defining the Problems," *The Journal of Neurotrauma*, 21(4), pp. 429-440 (Jul. 2004) (electronic publication).
Nussbaum et al., "Prion-like behaviour and tau-dependent cytotoxicity of pyroglutamylated amyloid-β," *Nature*, vol. 485, pp. 651-655 (May 2012) (electronic publication).
Oakley et al., "Intraneuronal β-Amyloid Aggregates, Neurodegeneration, and Neuron Loss in Transgenic Mice with Five Familial Alzheimer's Disease Mutations: Potential Factors in Amyloid Plaque Formation," *The Journal of Neuroscience*, 26(40), pp. 10129-10140 (Oct. 2006) (electronic publication).
Obermeier et a., "Development, maintenance and disruption of the blood-brain barrier," *Nature Medicine*, vol. 19, pp. 1584-1596 (Dec. 2013) (electronic publication).
Office Action in Chinese Application No. 201380048924.2, dated Apr. 13, 2018, English Translation, 7 pages.
Office Action in Chinese Application No. 201380048924.2, dated Jun. 17, 2016, Chinese Language, 6 pages.
Office Action in Chinese Application No. 201380048924.2, dated Jun. 17, 2016, English Translation, 5 pages.
Office Action in Chinese Application No. 201380048924.2, dated Mar. 21, 2017, Chinese Language, 5 pages.
Office Action in Chinese Application No. 201380048924.2, dated Mar. 21, 2017, English Translation, 7 pages.
Office Action in Chinese Application No. 201380048924.2, dated Sep. 26, 2017, English Translation, 6 pages.
Ohori et al., "Growth Factor Treatment and Genetic Manipulation Stimulate Neurogenesis and Oligodendrogenesis by Endogenous Neural Progenitors in the Injured Adult Spinal Cord," *Journal of Neuroscience*, 26(46), pp. 11948-11960 (Nov. 2006) (electronic publication).
Ojala et al., "Adeno-Associated Virus Vectors and Neurological Gene Therapy," *Neuroscientist*, 21(1), pp. 84-98 (Feb. 2015) (electronic publication).
Okada et al., "Conditional ablation of Stat3 or Socs3 discloses a dual role for reactive astrocytes after spinal cord injury," *Nature Medicine*, Jul. 2006, vol. 12, pp. 829-834 (Jun. 2006) (electronic publication).
Oproescu et al., "New Insights Into the Intricacies of Proneural Gene Regulation in the Embryonic and Adult Cerebral Cortex," *Frontier in Molecular Neuroscience*, 14(642016), pp. 1-24 (Feb. 2021) (electronic publication).
Ortinski et al., "Selective induction of astrocytic gliosis generates deficits in neuronal inhibition," *Nature Neuroscience*, 13(5), pp. 584-591 (Apr. 2010) (electronic publication).

(56) References Cited

OTHER PUBLICATIONS

Osborn et al., "Astrogliosis: An integral player in the pathogenesis of Alzheimer's disease," *Progress in Neurobiology*, vol. 144, pp. 121-141 (Sep. 2016) (electronic publication).
Ostrom et al., "CBTRUS Statistical Report: Primary Brain and Central Nervous System Tumors Diagnosed in the United States in 2008-2012," *Neuro-Oncology*, 17(suppl_4), pp. iv1-iv62 (Oct. 2015) (electronic publication).
Palop et al., "Amyloid-β-induced neuronal dysfunction in Alzheimer's disease: from synapses toward neural networks," *Nature Neuroscience*, 13(7), pp. 812-818 (Jun. 2010) (electronic publication).
Pang et al., "Induction of human neuronal cells by defined transcription factors," *Nature*, vol. 476, pp. 220-223 (May 2011) (electronic publication).
Panganiban et al., "Developmental functions of the Distal-less/Dlx homeobox genes," *Development*, 129(19), pp. 4371-4386 (Oct. 2002) (electronic publication).
Parkhurst et al., "Microglia Promote Learning-Dependent Synapse Formation through Brain-Derived Neurotrophic Factor," *Cell*, 155(7), pp. 1596-1609 (Dec. 2013) (electronic publication).
Paul et al., "Cystathionine γ-lyase deficiency mediates neurodegeneration in Huntington's disease," *Nature*, vol. 509, pp. 96-100 (Mar. 2014) (electronic publication).
Pawson, et al. Assembly of Cell Regulatory Systems Through Protein Interaction Domains, *Science*, vol. 300, pp. 445-452 (Apr. 2003) (London, UK).
Pereira et al., "Direct Reprogramming of Resident NG2 Glia into Neurons with Properties of Fast-Spiking Parvalbumin-Containing Interneurons," *Stem Cell Reports*, 9(3), pp. 742-751 (Sep. 2017) (electronic publication).
Perrin, "Preclinical research: Make mouse studies work," *Nature* vol. 507, pp. 423-425 (Mar. 2014) (electronic publication).
Petryniak et al., "Dlx1 and Dlx2 Control Neuronal versus Oligodendroglial Cell Fate Acquisition in the Developing Forebrain," *Neuron*, 55(3), pp. 417-433 (Aug. 2007) (electronic publication).
Pfisterer et al., "Direct conversion of human fibroblasts to dopaminergic neurons," *PNAS*, 108(25), pp. 10343-10348 (Jun. 2011) (electronic publication).
Pla et al., "Dlx1 and Dlx2 Promote Interneuron GABA Synthesis, Synaptogenesis, and Dendritogenesis," *Cerebral Cortex*, 28(11), pp. 3797-3815 (Nov. 2018) (electronic publication).
Porter et al., "Conditional Survival of All Primary Brain Tumor Patients by Age, Behavior, and Histology," *Neuroepidemiology*, vol. 36, pp. 230-239 (Jun. 2011) (electronic publication).
Pouladi et al., "Choosing an animal model for the study of Huntington's disease," *Nature Reviews Neuroscience*, vol. 14, pp. 708-721 (Sep. 2013) (electronic publication).
Prakash et al., "Blood-brain barrier breakdown and neovascularization processes after stroke and traumatic brain injury," *Curr Opin Neural.*, Author Manuscript, 28(6), pp. 556-554, (Dec. 2015) available online, DOI: doi:10.1097/WCO.0000000000000248.
Prinz et al., "Microglia and brain macrophages in the molecular age: from origin to neuropsychiatric disease," *Nature Reviews Neuroscience*, vol. 15, pp. 300-312 (Apr. 2014) (electronic publication).
Qin et al., "Chapter 16: ELISA Methodology to Quantify Astrocyte Production of Cytokines/Chemokines In Vitro," in Astrocytes, Methods in Molecular Biology vol. 814, Milner eds, Humana Press, Totowa, NJ pp. 235-249 (online publication, Nov. 2012).
Querfurth et al., "Mechanisms of disease," *The New England Journal of Medicine*, 362(4), pp. 329-344 (Jan. 2010) (electronic publication).
Rangel-Barajas et al., "Dysregulation of corticostriatal connectivity in Huntington's disease: a role for dopamine modulation," *Journal of Huntington's Disease*, 5(4), pp. 303-331 (Dec. 2016) (electronic publication).
Rao et al., "Molecular Mechanisms Underlying Ascl1-Mediated Astrocyte-to-Neuron Conversion," *Stem Cell Reports*, 16(3), pp. 534-547, (Mar. 2021) (electronic publication).

Reidling et al., "Human Neural Stem Cell Transplantation Rescues Functional Deficits in R6/2 and Q140 Huntington's Disease Mice," *Stem Cell Reports*, 10(1), pp. 58-72 (Jan. 2018) (electronic publication).
Reinius et al., "Conditional targeting of medium spiny neurons in the striatal matrix," *Frontiers in Behavioral Neuroscience*, 9(71) pp. 1-14 (Mar. 2015) (electronic publication).
Rexed, "A cytoarchitectonic atlas of the spinal coed in the cat," *Journal of Comparative Neurology*, 100(2), pp. 297-379 (Apr. 1954) (electronic publication).
Richardson et al., "Future applications: gene therapy," *Neurosurgery Clinics*, 20(2), pp. 219-224 (Apr. 2009) (electronic publication).
Richardson et al., "NG2-glia as Multipotent Neural Stem Cells: Fact or Fantasy?," *Neuron*, 70(4), pp. 661-673 (May 2011) (electronic publication).
Rikani et al., "The mechanism of degeneration of striatal neuronal subtypes in Huntington disease," *Annals of Neurosciences*, 21(3), pp. 112-114 (Jul. 2014) (electronic publication).
Römer et al., "Plant Pathogen Recognition Mediated by Promoter Activation of the Pepper Bs3 Resistance Gene," *Science*, 318(5850), pp. 645-648 (Oct. 2007) (electronic publication).
Roome et al., "A reproducible Endothelin-1 model of forelimb motor cortex stroke in the mouse," *Journal of Neuroscience Methods*, vol. 233, pp. 34-44 (Aug. 2014) (electronic publication).
Ross et al., "Huntington's disease: from molecular pathogenesis to clinical treatment," *The Lancet Neurology*, 10(1), pp. 83-98 (Jan. 2011) (electronic publication).
Roybon et al., "GABAergic Differentiation Induced by Mash1 Is Compromised by the bHLH Proteins Neurogenin2, NeuroD1, and NeuroD2," *Cerebral Cortex*, 20(5), pp. 1234-1244 (May 2010) (electronic publication).
Roybon et al., "Neurogenin2 Directs Granule Neuroblast Production and Amplification while NeuroD1 Specifies Neuronal Fate during Hippocampal Neurogenesis," *PLOS One*, 4(3):e4779, pp. 1-19 (Mar. 2009) (electronic publication).
Russo et al., "CRISPR-Mediated Induction of Neuron-Enriched Mitochondrial Proteins Boosts Direct Glia-to-Neuron Conversion," *Cell Stem Cell*, 28(3), pp. 524-534 (Mar. 2021) (electronic publication).
Sadleir et al., "Aβ reduction in BACE1 heterozygous null SXFAD mice is associated with transgenic APP level," *Molecular Neurodegeneration*, 10(1):1 (2015) (electronic publication).
Sandhu et al., "Glutamic acid decarboxylase 67 haplodeficiency impairs social behavior in mice," *Genes, Brain and Behavior*, 13(4), pp. 439-450 (Mar. 2014) (electronic publication).
Sanjana et al., "Improved vectors and genome-wide libraries for CRISPR screening," *Nature Methods*, vol. 11, pp. 783-784 (Jul. 2014) (electronic publication).
Santos et al., "Excitatory interneurons dominate sensory processing in the spinal substantia gelatinosa of rat," *The Journal of Physiology*, 581(1), pp. 241-254 (May 2007) (electronic publication).
Sassone et al., "Regenerative approaches in Huntington's disease: from mechanistic insights to therapeutic protocols," *Frontiers in Neuroscience*, 12(800), pp. 1-8 (Nov. 2018) (electronic publication).
Schmid et al., "Dysfunction of Somatostatin-Positive Interneurons Associated with Memory Deficits in an Alzheimer's Disease Model," *Neuron*, 92(1), pp. 114-125 (Oct. 2016) (electronic publication).
Schnütgen et al., "A directional strategy for monitoring Cre-mediated recombination at the cellular level in the mouse," *Nature Biotechnology*, 21(5), pp. 562-565 (Mar. 2003) (electronic publication).
Schornack et al., "Gene-for-gene-mediated recognition of nuclear-targeted AvrBs3-like bacterial effector proteins," *Journal of Plant Physiology*, 163(3), 256-272 (Feb. 2006) (electronic publication).
Schuster et al., "Biodistribution of adeno-associated virus serotype 9 (AAV9) vector after intrathecal and intravenous delivery in mouse," *Frontiers in Neuroanatomy*, vol. 8, article 42, pp. 1-14 (Jun. 2014) (electronic publication).
Servick, "Reprogrammed cells could tackle brain damage, Turning astrocytes into neurons improves symptoms in preliminary mouse studies," *Science*, 362 (6416), pp. 736-737 (Nov. 2019) (electronic publication).

(56)         References Cited

OTHER PUBLICATIONS

Shalem et al., "Genome-Scale CRISPR-Cas9 Knockout Screening in Human Cells," *Science*, 343(6166), pp. 84-87 (Dec. 2014) (electronic publication).

Sheng et al., "Direct reprogramming of Sertoli cells into multipotent neural stem cells by defined factors," *Cell Research*, 22(1), pp. 208-218 (Jan. 2012) (electronic publication).

Sheng et al., "Most Tissue-Resident Macrophages Except Microglia Are Derived from Fetal Hematopoietic Stem Cells," *Immunity*, 43(2), pp. 382-393 (Aug. 2015) (electronic publication).

Shin et al., "GABAergic Neurons from Mouse Embryonic Stem Cells Possess Functional Properties of Striatal Neurons In Vitro, and Develop into Striatal Neurons In Vivo in a Mouse Model of Huntington's Disease," *Stem Cell Reviews and Reports*, vol. 8, pp. 513-531 (Jul. 2012) (electronic publication).

Silver et al., "Regeneration beyond the filial scar," *Nature Reviews Neuroscience*, 5(2), pp. 146-156 (Feb. 2004) (electronic publication).

Sizemore et al., "Viral vector-based tools advance knowledge of basal ganglia anatomy and physiology," *Journal of Neurophysiology*, 115(4), pp. 2124-2146 (Apr. 2016) (electronic publication).

Skolnick et al., "From genes to protein structure and function: novel applications of computational approaches in the genomic era," *Trends in Biotechnology*, 18(1), pp. 34-39, (Jan. 2000) (electronic publication).

Smith et al., "Small Molecules Modulate Chromatin Accessibility to Promote NEUROG2-Mediated Fibroblast-to-Neuron Reprogramming," *Stem Cell Reports*, 7(5), pp. 955-969 (Nov. 2016).

Sofroniew, "Molecular dissection of reactive astrogliosis and glial scar formation," *Trends in Neurosciences*, 32(12), pp. 638-647 (Dec. 2009) (electronic publication).

Son et al., "Conversion of mouse and human fibroblasts into functional spinal motor neurons," *Cell Stem Cell*, 9(3), pp. 205-218, (Sep. 2011) (electronic publication).

Srivastava et al., "In Vivo Cellular Reprogramming: The Next Generation," *Cell*, 166(6), pp. 1386-1396 (Sep. 2016) (electronic publication).

Stamouli et al., "Pro-inflammatory cytokines in Alzheimer's disease," *Psychiatrike = Psychiatriki*, 27(4), pp. 264-275 (Oct. 2016) (electronic publication).

Stawinski et al., "Chapter 6: Di- and Oligonucleotides Synthesis Using H-Phosphonate Chemistry," in Oligonucleotide Synthesis: Methods and Application, vol. 288, Herdewijin (ed.), Humana Press, Totowa, NJ pp. 87-100 (Sep. 2004).

Stoica et al., "AAV-mediated gene transfer to the mouse CNS," *Current Protocols in Microbiology*, vol. 0 14, Unit14D.5, pp. 1-25 (Aug. 2013) (electronic publication).

Stühmer et al., "Ectopic expression of the Dlx genes induces glutamic acid decarboxylase and Dlx expression," *Development*, 129(1), pp. 245-252 (Jan. 2002) (electronic publication).

Su et al., "In vivo conversion of astrocytes to neurons in the injured adult spinal cord," *Nature Communications*, vol. 5, article 3338 pp. 1-5 (Feb. 2014) (electronic publication).

Sugio et al., "Two type III effector genes of Xanthomonas oryzae pv. oryzae control the induction of the host genes OsTFIIAγ1 and OsTFX1 during bacterial blight of rice," *Proceedings of the National Academy of Sciences*, 104(25): 10720-10725 (Jun. 2007) (electronic publication).

Takahashi et al., "Induction of Pluripotent Stem Cells from Adult Human Fibroblasts by Defined Factors," *Cell*, 131(5), pp. 861-872 (Nov. 2007) (electronic publication).

Takahashi et al., "Induction of Pluripotent stem cells from mouse embryonic and adult fibroblast cultures by defined factors," *Cell*, 126(4), pp. 663-676 (Aug. 2006) (electronic publication).

Takano et al., "Astrocytes and Ischemic Injury," *Stroke*, 40(3): suppl 1, pp. S8-S12 (Mar. 2009) (electronic publication).

Takashima et al., "Prolonged inhibition of hepatocellular carcinoma cell proliferation by combinatorial expression of defined transcription factors," *Cancer Science*, 109(11), pp. 3543-3553 (Sep. 2018) (electronic publication).

Tamamaki et al., "Green fluorescent protein expression and colocalization with calretinin, parvalbumin, and somatostatin in the GAD67-GFP knock-in mouse," *Journal of Comparative Neurology*, 467(1), pp. 60-79 (Oct. 2003) (electronic publication).

Taniguchi, "Genetic dissection of GABAergic neural circuits in mouse neocortex," *Frontiers in Cell Neuroscience*, 8:8 1-22 (Jan. 2014) (electronic publication).

Tong et al., "Astrocyte Kir4.1 ion channel deficits contribute to neuronal dysfunction in Huntington's disease model mice," *Nature Neuroscience*, vol. 17, pp. 694-703 (Mar. 2014) (electronic publication).

Torper et al., "Generation of induced neurons via direct conversion in vivo," *Proceedings of the National Academy of Sciences*, 110(17), pp. 7038-7043 (Mar. 2013) (electronic publication).

Torper et al., "In vivo reprogramming of striatal NG2 glia into functional neurons that integrate into local host circuitry," *Cell Reports*, 12(3), pp. 474-481 (Jul. 2015) (electronic publication).

Toy et al., "Role of Glial Cells in Axonal Regeneration," *Experimental Neurobiology*, 22(2), pp. 68-76, Jun. 27, 2013 (electronic publication).

Treutlein et al., "Dissecting direct reprogramming from fibroblast to neuron using single-cell RNA-seq," *Nature*, 534(7607), pp. 391-395 (Jun. 2016) (electronic publication).

Tsai et al., "Regional Astrocyte Allocation Regulates CNS Synaptogenesis and Repair," *Science*, 337(6092), pp. 358-362 (Jun. 2012) (electronic publication).

Tsoa et al., "Spatiotemporally different origins of NG2 progenitors produce cortical interneurons versus glia in the mammalian forebrain," *Proceedings of the National Academy of Sciences*, 111(20), pp. 7444-7449 (May 2014) (electronic publication).

Tsunemoto et al., "Diverse reprogramming codes for neuronal identity," *Nature*, vol. 557, pp. 375-380 (May 2018) (electronic publication).

Tuszynski et al., "Neural stem cell dissemination after grafting to CNS injury sites," *Cell*, 156(3), pp. 388-389 (Jan. 2014) (electronic publication).

Van Gijsel-Bonnello et al., "Metabolic changes and inflammation in cultured astrocytes from the 5xFAD mouse model of Alzheimer's disease: Alleviation by pantethine," *PLOS one*, 12(4):e0175369, pp. 1-22 (Apr. 2017) (electronic publication).

Vasan et al., "Direct Neuronal Reprogramming: Bridging the Gap Between Basic Science and Clinical Application," *Frontiers in Cell and Developmental Biology*, 9(68108), pp. 1-29 (Jul. 2021) (electronic publication).

Velasco et al., "A Multi-step Transcriptional and Chromatin State Cascade Underlies Motor Neuron Programming from Embryonic Stem Cells," *Cell Stem Cell*, 20(2), pp. 205-217 (Feb. 2017) (electronic publication).

Venegas et al., "Microglia-derived ASC specks cross-seed amyloid-β in Alzheimer's disease," Nature, vol. 552, pp. 355-361 (Dec. 2017) (electronic publication).

Verret et al., "Inhibitory Interneuron Deficit Links Altered Network Activity and Cognitive Dysfunction in Alzheimer Model," *Cell*, 149(3), pp. 708-721 (Apr. 2012) (electronic publication).

Victor et al., "Generation of Human Striatal Neurons by MicroRNA-Dependent Direct Conversion of Fibroblasts," *Neuron*, 84(2), pp. 311-323 (Oct. 2014) (electronic publication).

Vierbuchen et al., "Direct conversion of fibroblasts to functional neurons by defined factors, " *Nature*, vol. 463, pp. 1035-1041 (Jan. 2010) (electronic publication).

Viñals et al., "BMP-2 decreases Mash1 stability by increasing Id1 expression," *The EMBO Journal*, 23(17), pp. 3527-3537 (Sep. 2004) (electronic publication).

Walker, "Huntington's disease," *Lancet*, 369(9557), pp. 218-228 (Jan. 2007) (electronic publication).

Wang et al., "Dlx5 and Dlx6 Regulate the Development of Parvalbumin-Expressing Cortical Interneurons," *Journal of Neuroscience*, 30(15), pp. 5334-5345 (Apr. 2010) (electronic publication).

Wang et al., "The p53 Pathway Controls SOX2-Mediated Reprogramming in the Adult Mouse Spinal Cord," *Cell Reports*, 17(3), pp. 891-903 (Oct. 2016) (electronic publication).

(56) References Cited

OTHER PUBLICATIONS

Wang, "Developing hippocampal delivery of AAV-NeuroD1 as a novel therapy for Alzheimer's disease," *A Thesis in Molecular, Cellular and Integrative Biosciences*, 40 pages (May 2016) (electronic publication).

Wapinski et al., "Hierarchical mechanisms for direct reprogramming of fibroblasts to neurons," *Cell*, 155(3), pp. 621-635 (Oct. 2013) (electronic publication).

Wapinski et al., "Rapid Chromatin Switch in the Direct Reprogramming of Fibroblasts to Neurons," *Cell Reports*, 20(13), pp. 3236-3247 (Sep. 2017) (electronic publication).

Wannissorn et al., "11 Factors That Disrupt the Blood-Brain Barrier," SelfDecode pp. 1-13, (Nov. 2021) available online at https://health.selfdecode.com/blog/factors-and-disease-states-that-disrupt-the-blood-brain-barrier/ (printed Mar. 1, 2023) (electronic publication).

Wesson et al., "Olfactory dysfunction correlates with amyloid-fi burden in an Alzheimer's disease mouse model," *Journal of Neuroscience*, 30(2):505-514 (2010) (electronic publication).

Wolfson et al., "Alterations of regional cerebral blood flow and oxygen metabolism in Parkinson's disease," *Neurology*, 35(10), pp. 1399-1405, Abstract only (Oct. 1985) (electronic publication).

Wonders et al., "The origin and specification of cortical interneurons," *Nature Review Neuroscience*, vol. 7, pp. 687-696 (Aug. 2006) (electronic publication).

Wu et al., "A Chemical Recipe for Generation of Clinical-Grade Striatal Neurons from hESCs," *Stem Cell Reports*, 11(3), pp. 635-650 (Sep. 2018) (electronic publication).

Wu et al., "Gene therapy conversion of striatal astrocytes into GABAergic neurons in mouse models of Huntington's disease," *Nature Communications*, vol. 11, article 1105, pp. 1-18 (Feb. 2020) (electronic publication).

Wu et al., "Tonic inhibition in dentate gyrus impairs long-term potentiation and memory in an Alzheimer's disease model," *Nature Communications*, vol. 5, article 4159, pp. 1-13 (Jun. 2014) (electronic publication).

Xuan et al., "Genome-wide promoter extraction and analysis in human, mouse, and rat," *Genome Biology*, 6(8), article R72, pp. R72.1-R72.12 (Aug. 2005) (electronic publication).

Yamashita et al., "In vivo direct reprogramming of glial linage to mature neurons after cerebral ischemia," *Scientific Reports*, vol. 9, article 10956, pp. 1-7 (Jul. 2019) (electronic publication).

Yan et al., "A Huntingtin Knockin Pig Model Recapitulates Features of Selective Neurodegeneration in Huntington's Disease," *Cell*, 173(4), pp. 989-1002 (May 2018) (electronic publication).

Yang et al., "CRISPR/Cas9-mediated gene editing ameliorates neurotoxicity in mouse model of Huntington's disease," *The Journal of Clinical Investigation*, 127(7), pp. 2719-2724 (Jun. 2017) (electronic publication).

Yang et al., "Generation of pure GABAergic neurons by transcription factor programming," *Nature Methods*, 14(6):621-628 (May 2017) (electronic publication).

Yang et al., "Induced Neuronal Cells: How to Make and Define a Neuron," *Cell Stem Cell*, 9(6), pp. 517-525 (Dec. 2011) (electronic publication).

Yang et al., "Os8N3 is a host disease-susceptibility gene for bacterial blight of rice," *Proc. Natl. Acad. Sci. USA*, 103(27), pp. 10503-10508 (Jul. 2006) (electronic publication).

Yang et al., "Towards a transgenic model of Huntington's disease in a non-human primate," *Nature*, 453(7197), pp. 921-924 (May 2008) (electronic publication).

Yiu et al., "Glial inhibition of CNS axon regeneration," *Nature Reviews Neuroscience*, vol. 7, pp. 617-627 (Aug. 2006) (electronic publication).

Yokoyama et al., "Molecular cloning of a human neuroD from a neuroblastoma cell line specifically expressed in the fetal brain and adult cerebellum," *Molecular Brain Research*, 42(1), pp. 135-139 (Nov. 1996) (electronic publication).

Yoo et al., "MicroRNA-mediated conversion of human fibroblasts to neurons," *Nature*, vol. 476, pp. 228-231 (Jul. 2011) (electronic publication).

Yung et al., "Differential modulation of BMP signaling promotes the elaboration of cerebral cortical GABAergic neurons or oligodendrocytes from a common sonic hedgehog-responsive ventral forebrain progenitor species," *PNAS*, 99(25), pp. 16273-16278 (Dec. 2002) (electronic publication).

Zaiss et al., "Differential activation of inmate immune responses by adenovirus and adeno-associated virus vectors," *Journal of Virology*, 76(9), pp. 4580-4590 (May 2002) (electronic publication).

Zernicka-Goetz et al., "Following cell fate in the living mouse embryo," *Development*, 124(6), pp. 1133-1137 (Mar. 1997).

Zetsche et al., "Cpf1 is a single RNA-guided endonuclease of a class 2 CRISPR-Cas System," *Cell*, 163(3), pp. 759-771, (Oct. 2015) (electronic publication).

Zhang et al., "Astrocyte heterogeneity: an underappreciated topic in neurobiology," *Current Opinions in Neurobiology*, 20(5), pp. 588-594 (Oct. 2010) (electronic publication).

Zhang et al., "Development of Neuroregenerative Gene Therapy to Reverse Glial Scar Tissue Back to Neuron-Enriched Tissue," *Frontiers in Cell and Developmental Biology*, 14(594170), pp. 1-19 (Nov. 2020) (electronic publication).

Zhang et al., "Modeling the phenotype of spinal muscular atrophy by the direct conversion of human fibroblasts to motor neurons," *Oncotarget*, 8(7), pp. 10945-10953 (Feb. 2017) (electronic publication).

Zhang et al., "Reversing Glial Scar Back To Neural Tissue Through NeuroD1-Mediated Astrocyte-To-Neuron Conversion," *bioRxiv*, article 261438, 36 pages (Feb. 2018) (electronic publication).

Zhang, et al., "Small Molecules Efficiently Reprogram Human Astroglial Cells into Functional Neurons," *Cell Stem Cell*, 17(6), pp. 735-747 (Dec. 2015) (electronic publication).

Zhao et al., "Distinct morphological stages of dentate granule neuron maturation in the adult mouse hippocampus," *The Journal of Neuroscience*, 26(1), pp. 3-11 (Jan. 2006) (electronic publication).

Zhao et al., "Neuronal transcription factors induce conversion of human glioma cells to neurons and inhibit tumorigenesis," *PLoS One*, 7(7):e41506, pp. 1-11 (Jul. 2012) (electronic publication).

Zhao et al., "The ASH1-miR-375-YWHAZ Signaling Axis Regulates Tumor Properties in Hepatocellular Carcinoma," *Molecular Therapy Nucleic Acids*, vol. 11, pp. 538-553 (Jun. 2018) (electronic publication).

Zhao et al., "TRED: a Transcriptional Regulatory Element Database and a platform for in silico gene regulation studies," *Nucleic Acids Research*, 33(suppl_1), pp. D103-S107 (Jan. 2005) (electronic publication).

Zhong et al., "The Wnt receptor Ryk controls specification of GABAergic neurons versus oligodendrocytes during telencephalon development," *Development*, 138(3), pp. 409-419 (Feb. 2011) (electronic publication).

Zhuo et al., "Live astrocytes visualized by green fluorescent protein in transgenic mice," *Developmental Biology*, 187(1), pp. 36-42 (Jul. 1997) (electronic publication).

Altschul et al., "Basic local alignment search tool." *Journal of Molecular Biology*, 215(3):403-410 (1990).

Chenna et al., "Multiple sequence alignment with the Clustal series of programs," *Nucleic Acids Research*, 31: 3497-3500 (2003).

Larkin et al., "Clustal W and Clustal X version 2.0," *Bioinformatics*, 23(21): 2947-48 (2007).

Livak et al., "Analysis of Relative Gene Expression Data Using Real-Time Quantitative PCR and the 2-$\Delta\Delta$CT Method," *Methods*, 25(4):402-408 (2001).

Song et al., "Astroglia induce neurogenesis from adult neural stem cells," *Nature*, 417:39-44 (2002).

Thompson et al., "Clustal W: Improving the sensitivity of progressive multiple sequence alignment through sequence weighting, position-specific gap penalties and weight matrix choice," *Nucleic Acids Research*, 22: 4673-4680 (1994).

Bloom et al. "Influence of the microenvironment on cell fate determination and migration," *Physiol Genomics* 46(9), pp. 309-314, (May 2014), available online: DOI: 10.1152/physiolgenomics.00170.2013:10.1152/physiolgenomics.00170.2013, accessed Sep. 5, 2023.

(56)　　　　　References Cited

OTHER PUBLICATIONS

Boghdadi et al., "The Neuroprotective Role of Reactive Astrocytes after Central Nervous System Injury," *Journal of Neurotrauma*, 37, pp. 681-691, (Mar. 2020), available online: DOI: https://doi.org/10.1089/neu.2019.6938, accessed and printed Sep. 9, 2023.

Cepparulo et al.," Hemorrhagic Stroke Induces a Time-Dependent Upregulation of miR-150-5p and miR-181b-5p in the Bloodstream," *Front. Neurol.* vol. 12, Article 736474, pp. 1-12 (Oct. 2021) (electronic publication); available online: DOC: 10.3389/fneur.2021.736474.

Craig et al. "Evaluation of Gene Therapy as an Intervention Strategy to Treat Brain Injury from Stroke," *Frontiers in Molecular Neuroscience Mini Review Article*, 9(34), pp. 1-9, (May 2016), available online: DOI: https://doi.org/10.3389/fnmol.2016.00034.

Cyr,"Brain & Nervous System—Types of Neurons," Medically reviewed by Nicholas R. Metrus, MD, published Jan. 10, 2022 (accessed Jul. 27, 2023), 18 pages, available online: https://www.verywellhealth.com/types-of-neurons-5201172.

Domenger et al., "Next-generation AAV vectors-do not judge a virus (only) by its cover," *Human Molecular Genetics*, vol. 28, No. R1, pp. R3-R14 (Jul. 2019) available online: doi: 10.1093/hmg/ddz148 (electronic publication).

Finkel et al., "Diversity of Adult Neural Stem and Progenitor Cells in Physiology and Disease," *Cells*, vol. 10 (2045), pp. 1-23 (Aug. 2021) (electronic publication) available online: https://doi.org/10.3390/cells10082045.

Gadd et al., "Structural Basis for Partial Redundancy in a Class of Transcription Factors, the LIM Homeodomain Proteins, in Neural Cell Type Specification," *J Biol Chem* vol. 286, No. 50, pp. 42971-42980 (Dec. 2011) (electronic publication) available online: 10.1074/jbc.M111.248559.

GenBank Accession No. JX912274, submitted Jul. 1, 2014, 3 pages (electronic publication); available online: https://www.ncbi.nlm.nih.gov/nuccore/JX912274.

GenBank Accession No. NM_004316.4, "*Homo sapiens* achaete-scute family bHLH transcription factor 1 (ASCL1), mRNA," updated Nov. 23, 2023, 4 pages (accessed and printed Aug. 15, 2023); available at: https://www.ncbi.nlm.nih.gov/nuccore/NM_004316.4.

HGFAP-Cre (Plasmid #40591) Addgene, 2 pages, (Oct. 2001), (online publication). Accessed and printed online on Aug. 1, 2023 at https://www.addgene.org/40591/#:~:text=This%20plasmid%20encodes%20a%20transgene,human%20GFAP%20(hGFAP)%20gene.

Janowska et al., "Directed glial differentiation and transdifferentiation for neural tissue regeneration," *Experimental Neurology*, Vo. 319 (112813), pp. 1-14, (2019) (available online Aug. 2018) available: https://doi.org/10.1016/j.expneurol.2018.08.010.

Liu et al., "Systematic comparison of 2A peptides for cloning multi-genes in a polycistronic vector," *Scientific Reports*, 7(2193), 9 pages, (May 2017) (online publication), available at DOI: 10.1038/s41598-017-02460-2.

Maguire et al., "Gene Therapy for the Nervous System: Challenges and New strategies," *Neurotherapeutics*. 11(4), pp. 817-839, (Oct. 2014), available online: DOI: 10.1007/s13311-014-0299-5.

Mattugini et al., "Inducing Different Neuronal Subtypes from Astrocytes in the Injured Mouse Cerebral Cortex," *Neuron* vol. 103, Issue 6, pp. 1086-1095 (Sep. 2019) (electronic publication); available online: https://doi.org/10.1016/j.neuron.2019.08.009.

Nishiyama et al., "Astrocytes and NG2-glia: what's in a name?" *Journal of Anatomy*, 207(6), pp. 687-693, (Dec. 2005), available online: https://doi.org/10.1111/j.1469-7580.2005.00489.x.

Powell et al., "Viral Expression Cassette Elements to Enhance Transgene Target Specificity and Expression in Gene Therapy," *Discov Med.* 19(102), pp. 49-57, (Jan. 2015) (electronic publication), Available online: https://www.ncbi.nlm.nih.gov/pmc/articles/PMC4505817/.

Sato et al., "Usefulness of Double Gene Construct for Rapid Identification of Transgenic Mice Exhibiting Tissue-Specific Gene Expression," *Molecular Reproduction and Development*, vol. 60(4), pp. 446-456 (Dec. 2001) (electronic publication) available online: 10.1002/mrd.1109.

Szymczak et al., "Development of 2A peptide-based strategies in the design of multicistronic vectors," *Expert Opin Biol Ther* 5(5), pp. 627-638 (2005) (electronic publication); available online: DOI: 10.1517/14712598.5.5.627.

Trotter, et al., "NG2 cells: properties, progeny and origin," *Brain Res. Rev.*, 63(1-2), pp. 72-82, (May 2010), available online: DOI: 10.1016/j.brainresrev.2009.12.006.

"Types of Stroke and Treatment," *American Stroke Association*, pp. 1-4 (electronic publication). Available online https://www.stroke.org/en/about-stroke/types-of-stroke, accessed Aug. 1, 2023.

Wang et al., "Revisiting astrocyte to neuron conversion with lineage tracing in vivo," *Cell* vol. 184, pp. 5465-5481 (Oct. 2021) (electronic publication); available online: https://doi.org/10.1016/j.cell.2021.09.005.

Xie et al., "New AAV tools fail to detect Neurod1-mediated neuronal conversion of Muller glia and astrocytes in vivo," *EBioMedicine* 90 (104531), pp. 1-19 (Apr. 2023) (electronic publication); available online: https://doi.org/10.1016/j.ebiom.2023.104531.

AAV phSyn1(S)-FlpO-bGHpA (Plasmid # 51669), *Addgene Blog*, 6 pages, (accessed and printed Jan. 12, 2024) available at: https://www.addgene.org/51669/.

Alliot et al., "Astrocytic cell clones derived from established cultures of 8-day postnatal mouse cerebella," *Brain Res.*, 306(1-2), pp. 283-291, (Jul. 1984) (electronic publication), available online: DOI: 10.1016/0006-8993(84)90377-9.

Bao et al., "Silencing of A20 Aggravates Neuronal Death and Inflammation After Traumatic Brain Injury: A Potential Trigger of Necroptosis," *Front. Mol. Neurosci.*, 12(222), 21 pages, (Sep. 2019) (electronic publication), available online, DOI: https://doi.org/10.3389/fnmol.2019.00222.

Boone et al., "Effects of AAV-mediated knockdown of nNOS and GPx-1 gene expression in rat hippocampus after traumatic brain injury," *Plos ONE*, 12(10): e0185943, 22 pages, (Oct. 2017) (electronic publication), available online: https://doi.org/10.1371/journal.pone.0185943.

Chen et al., "Functional repair after ischemic injury through high efficiency in situ astrocyte-to-neuron conversion," *BioRxiv*, pp. 1-29, (Apr. 2018) (electronic publication), available online: DOI: http://dx.doi.org/10. 1 101/294967.

Extended European Search Report issued in European Patent Application No. 20876711.1, issued Oct. 13, 2023; 8 pages.

Extended European Search Report issued in European Patent Application No. 20875993.6, issued Oct. 13, 2023; 7 pages.

Extended European Search Report issued in European Patent Application No. 20875773.2, issued Oct. 6, 2023; 10 pages.

Extended European Search Report issued in European Patent Application No. 20894844.8, issued Nov. 17, 2023, 7 pages.

GenBank Accession No. EAW54861.1 "ISL1 transcription factor, LIM/homeodomain, (islet-1) [*Homo sapiens*]," published Mar. 23, 2015, 2 pages (accessed and printed Jan. 9, 2024, available at: https://www.ncbi.nlm.nih.gov/protein/EAW54861.

GenBank Accession No. AAH31213.1, "ISL LIM homeobox 1 [*Homo sapiens*]," published Jul. 17, 2007, 2 pages (accessed and printed Jan. 9, 2024) available online at: https://www.ncbi.nlm.nih.gov/protein/AAH31213.1.

GenBank Accession No. NP_002491.3, "neurogenic differentiation factor 1 [*Homo sapiens*]," published Dec. 4, 2023, 2 pages (accessed and printed Jan. 9, 2024) available online at: https://www.ncbi.nlm.nih.gov/protein/NP_002491.

GenBank Accession No. NM_002500.5, "*Homo sapiens* neuronal differentiation 1 (NEUROD1), transcript variant 1, mRNA]," published Dec. 4, 2023, 4 pages (accessed and printed Jan. 9, 2024) available online at: https://www.ncbi.nlm.nih.gov/nuccore/NM_002500.

GenBank Accession No. AC010327.8, "*Homo sapiens* chromosome 19 clone CTD-2587H24, complete sequence," published Aug. 1, 2002, 32 pages (accessed and printed Jan. 12, 2024), available online: https://www.ncbi.nlm.nih.gov/nuccore/AC010327.8.

(56) References Cited

OTHER PUBLICATIONS

Jones et al., "Proneural transcription factors D1x2 and Pax6 are altered in adult SVZ neural precursor cells following striatal cell loss," *Molecular and Cellular Neuroscience*, 47(1), pp. 53-60, (May 2011), (electronic publication) available online: https://doi.org/10.1016/j.men.2011.03.001.

Lashof-Sullivan et al., "Intravenously administered nanoparticles increase survival following blast trauma," *PNAS*, 111(28), pp. 10293-10298, (Jun. 2014) (electronic publication), available online: https://doi.org/10.1073/pnas.1406979111.

Logsdon et al., "Blast exposure elicits blood-brain barrier disruption and repair mediated by tight junction integrity and nitric oxide dependent processes," *Sci Rep*, 8(11344), (Jul. 2018) (electronic publication), available online: https://doi.org/10.1038/s41598-018-29341-6.

PAAV-FLEX-GFP (Plasmid #28304) Addgene Blog, 5 pages (accessed and printed Jan. 9, 2024) (online publication) available at: https://www.addgene.org/28304/.

PAAV-CaMKII-GFP (Plasmid #64545) Addgene Blog, 4 pages (accessed and printed Jan. 9, 2024) (online publication) available at: https://www.addgene.org/64545/.

PAAV-GFAP-hChR2(H134R)-mCherry (Plasmid #27055) Addgene Blog, 5 pages (accessed and printed Jan. 12, 2024, available at: https://www.addgene.org/27055/.

Richetin, "Genetic manipulation of adult-born hippocampal neurons rescues memory in a mouse model of Alzheimer's disease," *Brain*, 138(2), pp. 440-455, (Feb. 2015), (electronic publication) available online: https://doi.org/10.1093/brain/awu354.

Rodriguez et al. "Astroglia in dementia and Alzheimer's disease." *Cell Death & Differentiation*, 16(3), pp. 378-385, (Dec. 2009) (electronic publication), available online: DOI: https://doi.org/10.1038/cdd.2008.172.

Search Report issued in Chinese Patent Application No. 202080030149.8, dated Dec. 26, 2023, 8 pages.

Shen et al., "The potential application of gene therapy in the treatment of traumatic brain injury, " *Neurosurg Rev*, 30, pp. 291-298 (Aug. 2007) (electronic publication) available online: https://doi.org/10.1007/s10143-007-0094-4.

Smithsonian, "Numbers of Insects (Species and Individuals)," last visited Jan. 4, 2024, available online: https://www.si.edu/spotlight/buginfo/bugnos; 9pages, accessed and printed Apr. 1, 2024.

Stanley et al., "Complementation between mutants of CHO cells resistant to a variety of plant lectins," *Somatic Cell Genet.* 3(4), pp. 391-405, (Jul. 1977) (electronic publication), available online: DOI: 10.1007/BF01542968.

Steele et al., "Reactive astrocytes give neurons less support: implications for Alzheimer's disease," *Neurobiology of Aging*, 33(2), pp. 423-e1-423.e13, (Feb. 2012) (online publication), available online: DOI: https://doi.org/10.1016/j.neurobiolaging.2010.09.018.

Sukumari-Ramesh, et al., "Astrocyte-Specific Expression of Survivin after Intracerebral Hemorrhage in Mice: A Possible Role in Reactive Gliosis?" *Journal of Neurotrauma*, 29(18), pp. 2798-2804, (Dec. 2012), (electronic publication), available online: https://doi.org/10.1089/neu.2011.2243.

Ting et al. "Acute Brain Slice Methods for Adult and Aging Animals: Application of Targeted Patch Clamp Analysis and Optogenetics," *Methods in Molecular Biology*, 1183, pp. 221-242, (Jan. 2014) (electronic publication), available online: DOI: 10.1007/978-1-4939-1096-0 14.

Weston, "The Potential of Stem Cells in Treatment of Traumatic Brain Injury," *Current Neurology and Neuroscience Reports*, 18(1), pp. 1-10, (Jan. 2018), (electronic publication) available online: https://doi.org/10.1007/s11910-018-0812-z.

Wikipedia, "Mammal," accessed and printed Aug. 31, 2022, available online: en. wikipedia.org/wiki/Mammal, 49 pages.

Wikipedia, "Vertebrate," accessed and printed Jan. 4, 2024, available online: en. wikipedia.org/wiki/Vertebrates, 23 pages.

Windle et al., "An analysis of four different methods of producing focal cerebral ischemia with endothelin-1 in the rat," *Experimental Neurology*, 201(2), pp. 324-334, (Oct. 2006) (electronic publication), available online: https://doi.org/10.1016/j.expneurol.2006.04.012.

Wright et al., "ProTECT: A Randomized Clinical Trial of Progesterone for Acute Traumatic Brain Injury—Neurology/Original Research," *Annals of Emergency Medicine*, 49(4), pp. 391-402, (Apr. 2007) (electronic publication), available online, DOI: 10.1016/j.annemergmed.2006.07.932.

Wu et al., "γ-Aminobutyric Acid Type A (GABAA) Receptor α Subunits Play a Direct Role in Synaptic Versus Extrasynaptic Targeting," *The Journal of Biological Chemistry*, 287(33), pp. 27417-27430, (Aug. 2012) (electronic publication), available online: DOI: https://doi.org/10.1074/jbc.M112.360461.

You et al., "Necrostatin-1 reduces histopathology and improves functional outcome after controlled cortical impact in mice," *Journal of Cerebral Blood Flow & Metabolism*, 28, pp. 1564-1573, (May 2008) (electronic publication), available online: 10.1038/jcbfm.2008.44.

Yoshimura et al., FGF-2 regulates neurogenesis and degeneration in the dentate gyrus after traumatic brain injury in mice, *J Clin Invest.*, 112(8), pp. 1202-1210, (Oct. 2003) (electronic publication), available online: https://doi.org/10.1172/JCI16618.

Zhuo et al., "In vivo reprogramming of adult pancreatic exocrine cells to β-cells," *Nature*, 455(7213), pp. 627-632, (Oct. 2008) (available online), available online: DOI: 10.1038/nature07314.

International Search Report and Written Opinion, in International Application No. PCT/US/2020/056108, dated Feb. 12, 2021, 9 pages.

Altamirano et al., 2019, "Signaling within the pineal gland: A parallelism with the central nervous system," Seminars in Cell and Development Biology, 95:151-159.

Funato, T., "Gene Delivery using adeno-associated (AAV) vectors," Nippon-rinsho, 56(3):149-152, English Abstract 1998.

GenBank Accession No. LT738798.1, "Human ORFeome Gateway entry vector pENTR223-NEUROD1, complete sequence," Feb. 15, 2017.

GenBank Accession No. HQ258018.1, "Synthetic construct *Homo sapiens* clone Image: 100072327 distal-less homeobox 2 (DLX2) gene, encodes complete protein," Jul. 25, 2016.

Lee et al., 2008, "GFAP promoter elements required for region-specific and astrocyte-specific expression," Glia, vol. 56.

PUltra vector sequence (T2A sequence), 2014.

PGfa ABCID-nLac vector sequence (truncated hGFAp promoter), 2008.

PRc/CMV2 vector sequence (CMV enhancer), 2006.

PCI-Neo vector sequence (chimeric intron), 2008.

PcDNA3.1 vector sequence (bGH poly A), 2008.

Sun et al., 2016, "Direct Induction and Functional Maturation of Forebrain GABAergic Neurons from Human Pluripotent Stem Cells," Cell Reports, 16:1942-1953.

Wang et al., 2006, "Astrocytic expression of transgene in the rat brain mediated by baculovirus vectors containing an astrocyte-specific promoter," Gene Therapy, 13:1447-1456.

Wu et al., 2008, "Optimization of Self-complementary AAV Vectors for Liver-directed Expression Results in Sustained Correction of Hemophilia B at Low Vector Dose," MolTherpay, 16(2):280-289.

* cited by examiner

NXL-P35

NXL-P11

NXL-P39

NXL-P38

GFAP                                    SOX9

DAPI                            GFAP/SOX9/DAPI
                                    (Merged)

AAV9-P12, 3 x 10$^{10}$ vg/well

AAV9-P12, 1 x 10$^{10}$ vg/well

AAV9-P12, 2.5 x 10$^9$ vg/well

GFP NeuN/MAP2

DAPI GFP/NeuN/MAP2/DAPI
(Merged)

ND1                                              DAPI

ND1/DAPI
(Merged)

ND1                                                DAPI

ND1/DAPI
(Merged)

NeuN/MAP2                                          DAPI

NeuN/MAP2/DAPI
(Merged)

ND1                      DAPI

ND1/DAPI
(Merged)

ND1                                                      DAPI

ND1/DAPI
(Merged)

NeuN/MAP2                                    DAPI

NeuN/MAP2/DAPI
(Merged)

ND1                              GFP

DAPI              ND1/DAPI/GFP (Merged)

NeuN/MAP2

DAPI

NeuN/MAP2/DAPI
(Merged)

ND1                                        DAPI

ND1/ DAPI
(Merged)

ND1                                DAPI

ND1/ DAPI
(Merged)

NeuN/MAP2

DAPI

NeuN/MAP2/DAPI
(Merged)

ND1                                              DAPI

ND1/DAPI
(Merged)

ND1                   DAPI

ND1/ DAPI
(Merged)

ND1                                    DAPI

ND1/ DAPI
(Merged)

ND1                                    DAPI

ND1/ DAPI
(Merged)

ND1                                    DAPI

ND1/ DAPI
(Merged)

ND1                                            DAPI

ND1/ DAPI
(Merged)

*10 days post infection*

P12 Control Group

Cortex

P134 Group
High conversion

P138 Group
Low conversion

*30 days post infection*

P134 Group
High conversion

P138 Group
Low conversion

P12 Control Group

*10 days post infection*

P134 Group

SEQUENCE LISTING

```
<160> NUMBER OF SEQ ID NOS: 21

<210> SEQ ID NO 1
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tgcaggcagc tgcgcgctcg ctcgctcact gaggccgccc gggcgtcggg cgacctttgg      60
tcgcccggcc tcagtgagcg agcgagcgcg cagagaggga gtggccaact ccatcactag     120
gggttcct                                                              128

<210> SEQ ID NO 2
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
tgcaaagatg gataaagttt taaacagaga ggaatctttg cagctaatgg accttctagg      60
tcttgaaagg agtgggaatt ggctccggtg cccgtcagtg ggcagagcgc acatcgccca     120
```

-continued

```
cagtccccga gaagttgggg ggaggggtcg gca                          153

<210> SEQ ID NO 3
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaagcggag ctactaactt cagcctgctg aagcaggctg agacgtgga ggagaaccct     60 ggacct                                                            66

<210> SEQ ID NO 4
<211> LENGTH: 1667
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ctgcaagcag acctggcagc attgggctgg ccgcccccca gggcctcctc ttcatgccca     60
gtgaatgact caccttggca cagacacaat gttcggggtg ggcacagtgc ctgcttcccg    120
ccgcacccca gcccccctca aatgccttcc gagaagccca ttgagtaggg ggcttgcatt    180 gcacccagc ctgacagcct ggcatcttgg gataaaagca gcacagcccc ctaggggctg     240
cccttgctgt gtggcgccac cggcggtgga gaacaaggct ctattcagcc tgtgcccagg    300
aaaggggatc aggggatgcc caggcatgga cagtgggtgg cagggggga gaggagggct     360 gtctgcttcc cagaagtcca aggacacaaa tgggtgaggg gactgggcag ggttctgacc    420
ctgtgggacc agagtggagg gcgtagatgg acctgaagtc tccagggaca acagggccca    480
ggtctcaggc tcctagttgg gcccagtggc tccagcgttt ccaaacccat ccatccccag    540
aggttcttcc catctctcca ggctgatgtg tgggaactcg aggaaataaa tctccagtgg    600
gagacggagg ggtggccagg gaaacggggc gctgcaggaa taaagacgag ccagcacagc    660
cagctcatgc gtaacggctt tgtggagctg tcaaggcctg gtctctggga gagaggcaca    720
gggaggccag acaaggaagg ggtgacctgg agggacagat ccaggggcta aagtcctgat    780
aaggcaagag agtgccggcc ccctcttgcc ctatcaggac ctccactgcc acatagaggc    840
catgattgac ccttagacaa agggctggtg tccaatccca gccccagcc ccagaactcc     900 agggaatgaa tgggcagaga gcaggaatgt gggacatctg tgttcaaggg aaggactcca    960
ggagtctgct gggaatgagg cctagtagga aatgaggtgg cccttgaggg tacagaacag   1020
gttcattctt cgccaaattc ccagcacctt gcaggcactt acagctgagt gagataatgc   1080
ctgggttatg aaatcaaaaa gttggaaagc aggtcagagg tcatctggta cagcccttcc   1140
ttcccttttt ttttttttt ttttgtgaga caaggtctct ctctgttgcc caggctggag   1200
tggcgcaaac acagctcact gcagcctcaa cctactgggc tcaagcaatc ctccagcctc   1260
agcctcccaa agtgctggga ttacaagcat gagccacccc actcagccct ttccttcctt   1320
tttaattgat gcataataat tgtaagtatt catcatggtc caaccaaccc tttcttgacc   1380
caccttccta gagagagggt cctcttgatt cagcggtcag ggccccagac ccatggtctg   1440
gctccaggta ccacctgcct catgcaggag ttggcgtgcc caggaagctc tgcctctggg   1500
cacagtgacc tcagtggggt gaggggagct ctccccatag ctgggctgcg gcccaacccc   1560
```

-continued

```
acccccctcag gctatgccag ggggtgttgc caggggcacc cgggcatcgc cagtctagcc      1620
cactccttca taaagccctc gcatcccagg agcgagcaga gccagag                     1667

<210> SEQ ID NO 5
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gtaagtatca aggttacaag acaggtttaa ggagaccaat agaaactggg cttgtcgaga        60
cagagaagac tcttgcgttt ctgataggca cctattggtc ttactgacat ccactttgcc       120
tttctctcca cag                                                         133

<210> SEQ ID NO 6
<211> LENGTH: 1068
<212> TYPE: DNA
<213> ORGANISM: Homo sapiens

<400> SEQUENCE: 6
atgaccaaat cgtacagcga gagtgggctg atgggcgagc ctcagcccca aggtcctcca        60
agctggacag acgagtgtct cagttctcag gacgaggagc acgaggcaga caagaaggag       120
gacgacctcg aagccatgaa cgcagaggag gactcactga ggaacggggg agaggaggag       180
gacgaagatg aggacctgga agaggaggaa gaagaggaag aggaggatga cgatcaaaag       240
cccaagagac gcggccccaa aaagaagaag atgactaagg ctcgcctgga gcgttttaaa       300
ttgagacgca tgaaggctaa cgcccgggag cggaaccgca tgcacggact gaacgcggcg       360
ctagacaacc tgcgcaaggt ggtgccttgc tattctaaga cgcagaagct gtccaaaatc       420
gagactctgc gcttggccaa gaactacatc tgggctctgt cggagatcct gcgctcaggc       480
aaaagcccag acctggtctc cttcgttcag acgctttgca agggcttatc ccaacccacc       540
accaacctgg ttgcgggctg cctgcaactc aatcctcgga cttttctgcc tgagcagaac       600
caggacatgc cccccacct gccgacggcc agcgcttcct tccctgtaca cccctactcc       660
taccagtcgc ctgggctgcc cagtccgcct tacggtacca tggacagctc ccatgtcttc       720
cacgttaagc ctccgccgca cgcctacagc gcagcgctgg agcccttctt tgaaagccct       780
ctgactgatt gcaccagccc ttcctttgat ggacccctca gcccgccgct cagcatcaat       840
ggcaacttct ctttcaaaca cgaaccgtcc gccgagtttg agaaaaatta tgcctttacc       900
atgcactatc ctgcagcgac actggcaggg gcccaaagcc acggatcaat cttctcaggc       960
accgctgccc ctcgctgcga gatccccata gacaatatta tgtccttcga tagccattca      1020
catcatgagc gagtcatgag tgcccagctc aatgccatat ttcatgat                   1068

<210> SEQ ID NO 7
<211> LENGTH: 589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
aatcaacctc tggattacaa aatttgtgaa agattgactg gtattcttaa ctatgttgct        60
```

-continued

```
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact      240 ggttggggca ttgccaccac ctgtcagctc ctttccggga ctttcgcttt ccccctccct     300
attgccacgg cggaactcat cgccgcctgc cttgcccgct gctggacagg ggctcggctg     360
ttgggcactg acaattccgt ggtgttgtcg gggaaatcat cgtcctttcc ttggctgctc     420
gcctgtgttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgc                589
```

```
<210> SEQ ID NO 8
<211> LENGTH: 251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cgatccaccg gatctagata actgatcata atcagccata ccacatttgt agaggtttta      60
cttgctttaa aaaacctccc acacctcccc ctgaacctga aacataaaat gaatgcaatt     120
gttgttgtta acttgtttat tgcagcttat aatggttaca aataaagcaa tagcatcaca     180
aatttcacaa ataaagcatt tttttcactg cattctagtt gtggtttgtc caaactcatc     240
aatgtatctt a                                                         251
```

```
<210> SEQ ID NO 9
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag ctgcctgca                                                  139
```

```
<210> SEQ ID NO 10
<211> LENGTH: 356
<212> TYPE: PRT
<213> ORGANISM: Homo sapiens

<400> SEQUENCE: 10

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
                20                  25                  30

Glu His Glu Ala Asp Lys Lys Glu Asp Asp Leu Glu Ala Met Asn Ala
            35                  40                  45

Glu Glu Asp Ser Leu Arg Asn Gly Gly Glu Glu Glu Asp Glu Asp Glu
        50                  55                  60

Asp Leu Glu Glu Glu Glu Glu Glu Glu Glu Glu Asp Asp Asp Gln Lys
65                  70                  75                  80
```

-continued

```
Pro Lys Arg Arg Gly Pro Lys Lys Lys Met Thr Lys Ala Arg Leu
             85              90              95

Glu Arg Phe Lys Leu Arg Arg Met Lys Ala Asn Ala Arg Glu Arg Asn
            100             105             110

Arg Met His Gly Leu Asn Ala Ala Leu Asp Asn Leu Arg Lys Val Val
            115             120             125

Pro Cys Tyr Ser Lys Thr Gln Lys Leu Ser Lys Ile Glu Thr Leu Arg
    130             135             140

Leu Ala Lys Asn Tyr Ile Trp Ala Leu Ser Glu Ile Leu Arg Ser Gly
145             150             155             160

Lys Ser Pro Asp Leu Val Ser Phe Val Gln Thr Leu Cys Lys Gly Leu
            165             170             175

Ser Gln Pro Thr Thr Asn Leu Val Ala Gly Cys Leu Gln Leu Asn Pro
            180             185             190

Arg Thr Phe Leu Pro Glu Gln Asn Gln Asp Met Pro Pro His Leu Pro
            195             200             205

Thr Ala Ser Ala Ser Phe Pro Val His Pro Tyr Ser Tyr Gln Ser Pro
    210             215             220

Gly Leu Pro Ser Pro Pro Tyr Gly Thr Met Asp Ser Ser His Val Phe
225             230             235             240

His Val Lys Pro Pro Pro His Ala Tyr Ser Ala Ala Leu Glu Pro Phe
            245             250             255

Phe Glu Ser Pro Leu Thr Asp Cys Thr Ser Pro Ser Phe Asp Gly Pro
            260             265             270

Leu Ser Pro Pro Leu Ser Ile Asn Gly Asn Phe Ser Phe Lys His Glu
            275             280             285

Pro Ser Ala Glu Phe Glu Lys Asn Tyr Ala Phe Thr Met His Tyr Pro
    290             295             300

Ala Ala Thr Leu Ala Gly Ala Gln Ser His Gly Ser Ile Phe Ser Gly
305             310             315             320

Thr Ala Ala Pro Arg Cys Glu Ile Pro Ile Asp Asn Ile Met Ser Phe
            325             330             335

Asp Ser His Ser His His Glu Arg Val Met Ser Ala Gln Leu Asn Ala
            340             345             350

Ile Phe His Asp
            355

<210> SEQ ID NO 11
<211> LENGTH: 380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gacattgatt attgactagt tattaatagt aatcaattac ggggtcatta gttcatagcc       60
catatatgga gttccgcgtt acataactta cggtaaatgg cccgcctggc tgaccgccca      120
acgacccccg cccattgacg tcaataatga cgtatgttcc catagtaacg ccaatatggga      180 ctttccattg acgtcaatgg gtggactatt tacggtaaac tgcccacttg gcagtacatc      240
aagtgtatca tatgccaagt acgccccta ttgacgtcaa tgacggtaaa tggcccgcct      300
ggcattatgc ccagtacatg accttatggg actttcctac ttggcagtac atctacgtat      360
tagtcatcgc tattaccatg                                                  380
```

```
<210> SEQ ID NO 12
<211> LENGTH: 2214
<212> TYPE: DNA
<213> ORGANISM: Homo sapiens

<400> SEQUENCE: 12
cgcgtcccac ctccctctct gtgctgggac tcacagaggg agacctcagg aggcagtctg        60
tccatcacat gtccaaatgc agagcatacc ctgggctggg cgcagtggcg cacaactgta       120
attccagcac tttgggaggc tgatgtggaa ggatcacttg agcccagaag ttctagacca       180
gcctgggcaa catggcaaga ccctatctct acaaaaaaag ttaaaaaatc agccacgtgt       240
ggtgacacac acctgtagtc ccagctattc aggaggctga ggtgagggga tcacttaagg       300
ctgggaggtt gaggctgcag tgagtcgtgg ttgcgccact gcactccagc ctgggcaaca       360
gtgagaccct gtctcaaaag acaaaaaaaa aaaaaaaaa aaaagaaca tatcctggtg       420 tggagtaggg gacgctgctc tgacagaggc tcgggggcct gagctggctc tgtgagctgg       480
ggaggaggca gacagccagg ccttgtctgc aagcagacct ggcagcattg ggctggccgc       540
cccccagggc ctcctcttca tgcccagtga atgactcacc ttggcacaga cacaatgttc       600
ggggtgggca cagtgcctgc ttcccgccgc accccagccc ccctcaaatg ccttccgaga       660
agcccattga gcaggggct tgcattgcac cccagcctga cagcctggca tcttgggata       720
aaagcagcac agcccctag gggctgccct tgctgtgtgg cgccaccggc ggtggagaac       780
aaggctctat tcagcctgtg cccaggaaag gggatcaggg gatgcccagg catggacagt       840
gggtggcagg ggggagagg agggctgtct gcttcccaga agtccaagga cacaaatggg       900
tgaggggact gggcagggtt ctgaccctgt gggaccagag tggagggcgt agatggacct       960
gaagtctcca gggacaacag ggcccaggtc tcaggctcct agttgggccc agtggctcca      1020
gcgtttccaa acccatccat ccccagaggt tcttcccatc tctccaggct gatgtgtggg      1080
aactcgagga aataaatctc cagtgggaga cggaggggtg gccagggaaa cggggcgctg      1140
caggaataaa gacgagccag cacagccagc tcatgtgtaa cggctttgtg gagctgtcaa      1200
ggcctggtct ctgggagaga ggcacaggga ggccagacaa ggaaggggtg acctggaggg      1260
acagatccag gggctaaagt cctgataagg caagagagtg ccggcccct cttgccctat      1320 caggacctcc actgccacat agaggccatg attgaccctt agacaaaggg ctggtgtcca      1380
atcccagccc ccagccccag aactccaggg aatgaatggg cagagagcag gaatgtggga      1440
catctgtgtt caagggaagg actccaggag tctgctggga atgaggccta gtaggaaatg      1500
aggtggccct tgagggtaca gaacaggttc attcttcgcc aaattcccag caccttgcag      1560
gcacttacag ctgagtgaga taatgcctgg gttatgaaat caaaaagttg gaaagcaggt      1620
cagaggtcat ctggtacagc ccttccttcc ctttttttt ttttttttt gtgagacaag      1680 gtctctctct gttgcccagg ctggagtggc gcaaacacag ctcactgcag cctcaaccta      1740
ctgggctcaa gcaatcctcc agcctcagcc tcccaaagtg ctgggattac aagcatgagc      1800 cacccactc agcccttttcc ttcctttta attgatgcat aataattgta agtattcatc      1860
atggtccaac caacccttc ttgacccacc ttcctagaga gagggtcctc ttgcttcagc      1920
ggtcagggcc ccagacccat ggtctggctc caggtaccac ctgcctcatg caggagttgg      1980
cgtgcccagg aagctctgcc tctgggcaca gtgacctcag tggggtgagg ggagctctcc      2040
ccatagctgg gctgcggccc aaccccaccc cctcaggcta tgccagggg tgttgccagg      2100 ggcacccggg catcgccagt ctagcccact ccttcataaa gccctcgcat cccaggagcg      2160
```

-continued

```
agcagagcca gagcaggttg gagaggagac gcatcacctc cgctgctcgc cggg          2214

<210> SEQ ID NO 13
<211> LENGTH: 477
<212> TYPE: DNA
<213> ORGANISM: Homo sapiens

<400> SEQUENCE: 13
gggtggcatc cctgtgaccc ctccccagtg cctctcctgg ccctggaagt tgccactcca      60
gtgcccacca gccttgtcct aataaaatta agttgcatca ttttgtctga ctaggtgtcc     120
ttctataata ttatggggtg gaggggggtg gtatggagca aggggcaagt tgggaagaca     180
acctgtaggg cctgcggggt ctattgggaa ccaagctgga gtgcagtggc acaatcttgg     240
ctcactgcaa tctccgcctc ctgggttcaa gcgattctcc tgcctcagcc tcccgagttg     300
ttgggattcc aggcatgcat gaccaggctc agctaatttt tgtttttttg gtagagacgg     360
ggtttcacca tattggccag gctggtctcc aactcctaat ctcaggtgat ctacccacct     420
tggcctccca aattgctggg attacaggcg tgaaccactg ctcccttccc tgtcctt        477

<210> SEQ ID NO 14
<211> LENGTH: 208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
ctgtgccttc tagttgccag ccatctgttg tttgcccctc ccccgtgcct tccttgaccc      60
tggaaggtgc cactcccact gtcctttcct aataaaatga ggaaattgca tcgcattgtc     120
tgagtaggtg tcattctatt ctggggggtg gggtggggca ggacagcaag ggggaggatt     180
gggaagagaa tagcaggcat gctgggga                                         208

<210> SEQ ID NO 15
<211> LENGTH: 681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
aacatatcct ggtgtggagt aggggacgct gctctgacag aggctcgggg gcctgagctg      60
gctctgtgag ctggggagga ggcagacagc caggccttgt ctgcaagcag acctggcagc     120
attgggctgg ccgccccccca gggcctcctc ttcatgccca gtgaatgact caccttggca     180
cagacacaat gttcggggtg ggcacagtgc ctgcttcccg ccgcacccca gcccccctca     240
aatgccttcc gagaagccca ttgagcaggg ggcttgcatt gcaccccagc ctgacagcct     300
ggcatcttgg gataaaagca gcacagcccc ctaggggctg cccttgctgt gtggcgccac     360
cggcggtgga gaacaaggct ctattcagcc tgtgcccagg aaaggggatc aggggatgcc     420
caggcatgga cagtgggtgg caggggggga gaggagggct gtctgcttcc cagaagtcca     480
aggacacaaa tgggtgaggg gagagctctc cccatagctg ggctgcggcc caaccccacc     540
ccctcaggct atgccagggg gtgttgccag gggcacccgg gcatcgccag tctagcccac     600
tccttcataa agccctcgca tcccaggagc gagcagagcc agagcaggtt ggagaggaga     660
```

-continued

```
cgcatcacct ccgctgctcg c                                                 681

<210> SEQ ID NO 16
<211> LENGTH: 1062
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ggagtcgctg cgttgccttc gccccgtgcc ccgctccgcg ccgcctcgcg ccgcccgccc      60
cggctctgac tgaccgcgtt actcccacag gtgagcgggc gggacggccc ttctccctcc     120
gggctgtaat tagcgcttgg tttaatgacg gctcgtttct tttctgtggc tgcgtgaaag     180
ccttaaaggg ctccgggagg gcctttgtgc ggggggggagc ggctcggggg gtgcgtgcgt     240
gtgtgtgtgc gtggggagcg ccgcgtgcgg cccgcgctgc ccggcggctg tgagcgctgc     300
gggcgcggcg cggggctttg tgcgctccgc gtgtgcgcga ggggagcgcg ggccgggggc     360
ggtgccccgc ggtgcggggg ggctgcgagg ggaacaaagg ctgcgtgcgg ggtgtgtgcg     420 tggggggggtg agcagggggt gtgggcgcgg cggtcgggct gtaacccccc cctggcaccc     480
ccctccccga gttgctgagc acggcccggc ttcgggtgcg gggctccgtg cggggcgtgg     540 cgcgggggctc gccgtgccgg gcggggggtg gcggcaggtg ggggtgccgg gcggggcggg     600
gccgcctcgg gccgggggagg gctcgggggga ggggcgcggc ggccccggag cgccggcggc     660
tgtcgaggcg cggcgagccg cagccattgc cttttatggt aatcgtgcga gagggcgcag     720
ggacttcctt tgtcccaaat ctggcggagc cgaaatctgg gaggcgccgc cgcacccccct     780 ctagcgggcg cgggcgaagc ggtgcggcgc cggcaggaag gaaatgggcg gggagggcct     840
tcgtgcgtcg ccgcgccgcc gtccccttct ccatctccag cctcggggct gccgcagggg     900
gacggctgcc ttcggggggg acggggcagg gcggggttcg gcttctgcg tgtgaccggc     960 ggctttagag cctctgctaa ccatgttcat gccttcttct ttttcctaca gctcctgggc    1020
aacgtgctgg ttgttgtgct gtctcatcat tttggcaaag at                        1062

<210> SEQ ID NO 17
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
ggccactgtg aggcagaagt gaggaggggga tggggaaggg gggccttgtg agcagaaggg      60
gctgaatccc caagaaggag tgcccgagaa gtctcaggga ggggccgaac ctccctgctc     120
cctgggcctc cctacctctt gatggggcac tatccttgcc ccccaacatg atggggaggga    180 ccagaaacag gcccagggcc ccggggatct gatgcccgca tgccttctgc caggagtcca     240
gggtcccctc agcacctccc tactggggaa agcagtgcag gagcagcggg gcccctgtgt     300
ttcattcatg gctgggcttt gtgactgtgg gcagcgagct cacctattct gagcctgtgt     360
ccatataaag gaggagttgg aagcggagaa ggttgatgtc catgagggag attggattct     420
ggggtgaaga aagtgaggga aagagcaggc aggtctgggc gcaaagcaca ggtgactgcc     480
tgccaccagc ttgtgacccc catcaagtta ctttgacttg cacagctgtg aagcggtggt     540
cataataaaa ttcatttcaa aaggtggtta cctgggatca gaggaatccc caggggcatg     600
```

-continued

```
gcgcttcact gagctgacag gacatgcatg tgtgccttca agtgcaggag gacatgtgcg        660
tgtgtgtgtg tgtgtgtgca acagtgagtg tatgcttgtg gatgcgcctg tgtgagcaga        720
agcaggtgca ccaaccctga taaggcacct tagtaatgag ttaaggcaaa agcccacatc        780
tgctcatcct ccagacaagt cctctgtcta aggccccca accettaatc ctcctgctgc         840 tctactggtc ctgggtgggg gtggtctctg tgacagctgc ctcaagggag actgaggcag        900
gtattcaagt gtcctcagaa gagcctggac ccaggaatgt gtcccccac tccaggctcc         960 aggatgaaac caacctga                                                      978
```

```
<210> SEQ ID NO 18
<211> LENGTH: 581
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gagcatctta ccgccattta tacccatatt tgttctgttt ttcttgattt gggtatacat         60
ttaaatgtta ataaaacaaa atggtggggc aatcatttac atttttaggg atatgtaatt        120
actagttcag gtgtattgcc acaagacaaa catgttaaga aactttcccg ttatttacgc        180
tctgttcctg ttaatcaacc tctggattac aaaatttgtg aaagattgac tgatattctt        240
aactatgttg ctccttttac gctgtgtgga tatgctgctt tatagcctct gtatctagct        300
attgcttccc gtacggcttt cgtttctcc tccttgtata aatcctggtt gctgtctctt         360
ttagaggagt tgtggcccgt tgtccgtcaa cgtggcgtgg tgtgctctgt gtttgctgac        420
gcaaccccca ctggctgggg cattgccacc acctgtcaac tcctttctgg gactttcgct        480 ttcccctcc cgatcgccac ggcagaactc atcgccgcct gccttgcccg ctgctggaca         540
ggggctaggt tgctgggcac tgataattcc gtggtgttgt c                           581
```

```
<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19 ggaacccta gtgatggagt t                                                    21
```

```
<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cggcctcagt gagcga                                                         16
```

```
<210> SEQ ID NO 21
<211> LENGTH: 300
<212> TYPE: RNA
<213> ORGANISM: Artificial Sequence
<220> FEATURE:
<223> OTHER INFORMATION: Description of Artificial Sequence: Synthetic
```

-continued

```
        polynucleotide
<220> FEATURE:
<221> NAME/KEY: misc_feature
<222> LOCATION: (1)..(300)
<223> OTHER INFORMATION: This sequence may encompass 50-300 nucleotides
<220> FEATURE:
<223> OTHER INFORMATION: See specification as filed for detailed
        description of substitutions and preferred embodiments

<400> SEQUENCE: 21
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
```

NEUROD1 VECTOR

CROSS-REFERENCE TO RELATED APPLICATION

This application is a U.S. patent application which claims the benefit and priority to U.S. Provisional Application No. 63/084,908 filed Sep. 29, 2020, and 63/246,545 filed Sep. 21, 2021, each of which are incorporated by reference in their entireties herein.

INCORPORATION BY REFERENCE

A sequence listing contained in the file named P34822US02_SL.txt which is 21,632 bytes (measured in MS-Windows®) and created on Sep. 27, 2021, is filed electronically herewith and incorporated by reference in its entirety.

FIELD OF THE INVENTION

The present disclosure includes methods and compositions using an AAV vector comprising a nucleic acid sequence encoding human NeuroD1 to convert glial cells to neurons.

BACKGROUND OF THE INVENTION

Neurons are often killed or damaged and unable to regenerate in subjects with a neurological condition or following an injury to the central nervous system (CNS) or peripheral nervous system (PNS).

Glial cells become reactive following an injury to the CNS or PNS such as a brain injury or neurological condition.

Currently there are no methods available to regenerate functional new neurons in human subjects having a neurological condition using adeno-associated viruses (AAVs).

SUMMARY OF THE INVENTION

In one aspect, this disclosure provides, and includes, an adeno-associated virus (AAV) vector comprising a human neurogenic differentiation 1 (hNeuroD1) sequence comprising the nucleic acid sequence of SEQ ID NO: 6, where the hNeuroD1 sequence is operably linked to regulatory elements comprising: (a) a glial fibrillary acid protein (GFAP) promoter comprising a nucleic acid sequence selected from the group consisting of SEQ ID NOs: 4, 12, and 15; (b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence of SEQ ID NO: 5 or 16; (d) a woodchuck hepatitis virus posttranscriptional regulatory element (WPRE) comprising the nucleic acid sequence selected from the group consisting of SEQ ID NOs: 7 and 18; and (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

In one aspect, this disclosure provides, and includes, an adeno-associated virus (AAV) vector comprising a nucleic acid coding sequence encoding a human neurogenic differentiation 1 (hNeuroD1) protein comprising the amino acid sequence of SEQ ID NO: 10, where the coding sequence is operably linked to regulatory elements comprising: (a) a glial fibrillary acid protein (GFAP) promoter comprising a nucleic acid sequence selected from the group consisting of SEQ ID NOs: 4, 12, and 15; (b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence of SEQ ID NO: 5 or 16; (d) a woodchuck hepatitis virus posttranscriptional regulatory element (WPRE) comprising the nucleic acid sequence selected from the group consisting of SEQ ID NOs: 7 and 18; (e) and a SV40 polyadenylation signal sequence with a nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

In an aspect, this disclosure provides, and includes, an adeno-associated virus (AAV) vector comprising a neurogenic differentiation 1 (NeuroD1) nucleic acid coding sequence encoding a NeuroD1 protein, where the coding sequence is operably linked to regulatory elements comprising: (a) a glial fibrillary acid protein (GFAP) promoter; (b) an enhancer; (c) a chimeric intron; (d) a woodchuck hepatitis virus posttranscriptional regulatory element (WPRE); and (e) a polyadenylation signal sequence.

In an aspect, this disclosure provides, and includes, a composition comprising an adeno-associated virus (AAV) vector for converting glial cells to functional neurons in a human, where the AAV vector comprises a human neurogenic differentiation 1 (hNeuroD1) sequence having a nucleic acid sequence of SEQ ID NO: 6, and where the sequence is operably linked to regulatory elements comprising: (a) a human glial fibrillary acid protein (GFAP) promoter comprising a nucleic acid sequence selected from the group consisting of SEQ ID NOs: 4, 12, and 15; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic sequence of SEQ ID NO: 5 or 16; (d) a woodchuck hepatitis virus posttranscriptional regulatory element (WPRE) comprising the nucleic acid sequence selected from the group consisting of SEQ ID NOs: 7 and 18; and (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

In an aspect, this disclosure provides, and includes, a composition comprising an adeno-associated-virus (AAV) vector for converting glial cells to functional neurons in a human, where the AAV vector comprises a nucleic acid coding sequence encoding a human neurogenic differentiation 1 (hNeuroD1) protein comprising the amino acid sequence of SEQ ID NO: 10, and where the coding sequence is operably linked to regulatory elements comprising: (a) a human glial fibrillary acid protein (GFAP) promoter comprising a nucleic acid sequence selected from the group consisting of SEQ ID NOs: 4, 12, and 15; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence of SEQ ID NO: 5 or 16; (d) a woodchuck hepatitis virus posttranscriptional regulatory element (WPRE) comprising the nucleic acid sequence selected from the group consisting of SEQ ID NOs: 7 and 18; and (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

In an aspect, this disclosure provides, and includes, a composition comprising an adeno-associated virus (AAV) vector for the treatment of a subject in need thereof, where the AAV vector comprises a neurogenic differentiation 1 (NeuroD1) sequence operably linked to expression control elements comprising: (a) a glial fibrillary acid protein (GFAP) promoter; (b) an enhancer; (c) a chimeric intron; (d) a woodchuck hepatitis virus posttranscriptional regulatory element (WPRE); and (e) a polyadenylation signal.

In an aspect, this disclosure provides, and includes, a method of converting reactive astrocytes to functional neurons in a brain a living human comprising: injecting an adeno-associated virus (AAV) into a subject in need thereof, where the AAV comprises a DNA vector construct comprising a human neurogenic differentiation 1 (hNeuroD1) sequence comprising the nucleic acid sequence of SEQ ID NO: 6, where the sequence is operably linked to regulatory elements comprising: (a) a human glial fibrillary acid protein (GFAP) promoter comprising a nucleic acid sequence selected from the group consisting of SEQ ID NOs: 4, 12, and 15; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence of SEQ ID NO: 5 or 16; (d) a woodchuck hepatitis virus posttranscriptional regulatory element (WPRE) comprising the nucleic acid sequence selected from the group consisting of SEQ ID NO: 7 and 18; and (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

In an aspect, this disclosure provides, and includes, a method of converting reactive astrocytes to functional neurons in the brain of a living human brain comprising: injecting an adeno-associated virus (AAV) into a subject in need thereof, where the AAV comprises a DNA vector construct comprising a nucleic acid coding sequence encoding a human neurogenic differentiation 1 (hNeuroD1) protein comprising the amino acid sequence of SEQ ID NO: 10, where the coding sequence is operably linked to expression control elements comprising: (a) a human glial fibrillary acid protein (GFAP) promoter comprising a nucleic acid sequence selected from the group consisting of SEQ ID NOs: 4, 12, and 15; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence of SEQ ID NO: 5 or 16; (d) a woodchuck hepatitis virus posttranscriptional regulatory element (WPRE) comprising the nucleic acid sequence selected from the group consisting of SEQ ID NOs: 7 and 18; and (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

In an aspect, this disclosure provides, and includes, a method of converting glial cells to neurons in a subject in need thereof comprising: delivering an adeno-associated virus (AAV) to the subject in need thereof, where the AAV comprises a DNA vector construct comprising a neurogenic differentiation 1 (NeuroD1) sequence operably linked to expression control elements comprising: (a) a glial fibrillary acid protein (GFAP) promoter; (b) an enhancer; (c) a chimeric intron; (d) a woodchuck hepatitis virus posttranscriptional regulatory element (WPRE); and (e) and a polyadenylation signal sequence, where the vector is capable of converting at least one glial cell to a neuron in the subject in need thereof.

In an aspect, this disclosure provides, and includes, a method of treating a neurological condition in a subject in need thereof comprising: delivering an adeno-associated virus (AAV) to the subject, where the AAV comprises a DNA vector construct comprising a neurogenic differentiation 1 (NeuroD1) sequence operably linked to expression control elements comprising: (a) a glial fibrillary acid protein (GFAP) promoter; (b) an enhancer; (c) a chimeric intron; (d) a woodchuck hepatitis virus posttranscriptional regulatory element (WPRE); and (e) a polyadenylation signal to the subject in need thereof.

In one aspect, this disclosure provides, and includes, an adeno-associated virus (AAV) vector comprising a human neurogenic differentiation 1 (hNeuroD1) sequence comprising the nucleic acid sequence of SEQ ID NO: 6, where the hNeuroD1 sequence is operably linked to regulatory elements comprising: (a) a glial fibrillary acidic protein (GFAP) promoter comprising the nucleic acid sequence of SEQ ID NO: 15; (b) an enhancer from a human elongation factor-1 alpha (EF1-α) promoter comprising the nucleic acid sequence of SEQ ID NO: 2; (c) a chimeric intron comprising the nucleic acid sequence of SEQ ID NO: 16; (d) a woodchuck hepatitis virus posttranscriptional regulatory element (WPRE) comprising the nucleic acid sequence of SEQ ID NO: 18; and (e) a bGH polyadenylation sequence comprising the nucleic acid sequence of SEQ ID NO: 14.

In one aspect, this disclosure provides, and includes, an adeno-associated virus (AAV) vector comprising a human neurogenic differentiation 1 (hNeuroD1) sequence comprising the nucleic acid sequence of SEQ ID NO: 6, where the hNeuroD1 sequence is operably linked to regulatory elements comprising: (a) a glial fibrillary acidic protein (GFAP) promoter comprising the nucleic acid sequence of SEQ ID NO: 15; (b) a cytomegalovirus (CMV) enhancer comprising the nucleic acid sequence of SEQ ID NO: 11; (c) a chimeric intron comprising the nucleic acid sequence of SEQ ID NO: 16; (d) a woodchuck hepatitis virus posttranscriptional regulatory element (WPRE) comprising the nucleic acid sequence of SEQ ID NO: 18; and (e) a bGH polyadenylation sequence comprising the nucleic acid sequence of SEQ ID NO: 14.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9A presents the percentage transduction rate of AAV9-P12 (pGfaABC1D:GFP) and AAV5-P7 (pEF-1α:GFP) at MOI of 5×10⁵ vg/cell, 2×10⁵ vg/cell, and 5×10⁴ vg/cell. FIG. 9B presents the percentage transduction rate of AAV9-P12 (pGfaABC1D:GFP) in cells seeded at a series of densities of 2×10⁴ cell/well, 1.5×10⁴ cell/well, 1×10⁴ cell/well, and 5×10³ cell/well and infected with virus at a series of amounts of 2 μl, 1 μl, 0.5 μl, 0.25 μl, 0.125 μl of 1×10¹³ vg/ml virus in 100 μl of medium.

(right panel), AAV9-P9 (CE:GfaABC1D:NeuroD1:GFP) (middle panel), or AAV9-P11 (CE:GfaABC1D:NeuroD1: WPRE:SV40) (left panel).

Figure 11:
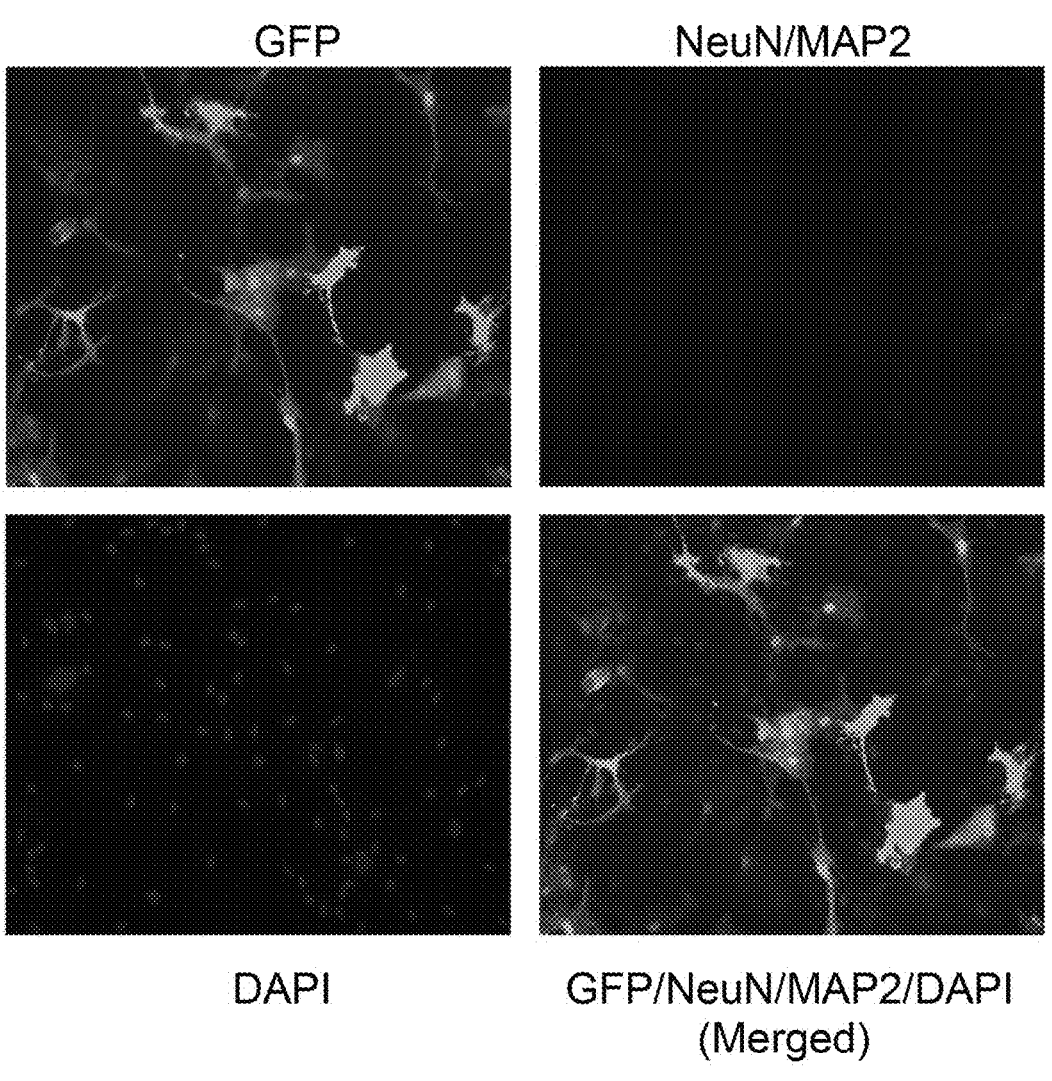

FIG. 11 depicts RCAs three weeks post transduction with control plasmid AAV9-P21 (CE-pGFA681-CI-GFP-WPRE-SV40pA) at 2×10¹⁰ vg/ml. Cells are immunostained with antibodies against neuronal markers NeuN and MAP2, and with DAPI (nuclear stain). GFP fluorescence indicates the presence of cells transduced with the control plasmid.

Figure 12:
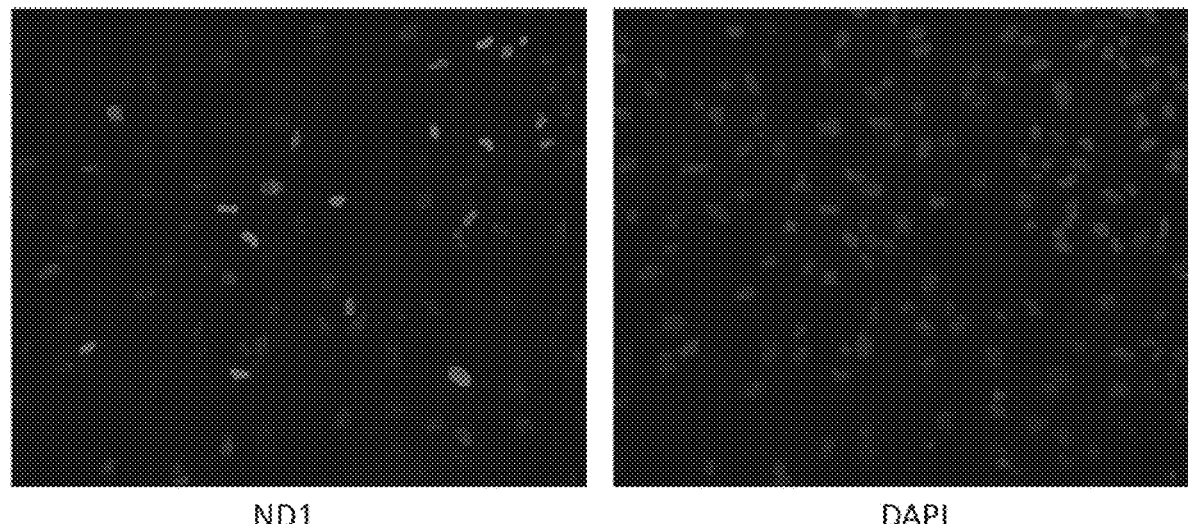
Figure 12:
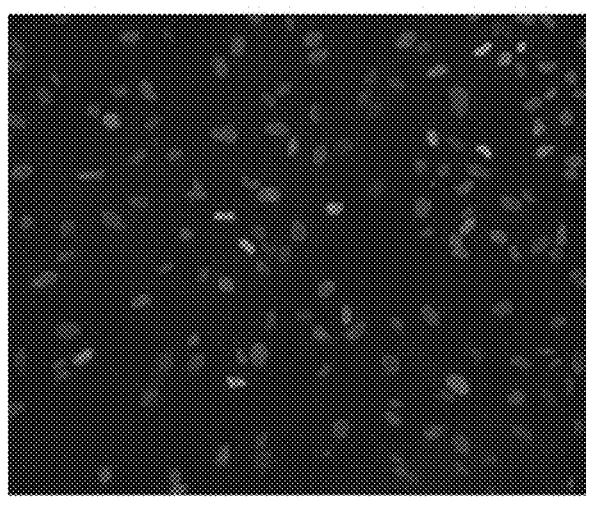

FIG. 12 depicts RCAs immunostained with an anti-NeuroD1(ND1) antibody and DAPI (nuclear stain) 24 hours post transfection with NXL-P134 (CE-pGfa681-CRGI-hND1-oPRE-bGHpA).

Figure 13:
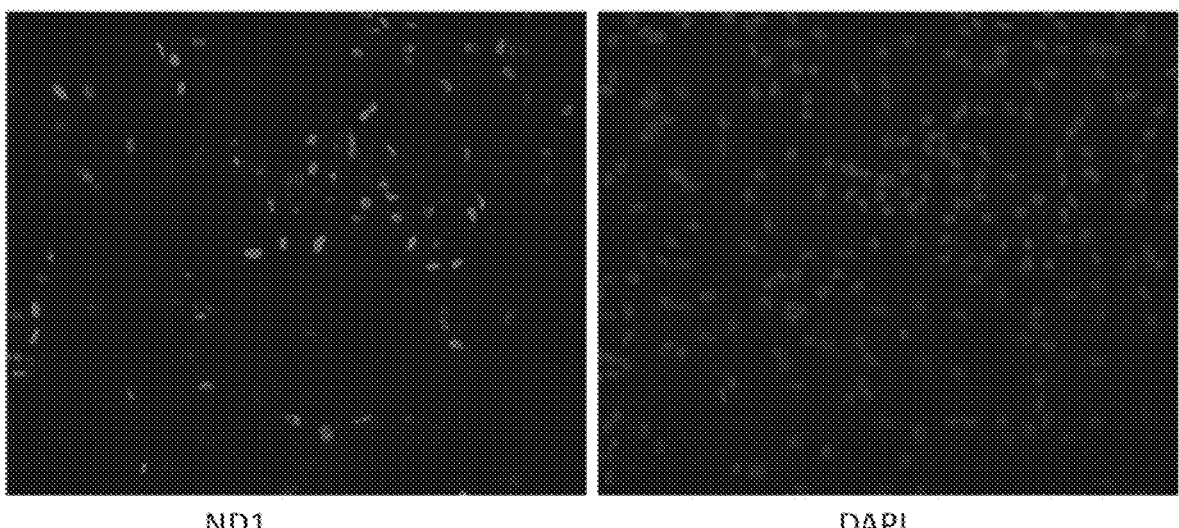
Figure 13:
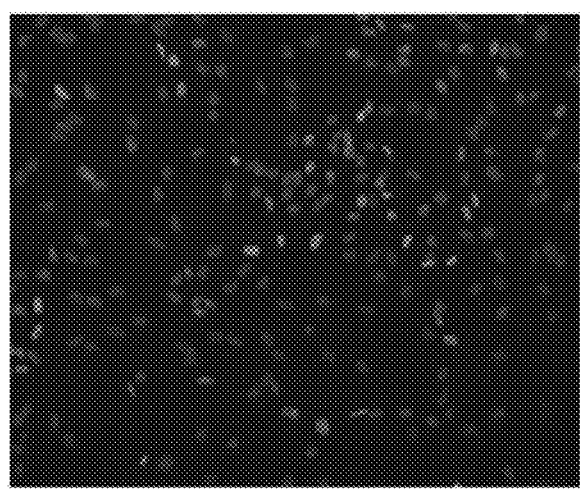

FIG. 13 depicts RCAs immunostained with an anti-ND1 antibody and DAPI (nuclear stain) 6 days post transduction with AAV9-P134 (CE-pGfa681-CRGI-hND1-oPRE-bGHpA) at 2×10¹⁰ vg/ml.

Figure 14:
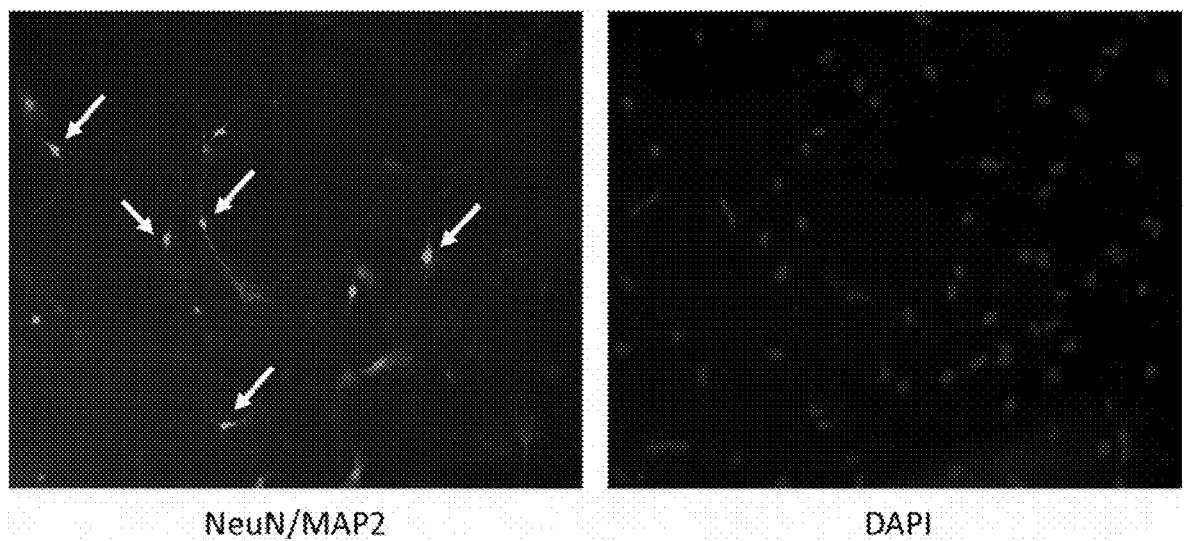
Figure 14:
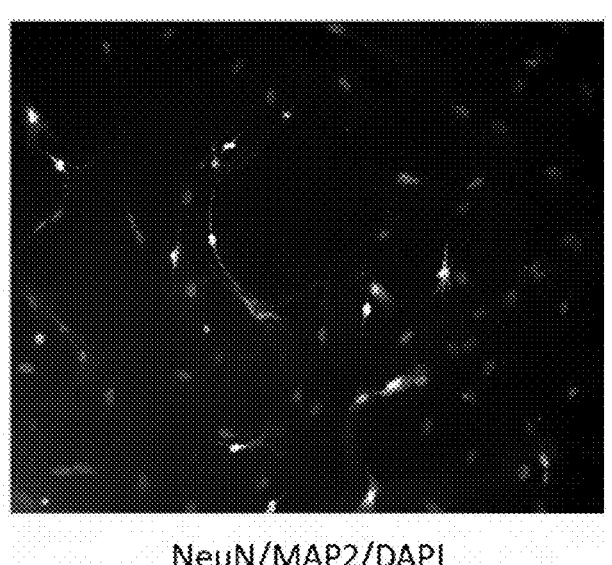

FIG. 14 depicts RCAs immunostained with anti-NeuN and anti-MAP2 antibodies and DAPI (nuclear stain) 3 weeks post transduction with AAV9-P134 (CE-pGfa681-CRGI-hND1-oPRE-bGHpA) at 2×10¹⁰ vg/ml. Transduction with the ND1-containing vector generates neurons (NeuN// MAP2+) from the astrocyte culture.

Figure 15:
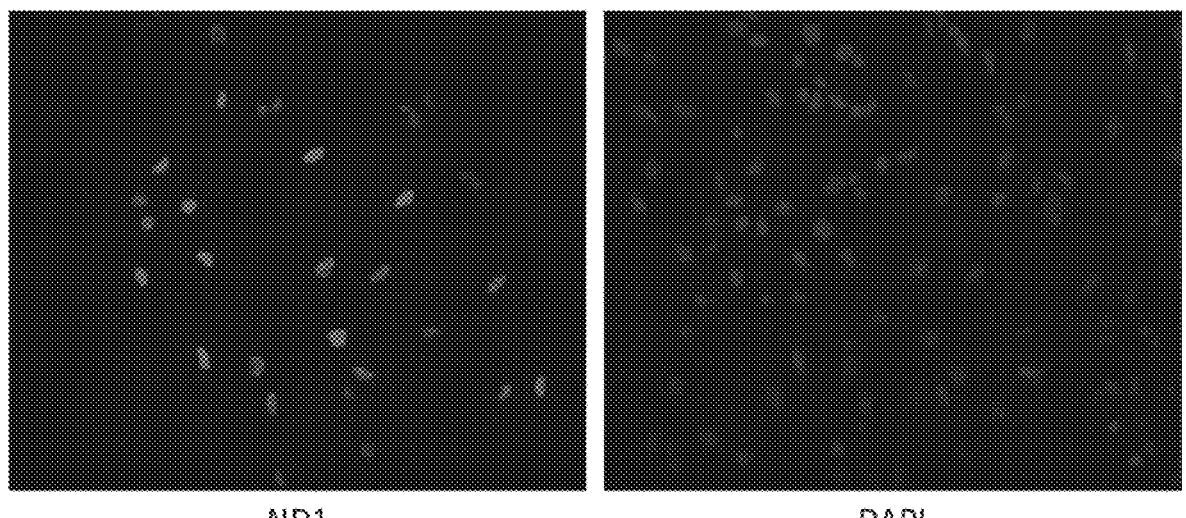
Figure 15:
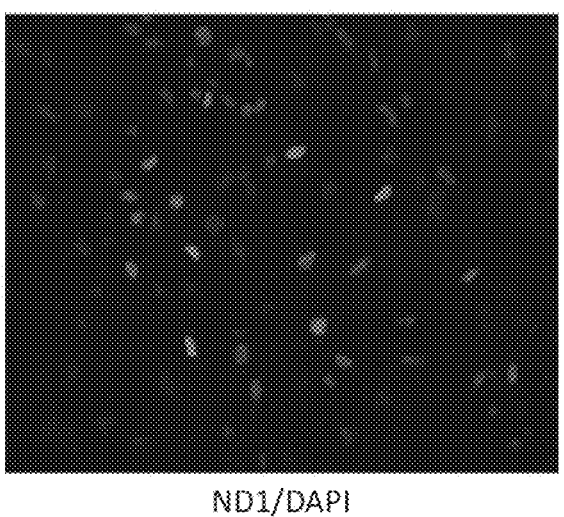

FIG. 15 depicts RCAs immunostained with an anti-ND1 antibody and DAPI (nuclear stain) 24 hours post transfection with NXL-P138 (EE-pGfa681-CRGI-hND1-oPRE-bGHpA).

Figure 16:
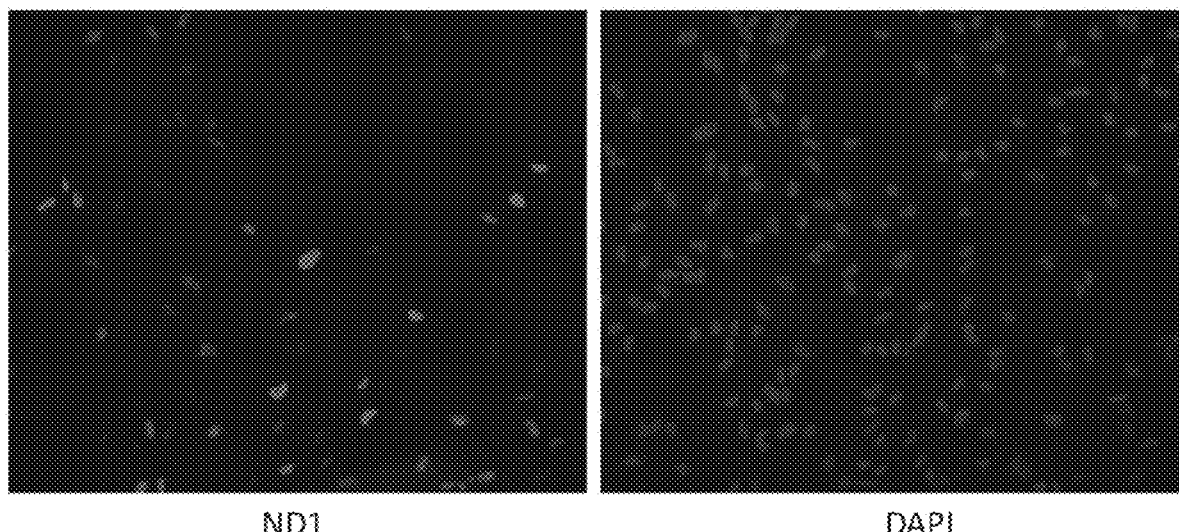
Figure 16:
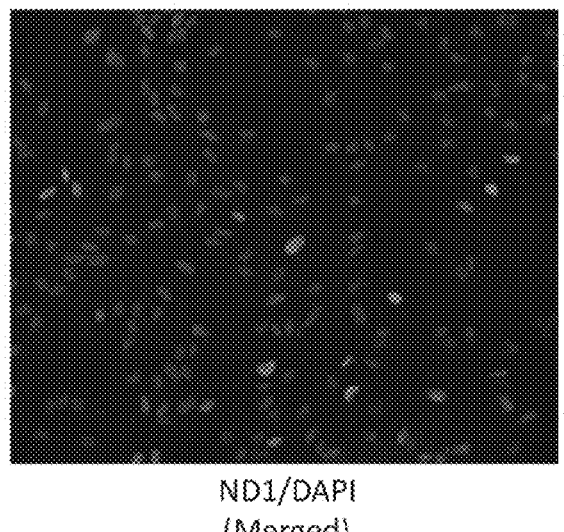

FIG. 16 depicts RCAs immunostained with an anti-ND1 antibody and DAPI (nuclear stain) 6 days post transduction with AAV9-P138 (EE-pGfa681-CRGI-hND1-oPRE-bGHpA) at 2×10¹⁰ vg/ml).

Figure 17:
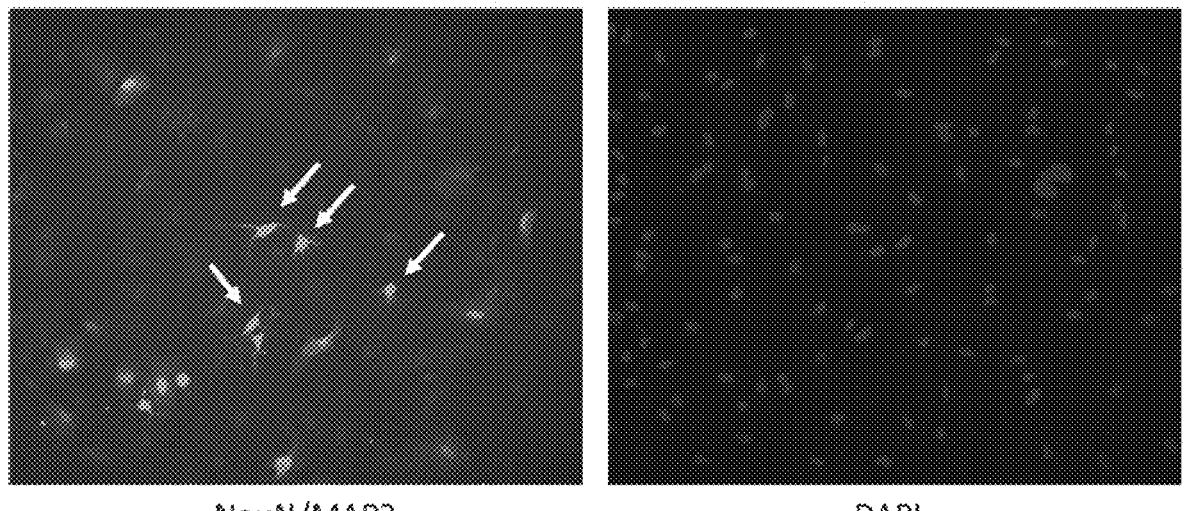
Figure 17:
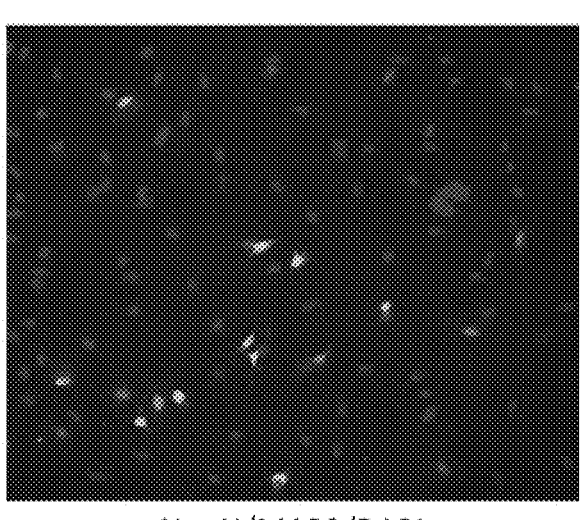

FIG. 17 depicts RCAs immunostained with anti-NeuN and anti-MAP2 antibodies and DAPI (nuclear stain) 3 weeks post transduction with AAV9-P138 (EE-pGfa681-CRGI-hND1-oPRE-bGHpA) at 2×10¹⁰ vg/ml). Transduction with the ND1-containing vector generates neurons (NeuN// MAP2+) from the astrocyte culture.

Figure 18:
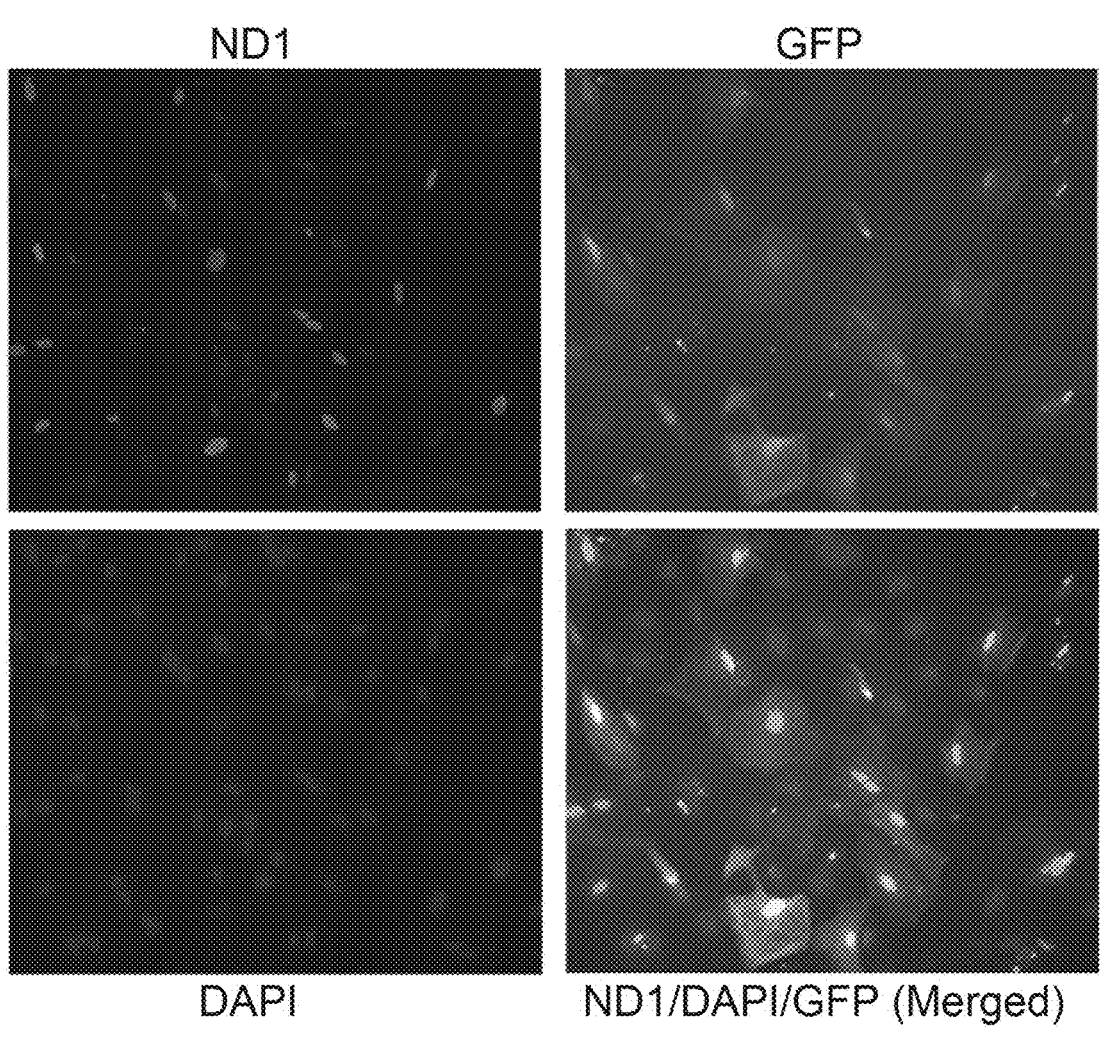

FIG. 18 depicts RCAs immunostained with an anti-ND1 antibody and DAPI (nuclear stain) 6 days post transduction with AAV9-P9 (CE-pGfa681-CI-hND1-p2A-GFP-WPRE-SV40pA) at 2×10¹⁰ vg/ml. GFP fluorescence indicates presence of transduced cells.

Figure 19:
Figure 19:
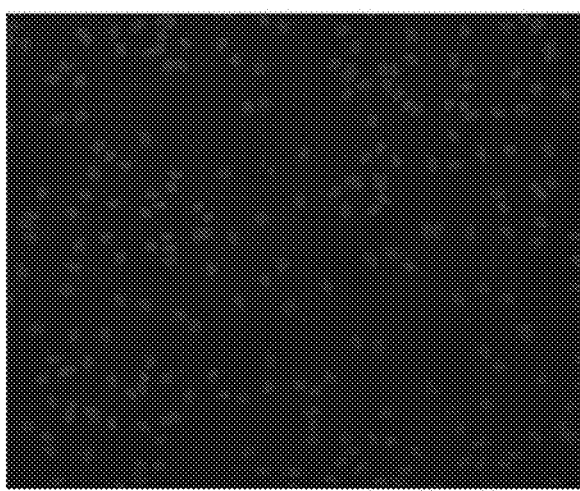
Figure 19:
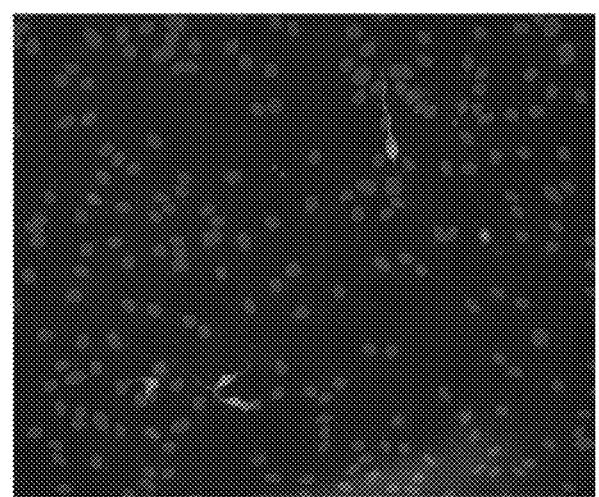

FIG. 19 depicts RCAs immunostained with anti-NeuN and anti-MAP2 antibodies and DAPI (nuclear stain) 3 weeks post transduction with AAV9-P9 (CE-pGfa681-CI-hND1-p2A-GFP-WPRE-SV40pA) at 2×10¹⁰ vg/ml. Transduction with the ND1-containing vector generates neurons (NeuN// MAP2+) from the astrocyte culture.

Figure 20:
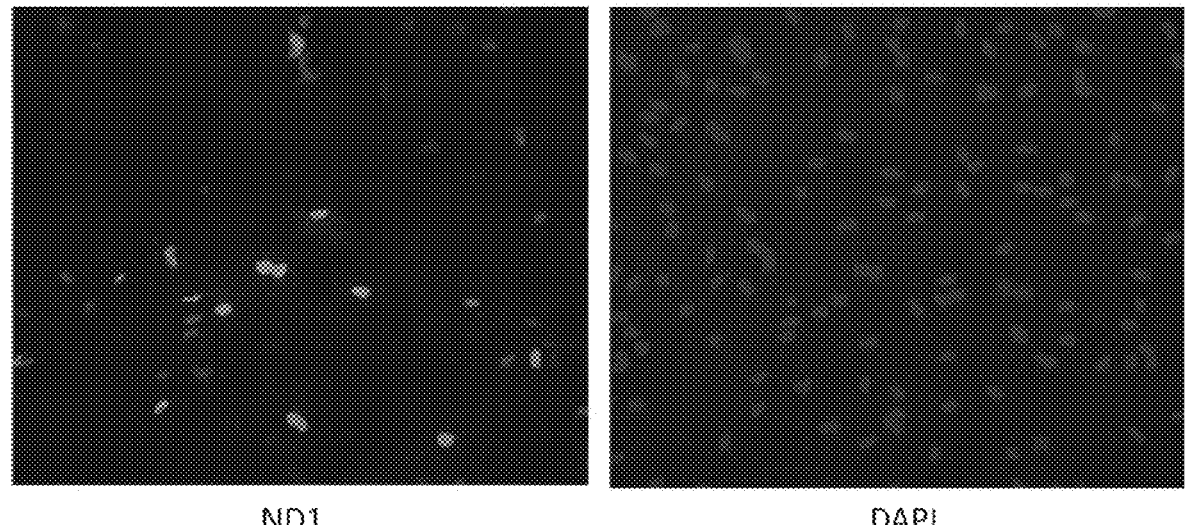
Figure 20:
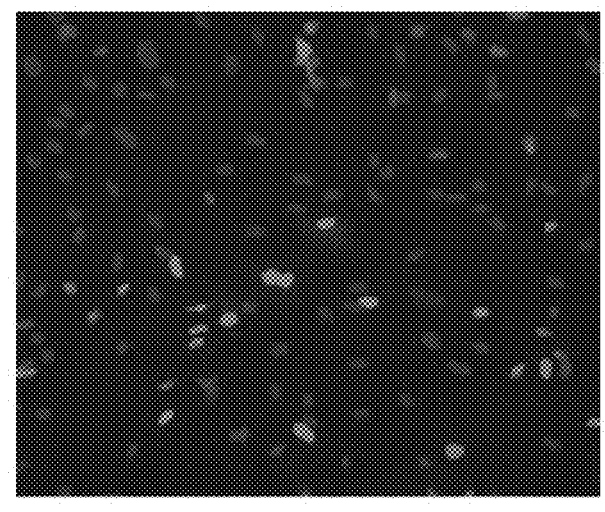

FIG. 20 depicts RCAs immunostained with an anti-ND1 antibody and DAPI (nuclear stain) 24 hours post transfection with NXL-P22 (CE-pGfa681-CI-hND1-WPRE-SV40pA).

Figure 21:
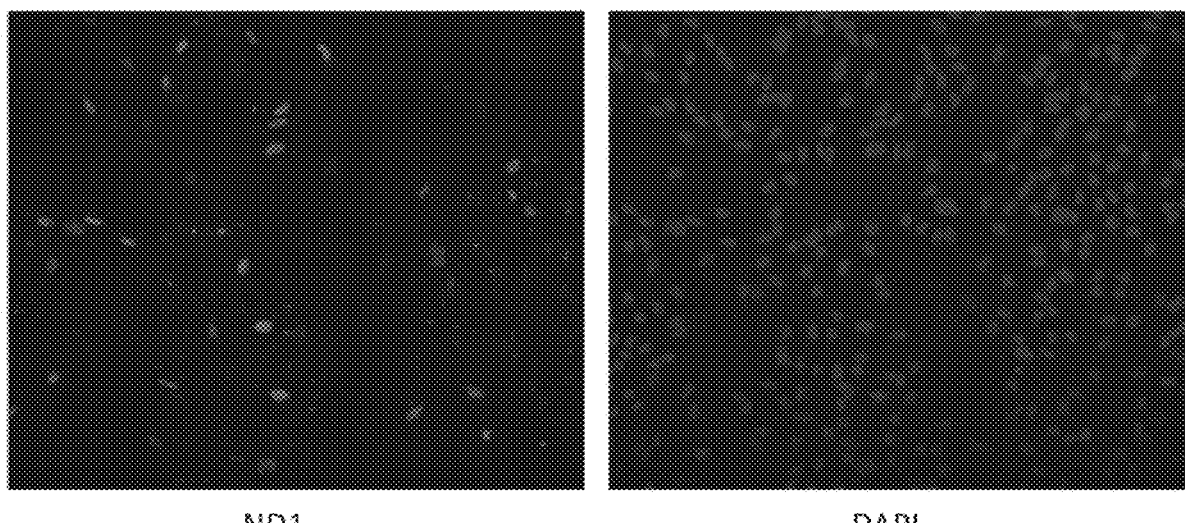
Figure 21:
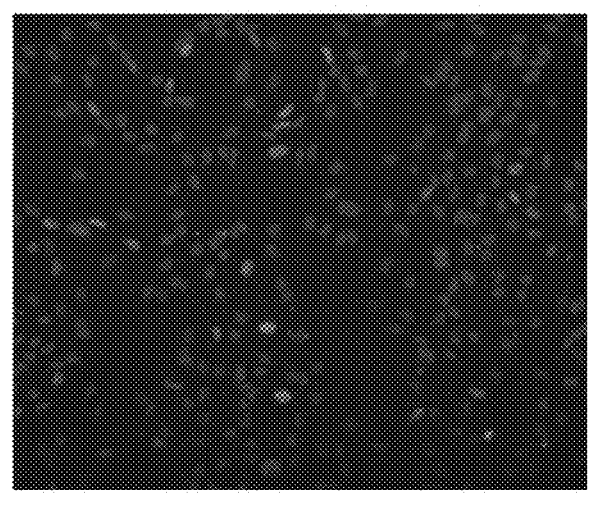

FIG. 21 depicts RCAs immunostained with an anti-ND1 antibody and DAPI (nuclear stain) 6 days post transduction with AAV9-P22 (CE-pGfa681-CI-hND1 WPRE-SV40pA) at 2×10¹⁰ vg/ml.

Figure 22:
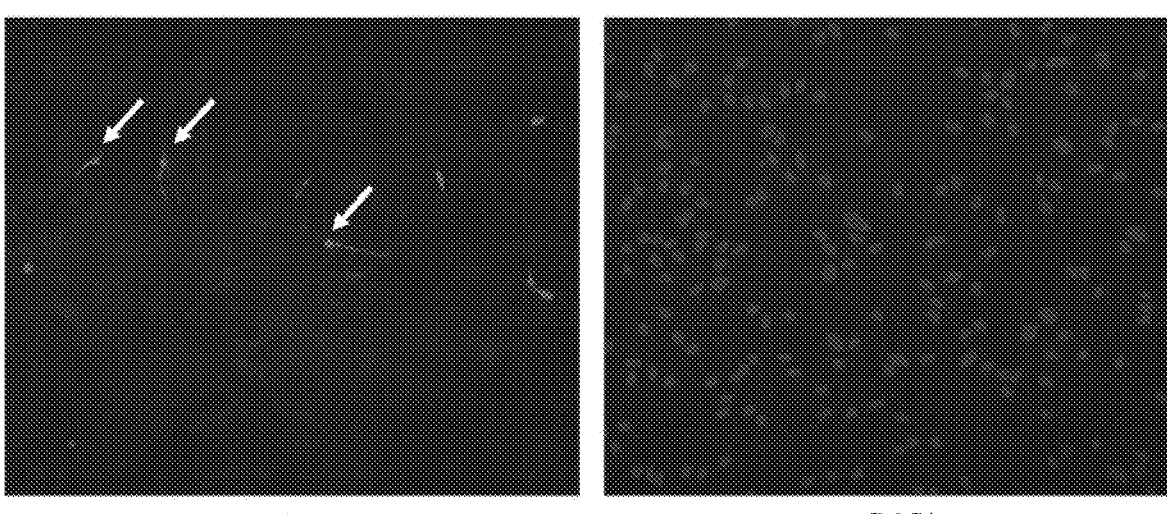
Figure 22:
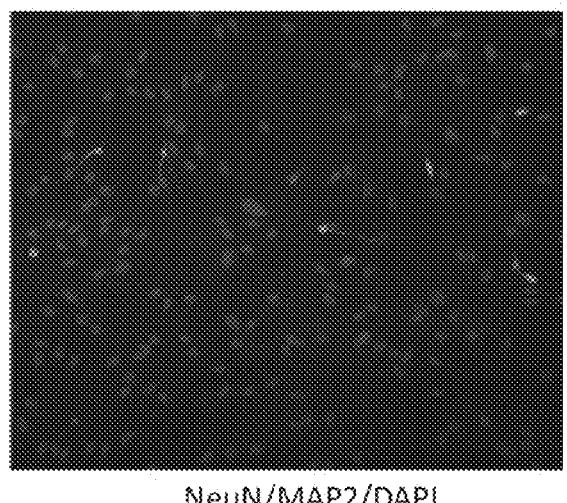

FIG. 22 depicts RCAs immunostained with anti-NeuN and anti-MAP2 antibodies and DAPI (nuclear stain) 3 weeks post transduction with AAV9-P22 (CE-pGfa681-CI-hND1-WPRE-SV40pA) at 2×10¹⁰ vg/ml. Transduction with the ND1-containing vector generates neurons (NeuN//MAP2+) from the astrocyte culture.

Figure 23:
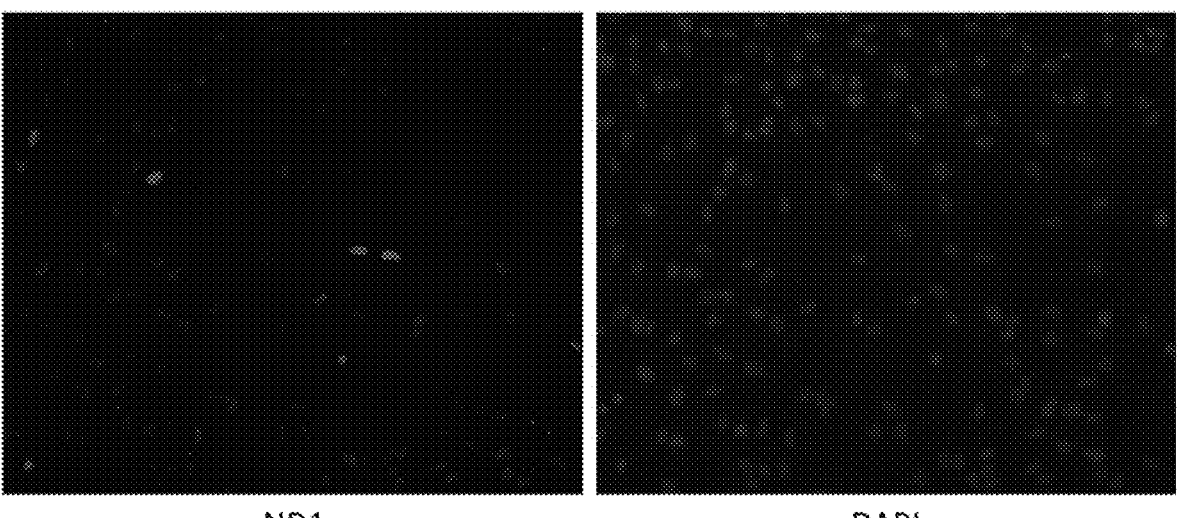
Figure 23:
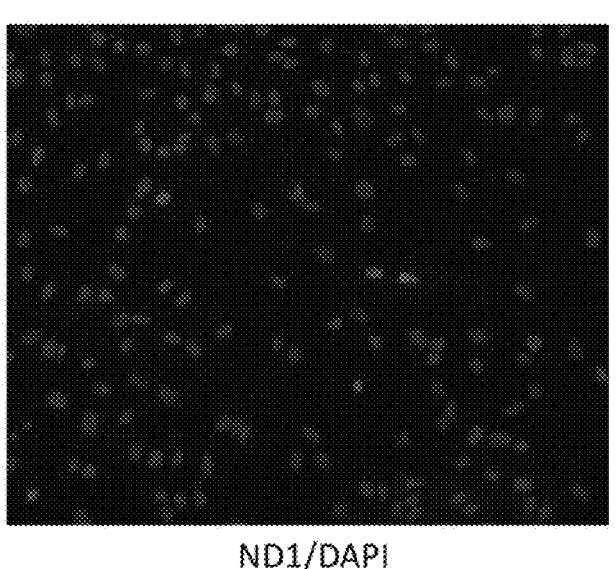

FIG. 23 depicts RCAs immunostained with an anti-ND1 antibody and DAPI (nuclear stain) 24 hours post transfection with NXL-P35 (EE-pGfa681-CI-hND1-WPRE-SV40pA).

7

Figure 24:
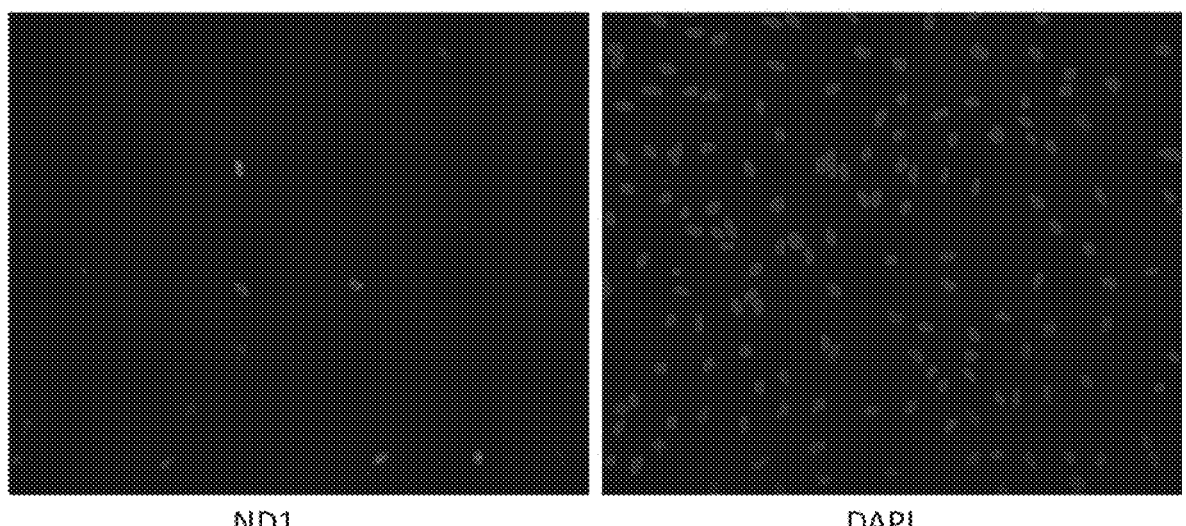
Figure 24:
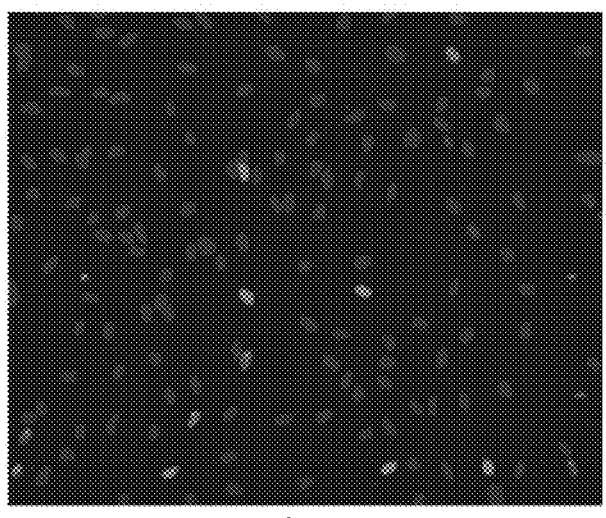

FIG. 24 depicts RCAs immunostained with an anti-ND1 antibody and DAPI (nuclear stain) 6 days post transduction with AAV9-P35 (EE-pGfa681-CI-hND1 WPRE-SV40pA) at 2×10¹⁰ vg/ml.

Figure 25:
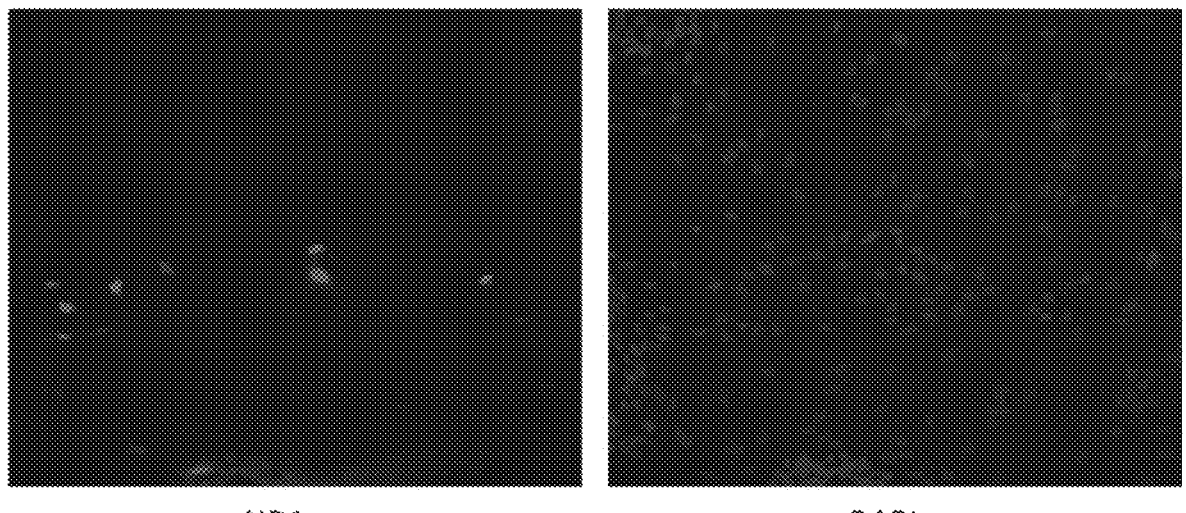
Figure 25:
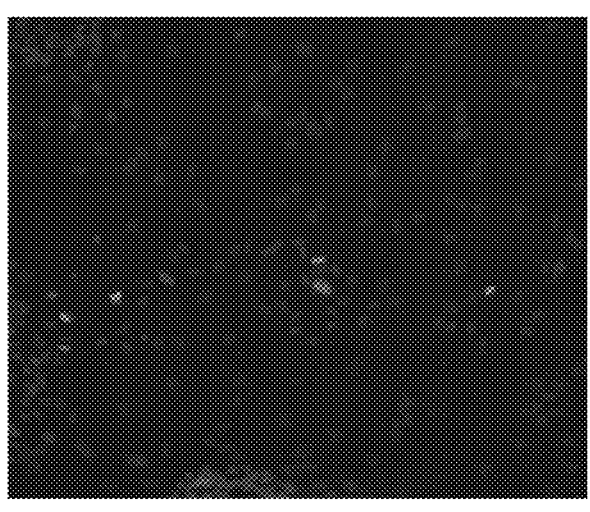

FIG. 25 depicts RCAs immunostained with an anti-NeuN antibody and DAPI (nuclear stain) 3 weeks post transduction with AAV9-P35 (EE-pGfa681-CI-hND1-WPRE-SV40pA) at 2×10¹⁰ vg/ml. Transduction with the ND1-containing vector generates neurons (NeuN+) from the astrocyte culture.

Figure 26:
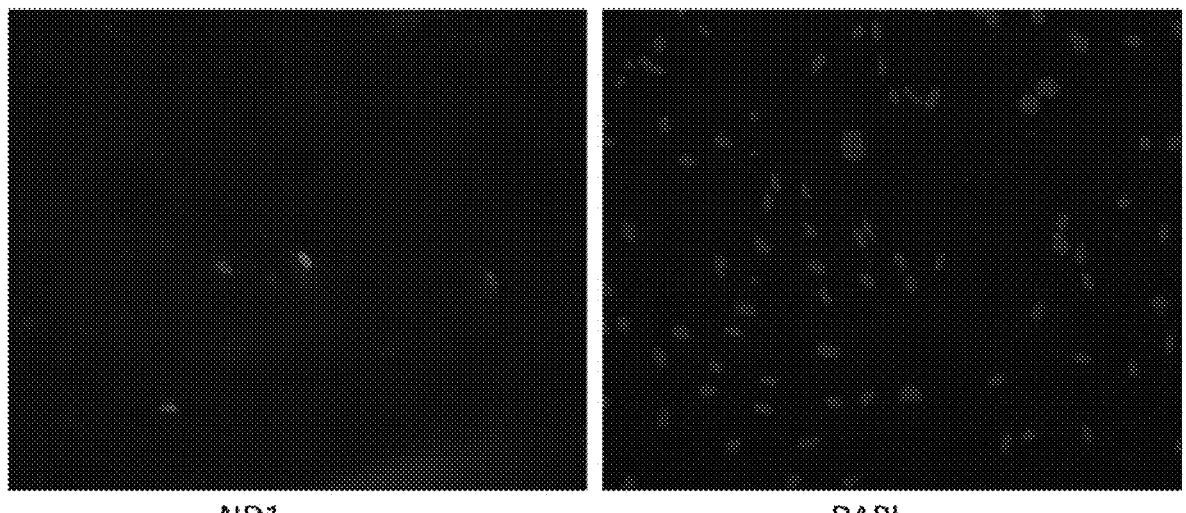
Figure 26:
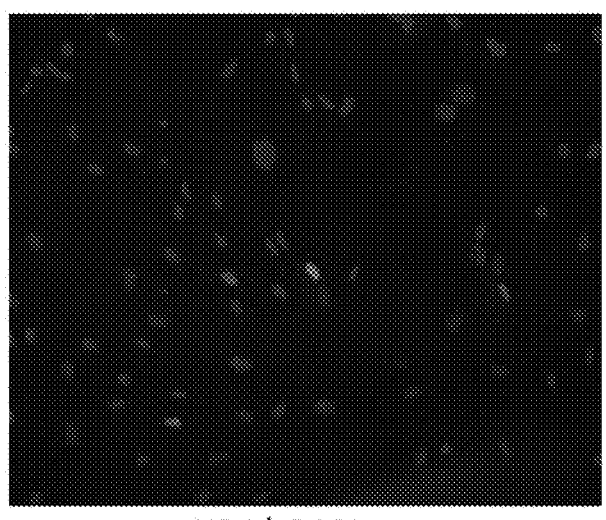

FIG. 26 depicts RCAs immunostained with an anti-ND1 antibody and DAPI (nuclear stain) 24 hours post transfection with NXL-P107 (CE-pGfa681-CI-hND1-bGHpA).

Figure 27:
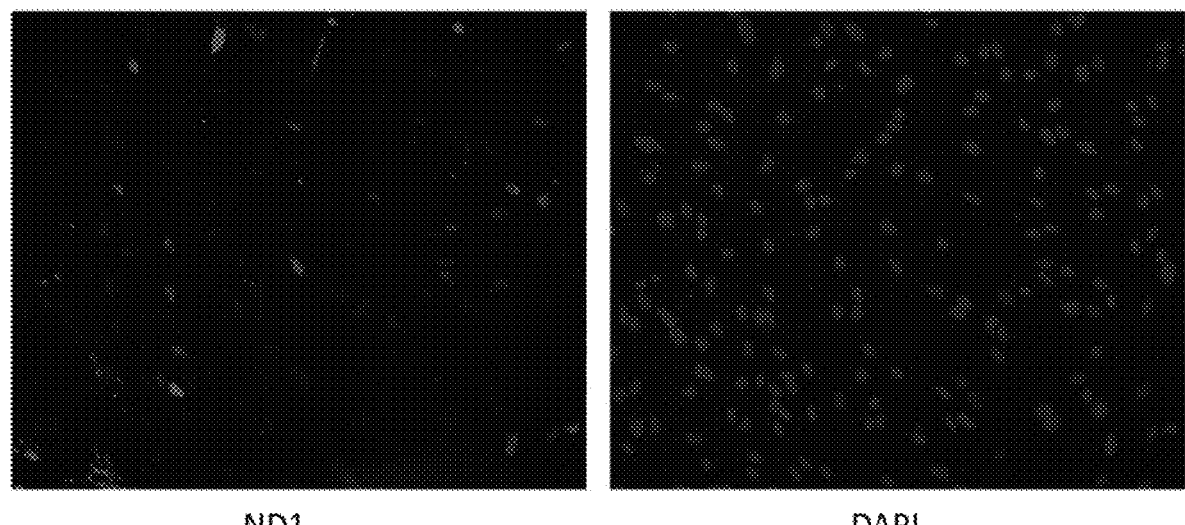
Figure 27:
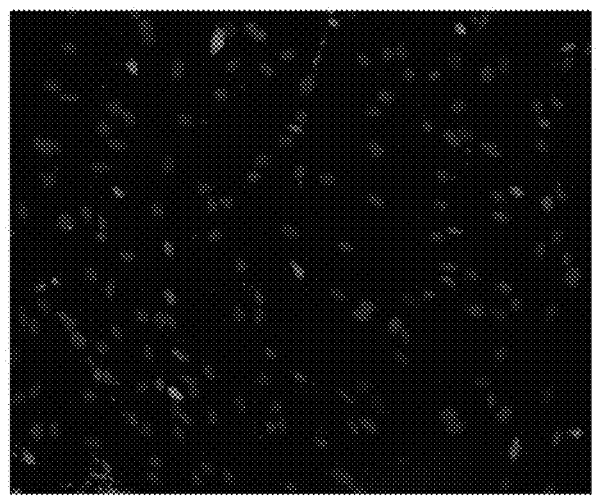

FIG. 27 depicts RCAs immunostained with an anti-ND1 antibody and DAPI (nuclear stain) 24 hours post transfection with NXL-P108 (CE-pGfa681-CI-hND1-oPRE-bGHpA).

Figure 28:
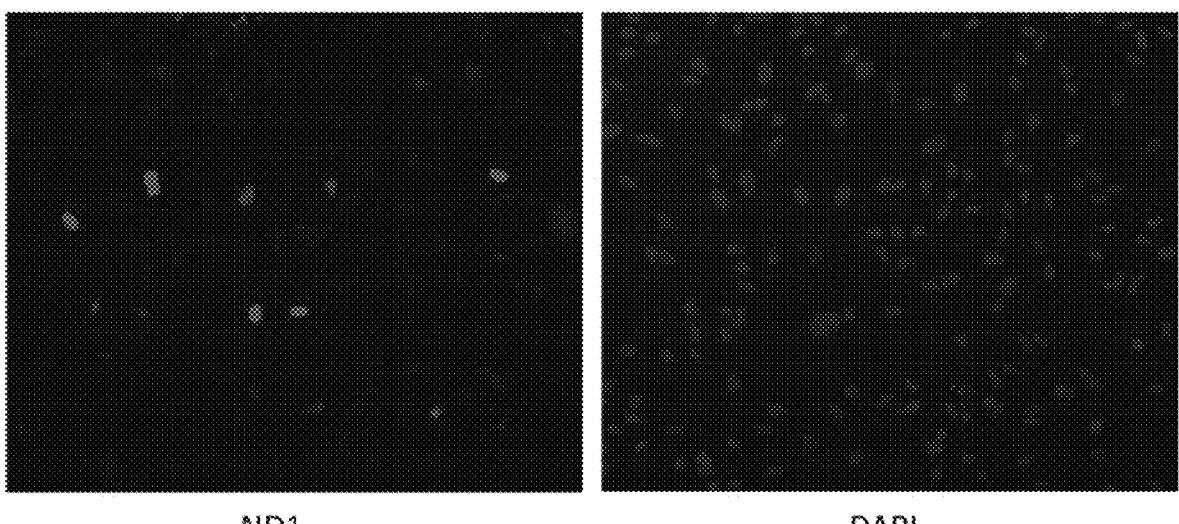
Figure 28:
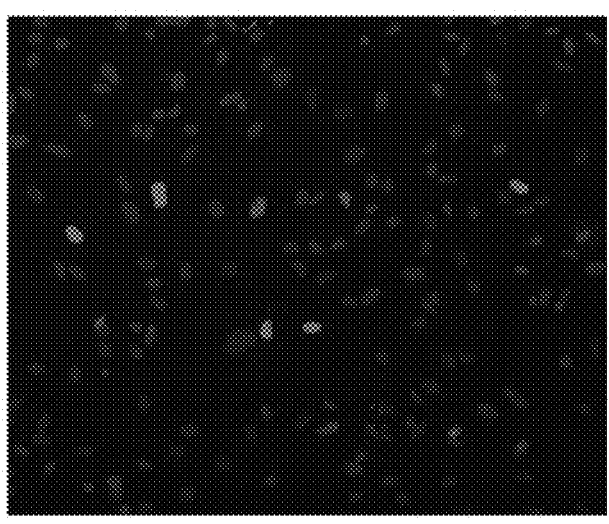

FIG. 28 depicts RCAs immunostained with an anti-ND1 antibody and DAPI (nuclear stain) 24 hours post transfection with NXL-P109 (CE-pGfa681-CRGI-hND1-bGHpA).

Figure 29:
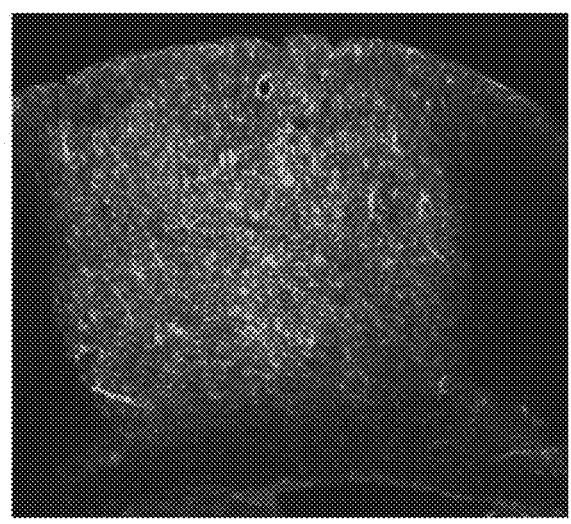
Figure 29:
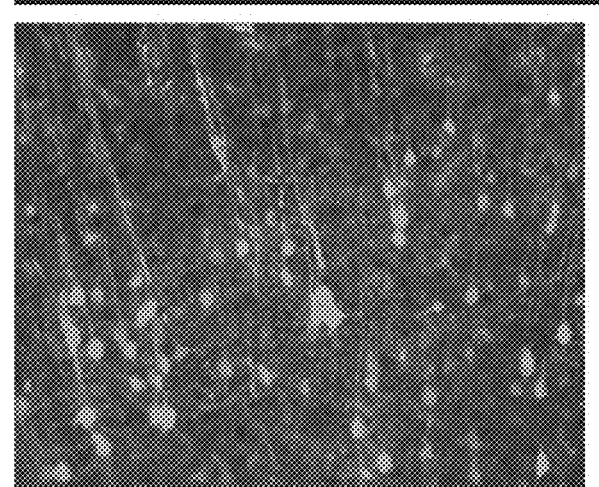
Figure 29:
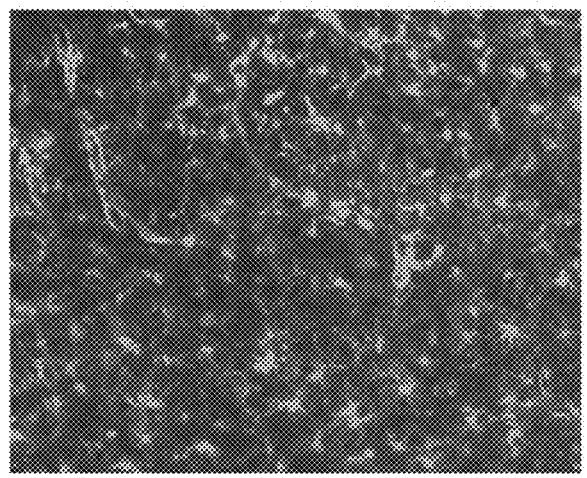

FIG. 29 depicts the brain cortex tissue of mice infected with AAV9-P12 (P12 control group), AAV9-P12+AAV9-P134 (P134 group), and AAV9-P12+AAV9-P138 (P138 group) at 10 days post infection (dpi).

Figure 30:
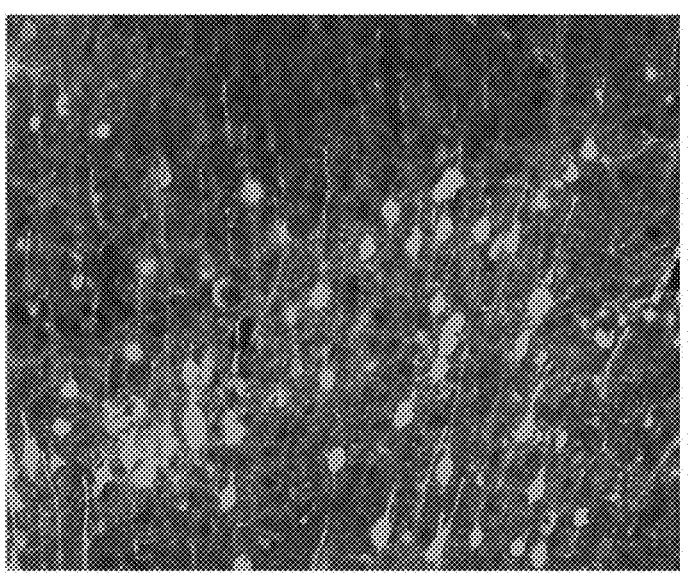
Figure 30:
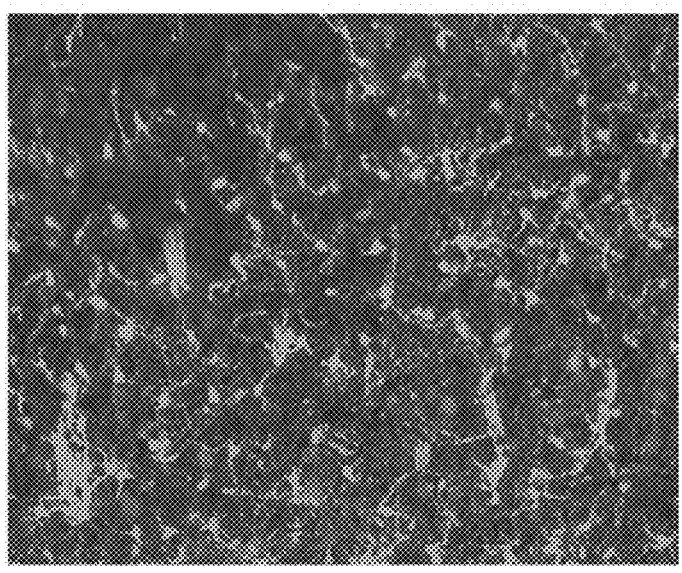

FIG. 30 depicts the brain cortex tissue of mice infected with AAV9-P12+AAV9-P134 (P134 group), and AAV9-P12+AAV9-P138 (P138 group) at 30 days post infection (dpi).

Figure 31:
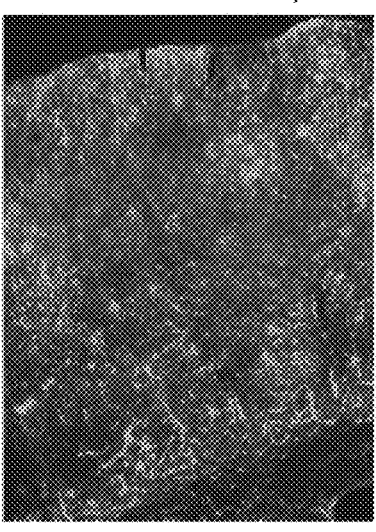
Figure 31:
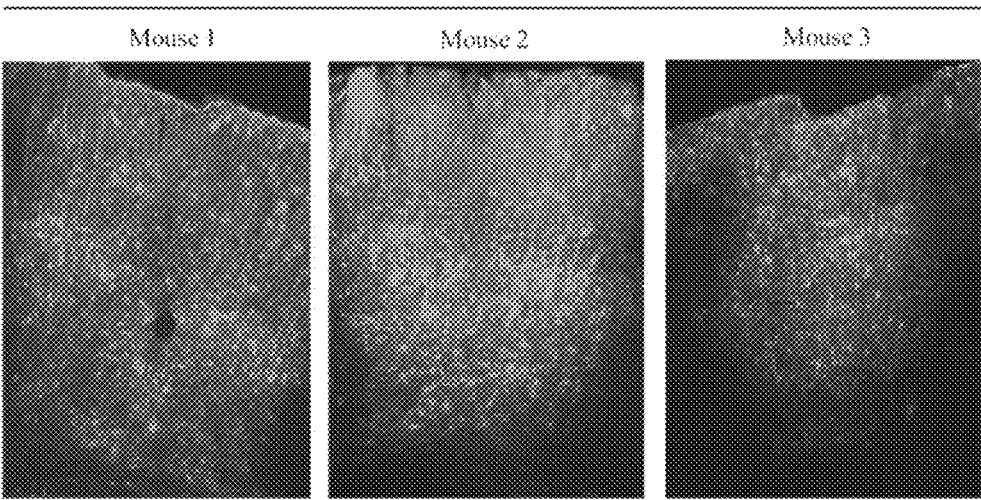

FIG. 31 depicts the brain cortex tissue of mice (bilateral injury model) infected with AAV9-P12 (P12 control group), and AAV9-P12+AAV9-P134 (P134 group) at 10 dpi.

Figure 32:
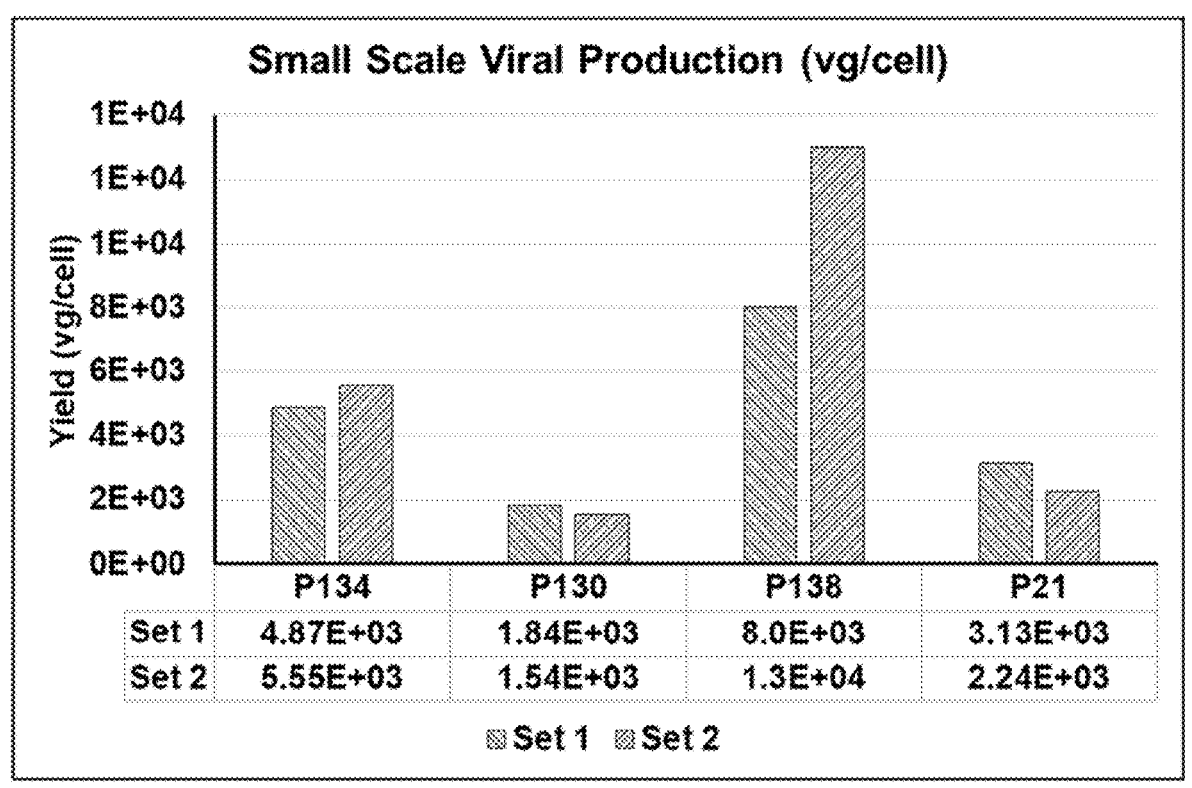

FIG. 32 is a plot of measurements of AAV virus production of the P134, P130, P138 and P21 plasmids. Titer analysis is performed by qPCR using primers amplifying gene of interest (GOI) and primers specific to the plasmids. Virus yield is calculated as vg/cell.

Figure 33:
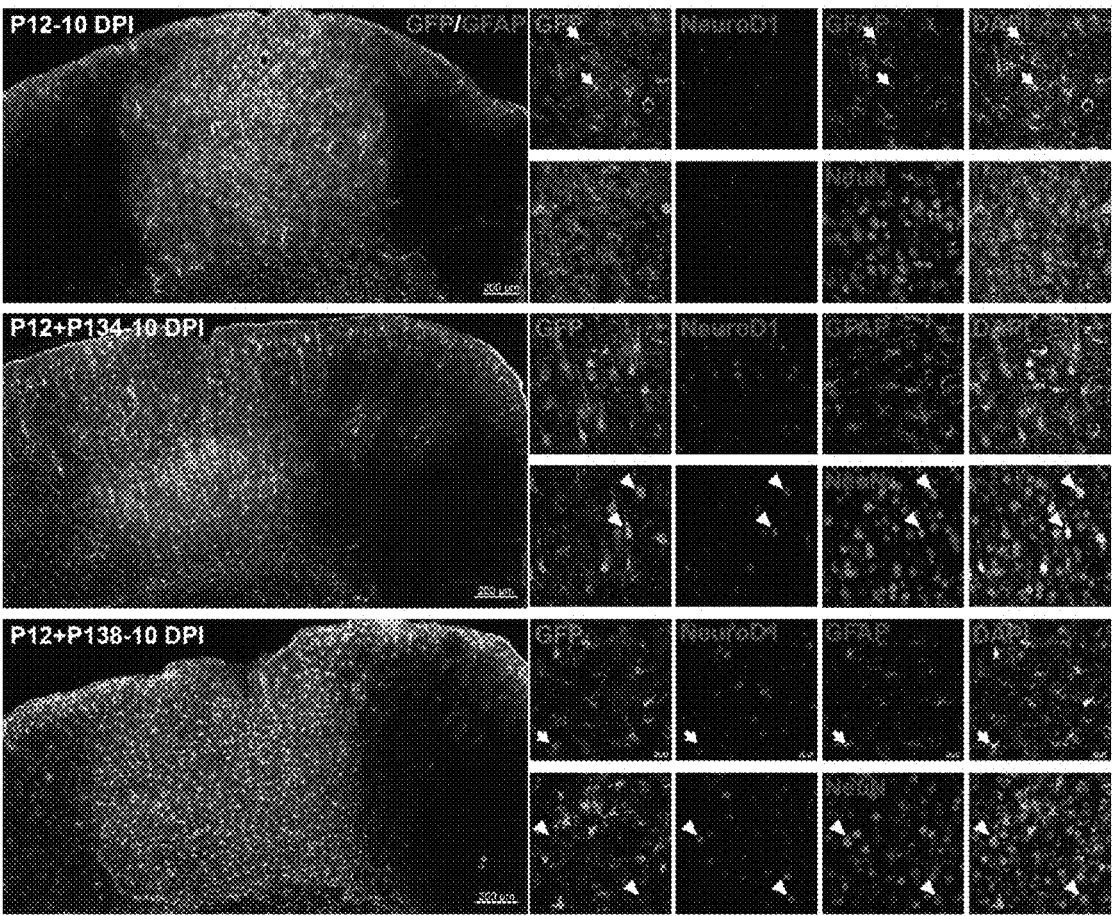

FIG. 33 depicts the brain cortex tissue of mice infected with AAV9-P12 (P12 control group), AAV9-P12+AAV9-P134 (P134 group), and AAV9-P12+AAV9-P138 (P138 group) at 10 days post infection (dpi). Cells are immunostained with antibodies against NeuroD1, GFAP, NeuN, and with DAPI (nuclear stain). GFP fluorescence indicates the presence of cells infected with the control virus.

Figure 34:
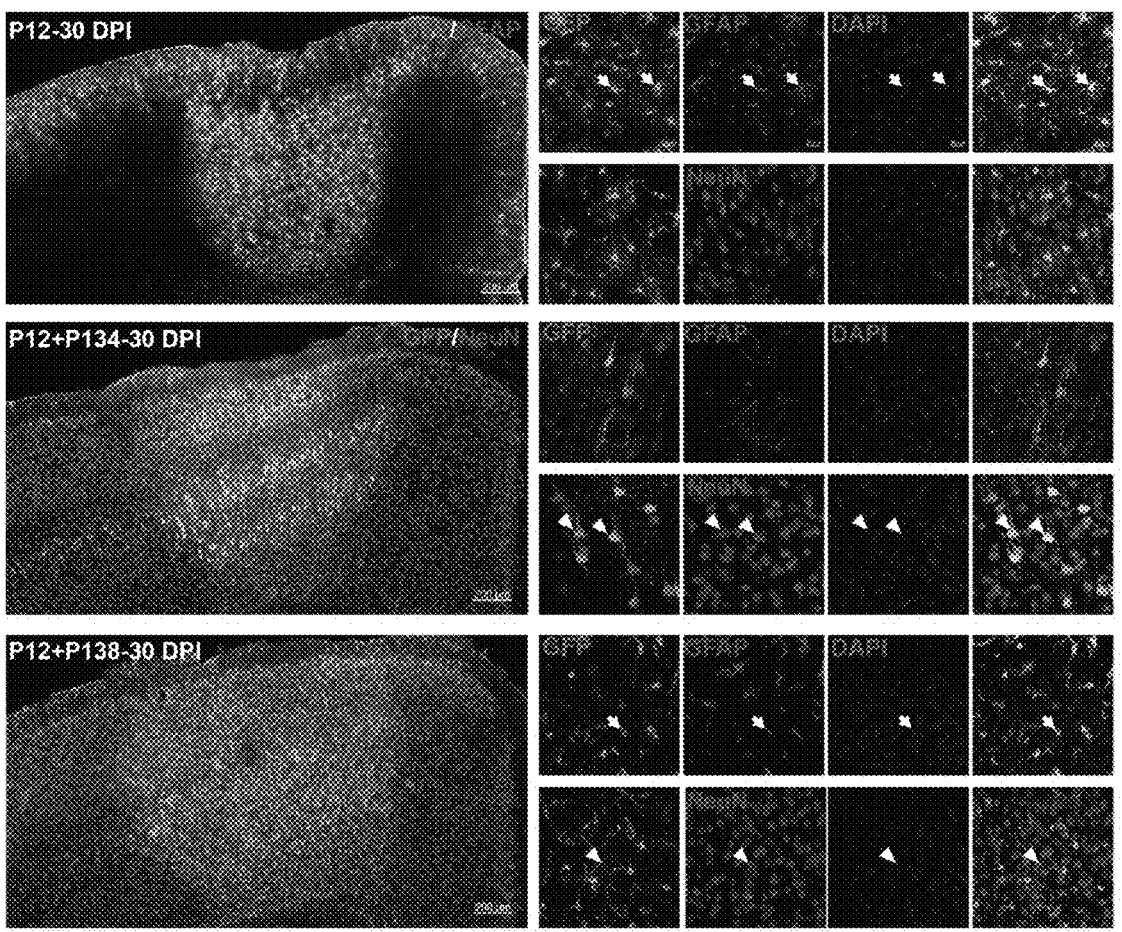

FIG. 34 depicts the brain cortex tissue of mice infected with AAV9-P12 (P12 control group), AAV9-P12+AAV9-P134 (P134 group), and AAV9-P12+AAV9-P138 (P138 group) at 30 days post infection (dpi). Cells are immunostained with antibodies against GFAP, NeuN, and with DAPI (nuclear stain). GFP fluorescence indicates the presence of cells infected with the control virus.

Figure 35:
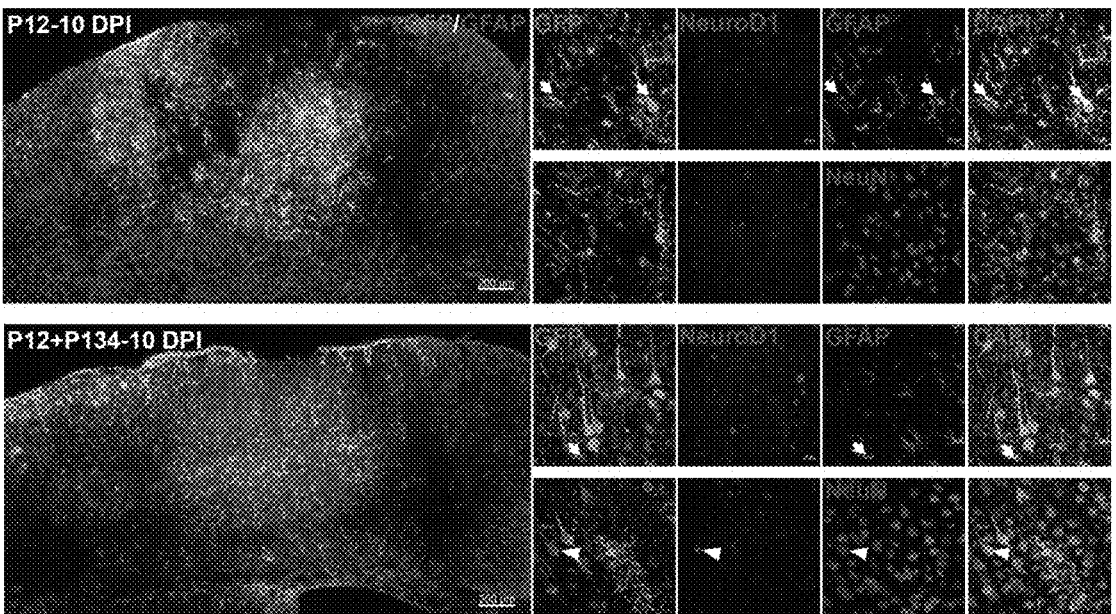

FIG. 35 depicts the brain cortex tissue of mice (bilateral injury model) infected with AAV9-P12 (P12 control group), and AAV9-P12+AAV9-P134 (P134 group) at 10 dpi. Cells are immunostained with antibodies against NeuroD1, GFAP, NeuN, and with DAPI (nuclear stain). GFP fluorescence indicates the presence of cells infected with the control virus.

Figure 36A:
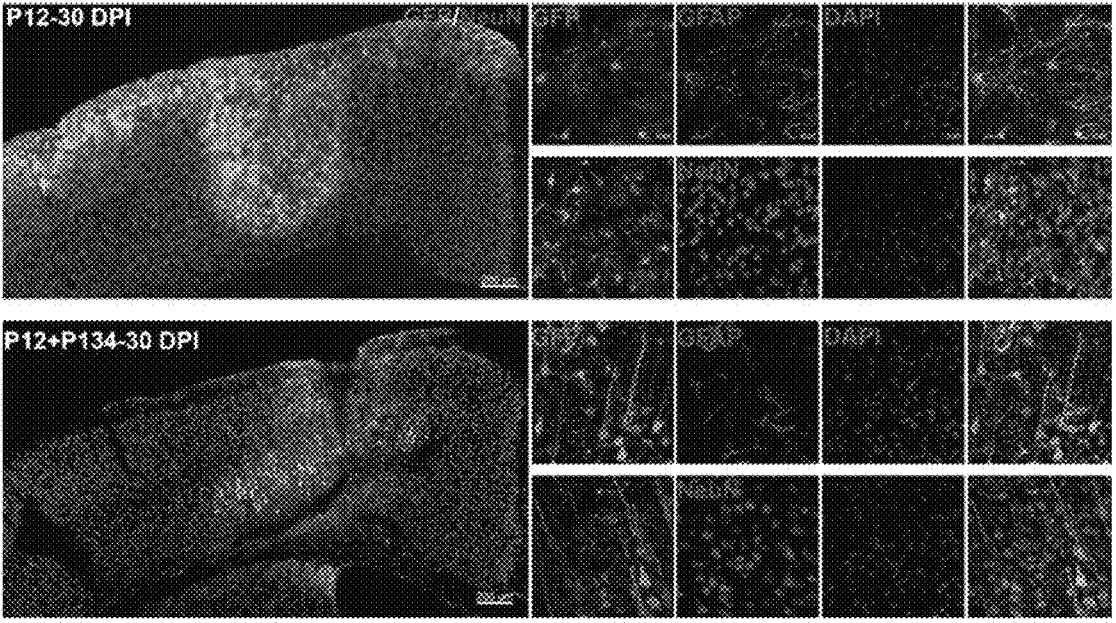
Figure 36B:
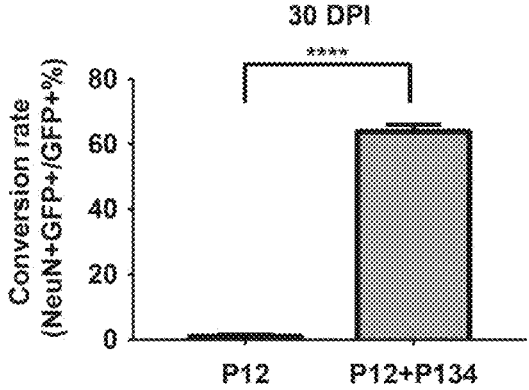

FIGS. 36A and 36B depicts the brain cortex tissue of mice (bilateral injury model) infected with AAV9-P12 (P12 control group), and AAV9-P12+AAV9-P134 (P134 group) at 30 dpi. FIG. 36A depicts the cells that are immunostained with antibodies against NeuroD1, GFAP, NeuN, and with DAPI (nuclear stain). GFP fluorescence indicates the presence of cells infected with the control virus. FIG. 36B is a quantification of the glial cell-to-neuron conversion rate at 30 dpi.

BRIEF DESCRIPTION OF SEQUENCES

A listing of nucleic acid sequences and amino acid sequences is provided in Table 1.

TABLE 1

| | | | Nucleic acid sequences |
|---|---|---|---|
| SEQ ID NO | Sequence Description | Sequence Type | Sequence |
| 1 | Upstream AAV2 ITR | Nucleic acid | TGCAGGCAGCTGCGCGCTCGCTCGCTCACTGAGGCCGCCCGG GCGTCGGGCGACCTTTGGTCGCCCGGCCTCAGTGAGCGAGCG AGCGCGCAGAGAGGGAGTGGCCAACTCCATCACTAGGGGTT CCT |
| 2 | Ef1a enhancer | Nucleic acid | TGCAAAGATGGATAAAGTTTTAAACAGAGAGGAATCTTTGC AGCTAATGGACCTTCTAGGTCTTGAAAGGAGTGGGAATTGGC TCCGGTGCCCGTCAGTGGGCAGAGCGCACATCGCCCACAGTC CCCGAGAAGTTGGGGGGAGGGGTCGGCA |
| 3 | p2A | Nucleic acid | GGAAGCGGAGCTACTAACTTCAGCCTGCTGAAGCAGGCTGG AGACGTGGAGGAGAACCCTGGACCT |
| 4 | Gfa1.6 promoter | Nucleic acid | CTGCAAGCAGACCTGGCAGCATTGGGCTGGCCGCCCCCCAG GGCCTCCTCTTCATGCCCAGTGAATGACTCACCTTGGCACAG ACACAATGTTCGGGGTGGGCACAGTGCCTGCTTCCCGCCGCA CCCCAGCCCCCCTCAAATGCCTTCCGAGAAGCCCATTGAGTA GGGGGCTTGCATTGCACCCCAGCCTGACAGCCTGGCATCTTG GGATAAAAGCAGCACAGCCCCTAGGGGCTGCCCTTGCTGTG TGGCGCCACCGGCGGTGGAGAACAAGGCTCTATTCAGCCTGT GCCCAGGAAAGGGGATCAGGGGATGCCCAGGCATGGACAGT GGGTGGCAGGGGGGAGAGGAGGGCTGTCTGCTTCCCAGAA GTCCAAGGACACAAATGGGTGAGGGGACTGGGCAGGGTTCT GACCCTGTGGGACCAGAGTGGAGGGCGTAGATGGACCTGAA GTCTCCAGGGACAACAGGGCCCAGGTCTCAGGCTCCTAGTTG GGCCCAGTGGCTCCAGCGTTTCCAAACCCATCCATCCCCAGA GGTTCTTCCCATCTCTCCAGGCTGATGTGTGGGAACTCGAGG AAATAAATCTCCAGTGGGAGACGGAGGGGTGGCCAGGGAAA CGGGGCGCTGCAGGAATAAAGACGAGCCAGCACAGCCAGCT CATGCGTAACGGCTTTGTGGAGCTGTCAAGGCCTGGTCTCTG GGAGAGAGGCACAGGGAGGCCAGACAAGGAAGGGGTGACC TGGAGGGACAGATCCAGGGGCTAAAGTCCTGATAAGGCAAG |

TABLE 1-continued

Nucleic acid sequences

| SEQ ID NO | Sequence Description | Sequence Type | Sequence |
|---|---|---|---|
| | | | AGAGTGCCGGCCCCCTCTTGCCCTATCAGGACCTCCACTGCC |
| | | | ACATAGAGGCCATGATTGACCCTTAGACAAAGGGCTGGTGTC |
| | | | CAATCCCAGCCCCCAGCCCCAGAACTCCAGGGAATGAATGG |
| | | | GCAGAGAGCAGGAATGTGGGACATCTGTGTTCAAGGGAAGG |
| | | | ACTCCAGGAGTCTGCTGGGAATGAGGCCTAGTAGGAAATGA |
| | | | GGTGGCCCTTGAGGGTACAGAACAGGTTCATTCTTCGCCAAA |
| | | | TTCCCAGCACCTTGCAGGCACTTACAGCTGAGTGAGATAATG |
| | | | CCTGGGTTATGAAATCAAAAAGTTGGAAAGCAGGTCAGAGG |
| | | | TCATCTGGTACAGCCCTTCCTTCCCTTTTTTTTTTTTTTTTTTT |
| | | | GTGAGACAAGGTCTCTCTCTGTTGCCCAGGCTGGAGTGGCGC |
| | | | AAACACAGCTCACTGCAGCCTCAACCTACTGGGCTCAAGCAA |
| | | | TCCTCCAGCCTCAGCCTCCCAAAGTGCTGGGATTACAAGCAT |
| | | | GAGCCACCCCACTCAGCCCTTTCCTTCCTTTTTAATTGATGCA |
| | | | TAATAATTGTAAGTATTCATCATGGTCCAACCAACCCTTTCTT |
| | | | GACCCACCTTCCTAGAGAGAGGGTCCTCTTGATTCAGCGGTC |
| | | | AGGGCCCCAGACCCATGGTCTGGCTCCAGGTACCACCTGCCT |
| | | | CATGCAGGAGTTGGCGTGCCCAGGAAGCTCTGCCTCTGGGCA |
| | | | CAGTGACCTCAGTGGGGTGAGGGGAGCTCTCCCCATAGCTGG |
| | | | GCTGCGGCCCAACCCCACCCCCTCAGGCTATGCCAGGGGGTG |
| | | | TTGCCAGGGGCACCCGGGCATCGCCAGTCTAGCCCACTCCTT |
| | | | CATAAAGCCCTCGCATCCCAGGAGCGAGCAGAGCCAGAG |
| 5 | Chimeric Intron | Nucleic acid | GTAAGTATCAAGGTTACAAGACAGGTTTAAGGAGACCAATA |
| | | | GAAACTGGGCTTGTCGAGACAGAGAAGACTCTTGCGTTTCTG |
| | | | ATAGGCACCTATTGGTCTTACTGACATCCACTTTGCCTTTCTC |
| | | | TCCACAG |
| 6 | hND1 (human NeuroD1) | Nucleic acid | ATGACCAAATCGTACAGCGAGAGTGGGCTGATGGGCGAGCC |
| | | | TCAGCCCCAAGGTCCTCCAAGCTGGACAGACGAGTGTCTCAG |
| | | | TTCTCAGGACGAGGAGCACGAGGCAGACAAGAAGGAGGACG |
| | | | ACCTCGAAGCCATGAACGCAGAGGAGGACTCACTGAGGAAC |
| | | | GGGGGAGAGGAGGAGGACGAAGATGAGGACCTGGAAGAGG |
| | | | AGGAAGAAGAGGAAGAGGAGGAGGATGACGATCAAAAGCCCAA |
| | | | GAGACGCGGCCCCAAAAAGAAGAAGATGACTAAGGCTCGCC |
| | | | TGGAGCGGTTTTAAATTGAGACGCATGAAGGCTAACGCCCGG |
| | | | GAGCGGAACCGCATGCACGGACTGAACGCGGCGCTAGACAA |
| | | | CCTGCGCAAGGTGGTGCCTTGCTATTCTAAGACGCAGAAGCT |
| | | | GTCCAAAATCGAGACTCTGCGCTTGGCCAAGAACTACATCTG |
| | | | GGCTCTGTCGGAGATCCTGCGCTCAGGCAAAAGCCCAGACCT |
| | | | GGTCTCCTTCGTTCAGACGCTTTGCAAGGGCTTATCCCAACC |
| | | | CACCACCAACCTGGTTGCGGGCTGCCTGCAACTCAATCCTCG |
| | | | GACTTTTCTGCCTGAGCAGAACCAGGACATGCCCCCCCCACCT |
| | | | GCCGACGGCCAGCGCTTCCTTCCCTGTACACCCCTACTCCTA |
| | | | CCAGTCGCCTGGGCTGCCCAGTCCGCCTTACGGTACCATGGA |
| | | | CAGCTCCCATGTCTTCCACGTTAAGCCTCCGCCGCACGCCTA |
| | | | CAGCGCAGCGCTGGAGCCCTTCTTTGAAAGCCCTCTGACTGA |
| | | | TTGCACCAGCCCTTCCTTTGATGGACCCCTCAGCCCGCCGCTC |
| | | | AGCATCAATGGCAACTTCTCTTTCAAACACGAACCGTCCGCC |
| | | | GAGTTTGAGAAAAATTATGCCTTTACCATGCACTATCCTGCA |
| | | | GCGACACTGGCAGGGGCCCAAAGCCACGGATCAATCTTCTC |
| | | | AGGCACCGCTGCCCCTCGCTGCGAGATCCCCATAGACAATAT |
| | | | TATGTCCTTCGATAGCCATTCACATCATGAGCGAGTCATGAG |
| | | | TGCCCAGCTCAATGCCATATTTCATGAT |
| 7 | WPRE (Woodchuck Hepatitis Virus Posttranscriptional Regulatory Element) | Nucleic acid | AATCAACCTCTGGATTACAAAATTTGTGAAAGATTGACTGGT |
| | | | ATTCTTAACTATGTTGCTCCTTTTACGCTATGTGGATACGCTG |
| | | | CTTTAATGCCTTTGTATCATGCTATTGCTTCCCGTATGGCTTT |
| | | | CATTTTCTCCTCCTTGTATAAATCCTGGTTGCTGTCTCTTTATG |
| | | | AGGAGTTGTGGCCCGTTGTCAGGCAACGTGGCGTGGTGTGCA |
| | | | CTGTGTTTGCTGACGCAACCCCCACTGGTTGGGGCATTGCCA |
| | | | CCACCTGTCAGCTCCTTTCCGGGACTTTCGCTTTCCCCCTCCC |
| | | | TATTGCCACGGCGGAACTCATCGCCGCCTGCCTTGCCCGCTG |
| | | | CTGGACAGGGGCTCGGCTGTTGGGCACTGACAATTCCGTGGT |
| | | | GTTGTCGGGGAAATCATCGTCCTTTCCTTGGCTGCTCGCCTGT |
| | | | GTTGCCACCTGGATTCTGCGCGGGACGTCCTTCTGCTACGTC |
| | | | CCTTCGGCCCTCAATCCAGCGGACCTTCCTTCCCGCGGCCTG |
| | | | CTGCCGGCTCTGCGGCCTCTTCCGCGTCTTCGCCTTCGCCCTC |
| | | | AGACGAGTCGGATCTCCCTTTGGGCCGCCTCCCCGC |
| 8 | SV40 poly(A) signal | Nucleic acid | CGATCCACCGGATCTAGATAACTGATCATAATCAGCCATACC |
| | | | ACATTTGTAGAGGTTTTACTTGCTTTAAAAAACCTCCCACAC |
| | | | CTCCCCCTGAACCTGAAACATAAAATGAATGCAATTGTTGTT |
| | | | GTTAACTTGTTTATTGCAGCTTATAATGGTTACAAATAAAGC |
| | | | AATAGCATCACAAATTTCACAAATAAAGCATTTTTTTCACTG |
| | | | CATTCTAGTTGTGGTTTGTCCAAACTCATCAATGTATCTTA |

TABLE 1-continued

| | | | |
|---|---|---|---|
| | Nucleic acid sequences | | |
| SEQ ID NO | Sequence Description | Sequence Type | Sequence |
| 9 | Downstream AAV2 ITR | Nucleic acid | AGGAACCCCTAGTGATGGAGTTGGCCACTCCCTCTCTGCGCG CTCGCTCGCTCACTGAGGCCGGGCGACCAAAGGTCGCCCGAC GCCCGGGCTTTGCCCGGGCGGCCTCAGTGAGCGAGCGAGCG CGCAGCTGCCTGCA |
| 10 | hND1 (human NeuroD1) | Amino Acid | MTKSYSESGLMGEPQPQGPPSWTDECLSSQDEEHEADKKEDDL EAMNAEEDSLRNGGEEEDEDEDLEEEEEEEEEDDDQKPKRRGP KKKKMTKARLERFKLRRMKANARERNRMHGLNAALDNLRKV VPCYSKTQKLSKIETLRLAKNYIWALSEILRSGKSPDLVSFVQTL CKGLSQPTTNLVAGCLQLNPRTFLPEQNQDMPPHLPTASASFPV HPYSYQSPGLPSPPYGTMDSSHVFHVKPPPHAYSAALEPFFESPL TDCTSPSFDGPLSPPLSINGNFSFKHEPSAEFEKNYAFTMHYPAA TLAGAQSHGSIFSGTAAPRCEIPIDNIMSFDSHSHHERVMSAQLN AIFHD |
| 11 | CMV enhancer ("CE") | Nucleic Acid | GACATTGATTATTGACTAGTTATTAATAGTAATCAATTACGG GGTCATTAGTTCATAGCCCATATATGGAGTTCCGCGTTACAT AACTTACGGTAAATGGCCCGCCTGGCTGACCGCCCAACGACC CCCGCCCATTGACGTCAATAATGACGTATGTTCCCATAGTAA CGCCAATAGGGACTTTCCATTGACGTCAATGGGTGGACTATT TACGGTAAACTGCCCACTTGGCAGTACATCAAGTGTATCATA TGCCAAGTACGCCCCCTATTGACGTCAATGACGGTAAATGGC CCGCCTGGCATTATGCCCAGTACATGACCTTATGGGACTTTC CTACTTGGCAGTACATCTACGTATTAGTCATCGCTATTACCAT G |
| 12 | hGFA2.2 promoter | Nucleic Acid | CGCGTCCCACCTCCCTCTCTGTGCTGGGACTCACAGAGGGAG ACCTCAGGAGGCAGTCTGTCCATCACATGTCCAAATGCAGAG CATACCCTGGGCTGGGCGCAGTGGCGCACAACTGTAATTCCA GCACTTTGGGAGGCTGATGTGGAAGGATCACTTGAGCCCAG AAGTTCTAGACCAGCCTGGGCAACATGGCAAGACCCTATCTC TACAAAAAAGTTAAAAAATCAGCCACGTGTGGTGACACAC ACCTGTAGTCCCAGCTATTCAGGAGGCTGAGGTGAGGGGATC ACTTAAGGCTGGGAGGTTGAGGCTGCAGTGAGTCGTGGTTGC GCCACTGCACTCCAGCCTGGGCAACAGTGAGACCCTGTCTCA AAAGACAAAAAAAAAAAAAAAAAAAAAAAGAACATATCCT GGTGTGGAGTAGGGGACGCTGCTCTGACAGAGGCTCGGGGG CCTGAGCTGGCTCTGTGAGCTGGGGAGGAGGCAGACAGCCA GGCCTTGTCTGCAAGCAGACCTGGCAGCATTGGGCTGGCCGC CCCCCAGGGCCTCCTCTTCATGCCCAGTGAATGACTCACCTT GGCACAGACACAATGTTCGGGGTGGGCACAGTGCCTGCTTCC CGCCGCACCCCAGCCCCCCTCAAATGCCTTCCGAGAAGCCCA TTGAGCAGGGGGCTTGCATTGCACCCCAGCCTGACAGCCTGG CATCTTGGGATAAAAGCAGCACAGCCCCCTAGGGGCTGCCCT TGCTGTGTGGCGCCACCGGCGGTGGAGAACAAGGCTCTATTC AGCCTGTGCCCAGGAAAGGGGATCAGGGGATGCCCCAGGCAT GGACAGTGGGTGGCAGGGGGGGAGAGGAGGGCTGTCTGCTT CCCAGAAGTCCAAGGACACAAATGGGTGAGGGGACTGGGCA GGGTTCTGACCCTGTGGGACCAGAGTGGAGGGCGTAGATGG ACCTGAAGTCTCCAGGGACAACAGGGCCCAGGTCTCAGGCT CCTAGTTGGGCCCAGTGGCTCCAGCGTTTCCAAACCCATCCA TCCCCAGAGGTTCTTCCCATCTCTCCAGGCTGATGTGTGGGA ACTCGAGGAAATAAATCTCCAGTGGGAGACGGAGGGGTGGC CAGGGAAACGGGGCGCTGCAGGAATAAAGACGAGCCAGCAC AGCCAGCTCATGTGTAACGGCTTTGTGGAGCTGTCAAGGCCT GGTCTCTGGGAGAGAGGCACAGGGAGGCCAGACAAGGAAG GGGTGACCTGGAGGGACAGATCCAGGGGCTAAAGTCCTGAT AAGGCAAGAGAGTGCCGGCCCCCTCTTGCCCTATCAGGACCT CCACTGCCACATAGAGGCCATGATTGACCCTTAGACAAAGG GCTGGTGTCCAATCCCAGCCCCCAGCCCCAGAACTCCAGGGA ATGAATGGGCAGAGAGCAGGAATGTGGGACATCTGTGTTCA AGGGAAGGACTCCAGGAGTCTGCTGGGAATGAGGCCTAGTA GGAAATGAGGTGGCCCTTGAGGGTACAGAACAGGTTCATTCT TCGCCAAATTCCCAGCACCTTGCAGGCACTTACAGCTGAGTG AGATAATGCCTGGGTTATGAAATCAAAAAGTTGGAAAGCAG GTCAGAGGTCATCTGGTACAGCCCTTCCTTCCCTTTTTTTTTT TTTTTTTTGTGAGACAAGGTCTCTCTCTGTTGCCCAGGCTGG AGTGGCGCAAACACAGCTCACTGCAGCCTCAACCTACTGGGC TCAAGCAATCCTCCAGCCTCAGCCTCCCAAAGTGCTGGGATT ACAAGCATGAGCCACCCCACTCAGCCCTTTCCTTCCTTTTTAA TTGATGCATAATAATTGTAAGTATTCATCATGGTCCAACCAA CCCTTTCTTGACCCACCTTCCTAGAGAGAGGGTCCTCTTGCTT CAGCGGTCAGGGCCCCAGACCCATGGTCTGGCTCCAGGTACC ACCTGCCTCATGCAGGAGTTGGCGTGCCCAGGAAGCTCTGCC |

TABLE 1-continued

| | | | Nucleic acid sequences |
|---|---|---|---|
| SEQ ID NO | Sequence Description | Sequence Type | Sequence |
| | | | TCTGGGCACAGTGACCTCAGTGGGGTGAGGGGAGCTCTCCCC ATAGCTGGGCTGCGGCCCAACCCCACCCCCTCAGGCTATGCC AGGGGGTGTTGCCAGGGGCACCCGGGCATCGCCAGTCTAGC CCACTCCTTCATAAAGCCCTCGCATCCCAGGAGCGAGCAGAG CCAGAGCAGGTTGGAGAGGAGACGCATCACCTCCGCTGCTC GCCGGG |
| 13 | hGH poly(A) signal | Nucleic Acid | GGGTGGCATCCCTGTGACCCCTCCCCAGTGCCTCTCCTGGCC CTGGAAGTTGCCACTCCAGTGCCCACCAGCCTTGTCCTAATA AAATTAAGTTGCATCATTTTGTCTGACTAGGTGTCCTTCTATA ATATTATGGGGTGGAGGGGGGTGGTATGGAGCAAGGGGCAA GTTGGGAAGACAACCTGTAGGGCCTGCGGGGTCTATTGGGA ACCAAGCTGGAGTGCAGTGGCACAATCTTGGCTCACTGCAAT CTCCGCCTCCTGGGTTCAAGCGATTCTCCTGCCTCAGCCTCCC GAGTTGTTGGGATTCCAGGCATGCATGACCAGGCTCAGCTAA TTTTTGTTTTTTTGGTAGAGACGGGGTTTCACCATATTGGCCA GGCTGGTCTCCAACTCCTAATCTCAGGTGATCTACCCACCTT GGCCTCCCAAATTGCTGGGATTACAGGCGTGAACCACTGCTC CCTTCCCTGTCCTT |
| 14 | bGH poly(A) signal (bGHpA) | Nucleic acid | CTGTGCCTTCTAGTTGCCAGCCATCTGTTGTTTGCCCCTCCCC CGTGCCTTCCTTGACCCTGGAAGGTGCCACTCCCACTGTCCTT TCCTAATAAAATGAGGAAATTGCATCGCATTGTCTGAGTAGG TGTCATTCTATTCTGGGGGGTGGGGTGGGGCAGGACAGCAA GGGGGAGGATTGGGAAGAGAATAGCAGGCATGCTGGGGA |
| 15 | pGfa681 promoter (also called "GfaABC1D promoter") | Nucleic acid | AACATATCCTGGTGTGGAGTAGGGGACGCTGCTCTGACAGA GGCTCGGGGGCCTGAGCTGGCTCTGTGAGCTGGGGAGGAGG CAGACAGCCAGGCCTTGTCTGCAAGCAGACCTGGCAGCATTG GGCTGGCCGCCCCCCAGGGCCTCCTCTTCATGCCCAGTGAAT GACTCACCTTGGCACAGACACAATGTTCGGGGTGGGCACAGT GCCTGCTTCCCGCCGCACCCCAGCCCCCCTCAAATGCCTTCC GAGAAGCCCATTGAGCAGGGGGCTTGCATTGCACCCCAGCCT GACAGCCTGGCATCTTGGGATAAAAGCAGCACAGCCCCCTA GGGGCTGCCCTTGCTGTGTGGCGCCACCGGCGGTGGAGAAC AAGGCTCTATTCAGCCTGTGCCCAGGAAAGGGGATCAGGGG ATGCCCAGGCATGGACAGTGGGTGGCAGGGGGGGAGAGGAG GGCTGTCTGCTTCCCAGAAGTCCAAGGACACAAATGGGTGA GGGGAGAGCTCTCCCCATAGCTGGGCTGCGGCCCAACCCCAC CCCCTCAGGCTATGCCAGGGGGTGTTGCCAGGGGCACCCGG GCATCGCCAGTCTAGCCCACTCCTTCATAAAGCCCTCGCATC CCAGGAGCGAGCAGAGCCAGAGCAGGTTGGAGAGGAGACG CATCACCTCCGCTGCTCGC |
| 16 | CRGI Chimeric Intron | Nucleic acid | GGAGTCGCTGCGTTGCCTTCGCCCCGTGCCCCGCTCCGCGCC GCCTCGCGCCGCCCGCCCCGGCTCTGACTGACCGCGTTACTC CCACAGGTGAGCGGGCGGGACGGCCCTTCTCCTCCGGGCTG TAATTAGCGCTTGGTTTAATGACGGCTCGTTTCTTTTCTGTGG CTGCGTGAAAGCCTTAAAGGGCTCCGGGAGGGCCTTTGTGCG GGGGGGAGCGGCTCGGGGGGTGCGTGCGTGTGTGTGCGT GGGGAGCGCCGCGTGCGGCCCGCGCTGCCCGGCGGCTGTGA GCGCTGCGGGCGCGGCGCGGGGCTTTGTGCGCTCCGCGTGTG CGCGAGGGGAGCGCGGGCCGGGGGCGGTGCCCCGCGGTGCG GGGGGGCTGCGAGGGGAACAAAGGCTGCGTGCGGGGTGTGT GCGTGGGGGGGTGAGCAGGGGGTGTGGGCGCGGCGGTCGGG CTGTAACCCCCCCCTGGCACCCCCCTCCCCGAGTTGCTGAGC ACGGCCCGGCTTCGGGTGCGGGGCTCCGTGCGGGGCGTGGC GCGGGGCTCGCCGTGCCGGGCGGGGGGTGGCGGCAGGTGGG GGTGCCGGGCGGGGCGGGGCCGCCTCGGGCCGGGGAGGGCT CGGGGGAGGGGCGCGGCGGCCCCCGGAGCGCCGGCGGCTGTC GAGGCGCGGCGAGCCGCAGCCATTGCCTTTTATGGTAATCGT GCGAGAGGGCGCAGGGACTTCCTTTGTCCCAAATCTGGCGGA GCCGAAATCTGGGAGGCGCCGCCGCACCCCCTCTAGCGGGC GCGGCGAAGCGGTGCGGCGCCGGCAGGAAGGAAATGGGC GGGGAGGGCCTTCGTGCGTCGCCGCGCCGCCGTCCCCTTCTC CATCTCCAGCCTCGGGGCTGCCGCAGGGGGACGGCTGCCTTC GGGGGGGACGGGGCAGGGCGGGGTTCGGCTTCTGGCGTGTG ACCGGCGGCTTTAGAGCCTCTGCTAACCATGTTCATGCCTTCT TCTTTTTCCTACAGCTCCTGGGCAACGTGCTGGTTGTTGTGCT GTCTCATCATTTTGGCAAAGAT |
| 17 | GFAP first intron (GI) | Nucleic acid | GGCCACTGTGAGGCAGAAGTGAGGAGGGGATGGGGAAGGG GGGCCTTGTGAGCAGAAGGGGCTGAATCCCCAAGAAGGAGT GCCCGAGAGTCTCAGGGAGGGGCCGAACCTCCCTGCTCCCT GGGCCTCCCTACCTCTTGATGGGGCACTATCCTTGCCCCCCA |

TABLE 1-continued

Nucleic acid sequences

| SEQ ID NO | Sequence Description | Sequence Type | Sequence |
|---|---|---|---|
| | | | ACATGATGGGAGGGACCAGAAACAGGCCCAGGGCCCCGGGG<br>ATCTGATGCCCGCATGCCTTCTGCCAGGAGTCCAGGGTCCCC<br>TCAGCACCTCCCTACTGGGGAAAGCAGTGCAGGAGCAGCGG<br>GGCCCCTGTGTTTCATTCATGGCTGGGCTTTGTGACTGTGGGC<br>AGCGAGCTCACCTATTCTGAGCCTGTGTCCATATAAAGGAGG<br>AGTTGGAAGCGGAGAAGGTTGATGTCCATGAGGGAGATTGG<br>ATTCTGGGGTGAAGAAAGTGAGGGAAAGAGCAGGCAGGTCT<br>GGGCGCAAAGCACAGGTGACTGCCTGCCACCAGCTTGTGAC<br>CCCCATCAAGTTACTTTGACTTGCACAGCTGTGAAGCGGTGG<br>TCATAATAAAATTCATTTCAAAAGGTGGTTACCTGGGATCAG<br>AGGAATCCCCAGGGGCATGGCGCTTCACTGAGCTGACAGGA<br>CATGCATGTGTGCCTTCAAGTGCAGGAGGACATGTGCGTGTG<br>TGTGTGTGTGTGTGCAACAGTGAGTGTATGCTTGTGGATGCG<br>CCTGTGTGAGCAGAAGCAGGTGCACCAACCCTGATAAGGCA<br>CCTTAGTAATGAGTTAAGGCAAAAGCCCACATCTGCTCATCC<br>TCCAGACAAGTCCTCTGTCTAAGGCCCCCCAACCCTTAATCC<br>TCCTGCTGCTCTACTGGTCCTGGGTGGGGGTGGTCTCTGTGA<br>CAGCTGCCTCAAGGGAGACTGAGGCAGGTATTCAAGTGTCCT<br>CAGAAGAGCCTGGACCCAGGAATGTGTCCCCCCACTCCAGG<br>CTCCAGGATGAAACCAACCTGA<br>GAGCATCTTACCGCCATTTATACCCATATTTGTTCTGTTTTTC |
| 18 | Optimized version of WPRE (oPRE), | Nucleic acid | TTGATTTGGGTATACATTTAAATGTTAATAAAACAAAATGGT<br>GGGGCAATCATTTACATTTTTAGGGATATGTAATTACTAGTT<br>CAGGTGTATTGCCACAAGACAAACATGTTAAGAAACTTTCCC<br>GTTATTTACGCTCTGTTCCTGTTAATCAACCTCTGGATTACAA<br>AATTTGTGAAAGATTGACTGATATTCTTAACTATGTTGCTCCT<br>TTTACGCTGTGTGGATATGCTGCTTTATAGCCTCTGTATCTAG<br>CTATTGCTTCCCGTACGGCTTTCGTTTTCTCCTCCTTGTATAA<br>ATCCTGGTTGCTGTCTCTTTTAGAGGAGTTGTGGCCCGTTGTC<br>CGTCAACGTGGCGTGGTGTGCTCTGTGTTTGCTGACGCAACC<br>CCCACTGGCTGGGGCATTGCCACCACCTGTCAACTCCTTTCT<br>GGGACTTTCGCTTTCCCCCTCCCGATCGCCACGGCAGAACTC<br>ATCGCCGCCTGCCTTGCCCGCTGCTGGACAGGGGCTAGGTTG<br>CTGGGCACTGATAATTCCGTGGTGTTGTC |
| 19 | Forward ITR primer | Nucleic acid | GGAACCCCTAGTGATGGAGTT |
| 20 | Reverse ITR primer | Nucleic acid | CGGCCTCAGTGAGCGA |

DETAILED DESCRIPTION

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to be inclusive of the edges of the range as well as any number between the defined edges of the range. For example, "between 1 and 10" includes any number between 1 and 10, as well as the number 1 and the number 10.

When the term "about" is used in reference to a number, it is understood to mean plus or minus 10%. For example, "about 100" would include from 90 to 110.

As used herein "hND1" refers to a human neuronal differentiation (NeuroD1) gene or protein.

As used herein "CE" refers to a cytomegalovirus (CMV) promoter enhancer sequence.

As used herein "EE" refers to an Ef1 alpha promoter enhancer sequence.

As used herein "pGfa681" refers to a human glial fibrillary acid protein (GFAP) promoter truncated sequence of 681 bp size.

As used herein "CI" refers to a chimeric intron composed of the 5'-donor site from the first intron of the human β-globin gene and the branch and 3'-acceptor site from the intron of an immunoglobulin gene heavy chain variable region.

As used herein "CRGI" refers to a chimeric intron of rabbit beta-globing and chicken beta actin similar in CAG promoter.

As used herein "GI" refers to a human glial fibrillary acid protein (GFAP) first intron.

As used herein "WPRE" refers to a Woodchuck Hepatitis Virus (WHV) Posttranscriptional Regulatory Element.

As used herein "oPRE" refers to an optimized version of WPRE.

As used herein "SV40pA" refers to a poly A signal of SV40 virus.

As used herein "bGHpA" refers to a poly A signal of bovine growth hormone.

As used herein "vg" refers to a viral genome.

As used herein "p2A" refers to a 2A self-cleavage peptide sequence from porcine teschovirus-1.

Any composition or vector provided herein is specifically envisioned for use with any method provided herein.

In an aspect, methods and compositions provided herein comprise a vector. As used herein, the term "vector" refers to a circular, double-stranded DNA molecule that is physically separate from chromosomal DNA. It should be noted that the term "vector" can be used interchangeably with the term "plasmid."

In an aspect, a vector provided herein is a recombinant vector. As used herein, the term "recombinant vector" refers to a vector that comprises a recombinant nucleic acid. As used herein, a "recombinant nucleic acid" refers to a nucleic acid molecule formed by laboratory methods of genetic recombination, such as, without being limiting, molecular cloning. A recombinant vector can be formed by laboratory methods of genetic recombination, such as, without being limiting, molecular cloning. Also, without being limiting, one skilled in the art can create a recombinant vector de novo via synthesizing a plasmid by individual nucleotides, or by splicing together nucleic acid molecules from different pre-existing vectors.

Adeno-associated viruses (AAVs) are replication-defective, non-enveloped *Dependoparvovirus* viruses that infect humans and additional primate species. AAVs are not known to cause disease in any species, although they can cause mild immune responses. AAVs can infect dividing and quiescent cells. AAVs are stably integrate into the human genome at a specific site in chromosome 19 termed the AAVS1 locus (nucleotides 7774-11429 of GenBank Accession No. AC010327.8), although random integrations at other loci in the human genome are possible.

AAVs comprise a linear genome with a single-stranded DNA of about 4700 nucleotides in length. The genome of AAVs also includes a 145 nucleotide-long inverted terminal repeat (ITR) at each end of the genome. The ITRs flank two viral genes rep (for replication, encoding non-structural proteins) and cap (for capsid, encoding structural proteins). The ITRs contain all of the cis-acting elements need for genome rescue, replication, and packaging of the AAV.

When used in gene therapy approaches, the rep and cap genes of the AAV genome sequence are removed and replaced with DNA of interest positioned between two AAV ITRs. As used herein, an "AAV vector construct" refers to a DNA molecule comprising a desired sequence inserted between two AAV ITR sequences. As used herein, an "AAV vector" refers to an AAV packaged with a DNA vector construct.

As used herein, the term "AAV vector serotype" mainly refers to a variation within the capsid proteins of an AAV vector.

In an aspect, an AAV vector is selected from the group consisting of AAV vector serotype 1, AAV vector serotype 2, AAV vector serotype 3, AAV vector serotype 4, AAV vector serotype 5, AAV vector serotype 6, AAV vector serotype 7, AAV vector serotype 8, AAV vector serotype 9, AAV vector serotype 10, AAV vector serotype 11, and AAV vector serotype 12. In one aspect, an AAV vector is selected from the group consisting AAV serotype 2, AAV serotype 5, and AAV serotype 9. In one aspect, an AAV vector is AAV serotype 1. In one aspect, an AAV vector is AAV serotype 2. In one aspect, an AAV vector is AAV serotype 3. In one aspect, an AAV vector is AAV serotype 4. In one aspect, an AAV vector is AAV serotype 5. In one aspect, an AAV vector is AAV serotype 6. In one aspect, an AAV vector is AAV serotype 7. In one aspect, an AAV vector is AAV serotype 8. In one aspect, an AAV vector is AAV serotype 9. In one aspect, an AAV vector is AAV serotype 10. In one aspect, an AAV vector is AAV serotype 11. In one aspect, an AAV vector is AAV serotype 12.

In an aspect, an AAV vector ITR is selected from the group consisting of an AAV serotype 1 ITR, an AAV serotype 2 ITR, an AAV serotype 3 ITR, an AAV serotype 4 ITR, an AAV serotype 5 ITR, an AAV serotype 6 ITR, an AAV serotype 7 ITR, an AAV serotype 8 ITR, an AAV serotype 9 ITR, an AAV serotype 10 ITR, an AAV serotype 11 ITR, and an AAV serotype 12 ITR. In one aspect, an AAV vector ITR is an AAV serotype 1 ITR. In one aspect, an AAV vector ITR is an AAV serotype 2 ITR. In one aspect, an AAV vector ITR is an AAV serotype 3 ITR. In one aspect, an AAV vector ITR is an AAV serotype 4 ITR. In one aspect, an AAV vector ITR is an AAV serotype 5 ITR. In one aspect, an AAV vector ITR is an AAV serotype 6 ITR. In one aspect, an AAV vector ITR is an AAV serotype 7 ITR. In one aspect, an AAV vector ITR is an AAV serotype 8 ITR. In one aspect, an AAV vector ITR is an AAV serotype 9 ITR. In one aspect, an AAV vector ITR is an AAV serotype 10 ITR. In one aspect, an AAV vector ITR is an AAV serotype 11 ITR. In one aspect, an AAV vector ITR is an AAV serotype 12 ITR.

In an aspect, at least one AAV vector ITR nucleic acid sequence is selected from the group consisting of SEQ ID NOs: 1 and 9. In one aspect, at least one AAV vector ITR nucleic acid sequence is SEQ ID NO: 1. In one aspect, at least one AAV vector ITR nucleic acid sequence is SEQ ID NO: 9.

In an aspect, an AAV ITR nucleic acid sequence comprises a sequence at least 70% identical to SEQ ID NO: 1, or the complement thereof. In one aspect, an AAV ITR nucleic acid sequence comprises a sequence at least 75% identical to SEQ ID NO: 1, or the complement thereof. In one aspect, an AAV ITR nucleic acid sequence comprises a sequence at least 80% identical to SEQ ID NO: 1, or the complement thereof. In one aspect, an AAV ITR nucleic acid sequence comprises a sequence at least 85% identical to SEQ ID NO: 1, or the complement thereof. In one aspect, an AAV ITR nucleic acid sequence comprises a sequence at least 90% identical to SEQ ID NO: 1, or the complement thereof. In one aspect, an AAV ITR nucleic acid sequence comprises a sequence at least 91% identical to SEQ ID NO:

1, or the complement thereof. In one aspect, an AAV ITR nucleic acid sequence comprises a sequence at least 92% identical to SEQ ID NO: 1, or the complement thereof. In one aspect, an AAV ITR nucleic acid sequence comprises a sequence at least 93% identical to SEQ ID NO: 1, or the complement thereof. In one aspect, an AAV ITR nucleic acid sequence comprises a sequence at least 94% identical to SEQ ID NO: 1, or the complement thereof. In one aspect, an AAV ITR nucleic acid sequence comprises a sequence at least 95% identical to SEQ ID NO: 1, or the complement thereof. In one aspect, an AAV ITR nucleic acid sequence comprises a sequence at least 96% identical to SEQ ID NO: 1, or the complement thereof. In one aspect, an AAV ITR nucleic acid sequence comprises a sequence at least 97% identical to SEQ ID NO: 1, or the complement thereof. In one aspect, an AAV ITR nucleic acid sequence comprises a sequence at least 98% identical to SEQ ID NO: 1, or the complement thereof. In one aspect, an AAV ITR nucleic acid sequence comprises a sequence at least 99% identical to SEQ ID NO: 1, or the complement thereof. In one aspect, an AAV ITR nucleic acid sequence comprises a sequence at least 99.5% identical to SEQ ID NO: 1, or the complement thereof. In one aspect, an AAV ITR nucleic acid sequence comprises a sequence at least 99.8% identical to SEQ ID NO: 1, or the complement thereof. In one aspect, an AAV ITR nucleic acid sequence comprises a sequence at least 99.9% identical to SEQ ID NO: 1, or the complement thereof. In one aspect, an AAV ITR nucleic acid sequence comprises a sequence 100% identical to SEQ ID NO: 1, or the complement thereof.

In an aspect, an AAV ITR nucleic acid sequence comprises a sequence at least 70% identical to SEQ ID NO: 9, or the complement thereof. In one aspect, an AAV ITR nucleic acid sequence comprises a sequence at least 75% identical to SEQ ID NO: 9, or the complement thereof. In one aspect, an AAV ITR nucleic acid sequence comprises a sequence at least 80% identical to SEQ ID NO: 9, or the complement thereof. In one aspect, an AAV ITR nucleic acid sequence comprises a sequence at least 85% identical to SEQ ID NO: 9, or the complement thereof. In one aspect, an AAV ITR nucleic acid sequence comprises a sequence at least 90% identical to SEQ ID NO: 9, or the complement thereof. In one aspect, an AAV ITR nucleic acid sequence comprises a sequence at least 91% identical to SEQ ID NO: 9, or the complement thereof. In one aspect, an AAV ITR nucleic acid sequence comprises a sequence at least 92% identical to SEQ ID NO: 9, or the complement thereof. In one aspect, an AAV ITR nucleic acid sequence comprises a sequence at least 93% identical to SEQ ID NO: 9, or the complement thereof. In one aspect, an AAV ITR nucleic acid sequence comprises a sequence at least 94% identical to SEQ ID NO: 9, or the complement thereof. In one aspect, an AAV ITR nucleic acid sequence comprises a sequence at least 95% identical to SEQ ID NO: 9, or the complement thereof. In one aspect, an AAV ITR nucleic acid sequence comprises a sequence at least 96% identical to SEQ ID NO: 9, or the complement thereof. In one aspect, an AAV ITR nucleic acid sequence comprises a sequence at least 97% identical to SEQ ID NO: 9, or the complement thereof. In one aspect, an AAV ITR nucleic acid sequence comprises a sequence at least 98% identical to SEQ ID NO: 9, or the complement thereof. In one aspect, an AAV ITR nucleic acid sequence comprises a sequence at least 99% identical to SEQ ID NO: 9, or the complement thereof. In one aspect, an AAV ITR nucleic acid sequence comprises a sequence at least 99.5% identical to SEQ ID NO: 9, or the complement thereof. In one aspect, an AAV ITR nucleic acid sequence comprises a sequence at least 99.8% identical to SEQ ID NO: 9, or the complement thereof. In one aspect, an AAV ITR nucleic acid sequence comprises a sequence at least 99.9% identical to SEQ ID NO: 9, or the complement thereof. In one aspect, an AAV ITR nucleic acid sequence comprises a sequence 100% identical to SEQ ID NO: 9, or the complement thereof.

The terms "percent identity" or "percent identical" as used herein in reference to two or more nucleotide or amino acid sequences is calculated by (i) comparing two optimally aligned sequences (nucleotide or amino acid) over a window of comparison (the "alignable" region or regions), (ii) determining the number of positions at which the identical nucleic acid base (for nucleotide sequences) or amino acid residue (for proteins and polypeptides) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

When percentage of sequence identity is used in reference to amino acids it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool® (BLAST™), etc., that can be used to compare the sequence identity or similarity between two or more nucleotide or amino acid sequences. Although other alignment and comparison methods are known in the art, the alignment and percent identity between two sequences (including the percent identity ranges described above) can be as determined by the ClustalW algorithm, see, e.g., Chenna et al., "Multiple sequence alignment with the Clustal series of programs," *Nucleic Acids Research* 31: 3497-3500 (2003); Thompson et al., "Clustal W: Improving the sensitivity of progressive multiple sequence alignment through sequence weighting, position-specific gap penalties and weight matrix choice," *Nucleic Acids Research* 22: 4673-4680 (1994); Larkin M A et al., "Clustal W and Clustal X version 2.0," *Bioinformatics* 23: 2947-48 (2007); and Altschul et al. "Basic local alignment search tool." *J. Mol. Biol.* 215:403-410 (1990), the entire contents and disclosures of which are incorporated herein by reference.

The terms "percent complementarity" or "percent complementary" as used herein in reference to two nucleotide sequences is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

The use of the term "polynucleotide," "nucleic acid sequence," or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In one aspect, a nucleic acid molecule provided herein is an RNA molecule. In one aspect, a nucleic acid molecule provided herein is single-stranded. In one aspect, a nucleic acid molecule provided herein is double-stranded. A nucleic acid molecule can encode a polypeptide or a small RNA.

As used herein, the term "polypeptide" refers to a chain of at least two covalently linked amino acids. Polypeptides can be encoded by polynucleotides provided herein. Proteins provided herein can be encoded by nucleic acid molecules provided herein. Proteins can comprise polypeptides provided herein. As used herein, a "protein" refers to a chain of amino acid residues that is capable of providing structure or enzymatic activity to a cell. As used herein, a "coding sequence" refers to a nucleic acid sequence that encodes a protein.

As used herein, the term "CpG site" or "CG site" refers to a region of DNA sequence where a cytosine and guanine is separated by only one phosphate group.

As used herein, the term "CpG island" of "CG island" refers to CpG sites that occur with a high frequency.

As used herein, the term "codon" refers to a sequence of three nucleotides.

As used herein, the term "codon optimized" refers to a code that is modified for enhanced expression in a host cell of interest by replacing at least one codon of a sequence with codons that are more frequently or most frequently used in the genes of the host cell while maintaining the original amino acid sequence.

As used herein, the term "enhancer" refers to a region of DNA sequence that operates to initiate, assist, affect, cause, and/or promote the transcription and expression of the associated transcribable DNA sequence or coding sequence, at least in certain tissue(s), developmental stage(s) and/or condition(s). In an aspect, an enhancer is a cis enhancer. In one aspect, an enhancer is a trans enhancer.

Enhancer sequences can be identified by utilizing genomic techniques well known in the art. Non-limiting examples include use of a reporter gene and next-generation sequencing methods such as chromatin immunoprecipitation sequencing (ChIP-seq), DNase I hypersensitivity sequencing (DNase-seq), micrococcal nuclease sequencing (MNase-seq), formaldehyde-assisted isolation of regulatory elements sequencing (FAIRE-seq), and assay for transposase accessible chromatin sequencing (ATAC-seq).

As used herein, the term "operably linked" refers to a functional linkage between a promoter or other regulatory element and an associated transcribable DNA sequence or coding sequence of a gene (or transgene), such that the promoter, etc., operates to initiate, assist, affect, cause, and/or promote the transcription and expression of the associated transcribable DNA sequence or coding sequence, at least in certain tissue(s), developmental stage(s) and/or condition(s). As used herein, "regulatory elements" refer to any sequence elements that regulate, positively or negatively, the expression of an operably linked sequence. "Regulatory elements" include, without being limiting, a promoter, an enhancer, a leader, a transcription start site (TSS), a linker, 5' and 3' untranslated regions (UTRs), an intron, a polyadenylation signal, and a termination region or sequence, etc., that are suitable, necessary or preferred for regulating or allowing expression of the gene or transcribable DNA sequence in a cell. Such additional regulatory element(s) can be optional and used to enhance or optimize expression of the gene or transcribable DNA sequence.

As used herein, the term "promoter" refers to a DNA sequence that contains an RNA polymerase binding site, a transcription start site, and/or a TATA box and assists or promotes the transcription and expression of an associated transcribable polynucleotide sequence and/or gene (or transgene). A promoter can be synthetically produced, varied, or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein.

As used herein, an "intron" refers to a nucleotide sequence that is removed by RNA splicing as a messenger RNA (mRNA) matures from a mRNA precursor.

As used herein, "mRNA" or "messenger RNA" refers to a single stranded RNA that corresponds to the genetic sequence of a gene.

Expression of mRNA can be measured using any suitable method known in the art. Non-limiting examples of measuring mRNA expression include quantitative reverse transcriptase polymerase chain reaction (qRT-PCR), RNA blot (e.g., a Northern blot), and RNA sequencing. Differences in expression can be described as an absolute quantification or a relative quantification. See, for example, Livak and Schmittgen, *Methods,* 25:402-408 (2001).

As used herein, the term "glial" or "glial cell" refers to a non-neuronal cell in the CNS or the PNS. In an aspect, at least one glial cell is selected from the group consisting of at least one oligodendrocyte, at least one astrocyte, at least one NG2 cell, at least one ependymal cell, and at least one microglia. In one aspect, at least one glial cell is at least one oligodendrocyte. In one aspect, at least one glial cell is at least one NG2 cell. In one aspect, at least one glial cell is at least one ependymal cell. In one aspect, at least one glial cell is at least one microglia. In one aspect, at least one glial cell is at least one reactive astrocyte. In one aspect, at least one astrocyte is at least one reactive astrocyte.

As used herein, the term "astrocyte" refers to a glial cell that is an important component of the brain. An astrocyte is involved in supporting neuronal functions such as synapse formation and plasticity, potassium buffering, nutrient supply, the secretion and absorption of neural or glial transmitters, and maintenance of the blood-brain barrier. As used herein, the term "reactive astrocytes" refers to an abnormal status of astrocytes after injury or disease.

As used herein, the term "NG2 cell" or "polydendrocyte" refers to a glial cell that expresses chondroitin sulfate proteoglycan (CSPG4) and the alpha receptor for platelet-derived growth factor (PDGFRA).

As used herein, the term "neuron" or "neuronal cell" refers to an electrically excitable cell that communicates with other neurons via synapses. In an aspect, a neuron is selected from the group consisting of an unipolar neuron, a bipolar neuron, a pseudounipolar neuron, and a multipolar neuron. In one aspect, a neuron is an unipolar neuron. In one aspect, a neuron is a bipolar neuron. In one aspect, a neuron is apseudounipolar neuron. In one aspect, a neuron is a bipolar neuron. In one aspect, a neuron is selected from the group consisting of a sensory neuron, a motor neuron, and an interneuron. In one aspect, a neuron is a sensory neuron. In one aspect, a neuron is a motor neuron. In one aspect, a neuron is an interneuron.

As used herein, the term "functional neuron" refers to a neuron that can perform biological process. Without being limiting, examples of biological processes include processing and transmission of information and communication via chemical and electrical synapses.

As used herein, the term "glutamatergic neurons" refers to a subclass of neurons that produce glutamate and establish excitatory synapses. As used herein, the term "excitatory synapse" refers to a synapse in which an action potential in a presynaptic neuron increases the probability of an action potential occurring in a postsynaptic cell. As used herein, the term "action potential" or "nerve impulse" refers to an electrical impulse across the membrane of an axon. As used herein, the term "axon" or "nerve fiber" refers to a neuron that conducts action potentials. As used herein, the term "GABAergic neurons" refers to a subset of neurons that produce GABA and establish inhibitory synapses. As used herein, the term "GABA" or "gamma-Aminobutyric acid" refers to a compound that opens ion channels to allow the flow of negatively charged chloride ions into the cell or positively charged potassium ions out of the cell. As used herein, the term "inhibitory synapse" refers to a synapse that moves the membrane potential of a postsynaptic neuron away from the threshold for generating action potentials. As used herein, the term "dopaminergic neuron" refers to a subset of neurons that produce dopamine. As used herein, the term "dopamine" refers to a type of neurotransmitter. As used herein, the term "neurotransmitter" refers to a class of endogenous chemicals that activate neurotransmissions. As used herein, the term "neurotransmission" refers to a process where neurotransmitters are released by the axon terminal of a neuron. As used herein, the term "acetyl cholinergic neuron" or "cholinergic neuron" refers to a subset of neurons that secrete acetylcholine. As used herein, the term "acetylcholine" refers to a type of neurotransmitter. As used herein, the term "seratonergic neuron" refers to a subset of neurons that synthesizes serotonin. As used herein, the term "serotonin" refers to a type of neurotransmitter. As used herein, an "epinephrinergic neuron" refers to a neuron that releases epinephrine as the neurotransmitter. As used herein, the term "motor neuron" refers to a subset of neurons where the cell body is located in the motor cortex, brainstem, or the spinal cord and the axon projects to the spinal cord or outside the spinal cord and directly or indirectly controls muscles and glands. As used herein, the term peptidergic neuron refers to a subset of neurons that utilize small peptide molecules as their neurotransmitter.

In an aspect, a neuron is a functional neuron. In one aspect, a functional neuron is selected from the group consisting of glutamatergic neurons, GABAergic neurons, dopaminergic neurons, cholinergic neurons, seratonergic neurons, epinephrinergic neurons, motor neurons, and peptidergic neurons. In one aspect, a functional neuron is a glutamatergic neuron. In one aspect, a functional neuron is a GABAergic neuron. In one aspect, a functional neuron is a dopaminergic neuron. In one aspect, a functional neuron is a cholinergic neuron. In one aspect, a functional neuron is a seratonergic neuron. In one aspect, a functional neuron is an epinephrinergic neuron. In one aspect, a functional neuron is a motor neuron. In one aspect, a functional neuron is a peptidergic neuron.

As used herein, the term "converting" or "converted" refers to a cell type changing its physical morphology and/or biological function into a different physical morphology and/or different biological function. In an aspect, this disclosure provides the conversion of at least one glial cell into at least one neuron. In one aspect, conversion of at least one glial cell to at least one neuron occurs in the CNS or PNS. In one aspect, conversion of at least one glial cell to at least one neuron occurs in the CNS. In one aspect, conversion of at least one glial cell to at least one neuron occurs in the PNS.

In an aspect, this disclosure provides, and includes, an adeno-associated virus (AAV) vector comprising a human neurogenic differentiation 1 (hNeuroD1) sequence comprising the nucleic acid sequence of SEQ ID NO: 6, where the hNeuroD1 sequence is operably linked to regulatory elements comprising: (a) a glial fibrillary acid protein (GFAP) promoter comprising a nucleic acid sequence selected from the group consisting of SEQ ID NOs: 4, 12, and 15; (b) an enhancer from a human elongation factor-1 alpha (EF1-α) promoter comprising the nucleic acid sequence of SEQ ID NO: 2 or cytomegalovirus (CMV) enhancer comprising the nucleic acid sequence of SEQ ID NO: 11; (c) a chimeric intron comprising the nucleic acid sequence of SEQ ID NO: 5 or 16; (d) a woodchuck hepatitis virus posttranscriptional regulatory element (WPRE) comprising the nucleic acid sequence selected from the group consisting of SEQ ID NO: 7 and 18; and (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

In an aspect, this disclosure provides an adeno-associated virus (AAV) vector comprising a nucleic acid coding sequence encoding a human neurogenic differentiation 1 (hNeuroD1) protein comprising the amino acid sequence if SEQ ID NO: 10, where the coding sequence is operably linked to regulatory elements comprising: (a) a glial fibrillary acid protein (GFAP) promoter comprising a nucleic acid sequence selected from the group consisting of SEQ ID NOs: 4, 12, and 15; (b) an enhancer from a human elongation factor-1 alpha (EF-1 alpha) promoter comprising the nucleic acid sequence of SEQ ID NO: 2 or cytomegalovirus (CMV) enhancer comprising the nucleic acid sequence of SEQ ID NO: 11; (c) a chimeric intron comprising the nucleic acid sequence of SEQ ID NO: 5 or 16; a woodchuck hepatitis virus posttranscriptional regulatory element (WPRE) comprising the nucleic acid sequence selected from the group consisting of SEQ ID NOs: 7 and 18; and a SV40 polyadenylation signal sequence with a nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

In an aspect, this disclosure provides, and includes, an adeno-associated virus (AAV) vector comprising a neurogenic differentiation 1 (NeuroD1) nucleic acid coding sequence encoding a NeuroD1 protein, where the coding sequence is operably linked to regulatory elements comprising: (a) a glial fibrillary acid protein (GFAP) promoter; (b) an enhancer; (c) a chimeric intron; (d) a woodchuck hepatitis virus posttranscriptional regulatory element (WPRE); and (e) a polyadenylation signal sequence.

In an aspect, this disclosure provides, and includes, a composition comprising an adeno-associated virus (AAV) vector for converting glial cells to functional neurons in a human, where the AAV vector comprises a human neurogenic differentiation 1 (hNeuroD1) sequence having a nucleic acid sequence of SEQ ID NO: 6, and where the sequence is operably linked to regulatory elements comprising: (a) a human glial fibrillary acid protein (GFAP) promoter comprising a nucleic acid sequence selected from the group consisting of SEQ ID NOs: 4, 12, and 15; (b) an enhancer from the human elongation factor-1 alpha (EF-1 alpha) promoter comprising the nucleic acid sequence of SEQ ID NO: 2 or cytomegalovirus (CMV) enhancer comprising the nucleic acid sequence of SEQ ID NO: 11; (c) a chimeric intron comprising the nucleic acid sequence of SEQ ID NO: 5 or 16; (d) a woodchuck hepatitis virus posttranscriptional regulatory element (WPRE) comprising the nucleic acid sequence selected from the group consisting of SEQ ID NOs: 7 and 18; and (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

In an aspect, this disclosure provides, and includes, a composition comprising an adeno-associated virus (AAV) vector for converting glial cells to functional neurons in a human, where the AAV vector comprises a nucleic acid coding sequence encoding a human neurogenic differentiation 1 (hNeuroD1) protein comprising the amino acid sequence of SEQ ID NO: 10, and where the coding sequence is operably linked to regulatory elements comprising: (a) a human glial fibrillary acid protein (GFAP) promoter comprising a nucleic acid sequence selected from the group consisting of SEQ ID NOs: 4, 12, and 15; (b) an enhancer from the human elongation factor-1 alpha (EF-1 alpha) promoter comprising the nucleic acid sequence of SEQ ID NO: 2 or cytomegalovirus (CMV) enhancer comprising the nucleic acid sequence of SEQ ID NO: 11; (c) a chimeric intron comprising the nucleic acid sequence of SEQ ID NO: 5 or 16; (d) a woodchuck hepatitis virus posttranscriptional regulatory element (WPRE) comprising the nucleic acid sequence selected from the group consisting of SEQ ID NOs: 7 and 18; and (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

In an aspect, this disclosure provides, and includes, a composition comprising an adeno-associated virus (AAV) vector for the treatment of a subject in need thereof, where the AAV vector comprises a neurogenic differentiation 1 (NeuroD1) sequence operably linked to expression control elements comprising: (a) a glial fibrillary acid protein (GFAP) promoter; (b) an enhancer; (c) a chimeric intron; (d) a woodchuck hepatitis virus posttranscriptional regulatory element (WPRE); and (e) a polyadenylation signal.

In an aspect, an AAV vector comprises a nucleic acid sequence encoding an AAV protein. In one aspect, an AAV vector comprises a nucleic acid sequence encoding a viral protein. Non-limiting examples of AAV proteins and viral proteins include rep and cap proteins.

Neurogenic differentiation 1 (NeuroD1; also referred to as β2) is a basic helix-loop-helix (bHLH) transcription factor that forms heterodimers with other bHLH proteins to activate transcription of genes that contain a DNA sequence known as an E-box.

In an aspect, a NeuroD1 sequence is a human NeuroD1 (hNeuroD1) sequence. In one aspect, a NeuroD1 sequence is selected from the group consisting of a chimpanzee NeuroD1 sequence, a bonobo NeuroD1 sequence, an orangutan NeuroD1 sequence, a gorilla NeuroD1 sequence, a macaque NeuroD1 sequence, a marmoset NeuroD1 sequence, a capuchin NeuroD1 sequence, a baboon NeuroD1 sequence, a gibbon NeuroD1 sequence, and a lemur NeuroD1 sequence. In one aspect, a NeuroD1 sequence is a chimpanzee NeuroD1 sequence. In one aspect, a NeuroD1 sequence is a bonobo NeuroD1 sequence. In one aspect, a NeuroD1 sequence is an orangutan NeuroD1 sequence. In one aspect, a NeuroD1 sequence is a gorilla NeuroD1 sequence. In one aspect, a NeuroD1 sequence is a macaque NeuroD1 sequence. In one aspect, a NeuroD1 sequence is a marmoset NeuroD1 sequence. In one aspect, a NeuroD1 sequence is a capuchin NeuroD1 sequence. In one aspect, a NeuroD1 sequence is a baboon NeuroD1 sequence. In one aspect, a NeuroD1 sequence is a gibbon NeuroD1 sequence. In one aspect, a NeuroD1 sequence is a lemur NeuroD1 sequence.

In an aspect, a NeuroD1 nucleic acid sequence comprises a sequence at least 70% identical to SEQ ID NO: 6, or the complement thereof. In one aspect, a NeuroD1 nucleic acid sequence comprises a sequence at least 75% identical to SEQ ID NO: 6, or the complement thereof. In one aspect, a NeuroD1 nucleic acid sequence comprises a sequence at least 80% identical to SEQ ID NO: 6, or the complement thereof. In one aspect, a NeuroD1 nucleic acid sequence comprises a sequence at least 85% identical to SEQ ID NO: 6, or the complement thereof. In one aspect, a NeuroD1 nucleic acid sequence comprises a sequence at least 90% identical to SEQ ID NO: 6, or the complement thereof. In one aspect, a NeuroD1 nucleic acid sequence comprises a sequence at least 91% identical to SEQ ID NO: 6, or the complement thereof. In one aspect, a NeuroD1 nucleic acid sequence comprises a sequence at least 92% identical to SEQ ID NO: 6, or the complement thereof. In one aspect, a NeuroD1 nucleic acid sequence comprises a sequence at least 93% identical to SEQ ID NO: 6, or the complement thereof. In one aspect, a NeuroD1 nucleic acid sequence comprises a sequence at least 94% identical to SEQ ID NO: 6, or the complement thereof. In one aspect, a NeuroD1 nucleic acid sequence comprises a sequence at least 95% identical to SEQ ID NO: 6, or the complement thereof. In one aspect, a NeuroD1 nucleic acid sequence comprises a sequence at least 96% identical to SEQ ID NO: 6, or the complement thereof. In one aspect, a NeuroD1 nucleic acid sequence comprises a sequence at least 97% identical to SEQ ID NO: 6, or the complement thereof. In one aspect, a NeuroD1 nucleic acid sequence comprises a sequence at least 98% identical to SEQ ID NO: 6, or the complement thereof. In one aspect, a NeuroD1 nucleic acid sequence comprises a sequence at least 99% identical to SEQ ID NO: 6, or the complement thereof. In one aspect, a NeuroD1 nucleic acid sequence comprises a sequence at least 99.5% identical to SEQ ID NO: 6, or the complement thereof. In one aspect, a NeuroD1 nucleic acid sequence comprises a sequence at least 99.8% identical to SEQ ID NO: 6, or the complement thereof. In one aspect, a NeuroD1 nucleic acid sequence comprises a sequence at least 99.9% identical to SEQ ID NO: 6, or the complement thereof. In one aspect, a NeuroD1 nucleic acid sequence comprises a sequence 100% identical to SEQ ID NO: 6, or the complement thereof.

In an aspect, a nucleic acid coding sequence encodes a NeuroD1 protein comprising an amino acid sequence at least 70% identical or similar to SEQ ID NO: 10. In one aspect, a nucleic acid coding sequence encodes a NeuroD1 protein comprising an amino acid sequence at least 75% identical or similar to SEQ ID NO: 10. In one aspect, a nucleic acid coding sequence encodes a NeuroD1 protein comprising an amino acid sequence at least 80% identical or similar to SEQ ID NO: 10. In one aspect, a nucleic acid coding sequence encodes a NeuroD1 protein comprising an amino acid sequence at least 85% identical or similar to SEQ ID NO: 10. In one aspect, a nucleic acid coding sequence encodes a NeuroD1 protein comprising an amino acid sequence at least 90% identical or similar to SEQ ID NO: 10. In one aspect, a nucleic acid coding sequence encodes a NeuroD1 protein comprising an amino acid sequence at least 91% identical or similar to SEQ ID NO: 10. In one aspect, a nucleic acid coding sequence encodes a NeuroD1 protein comprising an amino acid sequence at least 92% identical or similar to SEQ ID NO: 10. In one aspect, a nucleic acid coding sequence encodes a NeuroD1 protein comprising an amino acid sequence at least 93% identical or similar to SEQ ID NO: 10. In one aspect, a nucleic acid coding sequence encodes a NeuroD1 protein comprising an amino acid sequence at least 94% identical or similar to SEQ ID NO: 10. In one aspect, a nucleic acid coding sequence encodes a NeuroD1 protein comprising an amino acid sequence at least 95% identical or similar to SEQ ID NO: 10. In one aspect, a nucleic acid coding sequence encodes a NeuroD1 protein comprising an amino acid sequence at least 96% identical or similar to SEQ ID NO: 10. In one aspect, a nucleic acid coding sequence encodes a NeuroD1 protein comprising an amino acid sequence at least 97% identical or similar to SEQ ID NO: 10. In one aspect, a nucleic acid coding sequence encodes a NeuroD1 protein comprising an amino acid sequence at least 98% identical or similar to SEQ ID NO: 10. In one aspect, a nucleic acid coding sequence encodes a NeuroD1 protein comprising an amino acid sequence at least 99% identical or similar to SEQ ID NO: 10. In one aspect, a nucleic acid coding sequence encodes a NeuroD1 protein comprising an amino acid sequence at least 99.5% identical or similar to SEQ ID NO: 10. In one aspect, a nucleic acid coding sequence encodes a NeuroD1 protein comprising an amino acid sequence at least 99.8% identical or similar to SEQ ID NO: 10. In one aspect, a nucleic acid coding sequence encodes a NeuroD1 protein comprising an amino acid sequence at least 99.9% identical or similar to SEQ ID NO: 10. In one aspect, a nucleic acid coding sequence encodes a NeuroD1 protein comprising an amino acid sequence 100% identical or similar to SEQ ID NO: 10.

Glial fibrillary acid protein (GFAP); also referred to as glial fibrillary acidic protein is a member of the type III intermediate filament family of proteins that is expressed in the central nervous system and plays a role in cell communication and the functioning of the blood-brain barrier.

In an aspect, the promoter is selected from the group consisting of GFAP promoter, Sox9 promoter, S100b promoter, Aldh1l1 promoter, Lipocalin 2 (Lcn2) promoter, glutamine synthetase promoter, Aquaporin-4 (AQP4) promoter, oligodendrocyte transcription factor (Olig2) promoter, and synapsin promoter, NG2 promoter, ionized calcium binding adaptor molecule 1 (Iba1) promoter, cluster of differentiation 86 (CD86) promoter, platelet-derived growth factor receptor alpha (PDGFRA) promoter, platelet-derived growth factor receptor beta (PDGFRB) promoter, elongation factor 1-alpha (EF1a) promoter, CAG promoter, cytomegalovirus (CMV) promoter, ubiquitin promoter. In one aspect, the promoter is GFAP promoter. In one aspect, the promoter is a truncated GFAP promoter. In one aspect, the promoter is Sox9 promoter. In one aspect, the promoter is S100b promoter. In one aspect, the promoter is Aldh1l1 promoter. In one aspect, the promoter is Lcn2 promoter. In one aspect, the promoter is glutamine synthetase promoter. In one aspect, the promoter is AQP4 promoter. In one aspect, the promoter is Olig2 promoter. In one aspect, the promoter is synapsin promoter. In one aspect, the promoter is Iba1 promoter. In one aspect, the promoter is CD86 promoter. In one aspect, the promoter is PDGFRA promoter. In one aspect, the promoter is PDGFRB promoter. In one aspect, the promoter is EF1a promoter. In one aspect, the promoter is CAG promoter. In one aspect, the promoter is CMV promoter. In one aspect, the promoter is ubiquitin promoter.

In an aspect, a GFAP promoter is a promoter directing astrocyte-specific expression of a protein called glial fibrillary acidic protein (GFAP) in cells. In one aspect, a GFAP promoter sequence is a human GFAP (hGFAP) promoter sequence. In one aspect, a GFAP promoter is selected from the group consisting of GfaABC1D, Gfa1.6, and hGFA2.2. In one aspect, a GFAP promoter is selected from the group consisting of GfaABC1D, Gfa1.6, hGFA2.2, and pGfa681. In one aspect, a GFAP promoter is GfaABC1D. In one aspect, a GFAP promoter is Gfa1.6. In one aspect, a GFAP promoter is hGFA2.2. In one aspect, a GFAP promoter is pGfa681. In one aspect, pGfa681 is SEQ ID NO: 15. In one aspect, GFAP GfaABC1D is SEQ ID NO: 15. In one aspect, GFAP Gfa1.6 is SEQ ID NO: 4. In one aspect, hGFa2.2 is SEQ ID NO: 12. In one aspect, a GFAP promoter is selected from the group consisting of SEQ ID NOs: 4, 12, and 15. In one aspect, a GFAP promoter is SEQ ID NO: 15. In one aspect, a GFAP promoter is SEQ ID NO: 4. In one aspect, a GFAP promoter is SEQ ID NO: 12.

In one aspect, a GFAP promoter sequence is selected from the group consisting of a chimpanzee GFAP promoter sequence, a bonobo GFAP promoter sequence, an orangutan GFAP promoter sequence, a gorilla GFAP promoter sequence, a macaque GFAP promoter sequence, a marmoset GFAP promoter sequence, a capuchin GFAP promoter sequence, a baboon GFAP promoter sequence, a gibbon GFAP promoter sequence, and a lemur GFAP promoter sequence. In one aspect, a GFAP promoter sequence is a chimpanzee GFAP promoter sequence. In one aspect, a GFAP promoter sequence is a bonobo GFAP promoter sequence. In one aspect, a GFAP promoter sequence is an orangutan GFAP promoter sequence. In one aspect, a GFAP promoter sequence is a gorilla GFAP promoter sequence. In one aspect, a GFAP promoter sequence is a macaque GFAP promoter sequence. In one aspect, a GFAP promoter sequence is a marmoset GFAP promoter sequence. In one aspect, a GFAP promoter sequence is a capuchin GFAP promoter sequence. In one aspect, a GFAP promoter sequence is a baboon GFAP promoter sequence. In one aspect, a GFAP promoter sequence is a gibbon GFAP promoter sequence. In one aspect, a GFAP promoter sequence is a lemur GFAP promoter sequence.

In an aspect, a GFAP promoter sequence comprises at least 100 nucleotides. In one aspect, a GFAP promoter comprises at least 500 nucleotides. In a further aspect, a GFAP promoter comprises at least 1000 nucleotides. In still another aspect, a GFAP promoter comprises at least 1500 nucleotides.

It is appreciated in the art that a fragment of a promoter sequence can function to drive transcription of an operably linked nucleic acid molecule. For example, without being limiting, if a 1000 nucleotides promoter is truncated to 500 nucleotides, and the 500 nucleotides fragment is capable of driving transcription, the 500 nucleotides fragment is referred to as a "functional fragment."

In an aspect, a promoter comprises at least 10 nucleotides. In one aspect, a promoter comprises at least 50 nucleotides. In one aspect, a promoter comprises at least 100 nucleotides. In one aspect, an intron comprises at least 150 nucleotides. In one aspect, a promoter comprises at least 200 nucleotides. In one aspect, a promoter comprises at least 250 nucleotides. In one aspect, a promoter comprises at least 300 nucleotides. In one aspect, a promoter comprises at least 350 nucleotides. In one aspect, a promoter comprises at least 400 nucleotides. In one aspect, a promoter comprises at least 450 nucleotides. In one aspect, a promoter comprises at least 500 nucleotides. In one aspect, a promoter comprises between 50 nucleotides and 7500 nucleotides. In one aspect, a promoter comprises between 50 nucleotides and 5000 nucleotides. In one aspect, a promoter comprises between 50 nucleotides and 2500 nucleotides. In one aspect, a promoter comprises between 50 nucleotides and 1000 nucleotides. In one aspect, a promoter comprises between 50 nucleotides and 500 nucleotides. In one aspect, a promoter comprises between 10 nucleotides and 7500 nucleotides. In one aspect, a promoter comprises between 10 nucleotides and 5000 nucleotides. In one aspect, a promoter comprises between 10 nucleotides and 2500 nucleotides. In one aspect, a promoter comprises between 10 nucleotides and 1000 nucleotides. In one aspect, a promoter comprises between 10 nucleotides and 500 nucleotides In an aspect, a GFAP promoter nucleic acid sequence comprises a sequence at least 70% identical to a sequence selected from the group consisting of SEQ ID NOs: 4, 12, 15, and functional fragment thereof. In one aspect, a GFAP promoter nucleic acid sequence comprises a sequence at least 75% identical to a sequence selected from the group consisting of SEQ ID NOs: 4, 12, 15, and functional fragment thereof. In one aspect, a GFAP promoter nucleic acid sequence comprises a sequence at least 80% identical to a sequence selected from the group consisting of SEQ ID NOs: 4, 12, 15, and functional fragment thereof. In one aspect, a GFAP promoter nucleic acid sequence comprises a sequence at least 85% identical to a sequence selected from the group consisting of SEQ ID NOs: 4, 12, 15, and functional fragment thereof. In one aspect, a GFAP promoter nucleic acid sequence comprises a sequence at least 90% identical to a sequence selected from the group consisting of SEQ ID NOs: 4, 12, 15, and functional fragment thereof. In one aspect, a GFAP promoter nucleic acid sequence comprises a sequence at least 91% identical to a sequence selected from the group consisting of SEQ ID NOs: 4, 12, 15, and functional fragment thereof. In one aspect, a GFAP promoter nucleic acid sequence comprises a sequence at least 92% identical to SEQ ID NOs: 4, 12, 15, and functional fragment thereof. In one aspect, a GFAP promoter nucleic acid sequence comprises a sequence at least 93% identical to a sequence selected from the group consisting of SEQ ID NOs: 4, 12, 15, and functional fragment thereof. In one aspect, a GFAP promoter nucleic acid sequence comprises a sequence at least 94% identical to a sequence selected from the group consisting of SEQ ID NOs: 4, 12, 15, and functional fragment thereof. In one aspect, a GFAP promoter nucleic acid sequence comprises a sequence at least 95% identical to a sequence selected from the group consisting of SEQ ID NOs: 4, 12, 15, and functional fragment thereof. In one aspect, a GFAP promoter nucleic acid sequence comprises a sequence at least 96% identical to a sequence selected from the group consisting of SEQ ID NOs: 4, 12, 15, and functional fragment thereof. In one aspect, a GFAP promoter nucleic acid sequence comprises a sequence at least 97% identical to a sequence selected from the group consisting of SEQ ID NOs: 4, 12, 15, and functional fragment thereof. In one aspect, a GFAP promoter nucleic acid sequence comprises a sequence at least 98% identical to a sequence selected from the group consisting of SEQ ID NOs: 4, 12, 15, and functional fragment thereof. In one aspect, a GFAP promoter nucleic acid sequence comprises a sequence at least 99% identical to a sequence selected from the group consisting of SEQ ID NOs: 4, 12, 15, and functional fragment thereof. In one aspect, a GFAP promoter nucleic acid sequence comprises a sequence at least 99.5% identical to a sequence selected from the group consisting of SEQ ID NOs: 4, 12, 15, and functional fragment thereof. In one aspect, a GFAP promoter nucleic acid sequence comprises a sequence at least 99.8% identical to a sequence selected from the group consisting of SEQ ID NOs: 4, 12, 15, and functional fragment thereof. In one aspect, a GFAP promoter nucleic acid sequence comprises a sequence at least 99.9% identical to a sequence selected from the group consisting of SEQ ID NOs: 4, 12, 15, and functional fragment thereof. In one aspect, a GFAP promoter nucleic acid sequence comprises a sequence 100% identical to a sequence selected from the group consisting of SEQ ID NOs: 4, 12, 15, and functional fragment thereof.

In an aspect, a nucleic acid sequence as provided herein is codon optimized.

In an aspect, a nucleic acid sequence as provided herein is CpG site depleted.

As used herein, the term "brain" refers to an organ that functions as the center of the nervous system. In an aspect, a brain comprises a cerebrum, a cerebral cortex, a cerebellum, and/or a brain stem.

As used herein, the term "cerebral cortex" refers to the outer layer of neural tissue of the cerebrum.

As used herein, the term "striatum" or "corpus striatum" refers to a cluster of neurons in the subcortical basal ganglia of the forebrain and comprises the ventral striatum and dorsal striatum.

As used herein, the term "substantia nigra" refers to a cluster of neurons in the subcortical basal ganglia of the midbrain and comprises the pars compacta and the pars reticulata.

As used herein, the term "forebrain" refers to the forward-most portion of the brain.

As used herein, the term "putamen" refers to a round structure at the base of the forebrain and is a component of the dorsal striatum.

As used herein, the term "caudate nucleus" refers to a structure at the base of the forebrain and is a component of the dorsal striatum.

As used herein, the term "subcortical basal ganglia" refers to a cluster of neurons in the deep cerebral hemispheres of the brain.

As used herein, the term "spinal cord" refers to a structure that functions in the transmission of nerve signals from the motor cortex to the body.

As used herein, the term "motor cortex" refers to a region in the frontal lobe of the cerebral cortex that is involved in the planning, control, and execution of voluntary movements.

In one aspect, a method provided herein converts reactive astrocytes to functional neurons in the brain. In an aspect, a method provided herein converts reactive astrocytes to functional neurons in a cerebral cortex of the brain. In one aspect, a method provided herein coverts reactive astrocytes to functional neurons in a striatum of the brain. In one aspect, a method provided herein converts reactive astrocytes to functional neurons in a dorsal striatum of the brain. In one aspect, a method provided herein converts reactive astrocytes to functional neurons in a spinal cord of the brain. In one aspect, a method provided herein converts reactive astrocytes to functional neurons in a putamen of the brain. In one aspect, a method provided herein converts reactive astrocytes to functional neurons in a caudate nucleus of the brain. In one aspect, a method provided herein converts reactive astrocytes to functional neurons in a substantia nigra of the brain.

Elongation factor-1 alpha (EF-1 alpha; also referred to as eEF1a1) is an isoform of the alpha subunit of the elongation factor 1 complex. The complex is involved in the enzymatic delivery of aminoacyl tRNAs to the ribosome. The EF-1 alpha isoform is expressed in the brain, placenta, lung, liver, kidney, and pancreas.

In an aspect, an enhancer sequence from the EF-1 alpha promoter is a human enhancer sequence from the EF-1 alpha promoter. In one aspect, an enhancer sequence from the EF-1 alpha promoter is selected form the group consisting of a chimpanzee enhancer sequence from the EF-1 alpha promoter, a bonobo enhancer sequence from the EF-1 alpha promoter, an orangutan enhancer sequence from the EF-1 alpha promoter, a gorilla enhancer sequence from the EF-1 alpha promoter, a macaque enhancer sequence from the EF-1 alpha promoter, a marmoset enhancer sequence from the EF-1 alpha promoter, a capuchin enhancer sequence from the EF-1 alpha promoter, a baboon enhancer sequence from the EF-1 alpha promoter, a gibbon enhancer sequence from the EF-1 alpha promoter, and a lemur enhancer sequence from the EF-1 alpha promoter. In one aspect, an enhancer sequence from the EF-1 alpha promoter is a chimpanzee an enhancer sequence from the EF-1 alpha promoter. In one aspect, an enhancer sequence from the EF-1 alpha promoter is a bonobo enhancer sequence from the EF-1 alpha promoter. In one aspect, an enhancer sequence from the EF-1 alpha promoter is an orangutan enhancer sequence from the EF-1 alpha promoter. In one aspect, an enhancer sequence from the EF-1 alpha promoter is a gorilla enhancer sequence from the EF-1 alpha promoter. In one aspect, an enhancer sequence from the EF-1 alpha promoter is a macaque enhancer sequence from the EF-1 alpha promoter. In one aspect, enhancer sequence from the EF-1 alpha promoter is a marmoset enhancer sequence from the EF-1 alpha promoter. In one aspect, enhancer sequence from the EF-1 alpha promoter is a capuchin enhancer sequence from the EF-1 alpha promoter. In one aspect, enhancer sequence from the EF-1 alpha promoter is a baboon enhancer sequence from the EF-1 alpha promoter. In one aspect, enhancer sequence from the EF-1 alpha promoter is a gibbon enhancer sequence from the EF-1 alpha promoter. In one aspect, enhancer sequence from the EF-1 alpha promoter is a lemur enhancer sequence from the EF-1 alpha promoter.

In an aspect, an enhancer from the EF-1 alpha promoter nucleic acid sequence comprises a sequence at least 70% identical to SEQ ID NO: 2, or the complement thereof. In one aspect, an enhancer from the EF-1 alpha promoter nucleic acid sequence comprises a sequence at least 75% identical to SEQ ID NO: 2, or the complement thereof. In one aspect, an enhancer from the EF-1 alpha promoter nucleic acid sequence comprises a sequence at least 80% identical to SEQ ID NO: 2, or the complement thereof. In one aspect, an enhancer from the EF-1 alpha promoter nucleic acid sequence comprises a sequence at least 85% identical to SEQ ID NO: 2, or the complement thereof. In one aspect, an enhancer from the EF-1 alpha promoter nucleic acid sequence comprises a sequence at least 90% identical to SEQ ID NO: 2, or the complement thereof. In one aspect, an enhancer from the EF-1 alpha promoter nucleic acid sequence comprises a sequence at least 91% identical to SEQ ID NO: 2, or the complement thereof. In one aspect, an enhancer from the EF-1 alpha promoter nucleic acid sequence comprises a sequence at least 92% identical to SEQ ID NO: 2, or the complement thereof. In one aspect, an enhancer from the EF-1 alpha promoter nucleic acid sequence comprises a sequence at least 93% identical to SEQ ID NO: 2, or the complement thereof. In one aspect, an enhancer from the EF-1 alpha promoter nucleic acid sequence comprises a sequence at least 94% identical to SEQ ID NO: 2, or the complement thereof. In one aspect, an enhancer from the EF-1 alpha promoter nucleic acid sequence comprises a sequence at least 95% identical to SEQ ID NO: 2, or the complement thereof. In one aspect, an enhancer from the EF-1 alpha promoter nucleic acid sequence comprises a sequence at least 96% identical to SEQ ID NO: 2, or the complement thereof. In one aspect, an enhancer from the EF-1 alpha promoter nucleic acid sequence comprises a sequence at least 97% identical to SEQ ID NO: 2, or the complement thereof. In one aspect, an enhancer from the EF-1 alpha promoter nucleic acid sequence comprises a sequence at least 98% identical to SEQ ID NO: 2, or the complement thereof. In one aspect, an enhancer from the EF-1 alpha promoter nucleic acid sequence comprises a sequence at least 99% identical to SEQ ID NO: 2, or the complement thereof. In one aspect, an enhancer from the EF-1 alpha promoter nucleic acid sequence comprises a sequence at least 99.5% identical to SEQ ID NO: 2, or the complement thereof. In one aspect, an enhancer from the EF-1 alpha promoter nucleic acid sequence comprises a sequence at least 99.8% identical to SEQ ID NO: 2, or the complement thereof. In one aspect, an enhancer from the EF-1 alpha promoter nucleic acid sequence comprises a sequence at least 99.9% identical to SEQ ID NO: 2, or the complement thereof. In one aspect, an enhancer from the EF-1 alpha promoter nucleic acid sequence comprises a sequence 100% identical to SEQ ID NO: 2, or the complement thereof.

Cytomegalovirus (CMV) is a genus of viruses in the order Herpesvirale.

In an aspect, an enhancer sequence from the CMV is a human enhancer sequence from the CMV. In one aspect, an enhancer sequence from the CMV is selected form the group consisting of a chimpanzee enhancer sequence from the CMV, a bonobo enhancer sequence from the CMV, an orangutan enhancer sequence from the CMV, a gorilla enhancer sequence from the CMV, a macaque enhancer sequence from the CMV, a marmoset enhancer sequence from the CMV, a capuchin enhancer sequence from the CMV, a baboon enhancer sequence from the CMV, a gibbon enhancer sequence from the CMV, and a lemur enhancer sequence from the CMV. In one aspect, an enhancer sequence from the CMV is a chimpanzee an enhancer sequence from the CMV. In one aspect, an enhancer sequence from the CMV is a bonobo enhancer sequence from the CMV. In one aspect, an enhancer sequence from the CMV is an orangutan enhancer sequence from the CMV. In one aspect, an enhancer sequence from the CMV is a gorilla enhancer sequence from the CMV. In one aspect, an enhancer sequence from the CMV is a macaque enhancer sequence from the CMV. In one aspect, enhancer sequence from the CMV is a marmoset enhancer sequence from the CMV. In one aspect, enhancer sequence from the CMV is a capuchin enhancer sequence from the CMV. In one aspect, enhancer sequence from the CMV is a baboon enhancer sequence from the CMV. In one aspect, enhancer sequence from the CMV is a gibbon enhancer sequence from the CMV. In one aspect, enhancer sequence from the CMV is a lemur enhancer sequence from the CMV.

In an aspect, an enhancer from the CMV nucleic acid sequence comprises a sequence at least 70% identical to SEQ ID NO: 11, or the complement thereof. In one aspect, an enhancer from the CMV nucleic acid sequence comprises a sequence at least 75% identical to SEQ ID NO: 11, or the complement thereof. In one aspect, an enhancer from the CMV nucleic acid sequence comprises a sequence at least 80% identical to SEQ ID NO: 11, or the complement thereof. In one aspect, an enhancer from the CMV nucleic acid sequence comprises a sequence at least 85% identical to SEQ ID NO: 11, or the complement thereof. In one aspect, an enhancer from the CMV nucleic acid sequence comprises a sequence at least 90% identical to SEQ ID NO: 11, or the complement thereof. In one aspect, an enhancer from the CMV nucleic acid sequence comprises a sequence at least 91% identical to SEQ ID NO: 11, or the complement thereof. In one aspect, an enhancer from the CMV nucleic acid sequence comprises a sequence at least 92% identical to SEQ ID NO: 11, or the complement thereof. In one aspect, an enhancer from the CMV nucleic acid sequence comprises a sequence at least 93% identical to SEQ ID NO: 11, or the complement thereof. In one aspect, an enhancer from the CMV nucleic acid sequence comprises a sequence at least 94% identical to SEQ ID NO: 11, or the complement thereof. In one aspect, an enhancer from the CMV nucleic acid sequence comprises a sequence at least 95% identical to SEQ ID NO: 11, or the complement thereof. In one aspect, an enhancer from the CMV nucleic acid sequence comprises a sequence at least 96% identical to SEQ ID NO: 11, or the complement thereof. In one aspect, an enhancer from the CMV nucleic acid sequence comprises a sequence at least 97% identical to SEQ ID NO: 11, or the complement thereof. In one aspect, an enhancer from the CMV nucleic acid sequence comprises a sequence at least 98% identical to SEQ ID NO: 11, or the complement thereof. In one aspect, an enhancer from the CMV nucleic acid sequence comprises a sequence at least 99% identical to SEQ ID NO: 11, or the complement thereof. In one aspect, an enhancer from the CMV nucleic acid sequence comprises a sequence at least 99.5% identical to SEQ ID NO: 11, or the complement thereof. In one aspect, an enhancer from the CMV nucleic acid sequence comprises a sequence at least 99.8% identical to SEQ ID NO: 11, or the complement thereof. In one aspect, an enhancer from the CMV nucleic acid sequence comprises a sequence at least 99.9% identical to SEQ ID NO: 11, or the complement thereof. In one aspect, an enhancer from the CMV nucleic acid sequence comprises a sequence 100% identical to SEQ ID NO: 11, or the complement thereof.

In an aspect, an enhancer is selected from the group consisting of an enhancer from EF1-α promoter and CMV enhancer. In one aspect, an enhancer is from EF1-α promoter. In one aspect, an enhancer is an CMV enhancer.

In an aspect, a vector of the present disclosures comprises a chimeric intron. In an aspect the chimeric intron is composed of the 5'-donor site from the first intron of the human β-globin gene and the branch and 3'-acceptor site from the intron of an immunoglobulin gene heavy chain variable region. In an aspect, the chimeric intron is a chimeric intron of a rabbit beta-globing and a chicken beta actin similar in CAG promoter. In an aspect, a vector of the present disclosure comprises a glial fibrillary acid protein (GFAP) intron. In an aspect, a vector of the present disclosure comprises a glial fibrillary acid protein (GFAP) first intron.

Introns can be grouped into at least five classes, including: spliceosomal introns; transfer RNA introns; group I introns; group II introns; and group III introns. An intron can be synthetically produced, varied, or derived from a known or naturally occurring intron sequence or other intron sequence. An intron can also include a chimeric intron comprising a combination of two or more heterologous sequences. An intron of the present application can thus include variants of intron sequences that are similar in composition, but not identical to, other intron sequence(s) known or provided herein. In an aspect, an intron comprises at least 10 nucleotides. In one aspect, an intron comprises at least 50 nucleotides. In one aspect, an intron comprises at least 100 nucleotides. In one aspect, an intron comprises at least 150 nucleotides. In one aspect, an intron comprises at least 200 nucleotides. In one aspect, an intron comprises at least 250 nucleotides. In one aspect, an intron comprises at least 300 nucleotides. In one aspect, an intron comprises at least 350 nucleotides. In one aspect, an intron comprises at least 400 nucleotides. In one aspect, an intron comprises at least 450 nucleotides. In one aspect, an intron comprises at least 500 nucleotides. In one aspect, an intron comprises between 50 nucleotides and 7500 nucleotides. In one aspect, an intron comprises between 50 nucleotides and 5000 nucleotides. In one aspect, an intron comprises between 50 nucleotides and 2500 nucleotides. In one aspect, an intron comprises between 50 nucleotides and 1000 nucleotides. In one aspect, an intron comprises between 50 nucleotides and 500 nucleotides. In one aspect, an intron comprises between 10 nucleotides and 7500 nucleotides. In one aspect, an intron comprises between 10 nucleotides and 5000 nucleotides. In one aspect, an intron comprises between 10 nucleotides and 2500 nucleotides. In one aspect, an intron comprises between 10 nucleotides and 1000 nucleotides. In one aspect, an intron comprises between 10 nucleotides and 500 nucleotides.

In an aspect, a chimeric intron nucleic acid sequence comprises a sequence at least 70% identical to SEQ ID NO: 5, or the complement thereof. In one aspect, a chimeric intron nucleic acid sequence comprises a sequence at least 75% identical to SEQ ID NO: 5, or the complement thereof. In one aspect, a chimeric intron nucleic acid sequence comprises a sequence at least 80% identical to SEQ ID NO: 5, or the complement thereof. In one aspect, a chimeric intron nucleic acid sequence comprises a sequence at least 85% identical to SEQ ID NO: 5, or the complement thereof. In one aspect, a chimeric intron nucleic acid sequence comprises a sequence at least 90% identical to SEQ ID NO: 5, or the complement thereof. In one aspect, a chimeric intron nucleic acid sequence comprises a sequence at least 91% identical to SEQ ID NO: 5, or the complement thereof. In one aspect, a chimeric intron nucleic acid sequence comprises a sequence at least 92% identical to SEQ ID NO: 5, or the complement thereof. In one aspect, a chimeric intron nucleic acid sequence comprises a sequence at least 93% identical to SEQ ID NO: 5, or the complement thereof. In one aspect, a chimeric intron nucleic acid sequence comprises a sequence at least 94% identical to SEQ ID NO: 5, or the complement thereof. In one aspect, a chimeric intron nucleic acid sequence comprises a sequence at least 95% identical to SEQ ID NO: 5, or the complement thereof. In one aspect, a chimeric intron nucleic acid sequence comprises a sequence at least 96% identical to SEQ ID NO: 5, or the complement thereof. In one aspect, a chimeric intron nucleic acid sequence comprises a sequence at least 97% identical to SEQ ID NO: 5, or the complement thereof. In one aspect, a chimeric intron nucleic acid sequence comprises a sequence at least 98% identical to SEQ ID NO: 5, or the complement thereof. In one aspect, a chimeric intron nucleic acid sequence comprises a sequence at least 99% identical to SEQ ID NO: 5, or the complement thereof. In one aspect, a chimeric intron nucleic acid sequence comprises a sequence at least 99.5% identical to SEQ ID NO: 5, or the complement thereof. In one aspect, a chimeric intron nucleic acid sequence comprises a sequence at least 99.8% identical to SEQ ID NO: 5, or the complement thereof. In one aspect, a chimeric intron nucleic acid sequence comprises a sequence at least 99.9% identical to SEQ ID NO: 5, or the complement thereof. In one aspect, a chimeric intron nucleic acid sequence comprises a sequence 100% identical to SEQ ID NO: 5, or the complement thereof.

In an aspect, a chimeric intron nucleic acid sequence comprises a sequence at least 70% identical to SEQ ID NO: 16, or the complement thereof. In one aspect, a chimeric intron nucleic acid sequence comprises a sequence at least 75% identical to SEQ ID NO: 16, or the complement thereof. In one aspect, a chimeric intron nucleic acid sequence comprises a sequence at least 80% identical to SEQ ID NO: 16, or the complement thereof. In one aspect, a chimeric intron nucleic acid sequence comprises a sequence at least 85% identical to SEQ ID NO: 16, or the complement thereof. In one aspect, a chimeric intron nucleic acid sequence comprises a sequence at least 90% identical to SEQ ID NO: 16, or the complement thereof. In one aspect, a chimeric intron nucleic acid sequence comprises a sequence at least 91% identical to SEQ ID NO: 16, or the complement thereof. In one aspect, a chimeric intron nucleic acid sequence comprises a sequence at least 92% identical to SEQ ID NO: 16, or the complement thereof. In one aspect, a chimeric intron nucleic acid sequence comprises a sequence at least 93% identical to SEQ ID NO: 16, or the complement thereof. In one aspect, a chimeric intron nucleic acid sequence comprises a sequence at least 94% identical to SEQ ID NO: 16, or the complement thereof. In one aspect, a chimeric intron nucleic acid sequence comprises a sequence at least 95% identical to SEQ ID NO: 16, or the complement thereof. In one aspect, a chimeric intron nucleic acid sequence comprises a sequence at least 96% identical to SEQ ID NO: 16, or the complement thereof. In one aspect, a chimeric intron nucleic acid sequence comprises a sequence at least 97% identical to SEQ ID NO: 16, or the complement thereof. In one aspect, a chimeric intron nucleic acid sequence comprises a sequence at least 98% identical to SEQ ID NO: 16, or the complement thereof. In one aspect, a chimeric intron nucleic acid sequence comprises a sequence at least 99% identical to SEQ ID NO: 16, or the complement thereof. In one aspect, a chimeric intron nucleic acid sequence comprises a sequence at least 99.5% identical to SEQ ID NO: 16, or the complement thereof. In one aspect, a chimeric intron nucleic acid sequence comprises a sequence at least 99.8% identical to SEQ ID NO: 16, or the complement thereof. In one aspect, a chimeric intron nucleic acid sequence comprises a sequence at least 99.9% identical to SEQ ID NO: 16, or the complement thereof. In one aspect, a chimeric intron nucleic acid sequence comprises a sequence 100% identical to SEQ ID NO: 16, or the complement thereof.

In an aspect, an intron nucleic acid sequence comprises a sequence at least 70% identical to SEQ ID NO: 17, or the complement thereof. In one aspect, an intron nucleic acid sequence comprises a sequence at least 75% identical to SEQ ID NO: 17, or the complement thereof. In one aspect, an intron nucleic acid sequence comprises a sequence at least 80% identical to SEQ ID NO: 17, or the complement thereof. In one aspect, an intron nucleic acid sequence comprises a sequence at least 85% identical to SEQ ID NO: 17, or the complement thereof. In one aspect, an intron nucleic acid sequence comprises a sequence at least 90% identical to SEQ ID NO: 17, or the complement thereof. In one aspect, an intron nucleic acid sequence comprises a sequence at least 91% identical to SEQ ID NO: 17, or the complement thereof. In one aspect, an intron nucleic acid sequence comprises a sequence at least 92% identical to SEQ ID NO: 17, or the complement thereof. In one aspect, an intron nucleic acid sequence comprises a sequence at least 93% identical to SEQ ID NO: 17, or the complement thereof. In one aspect, an intron nucleic acid sequence comprises a sequence at least 94% identical to SEQ ID NO: 17, or the complement thereof. In one aspect, an intron nucleic acid sequence comprises a sequence at least 95% identical to SEQ ID NO: 17, or the complement thereof. In one aspect, an intron nucleic acid sequence comprises a sequence at least 96% identical to SEQ ID NO: 17, or the complement thereof. In one aspect, an intron nucleic acid sequence comprises a sequence at least 97% identical to SEQ ID NO: 17, or the complement thereof. In one aspect, an intron nucleic acid sequence comprises a sequence at least 98% identical to SEQ ID NO: 17, or the complement thereof. In one aspect, an intron nucleic acid sequence comprises a sequence at least 99% identical to SEQ ID NO: 17, or the complement thereof. In one aspect, an intron nucleic acid sequence comprises a sequence at least 99.5% identical to SEQ ID NO: 17, or the complement thereof. In one aspect, an intron nucleic acid sequence comprises a sequence at least 99.8% identical to SEQ ID NO: 17, or the complement thereof. In one aspect, an intron nucleic acid sequence comprises a sequence at least 99.9% identical to SEQ ID NO: 17, or the complement thereof. In one aspect, an intron nucleic acid sequence comprises a sequence 100% identical to SEQ ID NO: 17, or the complement thereof.

The woodchuck hepatitis virus posttranscriptional regulatory element (WPRE) is a DNA sequence that creates a tertiary structure enhancing expression of genes that are delivered in viral vectors.

In an aspect, a WPRE nucleic acid sequence is an optimized version of WPRE.

In an aspect, a WPRE nucleic acid sequence is selected from the group consisting of SEQ ID NOs: 7 and 18. In one aspect, a WPRE nucleic acid sequence is SEQ ID NO: 7. In one aspect, a WPRE nucleic acid sequence is SEQ ID NO: 18.

In an aspect, a WPRE nucleic acid sequence comprises a sequence at least 70% identical to SEQ ID NO: 7, or the complement thereof. In one aspect, a WPRE nucleic acid sequence comprises a sequence at least 75% identical to SEQ ID NO: 7, or the complement thereof. In one aspect, a WPRE nucleic acid sequence comprises a sequence at least 80% identical to SEQ ID NO: 7, or the complement thereof. In one aspect, a WPRE nucleic acid sequence comprises a sequence at least 85% identical to SEQ ID NO: 7, or the complement thereof. In one aspect, a WPRE nucleic acid sequence comprises a sequence at least 90% identical to SEQ ID NO: 7, or the complement thereof. In one aspect, a WPRE nucleic acid sequence comprises a sequence at least 91% identical to SEQ ID NO: 7, or the complement thereof. In one aspect, a WPRE nucleic acid sequence comprises a sequence at least 92% identical to SEQ ID NO: 7, or the complement thereof. In one aspect, a WPRE nucleic acid sequence comprises a sequence at least 93% identical to SEQ ID NO: 7, or the complement thereof. In one aspect, a WPRE nucleic acid sequence comprises a sequence at least 94% identical to SEQ ID NO: 7, or the complement thereof. In one aspect, a WPRE nucleic acid sequence comprises a sequence at least 95% identical to SEQ ID NO: 7, or the complement thereof. In one aspect, a WPRE nucleic acid sequence comprises a sequence at least 96% identical to SEQ ID NO: 7, or the complement thereof. In one aspect, a WPRE nucleic acid sequence comprises a sequence at least 97% identical to SEQ ID NO: 7, or the complement thereof. In one aspect, a WPRE nucleic acid sequence comprises a sequence at least 98% identical to SEQ ID NO: 7, or the complement thereof. In one aspect, a WPRE nucleic acid sequence comprises a sequence at least 99% identical to SEQ ID NO: 7, or the complement thereof. In one aspect, a WPRE nucleic acid sequence comprises a sequence at least 99.5% identical to SEQ ID NO: 7, or the complement thereof. In one aspect, a WPRE nucleic acid sequence comprises a sequence at least 99.8% identical to SEQ ID NO: 7, or the complement thereof. In one aspect, a WPRE nucleic acid sequence comprises a sequence at least 99.9% identical to SEQ ID NO: 7, or the complement thereof. In one aspect, a WPRE nucleic acid sequence comprises a sequence 100% identical to SEQ ID NO: 7, or the complement thereof.

In an aspect, a WPRE nucleic acid sequence comprises a sequence at least 70% identical to SEQ ID NO: 18, or the complement thereof. In one aspect, a WPRE nucleic acid sequence comprises a sequence at least 75% identical to SEQ ID NO: 18, or the complement thereof. In one aspect, a WPRE nucleic acid sequence comprises a sequence at least 80% identical to SEQ ID NO: 18, or the complement thereof. In one aspect, a WPRE nucleic acid sequence comprises a sequence at least 85% identical to SEQ ID NO: 18, or the complement thereof. In one aspect, a WPRE nucleic acid sequence comprises a sequence at least 90% identical to SEQ ID NO: 18, or the complement thereof. In one aspect, a WPRE nucleic acid sequence comprises a sequence at least 91% identical to SEQ ID NO: 18, or the complement thereof. In one aspect, a WPRE nucleic acid sequence comprises a sequence at least 92% identical to SEQ ID NO: 18, or the complement thereof. In one aspect, a WPRE nucleic acid sequence comprises a sequence at least 93% identical to SEQ ID NO: 18, or the complement thereof. In one aspect, a WPRE nucleic acid sequence comprises a sequence at least 94% identical to SEQ ID NO: 18, or the complement thereof. In one aspect, a WPRE nucleic acid sequence comprises a sequence at least 95% identical to SEQ ID NO: 18, or the complement thereof. In one aspect, a WPRE nucleic acid sequence comprises a sequence at least 96% identical to SEQ ID NO: 18, or the complement thereof. In one aspect, a WPRE nucleic acid sequence comprises a sequence at least 97% identical to SEQ ID NO: 18, or the complement thereof. In one aspect, a WPRE nucleic acid sequence comprises a sequence at least 98% identical to SEQ ID NO: 18, or the complement thereof. In one aspect, a WPRE nucleic acid sequence comprises a sequence at least 99% identical to SEQ ID NO: 18, or the complement thereof. In one aspect, a WPRE nucleic acid sequence comprises a sequence at least 99.5% identical to SEQ ID NO: 18, or the complement thereof. In one aspect, a WPRE nucleic acid sequence comprises a sequence at least 99.8% identical to SEQ ID NO: 18, or the complement thereof. In one aspect, a WPRE nucleic acid sequence comprises a sequence at least 99.9% identical to SEQ ID NO: 18, or the complement thereof. In one aspect, a WPRE nucleic acid sequence comprises a sequence 100% identical to SEQ ID NO: 18, or the complement thereof.

SV40 polyadenylation signal sequence (also refer as SV40 PolyA; Simian virus 40 PolyA; and PolyA) is a DNA sequence that can terminate transcription and add a PolyA tail to the 3' end of a messenger RNA (mRNA).

hGH polyadenylation signal sequence (also refer as hGH PolyA) is a DNA sequence the can terminate transcription and add a PolyA tail to the 3' end of a messenger RNA (mRNA).

bGH polyadenylation signal sequence (also refer as bGH PolyA or bGHpA) refers to a Poly A signal or PolyA tail of a bovine growth hormone.

As used herein, a "PolyA tail" refers to a stretch of RNA that only contains the nucleobase adenine. In an aspect, an RNA molecule transcribed from an AAV vector construct provided herein comprises a PolyA tail. In one aspect, a PolyA tail comprises at least two adenines. In one aspect, a PolyA tail comprises at least ten adenines. In one aspect, a PolyA tail comprises at least 50 adenines. In one aspect, a PolyA tail comprises at least 100 adenines. In one aspect, a PolyA tail comprises at least 150 adenines. In one aspect, a PolyA tail comprises at least 200 adenines. In one aspect, a PolyA tail comprises at least 250 adenines. In one aspect, a PolyA tail comprises between 50 adenines and 300 adenines.

In an aspect, a SV40 polyadenylation signal nucleic acid sequence comprises a sequence at least 70% identical to SEQ ID NO: 8, or the complement thereof. In one aspect, a SV40 polyadenylation signal nucleic acid sequence comprises a sequence at least 75% identical to SEQ ID NO: 8, or the complement thereof. In one aspect, a SV40 polyadenylation signal nucleic acid sequence comprises a sequence at least 80% identical to SEQ ID NO: 8, or the complement thereof. In one aspect, a SV40 polyadenylation signal nucleic acid sequence comprises a sequence at least 85% identical to SEQ ID NO: 8, or the complement thereof. In one aspect, a SV40 polyadenylation signal nucleic acid sequence comprises a sequence at least 90% identical to SEQ ID NO: 8, or the complement thereof. In one aspect, a SV40 polyadenylation signal nucleic acid sequence comprises a sequence at least 91% identical to SEQ ID NO: 8, or the complement thereof. In one aspect, a SV40 polyadenylation signal nucleic acid sequence comprises a sequence at least 92% identical to SEQ ID NO: 8, or the complement thereof. In one aspect, a SV40 polyadenylation signal nucleic acid sequence comprises a sequence at least 93% identical to SEQ ID NO: 8, or the complement thereof. In one aspect, a SV40 polyadenylation signal nucleic acid sequence comprises a sequence at least 94% identical to SEQ ID NO: 8, or the complement thereof. In one aspect, a SV40 polyadenylation signal nucleic acid sequence comprises a sequence at least 95% identical to SEQ ID NO: 8, or the complement thereof. In one aspect, a SV40 polyadenylation signal nucleic acid sequence comprises a sequence at least 96% identical to SEQ ID NO: 8, or the complement thereof. In one aspect, a SV40 polyadenylation signal nucleic acid sequence comprises a sequence at least 97% identical to SEQ ID NO: 8, or the complement thereof. In one aspect, a SV40 polyadenylation signal nucleic acid sequence comprises a sequence at least 98% identical to SEQ ID NO: 8, or the complement thereof. In one aspect, a SV40 polyadenylation signal nucleic acid sequence comprises a sequence at least 99% identical to SEQ ID NO: 8, or the complement thereof. In one aspect, a SV40 polyadenylation signal nucleic acid sequence comprises a sequence at least 99.5% identical to SEQ ID NO: 8, or the complement thereof. In one aspect, a SV40 polyadenylation signal nucleic acid sequence comprises a sequence at least 99.8% identical to SEQ ID NO: 8, or the complement thereof. In one aspect, a SV40 polyadenylation signal nucleic acid sequence comprises a sequence at least 99.9% identical to SEQ ID NO: 8, or the complement thereof. In one aspect, a SV40 polyadenylation signal nucleic acid sequence comprises a sequence 100% identical to SEQ ID NO: 8, or the complement thereof.

In an aspect, a hGH polyadenylation signal nucleic acid sequence comprises a sequence at least 70% identical to SEQ ID NO: 13, or the complement thereof. In one aspect, a hGH polyadenylation signal nucleic acid sequence comprises a sequence at least 75% identical to SEQ ID NO: 13, or the complement thereof. In one aspect, a hGH polyadenylation signal nucleic acid sequence comprises a sequence at least 80% identical to SEQ ID NO: 13, or the complement thereof. In one aspect, a hGH polyadenylation signal nucleic acid sequence comprises a sequence at least 85% identical to SEQ ID NO: 13, or the complement thereof. In one aspect, a hGH polyadenylation signal nucleic acid sequence comprises a sequence at least 90% identical to SEQ ID NO: 13, or the complement thereof. In one aspect, a hGH polyadenylation signal nucleic acid sequence comprises a sequence at least 91% identical to SEQ ID NO: 13, or the complement thereof. In one aspect, a hGH polyadenylation signal nucleic acid sequence comprises a sequence at least 92% identical to SEQ ID NO: 13, or the complement thereof. In one aspect, a hGH polyadenylation signal nucleic acid sequence comprises a sequence at least 93% identical to SEQ ID NO: 13, or the complement thereof. In one aspect, a hGH polyadenylation signal nucleic acid sequence comprises a sequence at least 94% identical to SEQ ID NO: 13, or the complement thereof. In one aspect, a hGH polyadenylation signal nucleic acid sequence comprises a sequence at least 95% identical to SEQ ID NO: 13, or the complement thereof. In one aspect, a hGH polyadenylation signal nucleic acid sequence comprises a sequence at least 96% identical to SEQ ID NO: 13, or the complement thereof. In one aspect, a hGH polyadenylation signal nucleic acid sequence comprises a sequence at least 97% identical to SEQ ID NO: 13, or the complement thereof. In one aspect, a hGH polyadenylation signal nucleic acid sequence comprises a sequence at least 98% identical to SEQ ID NO: 13, or the complement thereof. In one aspect, a hGH polyadenylation signal nucleic acid sequence comprises a sequence at least 99% identical to SEQ ID NO: 13, or the complement thereof. In one aspect, a hGH polyadenylation signal nucleic acid sequence comprises a sequence at least 99.5% identical to SEQ ID NO: 13, or the complement thereof. In one aspect, a hGH polyadenylation signal nucleic acid sequence comprises a sequence at least 99.13% identical to SEQ ID NO: 13, or the complement thereof. In one aspect, a hGH polyadenylation signal nucleic acid sequence comprises a sequence at least 99.9% identical to SEQ ID NO: 13, or the complement thereof. In one aspect, a hGH polyadenylation signal nucleic acid sequence comprises a sequence 100% identical to SEQ ID NO: 13, or the complement thereof In an aspect, a bGH polyadenylation signal nucleic acid sequence comprises a sequence at least 70% identical to SEQ ID NO: 14, or the complement thereof. In one aspect, a bGH polyadenylation signal nucleic acid sequence comprises a sequence at least 75% identical to SEQ ID NO: 14, or the complement thereof. In one aspect, a bGH polyadenylation signal nucleic acid sequence comprises a sequence at least 80% identical to SEQ ID NO: 14, or the complement thereof. In one aspect, a bGH polyadenylation signal nucleic acid sequence comprises a sequence at least 85% identical to SEQ ID NO: 14, or the complement thereof. In one aspect, a bGH polyadenylation signal nucleic acid sequence comprises a sequence at least 90% identical to SEQ ID NO: 14, or the complement thereof. In one aspect, a bGH polyadenylation signal nucleic acid sequence comprises a sequence at least 91% identical to SEQ ID NO: 14, or the complement thereof. In one aspect, a bGH polyadenylation signal nucleic acid sequence comprises a sequence at least 92% identical to SEQ ID NO: 14, or the complement thereof. In one aspect, a bGH polyadenylation signal nucleic acid sequence comprises a sequence at least 93% identical to SEQ ID NO: 14, or the complement thereof. In one aspect, a bGH polyadenylation signal nucleic acid sequence comprises a sequence at least 94% identical to SEQ ID NO: 14, or the complement thereof. In one aspect, a bGH polyadenylation signal nucleic acid sequence comprises a sequence at least 95% identical to SEQ ID NO: 14, or the complement thereof. In one aspect, a bGH polyadenylation signal nucleic acid sequence comprises a sequence at least 96% identical to SEQ ID NO: 14, or the complement thereof. In one aspect, a bGH polyadenylation signal nucleic acid sequence comprises a sequence at least 97% identical to SEQ ID NO: 14, or the complement thereof. In one aspect, a bGH polyadenylation signal nucleic acid sequence comprises a sequence at least 98% identical to SEQ ID NO: 14, or the complement thereof. In one aspect, a bGH polyadenylation signal nucleic acid sequence comprises a sequence at least 99% identical to SEQ ID NO: 14, or the complement thereof. In one aspect, a bGH polyadenylation signal nucleic acid sequence comprises a sequence at least 99.5% identical to SEQ ID NO: 14, or the complement thereof. In one aspect, a bGH polyadenylation signal nucleic acid sequence comprises a sequence at least 99.13% identical to SEQ ID NO: 14, or the complement thereof. In one aspect, a bGH polyadenylation signal nucleic acid sequence comprises a sequence at least 99.9% identical to SEQ ID NO: 14, or the complement thereof. In one aspect, a bGH polyadenylation signal nucleic acid sequence comprises a sequence 100% identical to SEQ ID NO: 14, or the complement thereof.

In an aspect, a vector of the present disclosure comprises a 2A self-cleavage peptide sequence. In an aspect, a vector of the present disclosure comprises a 2A self-cleavage peptide sequence from porcine teschovirus-1. In an aspect, a vector of the present disclosure comprises a nucleic acid sequence comprising SEQ ID NO: 3. In an aspect, a vector of the present disclosure comprises a nucleic acid sequence at least 70% identical to SEQ ID NO: 3. In an aspect, a vector of the present disclosure comprises a nucleic acid sequence at least 75% identical to SEQ ID NO: 3. In an aspect, a vector of the present disclosure comprises a nucleic acid sequence at least 80% identical to SEQ ID NO: 3. In an aspect, a vector of the present disclosure comprises a nucleic acid sequence at least 85% identical to SEQ ID NO: 3. In an aspect, a vector of the present disclosure comprises a nucleic acid sequence at least 90% identical to SEQ ID NO: 3. In an aspect, a vector of the present disclosure comprises a nucleic acid sequence at least 91% identical to SEQ ID NO: 3. In an aspect, a vector of the present disclosure comprises a nucleic acid sequence at least 92% identical to SEQ ID NO: 3. In an aspect, a vector of the present disclosure comprises a nucleic acid sequence at least 93% identical to SEQ ID NO: 3. In an aspect, a vector of the present disclosure comprises a nucleic acid sequence at least 94% identical to SEQ ID NO: 3. In an aspect, a vector of the present disclosure comprises a nucleic acid sequence at least 95% identical to SEQ ID NO: 3. In an aspect, a vector of the present disclosure comprises a nucleic acid sequence at least 96% identical to SEQ ID NO: 3. In an aspect, a vector of the present disclosure comprises a nucleic acid sequence at least 97% identical to SEQ ID NO: 3. In an aspect, a vector of the present disclosure comprises a nucleic acid sequence at least 98% identical to SEQ ID NO: 3. In an aspect, a vector of the present disclosure comprises a nucleic acid sequence at least 99% identical to SEQ ID NO: 3. In an aspect, a vector of the present disclosure comprises a nucleic acid sequence 100% identical to SEQ ID NO: 3.

As used herein, the term "central nervous system" or "CNS" refers to the brain and spinal cord of a bilaterally symmetric animal. The CNS also includes the retina, the optic nerve, olfactory nerves, and olfactory epithelium.

As used herein, the term "peripheral nervous system" or "PNS" refers to nerves and ganglia outside of the brain and spinal cord, excluding the retina, the optic nerve, olfactory nerves, and olfactory epithelium. In an aspect, the peripheral nervous system is divided into the somatic nervous system and the autonomic nervous system.

As used herein, the term "somatic nervous system" refers to the parts of the PNS that are associated with voluntary control of body movements.

As used herein, the term "autonomic nervous system" refers to the parts of the PNS that regulate the function of internal organs As used herein, the term "GFAP positive" refers to a cell having detectable protein accumulation of human glial fibrillary acid protein (GFAP) or detectable accumulation of GFAP mRNA expression using techniques standard in the art. In one aspect, a glial cell is GFAP positive.

As used herein, the term "detectable" refers to protein or mRNA accumulation that is identifiable.

Protein accumulation can be identified using antibodies. Non limiting examples of measuring protein accumulation include Western blots, enzyme linked immunosorbent assays (ELISAs), immunoprecipitations and immunofluorescence. An antibody provided herein can be a polyclonal antibody or a monoclonal antibody. An antibody having specific binding affinity for a protein provided herein can be generated using methods well known in the art. An antibody provided herein can be attached to a solid support such as a microtiter plate using methods known in the art.

As used herein, the term "multiplicity of infection" and "MOI" refers to a the number of virions that are added per cell during infection.

As used herein, the term "virion" refers to the infective form of a virus outside a host cell.

As used herein, the term "neurological condition" refers to a disorder, illness, sickness, injury, or disease, in the central nervous system or the peripheral nervous system. Non-limiting examples of neurological conditions can be found in Neurological Disorders: course and treatment, $2^{nd}$ Edition (2002) (Academic Press Inc.) and Christopher Goetz, Textbook of Clinical Neurology, $3^{rd}$ Edition (2007) (Saunders).

As used herein, the term "injury" refers to damage to the central nervous system or peripheral nervous system.

In one aspect, a neurological condition is selected from the group consisting of Alzheimer's Disease, Parkinson's Disease, amyotrophic lateral sclerosis (ALS), Huntington's Disease, epilepsy, physical injury, stroke, cerebral aneurysm, traumatic brain injury, concussion, a tumor, inflammation, infection, ataxia, brain atrophy, spinal cord atrophy, multiple sclerosis, traumatic spinal cord injury, ischemic or hemorrhagic myelopathy (myelopathy), global ischemia, hypoxic ischemic encephalopathy, embolism, fibrocartilage embolism myelopathy, thrombosis, nephropathy, chronic inflammatory disease, meningitis, and cerebral venous sinus thrombosis. In one aspect, a neurological condition is Alzheimer's Disease. In one aspect, a neurological condition is Parkinson's Disease. In one aspect, a neurological condition is ALS. In one aspect, a neurological condition is Huntington's Disease. In one aspect, a neurological condition is epilepsy. In one aspect, a neurological condition is a physical injury. In one aspect, a neurological condition is stroke. In one aspect, a neurological condition is ischemic stroke. In one aspect, a neurological condition is hemorrhagic stroke. In one aspect, a neurological condition is cerebral aneurysm. In one aspect, a neurological condition is traumatic brain injury. In one aspect, a neurological condition is concussion. In one aspect, a neurological condition is a tumor. In one aspect, a neurological condition is inflammation. In one aspect, a neurological condition is infection. In one aspect, a neurological condition is ataxia. In, one aspect, a neurological condition is brain atrophy. In, one aspect, a neurological condition is spinal cord atrophy. In one aspect, a neurological condition is multiple sclerosis. In one aspect, a neurological condition is traumatic spinal cord injury. In one aspect, a neurological condition is ischemic or hemorrhagic myelopathy (myelopathy). In one aspect, a neurological condition is global ischemia. In one aspect, a neurological condition is hypoxic ischemic encephalopathy. In one aspect, a neurological condition is embolism. In one aspect, a neurological condition is fibrocartilage embolism myelopathy. In one aspect, a neurological condition is thrombosis. In one aspect, a neurological condition is nephropathy. In one aspect, a neurological condition is chronic inflammatory disease. In one aspect, a neurological condition is meningitis. In one aspect, a neurological condition is cerebral venous sinus thrombosis.

In an aspect, a neurological condition comprises an injury to the CNS or to the PNS. In one aspect, a neurological condition comprises an injury to the CNS. In one aspect, a neurological condition comprises an injury to the PNS.

In an aspect, this disclosure provides, and includes, a method of converting reactive astrocytes to functional neurons in a brain of a living human brain comprising: injecting an adeno-associated virus (AAV) into a subject in need thereof, where the AAV comprises a DNA vector construct comprising a human neurogenic differentiation 1 (hNeuroD1) sequence comprising the nucleic acid sequence of SEQ ID NO: 6, where the sequence is operably linked to regulatory elements comprising: (a) a human glial fibrillary acid protein (GFAP) promoter comprising a nucleic acid sequence selected from the group consisting of SEQ ID NO: 4, 12, and 15; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence of SEQ ID NO: 5 or 16; (d) a woodchuck hepatitis virus posttranscriptional regulatory element (WPRE) comprising the nucleic acid sequence selected from the group consisting of SEQ ID NOs: 7 and 18; and (e) a SV40 polyadenylation signal sequence comprising the nucleic acid sequence of SEQ ID NO: 8, a hGH polyadenylation sequence comprising that nucleic acid sequence of SEQ ID NO: 13, or a bGH polyadenylation sequence comprising the nucleic acid sequence of SEQ ID NO: 14.

In an aspect, this disclosure, and includes, provides a method of converting reactive astrocytes to functional neurons in a brain of a living human brain comprising: injecting an adeno-associated virus (AAV) into a subject in need thereof, where the AAV comprises a DNA vector construct comprising a nucleic acid coding sequence encoding a human neurogenic differentiation 1 (hNeuroD1) protein comprising the amino acid sequence of SEQ ID NO: 10, where the coding sequence is operably linked to expression control elements comprising: (a) human glial fibrillary acid protein (GFAP) promoter comprising a nucleic acid sequence selected from the group consisting of SEQ ID NOs: 4, 12, and 15; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence of SEQ ID NO: 5 or 16; (d) a woodchuck hepatitis virus posttranscriptional regulatory element (WPRE) comprising the nucleic acid sequence selected from the group consisting of SEQ ID NOs: 7 and 18; and (e) a SV40 polyadenylation signal sequence comprising the nucleic acid sequence of SEQ ID NO: 8, a hGH polyadenylation sequence comprising that nucleic acid sequence of SEQ ID NO: 13, or a bGH polyadenylation sequence comprising the nucleic acid sequence of SEQ ID NO: 14.

In an aspect, this disclosure provides, and includes, a method of converting glial cells to neurons in a subject in need thereof comprising: delivering an adeno-associated virus (AAV) to the subject in need thereof, where the AAV comprises a DNA vector construct comprising a neurogenic differentiation 1 (NeuroD1) sequence operably linked to expression control elements comprising: (a) a glial fibrillary acid protein (GFAP) promoter; (b) an enhancer; (c) a chimeric intron; (d) a woodchuck hepatitis virus posttranscriptional regulatory element (WPRE); and (e) a polyadenylation signal sequence, where the AAV vector is capable of converting at least one glial cell to a neuron in the subject in need thereof.

In an aspect, this disclosure provides, and includes, a method of treating a neurological condition in a subject in need thereof comprising: delivering an adeno-associated virus (AAV) to the subject, where the AAV comprises a DNA vector construct comprising a neurogenic differentiation 1 (NeuroD1) sequence operably linked to expression control elements comprising: (a) a glial fibrillary acid protein (GFAP) promoter; (b) an enhancer; (c) a chimeric intron; (d) a woodchuck hepatitis virus posttranscriptional regulatory element (WPRE); and (e) a polyadenylation signal to the subject in need thereof.

In an aspect, a method as provided herein, is capable of converting at least one glial cell to a neuron. In one aspect, a method as provided herein converts at least one glial cell to a neuron.

Distal-less homeobox 2 (Dlx2; also referred to as TES1) is a member of the Dlx gene family and is a homeobox containing gene that plays a role in forebrain and craniofacial development.

Achaete-scute family BHLH transcription factor 1 (Ascl1; also referred to as ASH1, HASH1, MASH-1, and bHLHa46) encodes a member of the basic helix-loop-helix family of transcription factors and is a gene that plays a role in neuronal commitment and differentiation.

Insulin gene enhancer protein (ISL1; also known as ISL LIM homeobox-1 and ISLET1) is a gene that encodes a transcription factor containing two N-terminal LIM domains and one C-terminal homeodomain. The encoded protein plays a role in the embryogenesis of pancreatic islets of Langerhans.

LIM-homeobox 3 (LHX3; also known as LIM3 and CPHD3) gene encodes for a protein from a family of proteins with a unique cysteine-rich zinc-binding domain (LIM domain).

In an aspect, a method as provided herein uses an AAV vector comprising a NeuroD1 coding sequence in accordance with the present disclosure. In one aspect, a method as provided herein uses an AAV vector comprising a NeuroD1 coding sequence in combination with a second AAV vector comprising a second transcription factor coding sequence. In one aspect, a method as provided herein uses an AAV vector comprising a NeuroD1 coding sequence and a second transcription factor coding sequence. In one aspect, a second transcription factor is selected from the group consisting of Dlx2, Ascl1, ISL1, and LHX3. In one aspect, a second transcription factor is Dlx2. In one aspect, a second transcription factor is Ascl1. In one aspect, a second transcription factor is ISL1. In one aspect, a second transcription factor is LHX3. In one aspect, a method as provided herein uses an AAV vector comprising a NeuroD1 coding sequence and second NeuroD1 coding sequence. In one aspect, a method as provided herein uses an AAV vector comprising a NeuroD1 coding sequence in combination with a second AAV vector comprising a NeuroD1 coding sequence.

In an aspect, an AAV vector as provided herein, is measured for functionality by assessing transcription levels and protein levels of NeuN, doublecortin (DCX), β3-tubulin, (neurofilament 200) NF-200, (microtubule-associated protein 2) MAP2, ionized calcium binding adaptor molecule (Iba1).

As used herein, the term "NeuN" or "Fox-3" or "Rbfox2" or "Hexaribonucleotide Binding Protein-3" refers to a protein which is a homologue to the protein product of a sex-determining gene in *Caenorhabditis elegans* and is a neuronal nuclear antigen.

As used herein, the term "DCX" or "doubling" or "lissencephalin-X" refers to a microtubule-associated protein expressed by neuronal precursor cells and immature neurons in embryonic and adult cortical structures.

As used herein, the term "β3-tubulin" or "Class III β-tubulin" or "β-tubulin III" refers to a microtubule element of the tubulin family found in neurons.

As used herein, the term "NF-200" refers to a class of protein that is a type IV intermediate filaments found in the cytoplasm of neurons.

As used herein, the term "MAP2" refers to a protein that belongs to the microtubule-associated protein family and play a role in determining and stabilizing neuronal morphology during neuron development.

As used herein, the term "Iba1" refers to a microglia macrophage-specific calcium binding protein.

In an aspect, a composition as provided herein, is capable of converting at least one glial cell to a neuron. In one aspect, a composition as provided herein converts at least one glial cell to a neuron As used herein, the term "mammal" refers to any species classified in the class Mammalia.

As used herein, the term "human" refers to a *Homo sapiens*. In an aspect, a human has a neurological disorder.

As used herein, the term "living human" refers to a human that has heart, respiration and brain activity.

As used herein, the term "non-human primate" refers to any species or subspecies classified in the order Primates that are not *Homo sapiens*. Non-limiting examples of non-human primates include chimpanzee, bonobo, orangutan, gorilla, macaque, marmoset, capuchin, baboon, gibbon, and lemur.

As used herein, the term "delivering" or "delivery" refers to treating a mammal with an AAV vector or composition as provided herein. In an aspect, an AAV vector or composition as provided herein is delivered to a subject in need thereof. In one aspect, an AAV vector or composition as provided herein is formulated to be delivered to a subject in need thereof. In one aspect, delivering comprises local delivery. In one aspect, an AAV vector or composition as provided herein is formulated for local delivery. In one aspect, delivering comprises systemic delivery. In one aspect, an AAV vector or composition as provided herein is formulated for systemic delivery. In one aspect, delivery comprises injecting an AAV vector or composition as provided herein into a subject in need thereof. In one aspect, delivering is selected from the group consisting of intraperitoneal, intramuscular, intravenous, intrathecal, intracerebral, intracranial, intra lateral ventricle of the brain, intra cisterna magna, intra vitreous, intra-subretina, intraparenchymal, intranasal, or oral administration. In one aspect, delivery comprises intraperitoneal delivery. In one aspect, delivery comprises intramuscular delivery. In one aspect, delivery comprises intravenous delivery. In one aspect, delivery comprises intrathecal delivery. In one aspect, delivery comprises intracerebral delivery. In one aspect, delivery comprises intracranial delivery. In one aspect, delivery comprises intra lateral ventricle of the brain delivery. In one aspect, delivery comprises intra cisterna magna delivery. In one aspect, delivery comprises intra vitreous delivery. In one aspect, delivery comprises intra-subretina delivery. In one aspect, delivery comprises intraparenchymal delivery. In one aspect, delivery comprises intranasal delivery. In one aspect, delivery comprises oral administration.

As used herein, the term "injecting" refers to delivering an AAV vector or composition as provided herein under pressure and with force. As a non-limiting example, injecting can comprise the use of a syringe and needle.

In an aspect, an AAV vector or composition as provided herein is injected into a brain of a subject. In one aspect, an AAV vector or composition is injected into a cerebral cortex of a subject. In one aspect, an AAV vector or composition as provided herein is injected in to a spinal cord or a subject. In one aspect, an AAV vector or composition is injected in the striatum of a subject. In one aspect, an AAV vector or composition is injected in the dorsal striatum of a subject. In one aspect, an AAV vector or composition is injected in the putamen of a subject. In one aspect, an AAV vector or composition is injected in the caudate nucleus of a subject. In one aspect, an AAV vector or composition is injected in the substantia nigra of a subject.

In an aspect, an AAV vector or composition as provided herein has spread in the brain between about 1% and about 100%. In one aspect, an AAV vector or composition as provided herein has spread in the brain between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the cerebral cortex between about 1% and about 100%. In one aspect, an AAV vector or composition as provided herein has spread in the cerebral cortex between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the spinal cord between about 1% and about 100%. In one aspect, an AAV vector or composition as provided herein has spread in the spinal cord between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the striatum between about 1% and about 100%. In one aspect, an AAV vector or composition as provided herein has spread in the striatum between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the dorsal striatum between about 1% and about 100%. In one aspect, an AAV vector or composition as provided herein has spread in the dorsal striatum between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the putamen between about 1% and about 100%. In one aspect, an AAV vector or composition as provided herein has spread in the putamen between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the caudate nucleus between about 1% and about 100%. In one aspect, an AAV vector or composition as provided herein has spread in the caudate nucleus between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In and aspect, an AAV vector or composition as provided herein has a spread at from injection site between about 1% and about 100%. In one aspect, an AAV vector or composition as provided herein has a spread from injection site between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 60%, between about 40% and about 50%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the substantia nigra between about 1% and about 100%. In one aspect, an AAV vector or composition as provided herein has spread in the putamen between about 1% and about 10%, between 1% and about 20%, between 1% and about 30%, between 10% and about 20%, between 10% and about 30%, between about 10% and about 40%, between about 20% and about 30%, between about 20% and about 50%, between about 30% and about 40%, between about 30% and about 40%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

As used herein, the term "AAV particle" refers to packaged capsid forms of the AAV virus that transmits its nucleic acid genome to cells.

In an aspect, a composition comprising an AAV particle encoded by an AAV vector as provided herein is injected at a concentration between $10^{10}$ AAV particles/mL and $10^{14}$ AAV particles/mL. In one aspect, a composition comprising an AAV particle encoded by an AAV vector as provided herein is injected at a concentration between $10^{10}$ AAV particles/mL and $10^{11}$ AAV particles/mL, between $10^{10}$ AAV particles/mL and $10^{12}$ AAV particles/mL, between $10^{10}$ AAV particles/mL and $10^{13}$ AAV particles/mL, between $10^{11}$ AAV particles/mL and $10^{12}$ AAV particles/mL, between $10^{11}$ AAV particles/mL and $10^{13}$ AAV particles/mL, between $10^{11}$ AAV particles/mL and $10^{14}$ AAV particles/mL, between $10^{12}$ AAV particles/mL and $10^{13}$ AAV particles/mL, between $10^{12}$ AAV particles/mL and $10^{14}$ AAV particles/mL, or between $10^{13}$ AAV particles/mL and $10^{14}$ AAV particles/mL.

In an aspect, a composition comprising an AAV particle encoded by an AAV vector as provided herein is injected at volume between 10 µl and 1000 µl. In one aspect, a composition comprising an AAV particle encoded by an AAV vector as provided herein is injected at volume between 10 µl and 100 µl, between 10 µl and 200 µl, between 10 µl and 300 µl, between 100 µl and 200 µl, between 100 µl and 300 µl, between 100 µl and 400 µl, between 200 µl and 300 µl, between 200 µl and 400 µl, between 200 µl and 500 µl, between 300 µl and 400 µl, between 300 µl and 500 µl, between 300 µl and 600 µl, between 400 µl and 500 µl, between 400 µl and 600 µl, between 400 µl and 700 µl, between 500 µl and 600 µl, between 500 µl and 700 µl, between 500 µl and 800 µl, between 600 µl and 700 µl, between 600 µl and 800 µl, between 600 µl and 900 µl, between 700 µl and 800 µl, between 700 µl and 900 µl, between 700 µl and 1000 µl, between 800 µl and 900 µl, between 800 µl and 1000 µl, or between 900 µl and 1000 µl.

As used herein, the term "subject" refers to any animal subject. Non-limiting examples of animal subjects include humans, laboratory animals (e.g., non-human primates, rats, mice), livestock (e.g., cows, sheep, goats, pigs, turkeys, chickens), and household pets (e.g., dogs, cats, rodents, etc.).

As used herein, "a subject in need thereof" refers to a subject with a neurological condition. In an aspect, a subject in need thereof has a neurological condition selected from the group consisting of Alzheimer's Disease, Parkinson's Disease, amyotrophic lateral sclerosis (ALS), Huntington's Disease, epilepsy, physical injury, stroke, cerebral aneurysm, traumatic brain injury, concussion, a tumor, inflammation, infection, ataxia, brain atrophy, spinal cord atrophy, multiple sclerosis, traumatic spinal cord injury, ischemic or hemorrhagic myelopathy (myelopathy), global ischemia, hypoxic ischemic encephalopathy, embolism, fibrocartilage embolism myelopathy, thrombosis, nephropathy, chronic inflammatory disease, meningitis, and cerebral venous sinus thrombosis. In one aspect, a subject in need thereof has Alzheimer's Disease. In one aspect, a subject in need thereof has Parkinson's Disease. In one aspect, a subject in need thereof has ALS. In one aspect, a subject in need thereof has Huntington's Disease. In one aspect, a subject in need thereof has epilepsy. In one aspect, a subject in need thereof has a physical injury. In one aspect, a subject in need thereof has a stroke. In one aspect, a subject in need thereof has ischemic stroke. In one aspect, a subject in need thereof has hemorrhagic stroke. In one aspect, a subject in need thereof has a cerebral aneurysm. In one aspect, a subject in need thereof has traumatic brain injury. In one aspect, a subject in need thereof has concussion. In one aspect, a subject in need thereof has a tumor. In one aspect, a subject in need thereof has inflammation. In one aspect, a subject in need thereof has an infection. In, one aspect, a subject in need thereof has ataxia. In, one aspect, a subject in need thereof has brain atrophy. In one aspect, a subject in need thereof has spinal cord atrophy. In one aspect, a subject in need thereof has multiple sclerosis. In one aspect, a subject in need thereof has a traumatic spinal cord injury. In one aspect, a subject in need thereof has ischemic or hemorrhagic myelopathy (myelopathy). In one aspect, a subject in need thereof has global ischemia. In one aspect, a subject in need thereof has hypoxic ischemic encephalopathy. In one aspect, a subject in need thereof has an embolism. In one aspect, a subject in need thereof has fibrocartilage embolism myelopathy. In one aspect, a subject in need thereof has thrombosis. In one aspect, a subject in need thereof has nephropathy. In one aspect, a subject in need thereof has chronic inflammatory disease. In one aspect, a subject in need thereof has meningitis. In one aspect, a subject in need thereof has cerebral venous sinus thrombosis.

In an aspect, a subject in need thereof is a mammal. In one aspect, a subject in need thereof is a human. In one aspect, a subject in need thereof is a non-human primate. In one aspect, a subject in need thereof is selected from the group consisting of chimpanzee, bonobo, orangutan, gorilla, macaque, marmoset, capuchin, baboon, gibbon, and lemur. In one aspect, a subject in need thereof is a chimpanzee. In one aspect, a subject in need thereof is a bonobo. In one aspect, a subject in need thereof is orangutan. In one aspect, a subject in need thereof is gorilla. In one aspect, a subject in need thereof is a macaque. In one aspect, a subject in need thereof is marmoset. In one aspect, a subject in need thereof is a capuchin. In one aspect, a subject in need thereof is a baboon. In one aspect, a subject in need thereof is a gibbon. In one aspect, a subject in need thereof is lemur.

In one aspect, a subject in need thereof is a male. In one aspect, a subject in need thereof is a female. In one aspect, a subject in need thereof is gender neutral. In one aspect, a subject in need thereof is a premature newborn. In one aspect, a premature newborn is born before 36 weeks gestation. In one aspect, a subject in need thereof is a term newborn. In one aspect, a term newborn is below about 2 months old. In one aspect, a subject in need thereof is a neonate. In one aspect, a neonate is below about 1 month old. In one aspect, a subject in need thereof is an infant. In one aspect, an infant is between 2 months and 24 months old. In one aspect, an infant is between 2 months and 3 months, between 2 months and 4 months, between 2 months and 5 months, between 3 months and 4 months, between 3 months and 5 months, between 3 months and 6 months, between 4 months and 5 months, between 4 months and 6 months, between 4 months and 7 months, between 5 months and 6 months, between 5 months and 7 months, between 5 months and 8 months, between 6 months and 7 months, between 6 months and 8 months, between 6 months and 9 months, between 7 months and 8 months, between 7 months and 9 months, between 7 months and 10 months, between 8 months and 9 months, between 8 months and 10 months, between 8 months and 11 months, between 9 months and 10 months, between 9 months and 11 months, between 9 months and 12 months, between 10 months and 11 months, between 10 months and 12 months, between 10 months and 13 months, between 11 months and 12 months, between 11 months and 13 months, between 11 months and 14 months, between 12 months and 13 months, between 12 months and 14 months, between 12 months and 15 months, between 13 months and 14 months, between 13 months and 15 months, between 13 months and 16 months, between 14 months and 15 months, between 14 months and 16 months, between 14 months and 17 months, between 15 months and 16 months, between 15 months and 17 months, between 15 months and 18 months, between 16 months and 17 months, between 16 months and 18 months, between 16 months and 19 months, between 17 months and 18 months, between 17 months and 19 months, between 17 months and 20 months, between 18 months and 19 months, between 18 months and 20 months, between 18 months and 21 months, between 19 months and 20 months, between 19 months and 21 months, between 19 months and 22 months, between 20 months and 21 months, between 20 months and 22 months, between 20 months and 23 months, between 21 months and 22 months, between 21 months and 23 months, between 21 months and 24 months, between 22 months and 23 months, between 22 months and 24 months, and between 23 months and 24 months old. In one aspect, a subject in need thereof is a toddler. In one aspect, a toddler is between 1 year and 4 years old. In one aspect, a toddler is between 1 year and 2 years, between 1 year and 3 years, between 1 year and 4 years, between 2 years and 3 years, between 2 years and 4 years, and between 3 years and 4 years old. In one aspect, a subject in need thereof is a young child. In one aspect, a young child is between 2 years and 5 years old. In one aspect, a young child is between 2 years and 3 years, between 2 years and 4 years, between 2 years and 5 years, between 3 years and 4 years, between 3 years and 5 years, and between 4 years and 5 years old. In one aspect, a subject in need thereof is a child. In one aspect, a child is between 6 years and 12 years old. In one aspect, a child is between 6 years and 7 years, between 6 years and 8 years, between 6 years and 9 years, between 7 years and 8 years, between 7 years and 9 years, between 7 years and 10 years, between 8 years and 9 years, between 8 years and 10 years, between 8 years and 11 years, between 9 years and 10 years, between 9 years and 11 years, between 9 years and 12 years, between 10 years and 11 years, between 10 years and 12 years, and between 11 years and 12 years old. In one aspect, a subject in need thereof is an adolescent. In one aspect, an adolescent is between 13 years and 19 years old. In one aspect, an adolescent is between 13 years and 14 years, between 13 years and 15 years, between 13 years and 16 years, between 14 years and 15 years, between 14 years and 16 years, between 14 years and 17 years, between 15 years and 16 years, between 15 years and 17 years, between 15 years and 18 years, between 16 years and 17 years, between 16 years and 18 years, between 16 years and 19 years, between 17 years and 18 years, between 17 years and 19 years, and between 18 years and 19 years old. In one aspect, a subject in need thereof is a pediatric subject. In one aspect, a pediatric subject between 1 day and 18 years old. In one aspect, a pediatric subject is between 1 day and 1 year, between 1 day and 2 years, between 1 day and 3 years, between 1 year and 2 years, between 1 year and 3 years, between 1 year and 4 years, between 2 years and 3 years, between 2 years and 4 years, between 2 years and 5 years, between 3 years and 4 years, between 3 years and 5 years, between 3 years and 6 years, between 4 years and 5 years, between 4 years and 6 years, between 4 years and 7 years, between 5 years and 6 years, between 5 years and 7 years, between 5 years and 8 years, between 6 years and 7 years, between 6 years and 8 years, between 6 years and 9 years, between 7 years and 8 years, between 7 years and 9 years, between 7 years and 10 years, between 8 years and 9 years, between 8 years and 10 years, between 8 years and 11 years, between 9 years and 10 years, between 9 years and 11 years, between 9 years and 12 years, between 10 years and 11 years, between 10 years and 12 years, between 10 years and 13 years, between 11 years and 12 years, between 11 years and 13 years, between 11 years and 14 years, between 12 years and 13 years, between 12 years and 14 years, between 12 years and 15 years, between 13 years and 14 years, between 13 years and 15 years, between 13 years and 16 years, between 14 years and 15 years, between 14 years and 16 years, between 14 years and 17 years, between 15 years and 16 years, between 15 years and 17 years, between 15 years and 18 years, between 16 years and 17 years, between 16 years and 18 years, and between 17 years and 18 years old. In one aspect, a subject in need thereof is a geriatric subject. In one aspect, a geriatric subject is between 65 years and 95 or more years old. In one aspect, a geriatric subject is between 65 years and 70 years, between 65 years and 75 years, between 65 years and 80 years, between 70 years and 75 years, between 70 years and 80 years, between 70 years and 85 years, between 75 years and 80 years, between 75 years and 85 years, between 75 years and 90 years, between 80 years and 85 years, between 80 years and 90 years, between 80 years and 95 years, between 85 years and 90 years, and between 85 years and 95 years old. In one aspect, a subject in need thereof is an adult. In one aspect, an adult subject is between 20 years and 95 or more years old. In one aspect, an adult subject is between 20 years and 25 years, between 20 years and 30 years, between 20 years and 35 years, between 25 years and 30 years, between 25 years and 35 years, between 25 years and 40 years, between 30 years and 35 years, between 30 years and 40 years, between 30 years and 45 years, between 35 years and 40 years, between 35 years and 45 years, between 35 years and 50 years, between 40 years and 45 years, between 40 years and 50 years, between 40 years and 55 years, between 45 years and 50 years, between 45 years and 55 years, between 45 years and 60 years, between 50 years and 55 years, between 50 years and 60 years, between 50 years and 65 years, between 55 years and 60 years, between 55 years and 65 years, between 55 years and 70 years, between 60 years and 65 years, between 60 years and 70 years, between 60 years and 75 years, between 65 years and 70 years, between 65 years and 75 years, between 65 years and 80 years, between 70 years and 75 years, between 70 years and 80 years, between 70 years and 85 years, between 75 years and 80 years, between 75 years and 85 years, between 75 years and 90 years, between 80 years and 85 years, between 80 years and 90 years, between 80 years and 95 years, between 85 years and 90 years, and between 85 years and 95 years old. In one aspect, a subject in need thereof is between 1 year and 5 years, between 2 years and 10 years, between 3 years and 18 years, between 21 years and 50 years, between 21 years and 40 years, between 21 years and 30 years, between 50 years and 90 years, between 60 years and 90 years, between 70 years and 90 years, between 60 years and 80 years, or between 65 years and 75 years old. In one aspect, a subject in need thereof is a young old subject (65 to 74 years old). In one aspect, a subject in need thereof is a middle old subject (75 to 84 years old). In one aspect, a subject in need thereof is an old subject (>85 years old).

As used herein, the term "flow rate" refers to the rate of delivery of an AAV vector or composition. In an aspect, the flow rate is between 0.1 µL/minute and 5.0 µL/minute. In one aspect, the flow rate is between 0.1 µL/minute and 0.2 µL/minute, between 0.1 µL/minute and 0.3 µL/minute, between 0.1 µL/minute and 0.4 µL/minute, between 0.2 µL/minute and 0.3 µL/minute, between 0.2 µL/minute and 0.4 µL/minute, between 0.2 µL/minute and 0.5 µL/minute, between 0.3 µL/minute and 0.4 µL/minute, between 0.3 µL/minute and 0.5 µL/minute, between 0.3 µL/minute and 0.6 µL/minute, between 0.4 µL/minute and 0.5 µL/minute, between 0.4 µL/minute and 0.6 µL/minute, between 0.4 µL/minute and 0.7 µL/minute, between 0.5 µL/minute and 0.6 µL/minute, between 0.5 µL/minute and 0.7 µL/minute, between 0.5 µL/minute and 0.8 µL/minute, between 0.6 µL/minute and 0.7 µL/minute, between 0.6 µL/minute and 0.8 µL/minute, between 0.6 µL/minute and 0.9 µL/minute, between 0.7 µL/minute and 0.8 µL/minute, between 0.7 µL/minute and 0.9 µL/minute, between 0.7 µL/minute and 1.0 µL/minute, between 0.8 µL/minute and 0.9 µL/minute, between 0.8 µL/minute and 1.0 µL/minute, between 0.8 µL/minute and 1.1 µL/minute, between 0.9 µL/minute and 1.0 µL/minute, between 0.9 µL/minute and 1.1 µL/minute, between 0.9 µL/minute and 1.2 µL/minute, between 1.0 µL/minute and 1.1 µL/minute, between 1.0 µL/minute and 1.2 µL/minute, between 1.0 µL/minute and 1.3 µL/minute, between 1.1 µL/minute and 1.2 µL/minute, between 1.1 µL/minute and 1.3 µL/minute, between 1.1 µL/minute and 1.4 µL/minute, between 1.2 µL/minute and 1.3 µL/minute, between 1.2 µL/minute and 1.4 µL/minute, between 1.2 µL/minute and 1.5 µL/minute, between 1.3 µL/minute and 1.4 µL/minute, between 1.3 µL/minute and 1.5 µL/minute, between 1.3 µL/minute and 1.6 µL/minute, between 1.4 µL/minute and 1.5 µL/minute, between 1.4 µL/minute and 1.6 µL/minute, between 1.4 µL/minute and 1.7 µL/minute, between 1.5 µL/minute and 1.6 µL/minute, between 1.5 µL/minute and 1.7 µL/minute, between 1.5 µL/minute and 1.8 µL/minute, between 1.6 µL/minute and 1.7 µL/minute, between 1.6 µL/minute and 1.8 µL/minute, between 1.6 µL/minute and 1.9 µL/minute, between 1.7 µL/minute and 1.8 µL/minute, between 1.7 µL/minute and 1.9 µL/minute, between 1.7 µL/minute and 2.0 µL/minute, between 1.8 µL/minute and 1.9 µL/minute, between 1.8 µL/minute and 2.0 µL/minute, between 1.8 µL/minute and 2.1 µL/minute, between 1.9 µL/minute and 2.0 µL/minute, between 1.9 µL/minute and 2.1 µL/minute, between 1.9 µL/minute and 2.2 µL/minute, between 2.0 µL/minute and 2.1 µL/minute, between 2.0 µL/minute and 2.2 µL/minute, between 2.0 µL/minute and 2.3 µL/minute, between 2.1 µL/minute and 2.2 µL/minute, between 2.1 µL/minute and 2.3 µL/minute, between 2.1 µL/minute and 2.4 µL/minute, between 2.2 µL/minute and 2.3 µL/minute, between 2.2 µL/minute and 2.4 µL/minute, between 2.2 µL/minute and 2.5 µL/minute, between 2.3 µL/minute and 2.4 µL/minute, between 2.3 µL/minute and 2.5 µL/minute, between 2.3 µL/minute and 2.6 µL/minute, between 2.4 µL/minute and 2.5 µL/minute, between 2.4 µL/minute and 2.6 µL/minute, between 2.4 µL/minute and 2.7 µL/minute, between 2.5 µL/minute and 2.6 µL/minute, between 2.5 µL/minute and 2.7 µL/minute, between 2.5 µL/minute and 2.8 µL/minute, between 2.6 µL/minute and 2.7 µL/minute, between 2.6 µL/minute and 2.8 µL/minute, between 2.6 µL/minute and 2.9 µL/minute, between 2.7 µL/minute and 2.8 µL/minute, between 2.7 µL/minute and 2.9 µL/minute, between 2.7 µL/minute and 3.0 µL/minute, between 2.8 µL/minute and 2.9 µL/minute, between 2.8 µL/minute and 3.0 µL/minute, between 2.8 µL/minute and 3.1 µL/minute, between 2.9 µL/minute and 3.0 µL/minute, between 2.9 µL/minute and 3.1 µL/minute, between 2.9 µL/minute and 3.2 µL/minute, between 3.0 µL/minute and 3.1 µL/minute, between 3.0 µL/minute and 3.2 µL/minute, between 3.0 µL/minute and 3.3 µL/minute, between 3.1 µL/minute and 3.2 µL/minute, between 3.1 µL/minute and 3.3 µL/minute, between 3.1 µL/minute and 3.4 µL/minute, between 3.2 µL/minute and 3.3 µL/minute, between 3.2 µL/minute and 3.4 µL/minute, between 3.2 µL/minute and 3.5 µL/minute, between 3.3 µL/minute and 3.4 µL/minute, between 3.3 µL/minute and 3.5 µL/minute, between 3.3 µL/minute and 3.6 µL/minute, between 3.4 µL/minute and 3.5 µL/minute, between 3.4 µL/minute and 3.6 µL/minute, between 3.4 µL/minute and 3.7 µL/minute, between 3.5 µL/minute and 3.6 µL/minute, between 3.5 µL/minute and 3.7 µL/minute, between 3.5 µL/minute and 3.8 µL/minute, between 3.6 µL/minute and 3.7 µL/minute, between 3.6 µL/minute and 3.8 µL/minute, between 3.6 µL/minute and 3.9 µL/minute, between 3.7 µL/minute and 3.8 µL/minute, between 3.7 µL/minute and 3.9 µL/minute, between 3.7 µL/minute and 4.0 µL/minute, between 3.8 µL/minute and 3.9 µL/minute, between 3.8 µL/minute and 4.0 µL/minute, between 3.8 µL/minute and 4.1 µL/minute, between 3.9 µL/minute and 4.0 µL/minute, between 3.9 µL/minute and 4.1 µL/minute, between 3.9 µL/minute and 4.2 µL/minute, between 4.0 µL/minute and 4.1 µL/minute, between 4.0 µL/minute and 4.2 µL/minute, between 4.0 µL/minute and 4.3 µL/minute, between 4.1 µL/minute and 4.2 µL/minute, between 4.1 µL/minute and 4.3 µL/minute, between 4.1 µL/minute and 4.4 µL/minute, between 4.2 µL/minute and 4.3 µL/minute, between 4.2 µL/minute and 4.4 µL/minute, between 4.2 µL/minute and 4.5 µL/minute, between 4.3 µL/minute and 4.4 µL/minute, between 4.3 µL/minute and 4.5 µL/minute, between 4.3 µL/minute and 4.6 µL/minute, between 4.4 µL/minute and 4.5 µL/minute, between 4.4 µL/minute and 4.6 µL/minute, between 4.4 µL/minute and 4.7 µL/minute, between 4.5 µL/minute and 4.6 µL/minute, between 4.5 µL/minute and 4.7 µL/minute, between 4.5 µL/minute and 4.8 µL/minute, between 4.6 µL/minute and 4.7 µL/minute, between 4.6 µL/minute and 4.8 µL/minute, between 4.6 µL/minute and 4.9 µL/minute, between 4.7 µL/minute and 4.8 µL/minute, between 4.7 µL/minute and 4.9 µL/minute, between 4.7 µL/minute and 5.0 µL/minute, 4.8 µL/minute and 4.9 µL/minute, between 4.8 µL/minute and 5.0 µL/minute, or between 4.9 µL/minute and 5.0 µL/minute.

As used herein, the term "therapeutically effective dose" or "pharmaceutically active dose" refers to an amount of AAV particles or composition as provided herein which is effective in treating a neurological condition. In an aspect, an AAV particle or composition as provided herein can be provided together with a pharmaceutically acceptable carrier. As used herein, a "pharmaceutically acceptable carrier" refers to a non-toxic solvent, dispersant, excipient, adjuvant, or other material which is mixed with an AAV particles or composition as provided herein.

Non-limiting examples of a pharmaceutically acceptable carrier include a liquid (e.g., saline), gel, nanoparticles, exosomes, lipid vesicles, or solid form of diluents, adjuvant, excipients or an acid resistant encapsulated ingredient. Non-limiting examples of suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In an aspect, a therapeutic effective dose contains auxiliary substances such as wetting or emulsifying agents, stabilizing or pH buffering agents. In one aspect, a therapeutically effective dose of an AAV particle or composition as provided herein is injected to a subject. In one aspect, a therapeutically effective dose of an AAV particle or composition as provided herein is delivered into a subject. In one aspect, a therapeutically effective dose is administered with at least one pharmaceutically acceptable carrier. In one aspect, a therapeutic effective dose contains between about 1% and about 5%, between about 5% and about 10%, between about 10% and about 15%, between about 15% and about 20%, between about 20% and about 25%, between about 25% and about 30%, between about 30% and about 35%, between about 40 and about 45%, between about 50% and about 55%, between about 1% and about 95%, between about 2% and about 95%, between about 5% and about 95%, between about 10% and about 95%, between about 15% and about 95%, between about 20% and about 95%, between about 25% and about 95%, between about 30% and about 95%, between about 35% and about 95%, between about 40% and about 95%, between about 45% and about 95%, between about 50% and about 95%, between about 55% and about 95%, between about 60% and about 95%, between about 65% and about 95%, between about 70% and about 95%, between about 45% and about 95%, between about 80% and about 95%, or between about 85% and about 95% of AAV particle or composition as provided herein.

In an aspect, a therapeutically effective dose is delivered to subject in need thereof at least once daily or at least once weekly for at least two consecutive days or weeks. In one aspect, a therapeutically effective dose is delivered to subject in need thereof at least once daily or at least once weekly for at least 3, 4, 5, 6, 7, 8, 9, 10, 11, 12, 13, 14, or 15 consecutive days or weeks. In one aspect, a therapeutically effective dose is delivered to subject in need thereof at least once daily or at least once weekly for at least 1, 2, 3, 4, 5, 6, 7, 8, 9, 10, 11, or 12 consecutive weeks. In one aspect, a therapeutically effective dose is delivered to subject in need thereof at least once daily or at least once weekly for at most 4, 5, 6, 7, 8, 9, 10, 11, 12, 13, 14, 15, 16, 17, 18, 19, or 20 consecutive days or weeks. In one aspect, a therapeutically effective dose is delivered to subject in need thereof at least once daily or at least once weekly for at most 1, 2, 3, 4, 5, 6, 7, 8, 9, 10, 11, or 12 consecutive weeks or months. In one aspect, a therapeutically effective dose is delivered to subject in need thereof is administered at least once for at least 1, 2, 3, 4, 5, 6, 7, 8, 9, 10, 11, or 12 consecutive months or years, chronically for a subject's entire life span, or an indefinite period of time. In one aspect, a therapeutically effective dose is delivered to subject in need thereof once a year for 2 consecutive years, 3 consecutive years, or 5 consecutive years. In one aspect, a therapeutically effective dose is delivered to subject in need thereof once a year for 2 consecutive years. In one aspect, a therapeutically effective dose is delivered to subject in need thereof once a year for 3 consecutive years. In one aspect, a therapeutically effective dose is delivered to subject in need thereof once a year for 5 consecutive years.

As used herein, the term "remission", "cure," or "resolution rate" refers to the percentage of subjects in need thereof that are cured or obtain remission or complete resolution of a neurological condition in response to a therapeutically effective dose.

As used herein, the term "response rate" refers to the percentage of subjects in need thereof that respond positively (e.g., reduced severity or frequency of one or more symptoms) to a therapeutically effective dose.

In one aspect, a therapeutically effective dose achieves a remission, cure, response rate, or resolution rate of a neurological condition of at least about 50%. In one aspect, a therapeutically effective dose eliminates, reduces, slows, or delays, one or more neurological condition symptoms. Non-limiting examples of neurological condition symptoms include tremor, slowed movement (bradykinesia), rigid muscles, impaired posture and balance, loss of automatic movements, uncoordinated movement, uncontrolled movement, spontaneous jerking movement, speech changes, numbness, and writing changes. In an aspect, a neurological condition symptom is a movement symptom. Non-limiting examples of movement symptoms include impairment of an involuntary movement or an impairment of a voluntary movement. In one aspect, a neurological condition symptom is a cognitive symptom. Non-limiting examples of cognitive symptoms include fine motor skills, tremors, seizures, chorea, dystonia, dyskinesia, slow or abnormal eye movements, impaired gait, impaired posture, impaired balance, difficulty with speech, difficulty with swallowing, difficulty organizing, difficulty prioritizing, difficulty focusing on tasks, lack of flexibility, lack of impulse control, outbursts, lack of awareness of one's own behaviors and/or abilities, slowness in processing thoughts, difficulty in learning new information, difficulty in remember things, difficulty in communications, difficulty in following orders, difficulty in executing tasks.

In an aspect, neurological condition symptom is a psychiatric symptom. Non-limiting examples of psychiatric symptoms include depression, irritability, sadness or apathy, social withdrawal, insomnia, fatigue, lack of energy, obsessive-compulsive disorder, mania, bipolar disorder, and weight loss. In one aspect, a neurological condition symptom is at least one damaged blood vessel. In one aspect, a neurological condition symptom is a damaged blood brain barrier. In one aspect, a neurological condition symptom is damaged blood flow. Non-limiting examples of tests to evaluate the elimination, reduction, slow, or delay, of neurological condition symptoms include the unified Huntington's disease rating scale (UHDRS) score, UHDRS Total Functional Capacity (TFC), UHDRS Functional Assessment, UHDRS Gait score, UHDRS Total Motor Score (TMS), Hamilton depression scale (HAM-D), Columbia-suicide severity rating scale (C-SSRS), Montreal cognitive assessment (MoCA), modified Rankin Scale (mRS), National Institutes of Health Stroke Scale (NIHSS), and Barthel Index (BI), Timed Up and Go Test (TUG), Chedoke Arm and Hand Activity Inventory (CAHAI), Symbol Digit Modalities Test, Controlled Oral Word Association tasks, magnetic resonance imaging (MM), functional magnetic resonance imaging (fMRI), and positron emission tomography (PET) scanning.

In an aspect, a therapeutically effective dose achieves remission, cure, response rate, or resolution rate of a neurological condition of between about 10% and about 100% or more. In one aspect, a therapeutically effective dose achieves remission, cure, response rate, or resolution rate of a neurological condition between 10% and 100%, such as between 10% and 15%, between 10% and 20%, between 10% and 25%, between 15% and 20%, between 15% and 25%, between 15% and 30%, between 20% and 25%, between 20% and 30%, between 20% and 35%, between 25% and 30%, between 25% and 35%, between 25% and 40%, between 30% and 35%, between 30% and 40%, between 35% and 45%, between 35% and 50%, between 40% and 45%, between 40% and 50%, between 40% and 55%, between 45% and 50%, between 45% and 55%, between 45% and 60%, between 50% and 55%, between 50% and 60%, between 50% and 65%, between 55% and 60%, between 55% and 65%, between 55% and 70%, between 60% and 65%, between 60% and 70%, between 60% and 75%, between 65% and 70%, between 65% and 75%, between 65% and 80%, between 70% and 75%, between 70% and 80%, between 70% and 85%, between 75% and 80%, between 75% and 85%, between 75% and 90%, between 80% and 85%, between 80% and 90%, between 80% and 95%, between 85% and 90%, between 85% and 95%, between 85% and 100%, between 90% and 95%, between 90% and 100%, or between 95% and 100%.

In an aspect, a therapeutically effective dose eliminates, reduces, slows, or delays, one or more neurological condition symptoms between 10% and 100%, such as between 10% to about 15%, between 10% and 20%, between 10% and 25%, between 15% and 20%, between 15% and 25%, between 15% and 30%, between 20% and 25%, between 20% and 30%, between 20% and 35%, between 25 and 30%, between 25% and 35%, between 25% and 40%, between 30% and 35%, between 30% and 40%, between 35% and 45%, between 35% and 50%, between 40% and 45%, between 40% and 50%, between 40% and 55%, between 45% and 50%, between 45% and 55%, between 45% and 60%, between 50% and 55%, between 50% and 60%, between 50% and 65%, between 55% and 60%, between 55% and 65%, between 55% and 70%, between 60% and 65%, between 60% and 70%, between 60% and 75%, between 65% and 70%, between 65% and 75%, between 65% and 80%, between 70% and 75%, between 70% and 80%, between 70% and 85%, between 75% and 80%, between 75% and 85%, between 75% and 90%, between 80% and 85%, between 80% and 90%, between 80% and 95%, between 85% and 90%, between 85% and 95%, between 85% and 100%, between 90% and 95%, between 90% and 100%, or between 95% and 100%.

In an aspect, a neurological condition symptom is assessed on the day of treatment, 1 day post treatment, 3 months post treatment, 6 months post treatment, 1 year post treatment and every year thereafter post treatment.

In an aspect, a neurological condition symptom is assessed between 1 day post treatment and 7 days post treatment. In one aspect, symptoms can be assessed between 1 day post treatment and 2 days post treatment, between 1 day post treatment and 3 days post treatment, between 1 day post treatment and 4 days post treatment, between 2 days post treatment and 3 days post treatment, between 2 days post treatment and 4 days post treatment, between 2 days post treatment and 5 days post treatment, between 3 days post treatment and 4 days post treatment, between 3 days post treatment and 5 days post treatment, 3 days post treatment and 6 days post treatment, between 4 days post treatment and 5 days post treatment, between 4 days post treatment and 6 days post treatment, between 4 days post treatment and 7 days post treatment, between 5 days post treatment and 6 days post treatment, between 5 days post treatment and 7 days post treatment, or between 6 days post treatment and 7 days post treatment. In one aspect, symptoms can be assessed between 1 week post treatment and 4 weeks post treatment. In one aspect, symptoms can be assessed between 1 week post treatment and 2 weeks post treatment, between 1 week post treatment and 3 weeks post treatment, between 1 week post treatment and 4 weeks post treatment, between 2 weeks post treatment and 3 weeks post treatment, between 2 weeks post treatment and 4 weeks post treatment, or between 3 weeks post treatment and 4 weeks post treatment. In one aspect, symptoms can be assessed between 1 month post treatment and 12 months post treatment. In one aspect, symptoms can be assessed between 1 month post treatment and 2 months post treatment, between 1 month post treatment and 3 months post treatment, between 1 month post treatment and 4 months post treatment, between 2 months post treatment and 3 months post treatment, between 2 months post treatment and 4 months post treatment, between 2 months post treatment and 5 months post treatment, between 3 months post treatment and 4 months post treatment, between 3 months post treatment and 5 months post treatment, between 3 months post treatment and 6 months post treatment, between 4 months post treatment and 5 months post treatment, between 4 months post treatment and 6 months post treatment, between 4 months post treatment and 7 months post treatment, between 5 months post treatment and 6 months post treatment, between 5 months post treatment and 7 months post treatment, between 5 months post treatment and 8 months post treatment, between 6 months post treatment and 7 months post treatment, between 6 months post treatment and 8 months post treatment, between 6 months post treatment and 9 months post treatment, between 7 months post treatment and 8 months post treatment, between 7 months post treatment and 9 months post treatment, between 7 months post treatment and 10 months post treatment, between 8 months post treatment and 9 months post treatment, between 8 months post treatment and 10 months post treatment, between 8 months post treatment and 11 months post treatment, between 9 months post treatment and 10 months post treatment, between 9 months post treatment and 11 months post treatment, between 9 months post treatment and 12 months post treatment, between 10 months post treatment and 11 months post treatment, between 10 months post treatment and 12 months post treatment, or between 11 months post treatment and 12 months post treatment. In one aspect, symptoms can be assessed between 1 year post treatment and about 20 years post treatment. In one aspect symptoms can be assessed between 1 year post treatment and 5 years post treatment, between 1 year post treatment and 10 years post treatment, between 1 year post treatment and 15 years post treatment, between 5 years post treatment and 10 years post treatment, between 5 years post treatment and 15 years post treatment, between 5 years post treatment and 20 years post treatment, between 10 years post treatment and 15 years post treatment, between 10 years post treatment and 20 years post treatment, or between 15 years post treatment and 20 years post treatment.

As used herein, the term "survival rate" refers to a cohort of subjects in a treatment group still alive after a given period of time after diagnosis of a neurological condition.

In an aspect, a therapeutically effective dose achieves increase survival rate of between about 10% and 100% or more. In one aspect, a therapeutically effective dose achieves an increase in survival rate of between 10% and 100%, such as between 10% and 15%, between 10% and 20%, between 10% and 25%, between 15% and 20%, between 15% and 25%, between 15% and 30%, between 20% and 25%, between 20% and 30%, between 20% and 35%, between 25% and 30%, between 25% and 35%, between 25% and 40%, between 30% and 35%, between 30% and 40%, between 35% and 45%, between 35% and 50%, between 40% and 45%, between 40% and 50%, between 40% and 55%, between 45% and 50%, between 45% and 55%, between 45% and 60%, between 50% and 55%, between 50% and 60%, between 50% and 65%, between 55% and 60%, between 55% and 65%, between 55% and 70%, between 60% and 65%, between 60% and 70%, between 60% and 75%, between 65% and 70%, between 65% and 75%, between 65% and 80%, between 70% and 75%, between 70% and 80%, between 70% and 85%, between 75% and 80%, between 75% and 85%, between 75% and 90%, between 80% and 85%, between 80% and 90%, between 80% and 95%, between 85% and 90%, between 85% and 95%, between 85% and 100%, between 90% and 95%, between 90% and 100%, or between 95% and 100%.

As used herein, the term "life expectancy" refers to a period of time a subject is expected to live.

In an aspect, a therapeutically effective dose increases life expectancy of between about 10% and 100% or more. In one aspect, a therapeutically effective dose increases life expectancy of between 10% and 100%, such as between 10% and 15%, between 10% and 20%, between 10% and 25%, between 15% and 20%, between 15% and 25%, between 15% and 30%, between 20% and 25%, between 20% and 30%, between 20% and 35%, between 25% and 30%, between 25% and 35%, between 25% and 40%, between 30% and 35%, between 30% and 40%, between 35% and 45%, between 35% and 50%, between 40% and 45%, between 40% and 50%, between 40% and 55%, between 45% and 50%, between 45% and 55%, between 45% and 60%, between 50% and 55%, between 50% and 60%, between 50% and 65%, between 55% and 60%, between 55% and 65%, between 55% and 70%, between 60% and 65%, between 60% and 70%, between 60% and 75%, between 65% and 70%, between 65% and 75%, between 65% and 80%, between 70% and 75%, between 70% and 80%, between 70% and 85%, between 75% and 80%, between 75% and 85%, between 75% and 90%, between 80% and 85%, between 80% and 90%, between 80% and 95%, between 85% and 90%, between 85% and 95%, between 85% and 100%, between 90% and 95%, between 90% and 100%, or between 95% and 100%.

In an aspect, a therapeutically effective dose reduces the amount of atrophy within the brain of a subject in need thereof between about 10% and 100% or more. In one aspect, a therapeutically effective dose reduces the amount of atrophy within the brain of a subject in need thereof between 10% and 100%, such as between 10% and 15%, between 10% and 20%, between 10% and 25%, between 15% and 20%, between 15% and 25%, between 15% and 30%, between 20% and 25%, between 20% and 30%, between 20% and 35%, between 25% and 30%, between 25% and 35%, between 25% and 40%, between 30% and 35%, between 30% and 40%, between 35% and 45%, between 35% and 50%, between 40% and 45%, between 40% and 50%, between 40% and 55%, between 45% and 50%, between 45% and 55%, between 45% and 60%, between 50% and 55%, between 50% and 60%, between 50% and 65%, between 55% and 60%, between 55% and 65%, between 55% and 70%, between 60% and 65%, between 60% and 70%, between 60% and 75%, between 65% and 70%, between 65% and 75%, between 65% and 80%, between 70% and 75%, between 70% and 80%, between 70% and 85%, between 75% and 80%, between 75% and 90%, between 80% and 85%, between 85% and 90%, between 80% and 95%, between 85% and 90%, between 85% and 95%, between 85% and 100%, between 90% and 95%, between 90% and 100%, or between 95% and 100%.

In an aspect, the amount of atrophy within the brain of a subject in need thereof is assessed on the day of treatment, 1 day post treatment, 3 months post treatment, 6 months post treatment, 1 year post treatment and every year thereafter post treatment.

In an aspect, the amount of atrophy within the brain of a subject in need thereof is assessed between 1 day post treatment and 7 days post treatment. In one aspect, symptoms can be assessed between 1 day post treatment and 2 days post treatment, between 1 day post treatment and 3 days post treatment, between 1 day post treatment and 4 days post treatment, between 2 days post treatment and 3 days post treatment, between 2 days post treatment and 4 days post treatment, between 2 days post treatment and 5 days post treatment, between 3 days post treatment and 4 days post treatment, between 3 days post treatment and 5 days post treatment, 3 days post treatment and 6 days post treatment, between 4 days post treatment and 5 days post treatment, between 4 days post treatment and 6 days post treatment, between 4 days post treatment and 7 days post treatment, between 5 days post treatment and 6 days post treatment, between 5 days post treatment and 7 days post treatment, or between 6 days post treatment and 7 days post treatment. In one aspect, symptoms can be assessed between 1 week post treatment and 4 weeks post treatment. In one aspect, symptoms can be assessed between 1 week post treatment and 2 weeks post treatment, between 1 week post treatment and 3 weeks post treatment, between 1 week post treatment and 4 weeks post treatment, between 2 weeks post treatment and 3 weeks post treatment, between 2 weeks post treatment and 4 weeks post treatment, or between 3 weeks post treatment and 4 weeks post treatment. In one aspect, symptoms can be assessed between 1 month post treatment and 12 months post treatment. In one aspect, symptoms can be assessed between 1 month post treatment and 2 months post treatment, between 1 month post treatment and 3 months post treatment, between 1 month post treatment and 4 months post treatment, between 2 months post treatment and 3 months post treatment, between 2 months post treatment and 4 months post treatment, between 2 months post treatment and 5 months post treatment, between 3 months post treatment and 4 months post treatment, between 3 months post treatment and 5 months post treatment, between 3 months post treatment and 6 months post treatment, between 4 months post treatment and 5 months post treatment, between 4 months post treatment and 6 months post treatment, between 4 months post treatment and 7 months post treatment, between 5 months post treatment and 6 months post treatment, between 5 months post treatment and 7 months post treatment, between 5 months post treatment and 8 months post treatment, between 6 months post treatment and 7 months post treatment, between 6 months post treatment and 8 months post treatment, between 6 months post treatment and 9 months post treatment, between 7 months post treatment and 8 months post treatment, between 7 months post treatment and 9 months post treatment, between 7 months post treatment and 10 months post treatment, between 8 months post treatment and 9 months post treatment, between 8 months post treatment and 10 months post treatment, between 8 months post treatment and 11 months post treatment, between 9 months post treatment and 10 months post treatment, between 9 months post treatment and 11 months post treatment, between 9 months post treatment and 12 months post treatment, between 10 months post treatment and 11 months post treatment, between 10 months post treatment and 12 months post treatment, or between 11 months post treatment and 12 months post treatment. In one aspect, symptoms can be assessed between 1 year post treatment and about 20 years post treatment. In one aspect symptoms can be assessed between 1 year post treatment and 5 years post treatment, between 1 year post treatment and 10 years post treatment, between 1 year post treatment and 15 years post treatment, between 5 years post treatment and 10 years post treatment, between 5 years post treatment and 15 years post treatment, between 5 years post treatment and 20 years post treatment, between 10 years post treatment and 15 years post treatment, between 10 years post treatment and 20 years post treatment, or between 15 years post treatment and 20 years post treatment.

Non-limiting examples of tests to evaluate the amount of atrophy within the brain of a subject in need thereof include Nissle staining, MRI, functional magnetic resonance fMRI, and PET scanning While the present disclosure has been described with reference to preferred embodiments, it will be understood by those skilled in the art that various changes may be made and equivalents may be substituted for elements thereof to adapt to particular situations without departing from the scope of the present disclosure. Therefore, it is intended that the present disclosure not be limited to the particular embodiments disclosed as the best mode contemplated for carrying out the present disclosure, but that the present disclosure will include all embodiments falling within the scope and spirit of the appended claims.

The examples set out herein illustrate several embodiments of the present disclosure but should not be construed as limiting the scope of the present disclosure in any manner.

EXAMPLES

Example 1. AAV Vector Constructs

Figure 1A:
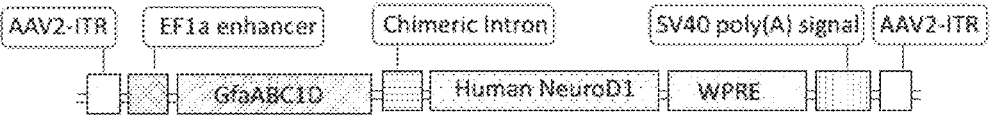
FIG. 1A depicts a map of a EF-1α:GfaABC1D:NeuroD1: WPRE:SV40 (P35).
Figure 1B:
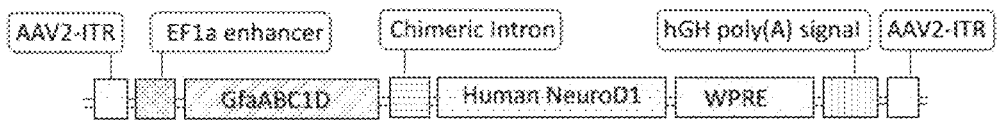
FIG. 1B depicts a map of a EF-1α:GfaABC1D:NeuroD1: WPRE:hGH.
Figure 1C:
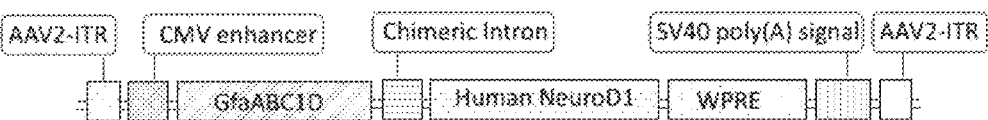
FIG. 1C depicts a map of a CE:GfaABC1D:NeuroD1: WPRE:SV40 (P11).
Figure 1D:
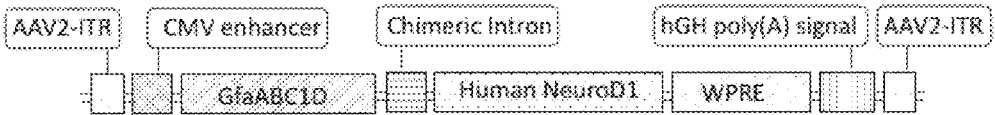
FIG. 1D depicts a map of a CE:GfaABC1D:NeuroD1: WPRE:hGH.
Figure 2A:
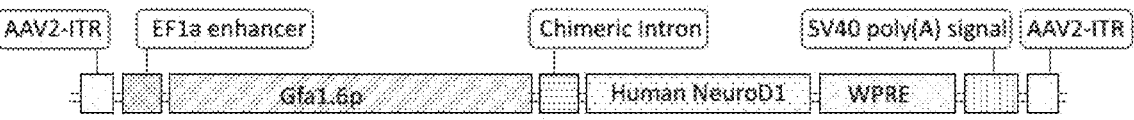
FIG. 2A depicts a map of a EF-1α:Gfa1.6:NeuroD1: WPRE:SV40 (P39).
Figure 2B:
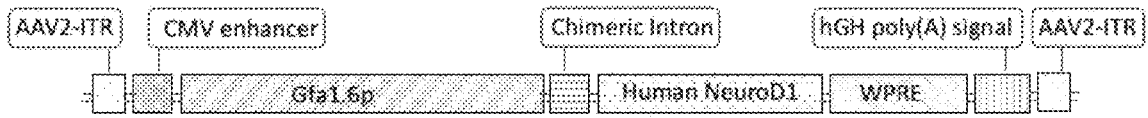
FIG. 2B depicts a map of a CE:Gfa1.6:NeuroD1:WPRE: hGH.
Figure 2C:
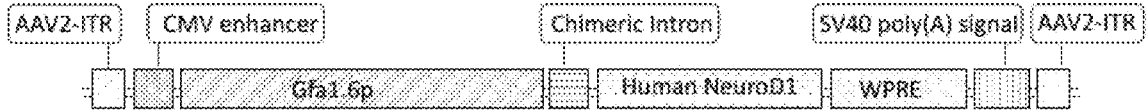
FIG. 2C depicts a map of a CE:Gfa1.6:NeuroD1:WPRE: SV40 (P38).
Figure 2D:
FIG. 2D depicts a map of a EF-1α:Gfa1.6:NeuroD1: WPRE:hGH.
Figure 3A:
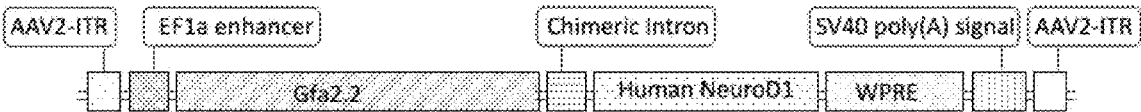
FIG. 3A depicts a map of a EF-1α:GFA2.2:NeuroD1: WPRE:SV40.
Figure 3B:
FIG. 3B depicts a map of a EF-1α:GFA2.2:NeuroD1: WPRE:hGH.
Figure 3C:
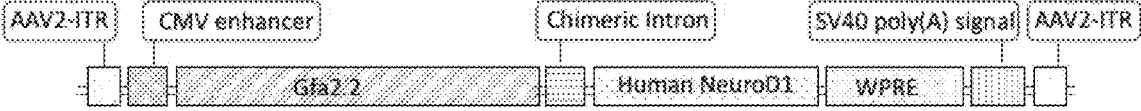
FIG. 3C depicts a map of a CE:GFA2.2:NeuroD1:WPRE: SV40.
Figure 3D:
FIG. 3D depicts a map of a CE:GFA2.2:NeuroD1:WPRE: hGH.

Twelve AAV vector constructs,
EF-1α:GfaABC1D:NeuroD1:WPRE:SV40 (P35) (FIG. 1A);
EF-1α:Gfa1.6:NeuroD1:WPRE:SV40 (P39) (FIG. 2A),
EF-1α:GFA2.2:NeuroD1:WPRE:SV40 (FIG. 3A),
EF-1α:GfaABC1D:NeuroD1:WPRE:hGH (FIG. 1B),
EF-1α:Gfa1.6:NeuroD1:WPRE:hGH (FIG. 2D),
EF-1α:GFA2.2:NeuroD1:WPRE:hGH (FIG. 3B),
CE:GfaABC1D:NeuroD1:WPRE:SV40 (P11) (FIG. 1C),
CE:Gfa1.6:NeuroD1:WPRE:SV40 (P38) (FIG. 2C),
CE:GFA2.2:NeuroD1:WPRE:SV40 (FIG. 3C),
CE:GfaABC1D:NeuroD1:WPRE:hGH (FIG. 1D),
CE:Gfa1.6:NeuroD1:WPRE:hGH (FIG. 2B), and
CE:GFA2.2:NeuroD1:WPRE:hGH are constructed (FIG. 3D).

All 12 vector constructs utilize pHSG-299 (Takara, Mountain View, CA), a pUC based vector construct which contains an origin of replication, a Kanamycin resistance gene and a multiple cloning site (MSC) with lacZ gene as backbone.

The 5' end of the expression cassette is an enhancer from a human elongation factor-1 alpha promoter (EF-1 alpha enhancer; SEQ ID NO: 2) or the cytomegalovirus enhancer (CMV enhancer; SEQ ID NO: 11) placed 5' to either a 681-nucleotide GFAP promoter (GfaABC1D; SEQ ID NO: 15), a 1667-nucleotide GFAP promoter (Gfa1.6; SEQ ID NO: 4), or a 2214-nucleotide GFAP promoter (GFA2.2 SEQ ID NO: 12).

Following (e.g., 3' to) the enhancer/GFAP promoter, several additional sequences are introduced into the expression cassette in 5' to 3' direction, including: a chimeric intron (SEQ ID NO: 5); a human NeuroD1 coding sequence (hNeuroD1; SEQ ID NO: 6); and a modified woodchuck hepatitis virus posttranscriptional regulatory element (WPRE; SEQ ID NO: 7 or SEQ ID NO: 18). These sequences are all operably linked to an SV40 poly(A) signal (SEQ ID NO: 8) or hGH poly (A) signal (SEQ ID NO: 13) or bGH poly (A) signal (SEQ ID NO: 14. The enhancer, GFAP promoter, chimeric intron, hNeuroD1 coding sequence, WPRE, and poly(A) signal are flanked by two AAV ITR sequences.

Example 2. AAV Virus Production

Each of the twelve plasmids is co-transfected into 293AAV cells using polyethylenimine along with Rep-Cap plasmid (a plasmid comprising a promoter driving the expression of AAV rep and cap genes) and Helper plasmid (a plasmid comprising a promoter driving the expression of E2A, E4, and VA RNA (of Adenovirus) to produce recombinant AAV virus particles.

Transfected cells are scraped and centrifuged at 72 hours after transfection. Cell pellets are frozen and thawed being placed in a dry ice/ethanol mixture followed by being placed in a 37° C. water bath. The freeze/thaw cycle is repeated three additional times. An AAV lysate is purified (e.g., cellular debris is removed) by ultra-centrifugation at 350,000 g for 1 hour in discontinuous iodixanol gradients. The virus-containing layer is collected and then concentrated by using Millipore Amicon Ultra Centrifugal Filters. Virus titers are then determined by qPCR using primers amplifying ITR region or gene/expression cassette specific sequences.

Example 3. Astrocyte Cell Cultures

Human cortical astrocytes (HA1800; ScienCell Research Laboratories, Inc., Carlsbad, California) are subcultured when they are over 90% confluent. For subculture, cells are trypsinized using TrypLE™ Select (Invitrogen, Carlsbad, California), centrifuged for 5 minutes at 200×g, then resuspended and plated on a medium comprising DMEM/F12 (Gibco); 10% fetal bovine serum (Gibco); penicillin/streptomycin (Gibco); 3.5 mM glucose (Sigma-Aldrich); B27 (Gibco); 10 ng/mL epidermal growth factor (Invitrogen); and 10 ng/mL fibroblast growth factor 2 (Invitrogen). The astrocytes are cultured on poly-D-lysine (Sigma-Aldrich) coated coverslips (12 mm) at a density of approximately 20,000 cells per coverslip in 24-well plates (BD Biosciences).

Rat primary astrocytes (isolated from Sprague Dawley Rat cortex or striatum) are cultured in media comprising DMEM/F12 (Gibco); 10% fetal bovine serum (Gibco), penicillin/streptomycin (Gibco); 3.5 mM glucose (Gibco).

All cells are maintained at 37° C. in humidified air with 5% carbon dioxide.

Example 4. Testing AAV Vector in Astrocyte Cell Cultures (In Vitro)

Recombinant AAV obtained from the method of Example 2 are used to infect human cortical astrocytes and rat primary astrocytes from Example 3 at a concentration range of $10^{10}$ particles/mL and $10^{14}$ particles/mL. Twenty-four hours after infection of the cells, the culture medium is replaced by differentiation medium comprising DMEM/F12 (Gibco); N2 supplement (Gibco); and 20 ng/mL brain-derived neurotrophic factor (Invitrogen). The differentiation medium is added to the cell cultures every four days. See Song et al., *Nature*, 417:39-44 (2002).

Empty space in the cell cultures is filled with additional human astrocytes to support the functional development of converted neurons as astrocytes or rat primary astrocytes convert to neurons.

Example 5. Testing of AAV Vector Potency

Recombinant AAV obtained from the method of Example 2 are used to infect human cortical astrocytes and rat primary astrocytes from Example 3 (or astrocytes from other brain regions or the spinal cord) at passage number 4 to 7 at a concentration range of $10^{10}$ particles/mL and $10^{14}$ particles/mL. qPCR, enzyme-linked immunosorbent (ELISA), and western blot are performed to determine expression of NeuroD1 transcript and protein levels.

Expression of NeuN, doublecortin (DCX), β3-tubulin, NF-200, and MAP2, are assessed by qPCR, ELISA, western blot, and immunostaining to determine functional output of recombinant AAV.

Example 6. Testing of AAV Vector Titration and Infection Rate

A purified AAV vector is treated with DNaseI to eliminate remnant plasmid contamination. A series of AAV vector dilutions are performed at 100 times, 500 times, 2500 times, and 12500 times. The AAV plasmid backbone is diluted to generate a standard curve by serial dilutions. The plasmid is diluted $10^4$, $10^5$, $10^6$, $10^7$, and $10^8$ molecules/W. qPCR is performed on the diluted AAV vectors and the diluted AAV plasmid. The primers used are against the ITR region (Forward ITR primer, 5'-GGAACCCCTAGTGATG-GAGTT, reverse ITR primer, 5'-CGGCCTCAGT-GAGCGA). The qPCR mix comprises 10 µl Universal SYBR Master Mix 2X, 2 µl of 5 µM forward ITR primer, 2 µl of 5 µM reverse ITR primer, 5 µl of tested sample or diluted standard and 1 µl H₂O. The qPCR program is 95° C. for 10 minutes followed by 40 cycles of 95° C. for 15 seconds, 60° C. for 30 seconds followed by a melt curve. The data is analyzed using the qPCR cyclers software. The physical titer of the AAV sample (viral genomes (vg)/ml) is calculated based on the standard curve.

The AAV vector infection rate is tested by using the 50% tissue culture infection dose (TCID50) assay performed using a standard protocol from the American Type Culture Collection (ATCC; Manassas, VA).

Example 7. Testing of AAV Dose Range (In Vivo)

Recombinant AAV obtained from the method of Example 2 is injected into C57/BL6 mice by bilateral intracranial injection into the motor cortex. Each AAV is injected at a dosage of $1\times10^{11}$, $3\times10^{11}$, $1\times10^{12}$, $3\times10^{12}$, $1\times10^{13}$ viral genomes/mL at 1 µl of volume. Each dosage is assessed at 4 days, 20 days, and 60 days post injection to determine the optimal effective dose (OED), maximum tolerable dose (MTD), and minimum effective dose (MED) at a cell and tissue level. There are three mice per time point. The OED, MTD, and MED, are determined by assessment of astrocyte-to-neuron conversion efficiency and potential toxicity via immunostaining of NeuroD1, GFAP, NeuN, and Iba1. If the first dose range is not sufficient to determine the OED, MTD, and MED, a second dosage range is performed at $1\times10^{10}$ GC/mL to $1\times10^{14}$ GC/mL, at 1 µl of volume.

Example 8. Dose Scale Assay in Non-Human Primates

The volume of brain tissue expressing NeuroD1 from Example 7 is divided by the number of vector genomes

64

(mm³/vector genomes) is used to determine the viral infection rate of brain tissue. The volume (mm³) of specific brain region to be treated in non-human primates is calculated and a dose range of vector genomes is according to the infection rate obtained in Example 7. A dose range study is performed as in Example 7 and the OED, MTD, and MED are determine by assessment of astrocyte-to-neuron conversion efficiency and potential toxicity via immunostaining of NeuroD1, GFAP, NeuN, and Iba1.

Example 9. Testing AAV Vector in Human Subjects (In Vivo)

Recombinant AAV obtained from the method of Example 2 are used to infect human brain or spinal cord astrocytes in vivo. Recombinant AAV is injected at a concentration range of $10^{10}$ particles/mL and 10" particles/mL with a volume ranging from 10 µl to 1 mL into the cerebral cortex of a human subject with a neurological condition. The human subject's neurological condition symptoms, brain or spinal cord imaging including MRI, PET scan, or combination of MRI and PET, and behavioral metrics are observed before, during, and post injection. Post injection observations are performed once a week until the first month post injection. After the first month post injection, observations are performed once a month for the next 11 months, and may be extended to 2 years following viral injection.

Example 10. Treatment of a Subject in Need Thereof with Stroke (In Vivo)

A subject with Stroke is treated with recombinant AAV obtained from the method of Example 2. The subject's neurological symptoms include speech changes, numbness, and writing changes. Recombinant AAV is injected at a concentration range of $10^{10}$ particles/mL and $10^{14}$ particles/mL with a volume ranging from 10 µl to 1000 µl into the cerebral cortex of a human subject with a neurological condition. The human subject's neurological condition symptoms, brain imaging including MRI, PET scan, or combination of MRI and PET, and behavioral metrics are observed before, during, and post injection. Post injection observations are performed once a week until the first month post injection. After the first month post injection, observations are performed once a month for the next 11 months, and may be extended to 2 years following viral injection.

Example 11. AAV Virus Production of P35

Figure 4:
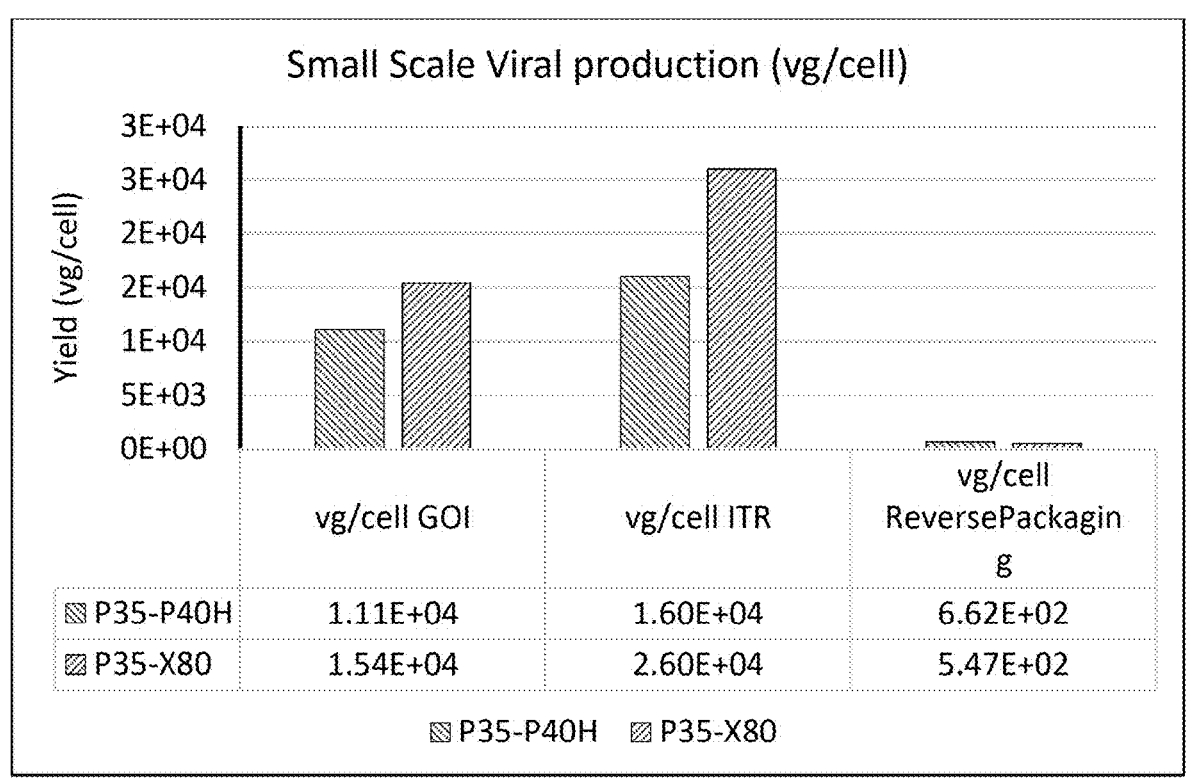
FIG. 4 is a plot of measurements of AAV virus production of the P35 plasmid. Titer analysis is performed using gene of interest (GOI) primers, ITR region primers, and reverse packaging primers. Virus yield is calculated as vg/cell.

Recombinant AAV is obtained as described in Example 2. The P35 plasmid is co-transfected into AAV293 cells with a Rep-Cap plasmid expressing serotype 9 capsid protein and the Helper plasmid P40Helper (P40H) or pALD-X80 (X80) to produce recombinant AAV virus particles (P35-P40H or P35-X80). Virus yields are determined by qPCR using primers amplifying gene of interest (GOI) primers specific to the P34 plasmid and the ITR region. Reverse packaging primers are used to evaluate nonspecific packaging. Increased viral production is observed with the X80 helper plasmid compared to the P40H helper plasmid (FIG. 4).

Example 12. Successful Establishment of Rat Astrocytes Primary Culture

Figure 5:
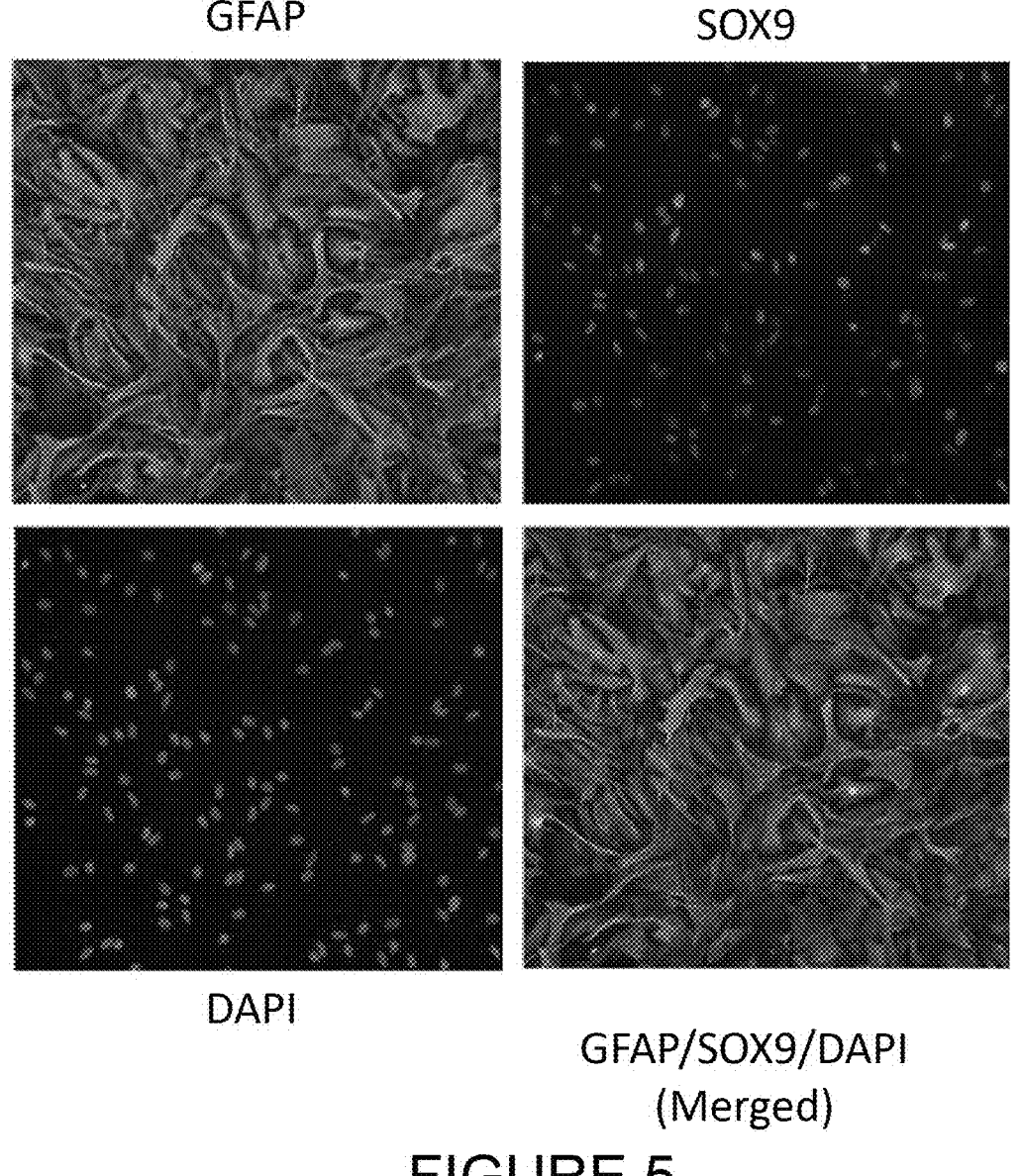
FIG. 5 depicts establishment of rat astrocyte primary culture from 3 day post-natal Sprague-Dawley rat brains. Upper left panel presents an image of GFAP stained cells. Upper right panel presents an image of SOX9 stained cells. Lower left panel presents an image of DAPI stained cells. Lower right panel presents a merge image of GFAP, SOX9, and DAPI stained cells.

Cortical and striatum tissue is isolated from 3-day post-natal Sprague-Dawley rat brains. Tissue is treated with papain to generate single cell suspension and seeded in flasks coated with poly-D-lysine. Cells are subcultured when 90% confluent. Cells of passage 6 are immunostained with GFAP antibody and SOX9 antibody. Cells are counter stained with DAPI antibody. More than 95% of cells are astrocytes identified by GFAP and SOX9 staining (FIG. 5). Upper left panel presents an image of GFAP stained cells. Upper right panel presents an image of SOX9 stained cells. Lower left panel presents an image of DAPI stained cells. Lower right panel presents a merge image of GFAP, SOX9, and DAPI stained cells.

Example 13. Successful Transfection of Rat Astrocytes

Figure 6:
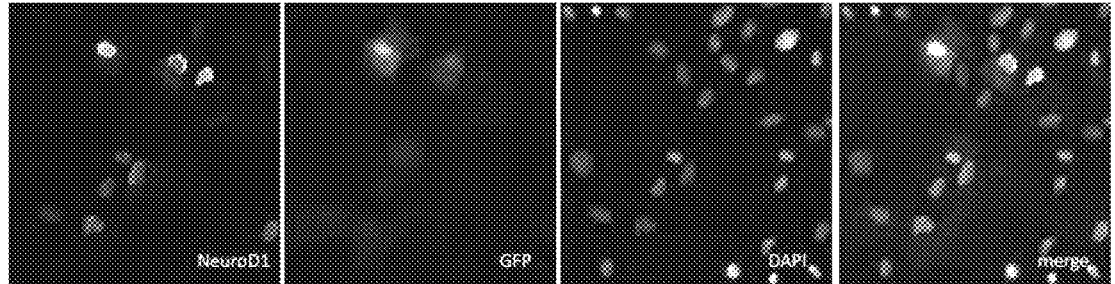
FIG. 6 depicts transfection of primary rat astrocytes with plasmid P5 (pEF-1α:hNeuroD1:GFP). Left panel presents an image of NeuroD1 stained cells. Middle left panel presents an image of GFP expressing cells. Middle right panel represents DAPI stained cells. Right panel represents a merge image of NeuroD1, GFP, and DAPI stained cells.

Primary rat astrocytes are seeded in 24-well plates with glass coverslip coated with poly-D-lysine and transfected with plasmid P5 (pEF-1α:hNeuroD1: GFP), a control plasmid, and Lipofectamine™ (a 3:1 mixture of (2,3-dioleoyloxy-N-[2(sperminecarboxamido)ethyl]-N,N-dimethyl-1-propaniminium trifluoroacetate) and 1,2-Dioleoyl-sn-glycerophosphoethanolamine) LTX reagent using a standard protocol from Thermo Fisher Scientific. Forty eight hours post transfection, cells are fixed and immunostained with anti-NeuroD1 antibody followed by a secondary antibody tagged with Alexa®-568. Cells are counter stained with DAPI to show all cell nuclei (FIG. 6). Left panel presents an image of NeuroD1 stained cells. Middle left panel presents an image of GFP expressing cells. Middle right panel represent DAPI stained cells. Right panel represents a merge image of NeuroD1, GFP, and DAPI stained cells.

Example 14. Comparison of Plasmid Transfection

Figure 7:
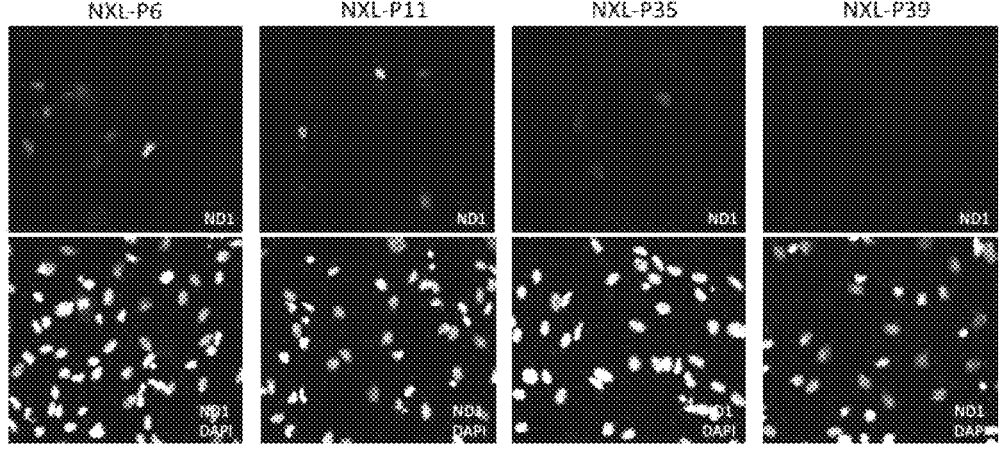
FIG. 7 depicts comparison of NeuroD1 expression level of plasmid. Primary rat astrocytes are transfected with either the P6 (pEF-1α:hNeuroD1:WPRE:SV40) expression vector, P11 (CE:GfaABC1D:NeuroD1:WPRE: SV40) expression vector, P35 (EF-1α: GfaABC1D:NeuroD1:WPRE: SV40) expression vector, or P39 (EF-1α:Gfa1.6:NeuroD1:WPRE: SV40). Top panels show NeuroD1 staining of cells, bottom panels show merged NeuroD1 and DAPI staining of cells.

Primary rat astrocytes are seeded and transfected as described in Example 11 with expression vectors P6 (pEF-1α:hNeuroD1:WPRE:SV40), P11 (CE:GfaABC1D:NeuroD1:WPRE:SV40), P35 (EF-1α:GfaABC1D:NeuroD1:WPRE:SV40), and P39 (EF-1α:Gfa1.6:NeuroD1:WPRE:SV40) to test the transfection efficiency of NeuroD1 into cells. P11 resulted in the highest NeuroD1 expression shown by NeuroD1 staining of cells (FIG. 7; top panels show NeuroD1 staining of cells, bottom panels show merged NeuroD1 and DAPI staining of cells).

Figure 8:
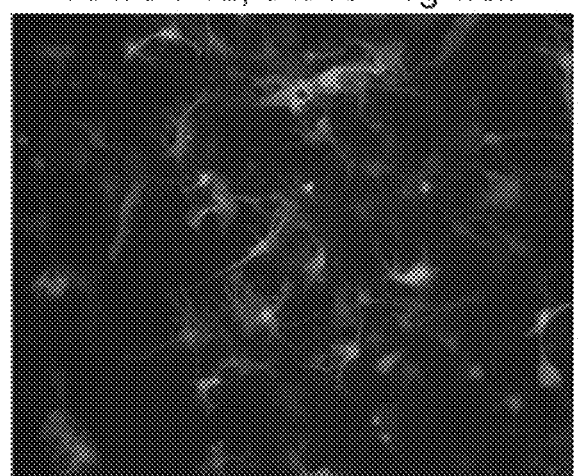
FIG. 8 depicts comparison of AAV virus particle transduction at different doses using AAV9-P12 (pGfaABC1D: GFP). Left panel shows a dose of 3×10¹⁰ vg/well. Middle panel shows a dose of 1×10¹⁰ vg/well. Right panel shows a dose of 2.5×10⁹ vg/well.
Figure 8:
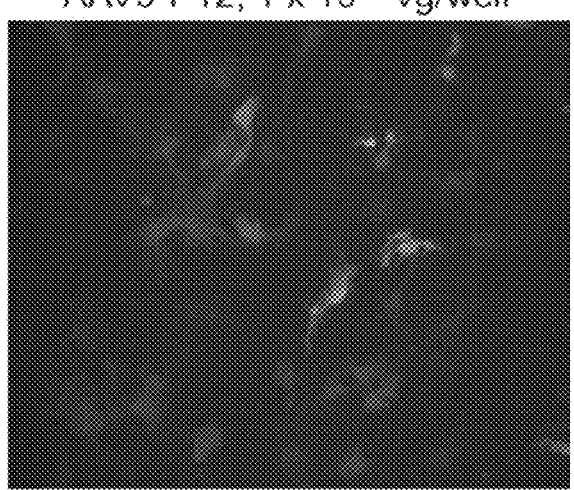
Figure 8:
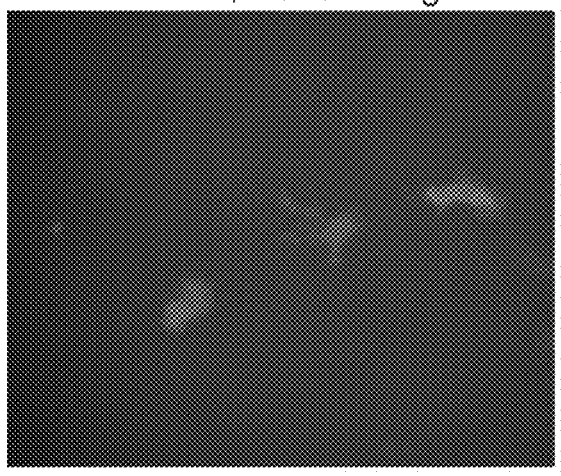

Example 15. Successful Transduction of AAV Virus Particles Into Primary Rat Astrocytes Recombinant AAV obtained from the method of Example 2 is transduced into primary rat astrocytes using control virus particles from AAV9-P12 (pGfaABC1D:GFP) at a transduction of either $3 \times 10^{10}$ vg/well, $1 \times 10^{10}$ vg/well, $2.5 \times 10^{19}$ vg/well in 100 ul media in a 96 well plate. RCAs of passage 5-7 are seeded on glass cover slips coated with poly-D-lysine (PDL) in 24-well plates at 30-50% confluency 24-48 hours prior to transduction. Cells are transduced with virus in fresh astrocyte media at the designated titer. Media are refreshed the next day and every 3-4 days. Images acquired six days post transduction of GFP positives cells show that the transduction rate is higher when virus titer is higher (FIG. 8).

Example 16. Quantitative Analysis of Transduction of AAV Virus Particles Into Primary Rat Astrocytes Recombinant AAV obtained from the method of Example 2 is transduced into primary rat astrocytes seeded in 24-well plates or 96-well plates with viral particles AAV9-P12

Figure 9A:
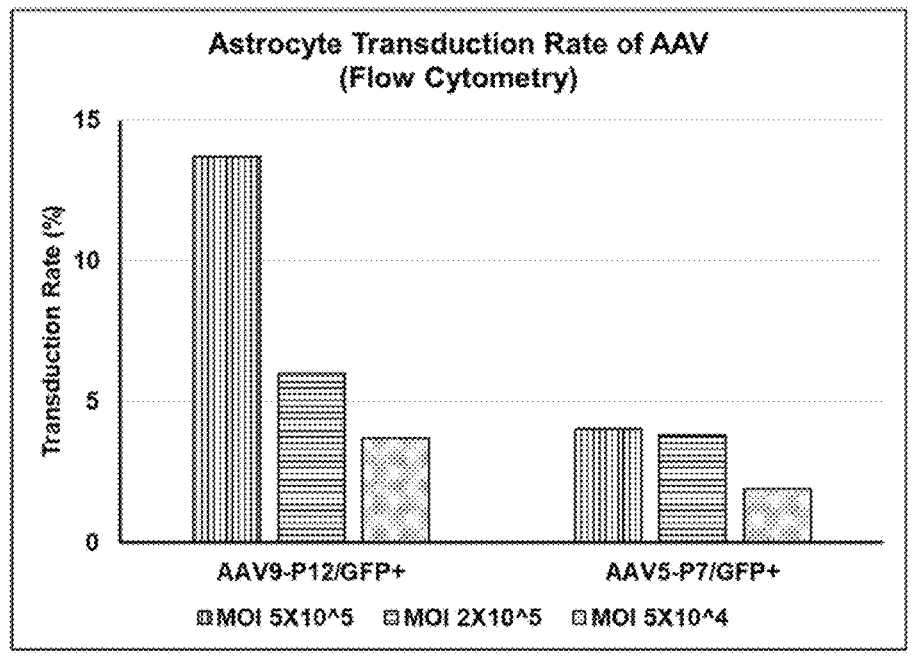
FIGS. 9A and 9B depicts quantitative analysis of AAV particle transduction into primary rate astrocytes.
Figure 9B:
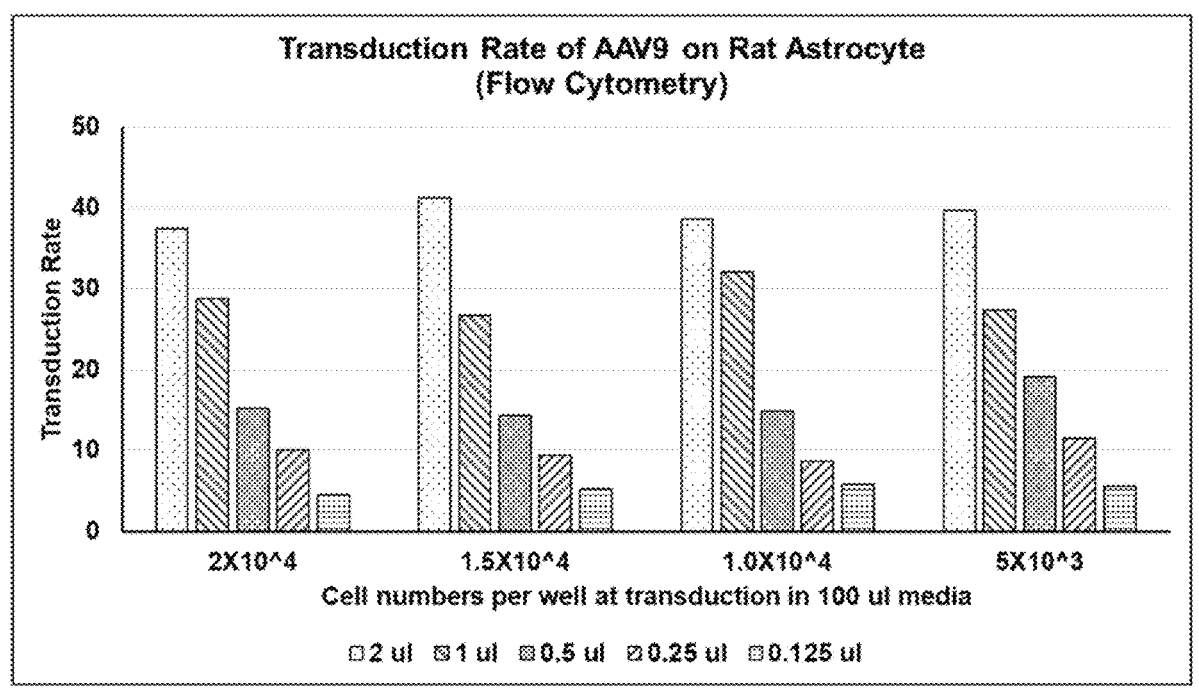

(pGfaABC1D:GFP). and AAVS-P7 (pEF-1α:GFP). Cells are harvested seven days post-infection by trypsinization. The cells are fixed, washed, and suspended in PBS. The viral transduction rate is analyzed using flow cytometry to count GFP positive cells compared with all cells (FIG. 9A-9B). FIG. 9A shows the % transduction rate at different MOI. Cells seeded in 24-well plates at $1 \times 10^5$ cells/well are infected at MOI of either $5 \times 10^5$ vg/cell, $2 \times 10^5$ vg/cell and $5 \times 10^4$ vg/cell. The viral transduction rate decreases as the MOI decreases. FIG. 9B shows the transduction rate of AAV viral particles in cells seeded in 96 well plates at a series of densities of $2 \times 10^4$ cells/well, $1.5 \times 10^4$ cells/well, $1 \times 10^4$ cells/well, and $5 \times 10^3$ cells/well, and infected with virus at a series of amounts of 2 μl, 1 μl, 0.5 μl, 0.25 μl, 0.125 μl of $1 \times 10^{13}$ vg/ml virus in 100 μl of medium. This is equivalent to $2 \times 10^{10}$ vg, $1 \times 10^{10}$ vg, $5 \times 10^9$ vg, $2.5 \times 10^9$ vg, and $1.25 \times 10^9$ vg each well respectively. The viral transduction rate is unchanged as the number of cells per well decreases.

Figure 10:
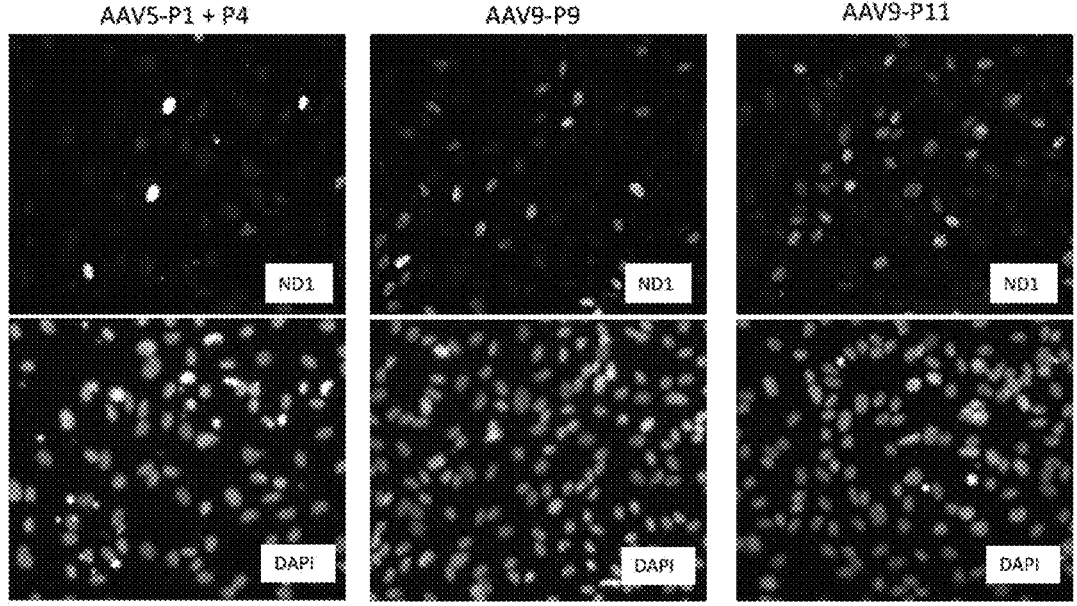
FIG. 10 depicts transduction of AAV virus particle comprising NeuroD1 into primary rat astrocytes. Primary rat astrocytes are transduced with AAV5-P1 (AAVS:pGfa2.2: cre) and AAV4-P4 (AAV5:pCAG:flex:hNeuroD1:GFP)

Example 17. Successful Transduction of AAV Virus Particles Containing NeuroD1 Into Primary Rat Astrocytes Recombinant AAV obtained from the method of Example 2 is transduced into primary rat astrocytes seeded in 24-well plates with viral particles 1) AAV5-P1 (AAV5:pGfa2.2:cre) and AAV4-P4 (AAV5:pCAG:flex:hNeuroD1:GFP); 2) AAV9-P9 (CE:GfaABC1D:NeuroD1:GFP); and 3) AAV9-P11 (CE:GfaABC1D:NeuroD1:WPRE: SV40). RCAs of passage 5-7 are seeded on glass cover slips coated with poly-D-lysine (PDL) in 24-well plates at 30-50% confluency 24-48 hours prior to transduction. Cells are transduced with virus in fresh astrocyte media at the titer of $2 \times 10^{10}$ vg/ml (MOI of $1 \times 10^6$ vg/cell). Media are refreshed the next day and every 3-4 days. Cells are fixed at six days post infection and immunostained for NeuroD1. The cells are counter stained with DAPI to identify the cell nuclei (FIG. 10). Cells transduced with the P1+P4 combination, P9 and P11 all show NeuroD1 expression.

Example 18. In Vitro Transgene Expression and Astrocyte-to-Neuron Conversion Induced By NeuroD1 Vectors

Materials and Methods

Primary Rat Astrocyte Culture: Rat cortical astrocytes (RCA) are isolated from 3-day postnatal Sprague Dawley rat cortical tissue. Cells are maintained in astrocyte media (AM) composed of DMEM supplemented with 10% FBS, 2.5 mM Glutamine, 3.5 mM Glucose, penn/strep. Cells are sub-cultured at 1:3-1:4 ratio for first two passages at low cell density to promote residual progenitor differentiation. Subsequent sub-cultures are at 1:2 or 1:3 ratio when reaching 90-100% confluent. Cells at passage 5-7 are used for transfection and transduction. Immunostaining with a GFAP antibody shows that >90% cells are GFAP positive astrocytes. Culture astrocytes are immunostained with astrocyte markers GFAP and Sox9 at passage 6 (FIG. 5).

Vectors: AAVs are produced with selected vectors and tested in vitro using rat astrocytes:
    NXL-P9 (CE-pGfa681-CI-hND1-p2A-GFP-WPRE-SV40pA)
    NXL-P22 (CE-pGfa681-CI-hND1-WRPE-SV40pA)
    NXL-P35 (EE-pGfa681-CI-hND1-WRPE-SV40pA)
    NXL-P37 (EE-pGfa681-CI-hND1-p2A-GFP-WPRE-SV40pA)

NXL-P107 (CE-pGfa681-CI-hND1-bGHpA)
NXL-P108 (CE-pGfa681-CI-hND1-oPRE-bGHpA)
NXL-P109 (CE-pGfa681-CRGI-hND1-bGHpA)
NXL-P130 (CE-pGfa681-GI-hND1-oPRE-bGHpA)
NXL-P134 (CE-pGfa681-CRGI-hND1-oPRE-bGHpA)
NXL-P136 (EE-Gfa681-CRGI-hND1-bGHpA)
NXL-P138 (EE-Gfa681-CRGI-hND1-oPRE-bGHpA)

Viral Production: Virus used for in vitro studies are produced using adherent AAV293 cells by triple transfections (GOI, helper, and Rep/Cap plasmids) with polyethylenimine (PEI). Virus recovery and purification is achieved via ultra-centrifugation or the use of commercial purification kits.

Specifically, AAV293 cells (Cell Biolabs, Cat # AAV-100) are seeded in 15-cm culture dishes 24 hours prior to transfection. Cells at 70-85% confluency are transfected per dish with 10 μg GOI, 10 μg of Rep/Cap, and 14 μg of pALD-X80 (Aldevron) or pHelper (Cell Biolabs) using polyethylenimine (PEI) at a DNA:PEI ratio of 1:4. Multiple dishes are transfected for production based on the scale needed. Culture media is refreshed daily. Seventy-two hours post transfection, cells are collected and lysed to harvest the virus using an AAVpro purification kit (Takara, Cat # 6666, 6675, 6235) following the manufacturer's protocol.

Viral titers are determined by real-time quantitative PCR using a primer pair in the ITR region, primers amplifying a gene of interest (GOI), or vector specific primers. Plasmid DNA is used as a standard. The production yield is $\sim 10^3$-$10^4$ vg/cell level. FIG. 32 depicts how each of the P134, P130, P138 and P21 plasmids co-transfected into AAV293 cells with a Rep-Cap plasmid expressing a serotype 9 capsid protein and the Helper plasmid pALD-X80 (X80) produced recombinant AAV virus particles as measured by qPCR.

Transfection and Immunofluorescence: Rat cortical astrocytes (RCAs) of passage 5-7 are seeded on glass cover slips coated with poly-D-lysine (PDL) in 24-well plates at 30-50% confluency 24-48 hours prior to transfection. Cells are transfected with 300 ng of vector DNA using Lipofectamine™ reagent (Thermo Fisher Cat # 15338) following the manufacturer's protocol. At 24-48 hours post transfection, cells are fixed with 4% paraformaldehyde in PBS and subsequently washed and immunostained with anti-NeuroD1 (anti-ND1) antibody (Abcam Cat #ab60704) and followed with secondary antibodies conjugated with fluorescent dyes (Invitrogen, Alexa Fluor®). Images are captured under a fluorescent microscope (Zeiss Axiovert A1, Zen Blue). Gene expression levels are assessed by comparing the fluorescence intensity.

Transduction and Immunofluorescence: RCAs of passage 5-7 are seeded on glass cover slips coated with poly-D-lysine (PDL) in 24-well plates at 30-50% confluency 24-48 hours prior to transduction. Cells are transduced with AAVs at $2$-$6 \times 10^{10}$ viral genome (vg)/ml in fresh astrocyte media. Media are refreshed the next day and every 3-4 days. Three to six days post transduction, cells are fixed with 4% paraformaldehyde in PBS and subsequently washed and immunostained with anti-ND1 antibody (Abcam Cat # ab60704) and followed with secondary antibodies conjugated with fluorescent dyes (Invitrogen, Alexa Fluor®) for observation and image capturing under a fluorescent microscope (Zeiss Axiovert A1, Zen Blue). Gene expression levels are assessed by comparing the fluorescence intensity.

Astrocyte-to-neuron conversion assessment RCAs of passage 5-7 are seeded on glass cover slips coated with poly-D-lysine (PDL) in 24-well plates at 30-50% confluency 24-48 hours prior to transduction. Cells are transduced with virus at $2$-$6 \times 10^{10}$ vg/ml in 500 μl of fresh astrocyte media (DMEM supplemented with 10% FBS, 2.5 mM Glutamine, 3.5 mM Glucose, penn/strep). At 48 hours post transduction, media is replaced with 5% FBS astrocyte media. Subsequently, 100 μl of conversion media (DMEM/F12+1% FBS+B27+N2 and 1 uM Rock inhibitor and 10 ng/ml BDNF) is added daily for 4 days. After the 4 days, the media is completely replaced with conversion media.

Cells are fixed with 4% paraformaldehyde in PBS at various desired time points (three days, one to five weeks post transduction) and subsequently washed and immunostained with antibodies against ND1 (Abcam Cat # ab60704), NeuN (Millipore, Cat # ABN78), Map2 (Invitrogen, Cat # PA5-17646), followed with secondary antibodies conjugated with fluorescent dyes (Invitrogen, Alexa Fluor®) for observation and imaging under a fluorescent microscope (Zeiss Axiovert A1, Zen Blue).

In Vitro Studies Results:

All tested NeuroD1 (ND1) plasmids are effective in driving the expression of NeuroD1 (FIGS. 12-28). The expression level of NeuroD1 is affected by the elements in the vector. Among three versions of the GFA promoter, the 681 bp promoter shows the highest NeuroD1 expression level and the 1.6 kb promoter shows the weakest NeuroD1 expression level. Promoter enhancer elements significantly affect the expression level of NeuroD1. The CMV enhancer increases the expression level of NeuroD1 more than the efl a enhancer. Chimeric introns and WPREs also increase the expression level of NeuroD1.

All tested ND1-containing AAVs are effective in driving the expression of ND1 and inducing an astrocyte-to-neuron conversion in cultured rat astrocytes as shown by positive staining of NeuN and/or MAP2 (FIGS. 14, 17, 19, 22, and 25). The conversion rate is higher when astrocytes are transduced by the vectors driving a higher ND1 expression. Vectors NXL-P134 and NXL-P138, and the viruses generated using these vectors, i.e., AAV9-P134 and AAV9-P138 respectively, are the most effective in driving expression of ND1 and inducing astrocyte-to-neuron conversion, with AAV-P134 being the most effective (FIGS. 12-17). Plasmid AAV9-P21 (CE-pGFA681-CI-GFP-WPRE-SV40pA), which does not contain an ND1 sequence, is used as a control, and it does not induce an astrocyte-to-neuron conversion, as shown by the lack of positive staining for NeuN and/or Map2 (FIG. 11).

NeuN/RBFOX3 (Neuronal nuclear protein) is a neuron differentiation marker, which stains nuclei and perinuclear cytoplasm in neurons. MAP2 (microtubule associated protein 2) is another neuronal marker which stains cytoplasm microtubules including dendrites in neurons.

One week post transduction by ND1-containing AAVs, small number of NeuN and MAP2 positive cells (neurons) are observed. By two and three weeks, more NeuN/MAP2 positive cells are observed. Some NeuN/MAP2 positive cells show typical neuronal morphology.

Example 19. In Vivo Transgene Expression and Astrocyte-to-Neuron Conversion Induced By NeuroD1 Viral Vectors AAV9-P134 and AAV9-P138 viruses are used for the in vivo studies. AAV9-P12, which drives the expression of GFP alone (no ND1) under a GFAP promoter, is used for the control and to identify cells expressing GFAP (astrocytes).

Single strand adenovirus-associated viral (ssAAV, AAV for short) vectors NXL-P12, NXL-P134 and NXL-P138 are packaged into AAV, serotype 9 (AAV9), followed by a subsequent iodixanol gradient ultracentrifuge and concentration. Purified AAV viruses are titered using a quantitative PCR-based method. All AAV used in this study is prepared in 0.001% Pluronic F-68 (Poloxamer 188 Solution, PFL01-100ML, Caisson Laboratories, Smithfield, UT, USA) in PBS (pH 7.4).

Normal C57BL/6J mice older than 8 weeks are injected with AAV9-P134, AAV-P138, and AAV9-P12 viruses as follows:

P12 control group: AAV9-P12 $5\times10^{11}$ GC/ml, 1 μL, 1 injection in cortex (unilateral) (n=6)

P134 group: AAV9-P12 $2.5\times10^{11}$ GC/ml+AAV9-P134 $2.5\times10^{11}$ GC/ml, 1 μL, 1 injection in cortex (unilateral) (n=6)

P138 group: AAV9-P12 $2.5\times10^{11}$ GC/ml+AAV9-P138 $2.5\times10^{11}$ GC/ml, 1 μL, 1 injection in cortex (unilateral) (n=6)

Mice are sacrificed and brain cortex tissue analyzed at 10 days post infection (dpi) and at 30 dpi. The animals are anesthetized with 1.25% Avertin and then sequentially perfused intracardially first with saline solution (0.9% NaCl) and then with 4% paraformaldehyde (PFA). The brains are collected and post-fixed in 4% PFA overnight and sequentially placed in 20% and 30% sucrose at 4° C. until the tissue sank. The dehydrated brains are embedded in Optimal Cutting Temperature (Tissue-Tek® O.C.T. Compound, Sakura® Finetek, Torrance, CA, USA), and then serially sectioned at the coronal plane on the cryostat (Thermo Scientific, Shanghai, China) at 30 μm thickness. For immunofluorescence, free floating brain sections are first washed with PBS and blocked for 1 hour at room temperature (RT) in 5% normal donkey serum, 3% bovine serum albumin and 0.3% TritonX-100 prepared in PBS, and then incubated overnight at 4° C. with primary antibodies diluted in blocking solution. After additional washing with 0.2% PBST (0.2% tween-20 in PBS), the samples are incubated with 0.5 μg/μL 4',6-diamidino-2-phenylindole (DAPI; F. Hoffmann-La Roche, Natley, NJ, USA) and appropriate donkey anti-mouse/rabbit secondary antibodies conjugated to Alexa Fluor® 555, goat anti-chicken secondary antibodies conjugated to Alexa Fluor® 488 (1:1000, Life technologies, Carlsbad, CA, USA), and goat anti-rat (Life technologies)/ guinea pig (Jackson immune research) secondary antibodies conjugated to Alexa Fluor® 647 (1:500) for 2 hours at room temperature, followed by extensive washing with PBS. Samples are finally mounted with VECTASHIELD® mounting medium (VECTOR Laboratories, Burlingame, CA, USA) and sealed with nail polish. Representative Images are taken with a confocal microscope (LSM880, Zeiss, Jena, Germany). Primary antibodies used are as follow: rat anti-GFAP (a marker for astrocytes, 1:1000, Cat # 13-0300, Invitrogen), guinea pig anti-NeuN (a marker for neurons 1:1000, Cat # ABN90, Millipore), mouse anti-NeuroD1 (1:500, Cat #ab60704, Abcam), and chicken anti-GFP (1:1000, Cat # ab13970, Abcam). Representative images are captured by either Zeiss Axioplan fluorescent microscope (Axio Imager Z2, Zeiss, Göttingen, Germany) or confocal microscope (LSM880, Zeiss, Jena, Germany). Quantitative analysis is performed based on 4 randomly chosen fields (212 μm×212 μm, acquired at 400 magnification from LSM880 confocal microscope) from 3 brain slices per mouse (3 mice per group). The data is shown as mean±SEM.

Control virus P12, which expresses GFP reporter alone, is first compared with NeuroD1-expressing viruses P134 and P138 (both added P12 together to trace converted neurons). When the control virus P12 is injected in the uninjured mouse cortex, the infected cells are primarily astrocytes without NeuroD1 expression at 10 dpi (days post injection, FIG. 33). In contrast, NeuroD1 expression is detected clearly in both P134 and P138 groups. While most NeuroD1-expressing cells in the P138 group at 10 dpi are still astrocytes, a portion of NeuroD1-expressing cells in P134 group are NeuN+ neurons already (FIG. 33), suggesting that P134 might have better conversion capability than P138. Additionally at 10 dpi, analysis of the cortex brain tissue of the mice in the P134 group shows a high level of conversion of astrocytes into neurons, as demonstrated by the morphological changes, such as the presence of long processes, in GFP positive cells (FIG. 29). The P138 group shows a lower level of conversion.

At 30 days after virus injection, the infected cells in the control group (P12) remain as astrocytes, but most GFP positive cells in the P134 group are neurons expressing NeuN (FIG. 34). However, the conversion rate of the P138 group is lower than the P134. Most infected cells in the P138 group at this stage are still astrocytes, and the GFP signal in the converted neurons is weak (FIG. 34). Additionally, at 30 dpi, analysis of the cortex brain tissue of the mice in the P134 group shows an even higher level of conversion of astrocytes into neurons, as demonstrated by the presence of long processes in GFP positive cells (FIG. 30).

The AAV9-P134 virus is also effective in a bilateral injury mouse model. Ischemic stroke is induced in normal C57BL/6J mice (older than 8 weeks) by injecting 1 μL of Endophilin 1, 1-31 aa (1 μg/μL) in each side of the cortex. Mice are anesthetized with 20 mg/kg 1.25% Avertin (a mixture of 12.5 mg/mL of 2,2,2-Tribromoethanol and 25 μL/mL 2-Methyl-2-butanol, Sigma, St. Louis, MO, USA) through intraperitoneal injection and then placed in a prone position in the stereotaxic frame. Endothelin-1 (ET-1) and virus is injected through glass pipette into motor cortex at the coordinate +0.2 mm anterior-posterior (AP from Bregma), −1.5 mm medial-lateral (ML from Bregma, left side), −0.7 mm dorsal-lateral (DV from dura). The injection speed is 80 nL/min. The pipette is kept in place after injection for about 10 minutes and then slowly withdrawn. Seven days after injection of Endothelin-1, mice are injected with the AAV9-P12 and AAV9-P134 viruses as follow:

P12 Group: AAV9-P12 $5\times10^{11}$ GC/ml, 1 μL, 1 injection in each side of cortex (bilateral)

P134 Group: AAV9-P12 $2.5\times10^{11}$ GC/ml+AAV9-P134 $2.5\times10^{11}$ GC/ml, 1 μL, 1 injection in each side of cortex (bilateral)

Mice are sacrificed at 10 days post injection (dpi) of the viruses and the brain cortex tissue analyzed. When the control virus P12 is injected in the ET-1 lesioned mouse cortex, the infected cells are primarily astrocytes without NeuroD1 expression at 10 dpi (days post injection, FIG. 35). In contrast, NeuroD1 expression is detected in the P134 group (FIG. 35). Additionally, at 10 dpi, analysis of the cortex brain tissue of the mice in the P134 group shows a high level of conversion of astrocytes into neurons, as demonstrated by the morphological changes observed in GFP positive cells, such as the presence of long processes (FIG. 31).

At 30 days after viral injection in the ET-1-injured mouse cortex, the infected cells in the control group (P12) remain as astrocytes, but most GFP positive cells in the P134 group become converted neurons expressing NeuN (FIG. 36A). The conversion rate of P134 in the ET-1 lesioned mouse cortex at 30 dpi is around 64% (FIG. 36B, NeuN⁺GFP⁺/ GFP⁺: P12, 1.0±0.2%; P12+P134, 63.8±1.2%, *P<0.0001, unpaired Student's t test). These studies demonstrate that P134 is a vector that can efficiently convert astrocytes into neurons in the ischemic injured mouse cortex in vivo.

A variety of further modifications and improvements in and to the compositions and methods of the present disclosure will be apparent to those skilled in the art based. The following non-limiting embodiments are envisioned:

1. An adeno-associated virus (AAV) vector comprising a human neurogenic differentiation 1 (hNeuroD1) sequence comprising the nucleic acid sequence of SEQ ID NO: 6, where the hNeuroD1 sequence is operably linked to regulatory elements comprising:
   (a) a glial fibrillary acidic protein (GFAP) promoter comprising a nucleic acid sequence selected from the group consisting of SEQ ID NOs: 4, 12, and 15;
   (b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11;
   (c) a chimeric intron comprising the nucleic acid sequence of SEQ ID NO: 5 or 16;
   (d) a woodchuck hepatitis virus posttranscriptional regulatory element (WPRE) comprising the nucleic acid sequence selected from the group consisting of SEQ ID NOs: 7 and 18; and
   (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

2. An adeno-associated virus (AAV) vector comprising a nucleic acid coding sequence encoding a human neurogenic differentiation 1 (hNeuroD1) protein comprising the amino acid sequence of SEQ ID NO: 10, wherein said coding sequence is operably linked to regulatory elements comprising:
   (a) a glial fibrillary acidic protein (GFAP) promoter comprising a nucleic acid sequence selected from the group consisting of SEQ ID NOs: 4, 12, and 15;
   (b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11;
   (c) a chimeric intron comprising the nucleic acid sequence of SEQ ID NO: 5 or 16;
   (d) a woodchuck hepatitis virus posttranscriptional regulatory element (WPRE) comprising the nucleic acid sequence selected from the group consisting of SEQ ID NOs: 7 and 18; and
   (e) a SV40 polyadenylation signal sequence with a nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

3. An adeno-associated virus (AAV) vector comprising a neurogenic differentiation 1 (NeuroD1) nucleic acid coding sequence encoding a NeuroD1 protein, wherein said coding sequence is operably linked to regulatory elements comprising:
   (a) a glial fibrillary acidic protein (GFAP) promoter;
   (b) an enhancer;
   (c) a chimeric intron;
   (d) a woodchuck hepatitis virus posttranscriptional regulatory element (WPRE); and
   (e) a polyadenylation signal sequence.

4. A composition comprising an adeno-associated virus (AAV) vector for converting glial cells to functional neurons in a human, wherein said AAV vector comprises a human neurogenic differentiation 1 (hNeuroD1) sequence having a nucleic acid sequence of SEQ ID NO: 6, and wherein said sequence is operably linked to regulatory elements comprising:
   (a) a human glial fibrillary acidic protein (GFAP) promoter comprising a nucleic acid sequence selected from the group consisting of SEQ ID NOs: 4, 12, and 15;
   (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11;
   (c) a chimeric intron comprising the nucleic acid sequence of SEQ ID NO: 5 or 16;
   (d) a woodchuck hepatitis virus posttranscriptional regulatory element (WPRE) comprising the nucleic acid sequence selected from the group consisting of SEQ ID NOs: 7 and 18; and
   (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

5. A composition comprising an adeno-associated-virus (AAV) vector for converting glial cells to functional neurons in a human, wherein said AAV vector comprises a nucleic acid sequence encoding a human neurogenic differentiation 1 (hNeuroD1) protein comprising the amino acid coding sequence of SEQ ID NO: 10, and wherein said coding sequence is operably linked to regulatory elements comprising:
   (a) a human glial fibrillary acidic protein (GFAP) promoter comprising a nucleic acid sequence selected from the group consisting of SEQ ID NOs: 4, 12, and 15;
   (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11;
   (c) a chimeric intron comprising the nucleic acid sequence of SEQ ID NO: 5 or 16;
   (d) a woodchuck hepatitis virus posttranscriptional regulatory element (WPRE) comprising the nucleic acid sequence selected from the group consisting of SEQ ID NOs: 7 and 18; and
   (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

6. A composition comprising an adeno-associated virus (AAV) vector for the treatment of a subject in need thereof, wherein said AAV vector comprises a neurogenic differentiation 1 (NeuroD1) sequence operably linked to expression control elements comprising:
   (a) a glial fibrillary acidic protein (GFAP) promoter;
   (b) an enhancer;
   (c) a chimeric intron;

(d) a woodchuck hepatitis virus posttranscriptional regulatory element (WPRE); and (e) a polyadenylation signal.

7. The AAV vector of any one of embodiments 1-3, or the composition of any one of embodiments 4-6, wherein said AAV vector is selected from the group consisting of AAV serotype 2, AAV serotype 5, and AAV serotype 9.

8. The AAV vector or composition of embodiment 7, wherein said AAV vector is AAV serotype 2.

9. The AAV vector or composition of embodiment 7, wherein said AAV vector is AAV serotype 5.

10. The AAV vector or composition of embodiment 7, wherein said AAV vector is AAV serotype 9.

11. The composition of embodiment 4 or 5, wherein said glial cells are reactive astrocytes.

12. The composition of embodiment 4 or 5, wherein said functional neurons are selected from the group consisting of glutamatergic neurons, GABAergic neurons, dopaminergic neurons, cholinergic neurons, seratonergic neurons, epinephrinergic neurons, motor neurons, and peptidergic neurons.

13. The composition of embodiment 4 or 5, wherein said human has a neurological condition.

14. The AAV vector of embodiment 3, or the composition of embodiment 6, wherein said NeuroD1 is a human NeuroD1 (hNeuroD1).

15. The AAV vector of embodiment 3, or the composition of embodiment 6, wherein said NeuroD1 is selected from the group consisting of a chimpanzee NeuroD1, a bonobo NeuroD1, an orangutan NeuroD1, a gorilla NeuroD1, a macaque NeuroD1, a marmoset NeuroD1, a capuchin NeuroD1, a baboon NeuroD1, a gibbon NeuroD1, and a lemur NeuroD1.

16. The AAV vector or composition of embodiment 14, wherein said hNeuroD1 comprises a nucleic acid coding sequence encoding an amino acid sequence at least 80% identical or similar to SEQ ID NO: 10.

17. The AAV vector or composition of embodiment 14, wherein said hNeuroD1 sequence comprises a nucleic acid sequence at least 80% identical to SEQ ID NO: 6, or the complement thereof.

18. The AAV vector of embodiment 3, or the composition of embodiment 6, wherein said GFAP promoter is a human GFAP (hGFAP) promoter.

19. The AAV vector of embodiment 3, or the composition of embodiment 6, wherein said GFAP promoter is selected from the group consisting of a chimpanzee GFAP promoter, a bonobo GFAP promoter, an orangutan GFAP promoter, a gorilla GFAP promoter, a macaque GFAP promoter, a marmoset GFAP promoter, a capuchin GFAP promoter, a baboon GFAP promoter, a gibbon GFAP promoter, and a lemur GFAP promoter.

20. The AAV vector or composition of any one of the preceding embodiments, wherein the AAV vector further comprises a 2A self-cleavage peptide sequence at least 80% identical to SEQ ID NO: 3 or the complementement thereof.

21. The AAV vector or composition of embodiment 18, wherein said hGFAP promoter comprises a nucleic acid sequence at least 80% identical to SEQ ID NO: 4 or the complement thereof.

22. The AAV vector or composition of embodiment 18, wherein said hGFAP promoter comprises a nucleic acid sequence at least 80% identical to SEQ ID NOs: 12 or the complement thereof.

23. The AAV vector or composition of embodiment 18, wherein said hGFAP promoter comprises a nucleic acid sequence at least 80% identical to SEQ ID NOs: 15 or the complement thereof.

24. The AAV vector of embodiment 3, or the composition of embodiment 6, wherein said enhancer is selected from the group consisting of an enhancer from human elongation factor-1 alpha (EF1-α) promoter and cytomegalovirus (CMV) enhancer.

25. The AAV vector or composition of embodiment 24, wherein said EF1-α comprises a nucleic acid sequence at least 80% identical to SEQ ID NO: 2, or the complement thereof.

26. The AAV vector or composition of embodiment 24, wherein said CMV enhancer comprises a nucleic acid sequence at least 80% identical to SEQ ID NO: 11, or the complement thereof.

27. The AAV vector of embodiment 3, or the composition of embodiment 6, wherein said chimeric intron comprises a nucleic acid sequence at least 80% identical to SEQ ID NO: 5 or the complement thereof.

28. The AAV vector of embodiment 3, or the composition of embodiment 6, wherein said chimeric intron comprises a nucleic acid sequence at least 80% identical to SEQ ID NO: 16 or the complement thereof.

29. The AAV vector of embodiment 3, or the composition of embodiment 6, wherein said WPRE comprises a nucleic acid sequence at least 80% identical to a nucleic acid sequence selected from the group consisting of SEQ ID NOs: 7 and 18, or the complement thereof.

30. The AAV vector of embodiment 3, or the composition of embodiment 6, wherein said polyadenylated signal is selected from the group consisting of SV40 polyadenylation signal and a hGH polyadenylation signal.

31. The AAV vector or composition of embodiment 30, wherein said SV40 polyadenylated signal comprises a nucleic acid sequence at least 80% identical to SEQ ID NO: 8, or the complement thereof.

32. The AAV vector or composition of embodiment 30, wherein said hGH polyadenylated signal comprises a nucleic acid sequence at least 80% identical to SEQ ID NO: 13, or the complement thereof.

33. The AAV vector or composition of embodiment 30, wherein said bGH polyadenylated signal comprises a nucleic acid sequence at least 80% identical to SEQ ID NO: 14, or the complement thereof.

34. The AAV vector of embodiment 3, or the composition of embodiment 6, wherein said AAV vector further comprises a nucleic acid sequence encoding an AAV protein sequence.

35. The AAV vector of any one of embodiments 1-3, or the composition of any one of embodiments 4-6, wherein said AAV vector comprises AAV serotype 2 inverted terminal repeats (ITRs).

36. The AAV vector of any one of embodiments 1-3, or the composition of any one of embodiments 4-6, wherein said AAV vector comprises AAV serotype 5 inverted terminal repeats (ITRs).

37. The AAV vector of any one of embodiments 1-3, or the composition of any one of embodiments 4-6, wherein said AAV vector comprises AAV serotype 9 inverted terminal repeats (ITRs).

38. The AAV vector of any one of embodiments 1-3, or the composition of any one of embodiments 4-6, wherein said AAV vector comprises at least one ITR nucleic acid sequence at least 80% identical to SEQ ID NO: 1.

39. The AAV vector of any one of embodiments 1-3, or the composition of any one of embodiments 4-6, wherein said AAV vector comprises at least one ITR nucleic acid sequence at least 80% identical to SEQ ID NO: 9.

40. The composition of embodiment 6, wherein said subject in need thereof is a mammal.

41. The composition of embodiment 40, wherein said mammal is a human.

42. The composition of embodiment 40, wherein said mammal is a non-human primate.

43. The composition of embodiment 6, wherein said subject in need thereof has a neurological condition.

44. The composition of embodiment 13 or 43, wherein said neurological condition comprises an injury to the central nervous system (CNS) or peripheral nervous system.

45. The composition of embodiment 13 or 43, wherein said wherein said neurological condition comprises an injury to the CNS.

46. The composition of embodiment 13 or 43, wherein said neurological condition is selected from the group consisting of Alzheimer's Disease, Parkinson's Disease, amyotrophic lateral sclerosis (ALS), Huntington's Disease, epilepsy, physical injury, stroke, cerebral aneurysm, traumatic brain injury, concussion, a tumor, inflammation, infection, ataxia, brain atrophy, spinal cord atrophy, multiple sclerosis, traumatic spinal cord injury, ischemic or hemorrhagic myelopathy (myelopathy), global ischemia, hypoxic ischemic encephalopathy, embolism, fibrocartilage embolism myelopathy, thrombosis, nephropathy, chronic inflammatory disease, meningitis, and cerebral venous sinus thrombosis.

47. The composition of embodiment 13 or 43, wherein said neurological condition is Alzheimer's Disease.

48. The composition of embodiment 13 or 43, wherein said neurological condition is Parkinson's Disease.

49. The composition of embodiment 13 or 43, wherein said neurological condition is ALS.

50. The composition of embodiment 13 or 43, wherein said neurological condition is Huntington's Disease.

51. The composition of embodiment 13 or 43, wherein said neurological condition is a stroke.

52. The composition of embodiment 51, wherein said stroke is an ischemic stroke.

53. The composition of embodiment 51, wherein said stroke is a hemorrhagic stroke.

54. The composition of embodiment 43, wherein said composition is capable of converting at least one glial cell to a neuron.

55. The composition of embodiment 54, wherein said glial cells are selected from the group consisting of astrocytes and NG2 cells.

56. The composition of embodiment 54, wherein said glial cells are astrocytes.

57. The composition of embodiment 56, wherein said astrocytes are reactive astrocytes.

58. The composition of embodiment 54, wherein said glial cells are GFAP positive.

59. The composition of embodiment 54, wherein said neurons are functional neurons.

60. The composition of embodiment 54, wherein said functional neurons are selected from the group consisting of glutamatergic neurons, GABAergic neurons. dopaminergic neurons, cholinergic neurons, seratonergic neurons, epinephrinergic neurons, motor neurons, and peptidergic neurons.

61. The composition of embodiment 60, wherein said functional neurons are glutamatergic neurons.

62. The composition of embodiment 6, wherein said composition is formulated to be delivered to a subject in need thereof.

63. The composition of embodiment 62, wherein said composition is formulated for local delivery.

64. The composition of embodiment 62, wherein said composition is formulated for systemic delivery.

65. The composition of any one of embodiments 62-64, wherein said composition is formulated for delivery via intraperitoneal, intramuscular, intravenous, intrathecal, intracerebral, intracranial, intra lateral ventricle of the brain, intra cisterna magna, intra vitreous, intra-subretina, intraparenchymal, intranasal, or oral administration.

66. A method comprising delivering the composition of embodiment 6 to said subject in need thereof.

67. The method of embodiment 66, wherein said composition is formulated to be delivered to a subject in need thereof.

68. The method of embodiment 66, wherein said delivering comprises local administration.

69. The method of embodiment 66, wherein said delivering comprises systemic administration.

70. The method of any one of embodiments 66-69, wherein said delivering comprises an intraperitoneal, intramuscular, intravenous, intrathecal, intracerebral, intracranial, intra lateral ventricle of the brain, intra cisterna magna, intra vitreous, intra-subretina, intraparenchymal, intranasal, or oral administration.

71. A method of converting reactive astrocytes to functional neurons in a brain of a living human comprising: injecting an adeno-associated virus (AAV) into a subject in need thereof, wherein said AAV comprises a DNA vector construct comprising a human neurogenic differentiation 1 (hNeuroD1) sequence comprising the nucleic acid sequence of SEQ ID NO: 6, wherein said sequence is operably linked to regulatory elements comprising:

(a) a human glial fibrillary acid protein (GFAP) promoter comprising a nucleic acid sequence selected from the group consisting of SEQ ID NOs: 4, 12, and 15;

(b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11;

(c) a chimeric intron comprising the nucleic acid sequence of SEQ ID NO: 5 or 16;

(d) a woodchuck hepatitis virus posttranscriptional regulatory element (WPRE) comprising the nucleic acid sequence selected from the group consisting of SEQ ID NOs: 7 and 18; and (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

72. A method of converting reactive astrocytes to functional neurons in a brain of a living humancomprising: injecting an adeno-associated virus (AAV) into a subject in need thereof, wherein said AAV comprises a DNA vector construct comprising a nucleic acid sequence encoding a human neurogenic differentiation 1 (hNeuroD1) protein comprising the amino acid coding sequence of SEQ ID NO: 10, wherein said coding sequence is operably linked to expression control elements comprising:

(a) a human glial fibrillary acid protein (GFAP) promoter comprising a nucleic acid sequence selected from the group consisting of SEQ ID NOs: 4, 12, and 15;

(b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11;

(c) a chimeric intron comprising the nucleic acid sequence of SEQ ID NO: 5 or 16;

(d) a woodchuck hepatitis virus posttranscriptional regulatory element (WPRE) comprising the nucleic acid sequence selected from the group consisting of SEQ ID NOs: 7 and 18; and (e) a SV40 polyadenylation signal sequence comprising the nucleic acid sequence of SEQ ID NO: 8, a hGH polyadenylation sequence comprising the nucleic acid sequence of SEQ ID NO: 13, or a bGH polyadenylation sequence comprising the nucleic acid sequence of SEQ ID NO: 14.

73. A method of converting glial cells to neurons in a subject in need thereof comprising: delivering an adeno-associated virus (AAV) to said subject in need thereof, wherein said AAV comprises a DNA vector construct comprising a neurogenic differentiation 1 (NeuroD1) sequence operably linked to expression control elements comprising:

(a) a glial fibrillary acid protein (GFAP) promoter;

(b) an enhancer;

(c) a chimeric intron;

(d) a woodchuck hepatitis virus posttranscriptional regulatory element (WPRE); and (e) and a polyadenylation signal sequence, wherein said vector is capable of converting at least one glial cell to a neuron in said subject in need thereof.

74. A method of treating a neurological condition in a subject in need thereof comprising: delivering an adeno-associated virus (AAV) to said subject, wherein said AAV comprises a DNA vector construct comprising a neurogenic differentiation 1 (NeuroD1) sequence operably linked to expression control elements comprising:

(a) a glial fibrillary acid protein (GFAP) promoter;

(b) an enhancer;

(c) a chimeric intron;

(d) a woodchuck hepatitis virus posttranscriptional regulatory element (WPRE); and (e) a polyadenylation signal to said subject in need thereof.

75. The method of any one of embodiments 71-74, wherein said AAV is selected from the group consisting of AAV serotype 2, AAV serotype 5, and AAV serotype 9.

76. The method of embodiment 75, wherein said AAV is AAV serotype 2.

77. The method of embodiment 75, wherein said AAV is AAV serotype 5.

78. The method of embodiment 75, wherein said AAV is AAV serotype 9.

79. The method of embodiments 71 or 72, wherein said functional neurons are glutamatergic neurons, GABAergic neurons, dopaminergic neurons, cholinergic neurons, seratonergic neurons, epinephrinergic neurons, motor neurons, and peptidergic neurons.

80. The method of embodiments 73 or 74, wherein said NeuroD1 is human NeuroD1 (hNeuroD1).

81. The method of embodiments 73 or 74, wherein said NeuroD1 is selected from the group consisting of a chimpanzee NeuroD1, a bonobo NeuroD1, an orangutan NeuroD1, a gorilla NeuroD1, a macaque NeuroD1, a marmoset NeuroD1, a capuchin NeuroD1, a baboon NeuroD1, a gibbon NeuroD1, and a lemur NeuroD1.

82. The method of embodiment 80, wherein said hNeuroD1 comprises a amino acid sequence encoding an amino acid coding sequence at least 80% identical or similar to SEQ ID NO: 10.

83. The method of embodiment 80, wherein said hNeuroD1 sequence comprises a nucleic acid sequence at least 80% identical to SEQ ID NO: 6, or the complement thereof.

84. The method of embodiments 73 or 74, wherein said GFAP promoter is a human GFAP (hGFAP) promoter.

85. The method of embodiments 73 or 74, wherein said GFAP promoter is selected from the group consisting of a chimpanzee GFAP promoter, a bonobo GFAP promoter, an orangutan GFAP promoter, a gorilla GFAP promoter, a macaque GFAP promoter, a marmoset GFAP promoter, a capuchin GFAP promoter, a baboon GFAP promoter, a gibbon GFAP promoter, and a lemur GFAP promoter.

86. The method of any one of embodiments 71-85, wherein the DNA vector construct further comprises a 2A self-cleavage peptide sequence at least 80% identical to SEQ ID NO: 3 or the completement thereof.

87. The method of embodiment 84, wherein said hGFAP promoter comprises a nucleic acid sequence at least 80% identical to SEQ ID NO: 4, or the complement thereof.

88. The method of embodiment 84, wherein said hGFAP promoter comprises a nucleic acid sequence at least 80% identical to SEQ ID NO: 12, or the complement thereof.

89. The method of embodiment 84, wherein said hGFAP promoter comprises a nucleic acid sequence at least 80% identical to SEQ ID NO: 15, or the complement thereof.

90. The method of embodiments 73 or 74, wherein said enhancer is selected from the group consisting of an enhancer from human elongation factor-1 alpha (EF1-α) promoter and cytomegalovirus (CMV) enhancer.

91. The method of embodiment 90, wherein said EF1-α comprises a nucleic acid sequence at least 80% identical to SEQ ID NO: 2, or the complement thereof.

92. The method of embodiment 90 wherein said CMV enhancer comprises a nucleic acid sequence at least 80% identical to SEQ ID NO: 11, or the complement thereof.

93. The method of embodiments 73 or 74, wherein said chimeric intron comprises a nucleic acid sequence at least 80% identical to SEQ ID NO: 5, or the complement thereof.

94. The method of embodiments 73 or 74, wherein said chimeric intron comprises a nucleic acid sequence at least 80% identical to SEQ ID NO: 16, or the complement thereof.

95. The method of embodiments 73 or 74, wherein said WPRE comprises a nucleic acid sequence at least 80% identical to a nucleic acid sequence selected from the group consisting of SEQ ID NOs: 7 and 18, or the complement thereof.

96. The method of embodiments 73 or 74, wherein said polyadenylated signal is selected from the group consisting of SV40 polyadenylation signal, a hGH polyadenylation signal, and a bGH polyadenylation signal.

97. The method of embodiments 73 or 74, wherein said SV40 polyadenylated signal comprises a nucleic acid sequence at least 80% identical to SEQ ID NO: 8, or the complement thereof.

98. The method of embodiments 73 or 74 wherein said hGH polyadenylated signal comprises a nucleic acid sequence at least 80% identical to SEQ ID NO: 13, or the complement thereof.

99. The method of embodiments 73 or 74 wherein said bGH polyadenylated signal comprises a nucleic acid sequence at least 80% identical to SEQ ID NO: 14, or the complement thereof.

100. The method of embodiments 73 or 74, wherein said vector further comprises a nucleic acid sequence encoding an AAV protein sequence.

101. The method of any one of embodiments 71-74, wherein said vector comprises AAV serotype 2 inverted terminal repeats (ITRs).

102. The method of any one of embodiments 71-74, wherein said vector comprises AAV serotype 5 inverted terminal repeats (ITRs).

103. The method of any one of embodiments 71-74, wherein said vector comprises AAV serotype 9 inverted terminal repeats (ITRs).

104. The method of any one of embodiments 71-74, wherein said vector comprises at least one ITR nucleic acid sequence at least 80% identical to SEQ ID NO: 1.

105. The method of any one of embodiments 71-74, wherein said vector comprises at least one ITR nucleic acid sequence at least 80% identical to SEQ ID NO: 9.

106. The method of embodiment 71, wherein said converting occurs in the central nervous system (CNS) or peripheral nervous system.

107. The method of embodiment 73, wherein said converting occurs in the CNS.

108. The method of embodiment 73 or 74, wherein said subject in need thereof is a mammal.

109. The method of embodiment 108, wherein said mammal is a human.

110. The method of embodiment 108, wherein said mammal is a non-human primate.

111. The method of embodiment 73 or 74, wherein said delivering comprises a local administration.

112. The method of embodiment 73 or 74, wherein said delivering comprises systemic administration.

113. The method of embodiment 73 or 74, wherein said delivering comprises an administration selected from the group consisting of an intraperitoneal administration, intramuscular administration, intravenous administration, intrathecal administration, intracerebral administration, intracranial, intra lateral ventricle of the brain, intra cisterna magna, intra vitreous, intra-subretina, intraparenchymal administration, intranasal administration, and oral administration.

114. The method of embodiment 71 or 72, wherein said injecting comprises an injection selected from the group consisting of an intraperitoneal injection, intramuscular injection, intravenous injection, intrathecal injection, intracerebral injection, intracranial, intra lateral ventricle of the brain, intra cisterna magna, intra vitreous, intra-subretina, intraparenchymal injection, intranasal injection, and oral injection.

115. The method of embodiments 73 or 74, wherein said delivering comprises injecting.

116. The method of any one of embodiments 71, 72, or 115, wherein said injecting is performed at a concentration of between $10^{10}$ particles/mL and $10^{14}$ particles/mL.

117. The method of embodiment 116, wherein said injecting further comprises a flow rate of between 0.1 ul/minute and 5.0 ul/minute.

118. The method of embodiment 73, wherein said at least one glial cell is selected from the group consisting of at least one astrocyte and at least one NG2 cell.

119. The method of embodiment 71, wherein said at least one glial cell is at least one astrocyte.

120. The method of embodiment 118 or 119, wherein said at least one astrocyte is a reactive astrocyte.

121. The method of embodiment 73, wherein said neuron is a functional neuron.

122. The method of any one of embodiments 71, 72, and 121, wherein said functional neurons are selected from the group consisting of glutamatergic neurons, GABAergic neurons, dopaminergic neurons, cholinergic neurons, seratonergic neurons, epinephrinergic neurons, motor neurons, and peptidergic neurons.

123. The method of embodiment 73, wherein said subject exhibits an improvement of at least one neurological condition symptom as compared to said subject prior to said delivering.

124. The method of embodiment 123, wherein said improvement is measured within 1 year of said delivering.

125. The method of any one of embodiments 71, 72, or 115, wherein said method comprises directly injecting said AAV into the brain of said subject.

126. The method of any one of embodiments 71 or 72, wherein said converting is in the cerebral cortex of said brain.

127. The method of any one of embodiments 71, 72, or 115, wherein said method comprises directly injecting said AAV into the spinal cord of said subject.

128. The method of embodiment 74, wherein said neurological condition comprises an injury to the central nervous system (CNS) or peripheral nervous system.

129. The method of embodiment 74, wherein said neurological condition is selected from the group consisting of Alzheimer's Disease, Parkinson's Disease, amyotrophic lateral sclerosis (ALS), Huntington's Disease, epilepsy, physical injury, stroke, cerebral aneurysm, traumatic brain injury, concussion, a tumor, inflammation, infection, ataxia, brain atrophy, spinal cord atrophy, multiple sclerosis, traumatic spinal cord injury, ischemic or hemorrhagic myelopathy (myelopathy), global ischemia, hypoxic ischemic encephalopathy, embolism, fibrocartilage embolism myelopathy, thrombosis, nephropathy, chronic inflammatory disease, meningitis, and cerebral venous sinus thrombosis.

130. The method of embodiment 74, wherein said neurological condition is Alzheimer's Disease.

131. The method of embodiment 74, wherein said neurological condition is Parkinson's Disease.

132. The method of embodiment 74, wherein said neurological condition is ALS.

133. The method of embodiment 74, wherein said neurological condition is Huntington's Disease.

134. The method of embodiment 74, wherein said neurological condition is a stroke.

135. The method of embodiment 134, wherein said stroke is an ischemic stroke.

136. The method of embodiment 134, wherein said stroke is a hemorrhagic stroke.

137. The method of embodiment 74, wherein said method is capable of converting at least one glial cell into a neuron.

138. The method of embodiment 137, wherein said glial cells are selected from the group consisting of astrocytes and NG2 cells.

139. The method of embodiment 137, wherein said glial cells are astrocytes.

140. The method of embodiment 139, wherein said astrocytes are reactive astrocytes.

141. The method of embodiment 137, wherein said glial cells are GFAP positive.

142. The method of embodiment 137, wherein said neurons are functional neurons.

143. The method of embodiment 142, wherein said functional neurons are selected from the group consisting of glutamatergic neurons, GABAergic neurons, dopaminergic neurons, cholinergic neurons, seratonergic neurons, epinephrinergic neurons, motor neurons, and peptidergic neurons.

144. The method of embodiments 71 or 72, wherein a therapeutically effective dose of said AAV vector is injected into said subject.

145. The method of embodiments 73 or 74, wherein a therapeutically effective dose of said AAV vector is delivered to said subject.

146. The method of embodiment 144 or 145, wherein said therapeutically effective dose is administered with a pharmaceutically acceptable carrier.

147. An adeno-associated virus (AAV) vector comprising a human neurogenic differentiation 1 (hNeuroD1) sequence comprising the nucleic acid sequence of SEQ ID NO: 6, where the hNeuroD1 sequence is operably linked to regulatory elements comprising:
   (a) a glial fibrillary acidic protein (GFAP) promoter comprising the nucleic acid sequence of SEQ ID NO: 15;
   (b) an enhancer from a human elongation factor-1 alpha (EF1-α) promoter comprising the nucleic acid sequence of SEQ ID NO: 2;
   (c) a chimeric intron comprising the nucleic acid sequence of SEQ ID NO: 16;
   (d) a woodchuck hepatitis virus posttranscriptional regulatory element (WPRE) comprising the nucleic acid sequence of SEQ ID NO: 18; and
   (e) a bGH polyadenylation sequence comprising the nucleic acid sequence of SEQ ID NO: 14.

148. An adeno-associated virus (AAV) vector comprising a human neurogenic differentiation 1 (hNeuroD1) sequence comprising the nucleic acid sequence of SEQ ID NO: 6, where the hNeuroD1 sequence is operably linked to regulatory elements comprising:
   (a) a glial fibrillary acidic protein (GFAP) promoter comprising the nucleic acid sequence of SEQ ID NO: 15;
   (b) a cytomegalovirus (CMV) enhancer comprising the nucleic acid sequence of SEQ ID NO: 11;
   (c) a chimeric intron comprising the nucleic acid sequence of SEQ ID NO: 16;
   (d) a woodchuck hepatitis virus posttranscriptional regulatory element (WPRE) comprising the nucleic acid sequence of SEQ ID NO: 18; and
   (e) a bGH polyadenylation sequence comprising the nucleic acid sequence of SEQ ID NO: 14.

---

The invention claimed is:

1. An adeno-associated virus (AAV) vector comprising a human neurogenic differentiation 1 (hNeuroD1) sequence, wherein said hNeuroD1 sequence comprises a nucleic acid sequence at least 99% identical to SEQ ID NO:6; wherein the AAV vector does not encode another heterologous polypeptide; and wherein said hNeuroD1 sequence is operably linked to regulatory elements comprising:

(a) a glial fibrillary acidic protein (GFAP) promoter comprising a nucleic acid sequence at least 95% identical to the sequence set forth in SEQ ID NO:15;

(b) a cytomegalovirus (CMV) enhancer comprising a nucleic acid sequence at least 95% identical to the sequence set forth in SEQ ID NO:11;

(c) a chimeric intron comprising a nucleic acid sequence at least 95% identical to the sequence set forth in SEQ ID NO:16;

(d) a woodchuck hepatitis virus posttranscriptional regulatory element (WPRE) comprising the nucleic acid sequence set forth in SEQ ID NO:18; and (e) a bGH polyadenylation sequence comprising a nucleic acid sequence at least 95% identical to the sequence set forth in SEQ ID NO:14.

2. The AAV vector of claim 1, wherein:

(a) said GFAP promoter comprises the nucleic acid sequence set forth in SEQ ID NO: 15;

(b) said CMV enhancer comprises the nucleic acid sequence set forth in SEQ ID NO: 11;

(c) said chimeric intron comprises the nucleic acid sequence set forth in SEQ ID NO: 16;

(d) said bGH polyadenylation sequence comprises the nucleic acid sequence set forth in SEQ ID NO:14; or (e) said nucleic acid sequence encoding said hNeuroD1 sequence is at least 99.5% identical to the sequence set forth in SEQ ID NO:6.

3. The AAV vector of claim 1, wherein said AAV vector is selected from the group consisting of AAV serotype 2, AAV serotype 5, and AAV serotype 9.

4. The AAV vector of claim 1, wherein said hNeuroD1 sequence comprises the nucleic acid sequence set forth in SEQ ID NO:6.

5. The AAV vector of claim 1, wherein said AAV vector further comprises a 2A self-cleavage peptide coding sequence that is at least 80% identical to (i) the sequence set forth in SEQ ID NO:3 or (ii) the complementary sequence set forth in SEQ ID NO:3.

6. The AAV vector of claim 1, wherein said AAV vector comprises at least one inverted terminal repeat nucleic acid sequence at least 80% identical to the sequence set forth in SEQ ID NO: 1 or SEQ ID NO:9.

7. An adeno-associated virus (AAV) vector comprising, in order from 5' to 3':

(a) a cytomegalovirus (CMV) enhancer comprising a nucleic acid sequence at least 95% identical to the sequence set forth in SEQ ID NO:11;

(b) a glial fibrillary acidic protein (GFAP) promoter comprising a nucleic acid sequence at least 95% identical to the sequence set forth in SEQ ID NO:15;

(c) a chimeric intron comprising a nucleic acid sequence at least 95% identical to the sequence set forth in SEQ ID NO:16;

(d) a human neurogenic differentiation 1 (hNeuroD1) sequence comprising a nucleic acid sequence at least 99% identical to the sequence set forth in SEQ ID NO:6;

(e) a woodchuck hepatitis virus posttranscriptional regulatory element (WPRE) comprising the nucleic acid sequence set forth in SEQ ID NO:18; and (f) a bGH polyadenylation sequence comprising a nucleic acid sequence at least 95% identical to the sequence set forth in SEQ ID NO:14;

wherein the AAV vector does not encode another heterologous polypeptide.

8. The AAV vector of claim 7, wherein said AAV vector comprises at least one inverted terminal repeat nucleic acid sequence at least 80% identical to the sequence set forth in SEQ ID NO:1 or SEQ ID NO:9.

9. The AAV vector of claim 7, wherein:

(a) said GFAP promoter comprises the nucleic acid sequence set forth in SEQ ID NO: 15;

(b) said CMV enhancer comprises the nucleic acid sequence set forth in SEQ ID NO: 11;

(c) said chimeric intron comprises the nucleic acid sequence set forth in SEQ ID NO: 16;

(d) said bGH polyadenylation sequence comprises the nucleic acid sequence set forth in SEQ ID NO:14; and (e) said hNeuroD1 sequence comprises a nucleic acid sequence at least 99.5% identical to the sequence set forth in SEQ ID NO:6.

10. The AAV vector of claim 1, wherein said AAV vector further comprises a 2A self-cleavage peptide coding sequence at least 90% identical to (i) the sequence set forth in SEQ ID NO:3 or (ii) the complementary sequence set forth in SEQ ID NO:3.

11. The AAV vector of claim 1, wherein said AAV vector further comprises a 2A self-cleavage peptide coding sequence comprising the nucleic acid sequence set forth in SEQ ID NO:3 or the complementary sequence set forth in SEQ ID NO:3.

12. The AAV vector of claim 1, wherein said AAV vector comprises at least one inverted terminal repeat nucleic acid sequence at least 90% identical to the sequence set forth in SEQ ID NO:1 or SEQ ID NO:9.

13. The AAV vector of claim 1, wherein said AAV vector comprises at least one inverted terminal repeat nucleic acid sequence set forth in SEQ ID NO:1 or SEQ ID NO:9.

14. The AAV vector of claim 7, wherein said AAV vector is selected from the group consisting of AAV serotype 2, AAV serotype 5, and AAV serotype 9.

15. The AAV vector of claim 7, wherein said AAV vector further comprises a 2A self-cleavage peptide coding sequence at least 90% identical to (i) the sequence set forth in SEQ ID NO:3 or (ii) the complementary sequence set forth in SEQ ID NO:3.

16. The AAV vector of claim 7, wherein said AAV vector further comprises a 2A self-cleavage peptide coding sequence comprising the nucleic acid sequence set forth in SEQ ID NO:3 or the complementary sequence set forth in SEQ ID NO:3.

17. The AAV vector of claim 7, wherein said AAV vector comprises at least one inverted terminal repeat nucleic acid sequence at least 90% identical to the sequence set forth in SEQ ID NO: 1 or SEQ ID NO: 9.

18. The AAV vector of claim 7, wherein said AAV vector comprises at least one inverted terminal repeat nucleic acid sequence set forth in SEQ ID NO: 1 or SEQ ID NO:9.

19. The AAV vector of claim 1, wherein said hNeuroD1 sequence comprises the amino acid sequence set forth in SEQ ID NO:10.

* * * * *